US011155821B2

(12) United States Patent
Palmer et al.

(10) Patent No.: US 11,155,821 B2
(45) Date of Patent: Oct. 26, 2021

(54) COMPOSITIONS AND METHODS FOR TAGGING RIBONUCLEIC ACIDS

(71) Applicants: The Regents of the University of Colorado, a body corporate, Denver, CO (US); Institute of Organic Chemistry POS, Warsaw (PL)

(72) Inventors: Amy E. Palmer, Boulder, CO (US); Esther Braselmann, Arvada, CO (US); Robert T. Batey, Boulder, CO (US); Dorota Gryko, Warsaw (PL)

(73) Assignees: The Regents of the University of Colorado, a body corporate, Denver, CO (US); Institute of Organic Chemistry POS, Warsaw (PL)

( * ) Notice: Subject to any disclaimer, the term of this patent is extended or adjusted under 35 U.S.C. 154(b) by 121 days.

(21) Appl. No.: 16/526,835

(22) Filed: Jul. 30, 2019

(65) Prior Publication Data
US 2020/0149046 A1 May 14, 2020

Related U.S. Application Data

(60) Provisional application No. 62/712,832, filed on Jul. 31, 2018.

(51) Int. Cl.
*C12N 15/115* (2010.01)
*C12Q 1/68* (2018.01)

(52) U.S. Cl.
CPC ........ *C12N 15/115* (2013.01); *C12N 2310/16* (2013.01); *C12N 2310/3517* (2013.01); *C12N 2310/3519* (2013.01); *C12N 2310/531* (2013.01); *C12N 2310/532* (2013.01)

(58) Field of Classification Search
None
See application file for complete search history.

(56) References Cited

U.S. PATENT DOCUMENTS 8,313,901 B2    11/2012  Breaker et al. ............... 435/6.1
2011/0151471 A1  6/2011  Breaker et al. ............. 435/6.13

FOREIGN PATENT DOCUMENTS

WO    WO2005025512    3/2005

OTHER PUBLICATIONS

Andreassi and Riccio, "To Localize or Not to Localize: mRNA Fate Is in 3'UTR Ends." *Trends Cell Biol*, 19(9):465-474 (2009).
Arora, et al., "Dual-Colour Imaging of mRNA Using Quencher- and Fluorophore-Binding Aptamers." *Nucleic acids research*, 43(21):e144-e144 (2015).
Autour, et al., "Fluorogenic RNA Mango Aptamers for Imaging Small Non-Coding mRNA in Mammalian Cells." *Nature communications*, 9(1):1-12 (2018).
Babendure, et al., "Aptamers Switch on Fluorescence of Triphenylmethane Dyes." *Journal of the American Chemical Society*, 125(48):14716-14717 (2003).
Batey, "Basis of Gene Regulation by Purine and Cobalamin Riboswitches." 2R01GM073850-10. Project start date: Apr. 1, 2005. abstract only. Downloaded Apr. 17, 2018.
Beckley, et al., "Reduction of Target Gene Expression by a Modified U1 snRNA." *Molecular and Cellular Biology*, 21(8):2815-2825 (2001).
Ben-Ari, et al., "The Life of an mRNA in Space and Time." *J Cell Sci*, 123(Pt 10):1761-1774 (2010).
Bertrand, et al., "Localization of Ash1 mRNA Particles in Living Yeast." *Mol Cell*, 2(4):437-445 (1998).
Buchan and Parker, "Eukaryotic Stress Granules: The Ins and Outs of Translation." *Molecular Cell*, 36(6):932-941 (2009).
Buxbaum, et al., "Single B-Actin mRNA Detection in Neurons Reveals a Mechanism for Regulating Its Translatability." *Science*, 343(6169):419-422 (2014).
Buxbaum, et al., "In the Right Place at the Right Time: Visualizing and Understanding mRNA Localization." *Nat Rev Mol Cell Biol*, 16(2):95-109 (2015).
Ceres, et al., "Modularity of Select Riboswitch Expression Platforms Enables Facile Engineering of Novel Genetic Regulatory Devices." *ACS synthetic biology*, 2(8):463-472 (2013A).
Ceres, et al., "Engineering Modular 'On' RNA Switches Using Biological Components." *Nucleic acids research*, 41(22):10449-10461 (2013B).
Chao, et al., "Structural Basis for the Coevolution of a Viral mRNA—Protein Complex." *Nat Struct Mol Biol*, 15(1):103-105 (2008).
Chromiński and Gryko, ""Clickable" Vitamin B12 Derivative." *Chemistry—A European Journal*, 19(16):5141-5148 (2013).
Condeelis and Singer, "How and Why Does B-Actin mRNA Target?" *Biology of the Cell*, 97(1):97-110 (2005).
Custer and Walter, "In Vitro Labeling Strategies for in Cellulo Fluorescence Microscopy of Single Ribonucleoprotein Machines." *Protein Sci*, 26(7):1363-1379 (2017).
Dean and Palmer, "Advances in Fluorescence Labeling Strategies for Dynamic Cellular Imaging." *Nat Chem Biol*, 10(7):512-523 (2014).

(Continued)

*Primary Examiner* — Sean McGarry
(74) *Attorney, Agent, or Firm* — Medlen & Carroll, LLP

(57) ABSTRACT

This invention relates to the field of ribonucleic acid (RNA) regulation of intracellular activity. In particular, the invention relates to compositions and methods of identifying and tracking specific intracellular RNAs. For example, a fluorescently tagged RNA probe may be tracked by in vivo live imaging throughout its intracellular lifetime in order to determine its purpose and identify regulatory targets to modify its effects. Alternatively, an RNA probe may carry a therapeutic payload for treatment of medical condition or disorder.

19 Claims, 55 Drawing Sheets
(41 of 55 Drawing Sheet(s) Filed in Color)
Specification includes a Sequence Listing.

(56) References Cited

OTHER PUBLICATIONS

Decker and Parker, "P-Bodies and Stress Granules: Possible Roles in the Control of Translation and mRNA Degradation." *Cold Spring Harbor perspectives in biology*, 4(9):a012286 (2012).
Dolgosheina, et al., "RNA Mango Aptamer-Fluorophore: A Bright, High-Affinity Complex for RNA Labeling and Tracking." *ACS Chemical Biology*, 9(10):2412-2420 (2014).
Edwards, et al., Determining Structures of RNA Aptamers and Riboswitches by X-Ray Crystallography *Nucleic Acid and Peptide Aptamers* (pp. 135-163): Springer. (2009).
Fedosov, et al., "Application of a Fluorescent Cobalamin Analogue for Analysis of the Binding Kinetics: A Study Employing Recombinant Human Transcobalamin and Intrinsic Factor." *The FEBS journal*, 273(20):4742-4753 (2006).
Filonov, et al., "Broccoli: Rapid Selection of an RNA Mimic of Green Fluorescent Protein by Fluorescence-Based Selection and Directed Evolution." *Journal of the American Chemical Society*, 136(46):16299-16308 (2014).
Filonov, et al., "In-Gel Imaging of RNA Processing Using Broccoli Reveals Optimal Aptamer Expression Strategies." *Chemistry & Biology*, 22(5):649-660 (2015).
Filonov and Jaffrey, "RNA Imaging with Dimeric Broccoli in Live Bacterial and Mammalian Cells." *Current Protocols in Chemical Biology*, 8(1):1-28 (2016).
Fowler, et al., "Uptake and Transport of B12-Conjugated Nanoparticles in Airway Epithelium." *J Control Release*, 172(1):374-381 (2013).
Fusco, et al., "Single Mrna Molecules Demonstrate Probabilistic Movement in Living Mammalian Cells." *Current Biology*, 13(2):161-167 (2003).
Garcia and Parker, "MS2 Coat Proteins Bound to Yeast mRNAs Block 5' to 3' Degradation and Trap mRNA Decay Products: Implications for the Localization of mRNA s by MS2-MCP System." *RNA*, 21(8):1393-1395 (2015).
Gerstberger, et al., "A Census of Human mRNA-Binding Proteins." *Nature Reviews Genetics*, 15(12):829-845 (2014).
Gilbert and Batey, Monitoring RNA—Ligand Interactions Using Isothermal Titration Calorimetry *Riboswitches* (pp. 97-114): Springer. (2009).
Golding and Cox, "RNA Dynamics in Live *Escherichia coli* Cells." *Proceedings of the National Academy of Sciences of the United States of America*, 101(31):11310-11315 (2004).
Grimm, et al., "A General Method to Fine-Tune Fluorophores for Live-Cell and in Vivo Imaging" *Nature methods*, 14(10):987 (2017).
Han, et al., "Understanding the Photophysics of the Spinach—DFHBI RNA Aptamer—Fluorogen Complex to Improve Live-Cell RNA Imaging." *Journal of the American Chemical Society*, 135(50):19033-19038 (2013).
Hayashi-Takanaka, et al., "Tracking Epigenetic Histone Modifications in Single Cells Using Fab-Based Live Endogenous Modification Labeling." *Nucleic acids research*, 39(15):6475-6488 (2011).
Hutten, et al., "A Role for the Cajal-Body-Associated SUMO Isopeptidase USPL1 in snRNA Transcription Mediated by RNA Polymerase II." *Journal of cell science*, 127(5):1065-1078 (2014).
Ishikawa, et al., "Identification of Truncated Forms of U1 snRNA Reveals a Novel RNA Degradation Pathway During snRNP Biogenesis." *Nucleic acids research*, 42(4):2708-2724 (2014).
Jeng, et al., "Fluorophore Ligand Binding and Complex Stabilization of the RNA Mango and RNA Spinach Aptamers." *RNA*, 22(12):1884-1892 (2016).
Johnson Jr, et al., "B12 Cofactors Directly Stabilize an mRNA Regulatory Switch." *Nature*, 492(7427):133-137 (2012).
Katz, et al., "Mapping Translation 'hot-Spots' in Live Cells by Tracking Single Molecules of mRNA and Ribosomes." *Elife*, 5:e10415 (2016).
Kedersha, et al., "Real-Time and Quantitative Imaging of Mammalian Stress Granules and Processing Bodies." *Methods in enzymology*, 448:521-552 (2008).

Kollmannsperger, et al., "Live-Cell Protein Labelling with Nanometre Precision by Cell Squeezing." *Nature Communications*, 7(1):10372 (2016).
Konopka and Bednarek, "Variable-Angle Epifluorescence Microscopy: A New Way to Look at Protein Dynamics in the Plant Cell Cortex." *Plant J*, 53(1):186-196 (2008).
Lakowicz (ed.), Quenching of Fluorescence. Chapter 8. In Principles of Fluorescence Spectroscopy, pp: 277-330 (Springer) 2006.
Lee and Grissom, "Design, Synthesis, and Characterization of Fluorescent Cobalamin Analogues with High Quantum Efficiencies." *Organic letters*, 11(12):2499-2502 (2009).
Lee, et al., "Therapeutic Applications of Aptamer-Based Riboswitches." *Nucleic Acid Ther*, 26(1):44-51 (2016).
Lifland, et al., "Dynamics of Native B-Actin mRNA Transport in the Cytoplasm." *Traffic*, 12(8):1000-1011 (2011).
Loska, et al., "Design and Synthesis of Protoporphyrin IX/Vitamin B12 Molecular Hybrids Via CUAAC Reaction." *Journal of Porphyrins and Phthalocyanines*, 17(01n02):104-117 (2013).
Lyon and Stasevich, "Imaging Translational and Post-Translational Gene Regulatory Dynamics in Living Cells with Antibody-Based Probes." *Trends Genet*, 33(5):322-335 (2017).
Ma, et al., "Huntingtin Mediates Dendritic Transport of B-Actin mRNA in Rat Neurons." *Sci Rep*, 1:140 (2011).
Matera and Wang, "A Day in the Life of the Spliceosome." *Nature reviews Molecular cell biology*, 15(2):108-121 (2014).
McCloskey, et al., "HNRNP C Tetramer Measures RNA Length to Classify RNA Polymerase II Transcripts for Export." *Science*, 335(6076):1643-1646 (2012).
McNeil and Warder, "Glass Beads Load Macromolecules into Living Cells." *Journal of cell science*, 88(5):669-678 (1987).
Mollet, et al., "Translationally Repressed mRNA Transiently Cycles through Stress Granules During Stress." *Mol Biol Cell*, 19(10):4469-4479 (2008).
Morisaki, et al., "Real-Time Quantification of Single RNA Translation Dynamics in Living Cells." *Science*, 352(6292):1425-1429 (2016).
Nahvi, et al., "Coenzyme B12 Riboswitches Are Widespread Genetic Control Elements in Prokaryotes." *Nucleic acids research*, 32(1):143-150 (2004).
Nelles, et al., "Programmable RNA Tracking in Live Cells with Crispr/Cas9." *Cell*, 165(2):488-496 (2016).
Nguyen, et al., "Binding to an RNA Aptamer Changes the Charge Distribution and Conformation of Malachite Green." *Journal of the American Chemical Society*, 124(50):15081-15084 (2002).
Ni, et al., "Crystal Structure of the MS2 Coat Protein Dimer: Implications for RNA Binding and Virus Assembly." *Structure*, 3(3):255-263 (1995).
Ouellet ,"RNA Fluorescence with Light-up Aptamers." *Front Chem*, 4:29 (2016).
Paige, et al., "RNA Mimics of Green Fluorescent Protein." *Science*, 333(6042):642-646 (2011).
Park, et al., "Visualization of Dynamics of Single Endogenous mRNA Labeled in Live Mouse." *Science*, 343(6169):422-424 (2014).
Pitchiaya, et al., "Intracellular Single Molecule Microscopy Reveals Two Kinetically Distinct Pathways for Microrna Assembly." *EMBO Rep*, 13(8):709-715 (2012).
Pitchiaya, et al., "Resolving Subcellular miRNA Trafficking and Turnover at Single-Molecule Resolution." *Cell Rep*, 19(3):630-642 (2017).
Polaski, et al., "Mechanistic Insights into Cofactor-Dependent Coupling of RNA Folding and mRNA Transcription/Translation by a Cobalamin Riboswitch." *Cell reports*, 15(5):1100-1110 (2016).
Ponchon and Dardel, "Recombinant RNA Technology: The tRNA Scaffold." *Nature methods*, 4(7):571-576 (2007).
Quadros and Sequeira, "Cellular Uptake of Cobalamin. Transcobalamin and the TCBLR/CD320 Receptor." *Biochimie*, 95(5):1008-1018 (2013).
Querido and Chartrand, "Using Fluorescent Proteins to Study mRNA Trafficking in Living Cells." *Methods Cell Biol*, 85:273-292 (2008).
Santangelo, et al., "Single Molecule-Sensitive Probes for Imaging RNA in Live Cells." *Nat Methods*, 6(5):347-349 (2009).

(56) References Cited

OTHER PUBLICATIONS

Sauer and Paeschke, "G-Quadruplex Unwinding Helicases and Their Function in Vivo." *Biochem Soc Trans*, 45(5):1173-1182 (2017).
Schmidt, et al., "Live Cell Imaging Reveals the Dynamics of Telomerase Recruitment to Telomeres." *Cell*, 166(5):1188-1197 e1189 (2016).
Shav-Tal, et al., "Dynamics of Single mRNps in Nuclei of Living Cells." *Science*, 304(5678):1797-1800 (2004).
Shpargel, et al., "Control of Cajal Body Number Is Mediated by the Coilin C-Terminus." *Journal of cell science*, 116(2):303-312 (2003).
Shpargel and Matera, "Gemin Proteins Are Required for Efficient Assembly of Sm-Class Ribonucleoproteins." *Proceedings of the National Academy of Sciences*, 102(48): 17372-17377 (2005).
Smeltzer, et al., "Synthesis and Characterization of Fluorescent Cobalamin (Cobalafluor) Derivatives for Imaging." *Organic letters*, 3(6):799-801 (2001).
Song, et al., "Imaging RNA Polymerase IIITranscription Using a Photostable RNA—Fluorophore Complex." *Nature chemical biology*, 13(11):1187 (2017).
Specht, et al., "A Critical and Comparative Review of Fluorescent Tools for Live-Cell Imaging." *Annu Rev Physiol*, 79:93-117 (2017).
Strack, et al., "A Superfolding Spinach2 Reveals the Dynamic Nature of Trinucleotide Repeat-Containing Rna." *Nat Methods*, 10(12):1219-1224 (2013).
Sunbul and Jäschke, "Contact-Mediated Quenching for RNA Imaging in Bacteria with a Fluorophore-Binding Aptamer." *Angewandte Chemie*, 125(50):13643-13646 (2013).
Tan, et al., "Fluoromodules Consisting of a Promiscuous RNA Aptamer and Red or Blue Fluorogenic Cyanine Dyes: Selection, Characterization, and Bioimaging." *Journal of the American Chemical Society*, 139(26):9001-9009 (2017).
Tanenbaum, et al., "A Protein-Tagging System for Signal Amplification in Gene Expression and Fluorescence Imaging." *Cell*, 159(3):635-646 (2014).
Teng, et al., "Delivery of Fluorescent Probes Using Streptolysin O for Fluorescence Microscopy of Living Cells." *Curr Protoc Protein Sci*, 93(1):e60 (2018).
Tinevez, et al., "Trackmate: An Open and Extensible Platform for Single-Particle Tracking." *Methods*, 115:80-90 (2017).
Tokunaga, et al., "Highly Inclined Thin Illumination Enables Clear Single-Molecule Imaging in Cells." *Nat Methods*, 5(2):159-161 (2008).
Trachman, et al., "Structural Basis for High-Affinity Fluorophore Binding and Activation by RNA Mango." *Nat Chem Biol*, 13(7):807-813 (2017).
Trausch and Batey, Chapter Three "Design of Modular "Plug-and-Play" Expression Platforms Derived from Natural Riboswitches for Engineering Novel Genetically Encodable RNA Regulatory Devices." In, Methods in Enzymology, vol. 550, pp. 41-71. Abstract only. 2015. Epub 2014.
Tsalikis, et al., "Intracellular Bacterial Pathogens Trigger the Formation of U Small Nuclear RNA Bodies (U Bodies) through Metabolic Stress Induction." *Journal of Biological Chemistry*, 290(34):20904-20918 (2015).
Tutucci, et al., "An Improved MS2 System for Accurate Reporting of the mRNA Life Cycle." *Nature methods*, 15(1):81-89 (2018).
Vargas, et al., "Mechanism of mRNA Transport in the Nucleus." *Proceedings of the National Academy of Sciences of the United States of America*, 102(47):17008-17013 (2005).
Viswanathan, et al., "High-Performance Probes for Light and Electron Microscopy." *Nat Methods*, 12(6):568-576 (2015).
Voigt, et al., "Single-Molecule Quantification of Translation-Dependent Association of mRNAs with the Endoplasmic Reticulum." *Cell Rep*, 21(13):3740-3753 (2017).
Wagner, et al., "Classification and Segmentation of Nanoparticle Diffusion Trajectories in Cellular Micro Environments." *PloS one*, 12(1):e0170165-e0170165 (2017).
Wang, et al., "Real-Time Imaging of Translation on Single mRNA Transcripts in Live Cells." *Cell*, 165(4):990-1001 (2016).
Warner, et al., "Structural Basis for Activity of Highly Efficient RNA Mimics of Green Fluorescent Protein." *NaturE Structural & Molecular Biology*, 21(8):658-663 (2014).
Wheeler, et al., Distinct Stages in Stress Granule Assembly and Disassembly. Elife 5: e18413 (2016).
Wu, et al., "Fluorescence Fluctuation Spectroscopy Enables Quantitative Imaging of Single mRNAs in Living Cells." *Biophysical journal*, 102(12):2936-2944 (2012).
Wu, et al., "Background Free Imaging of Single mRNAs in Live Cells Using Split Fluorescent Proteins." *Scientific reports*, 4(1):1-3 (2014).
Wu, et al., "Translation Dynamics of Single mRNA s in Live Cells and Neurons." *Science*, 352(6292):1430-1435 (2016).
Xi, et al., "A Novel Two-Step Genome Editing Strategy with Crispr-Cas9 Provides New Insights into Telomerase Action and Tert Gene Expression." *Genome biology*, 16(1):1-17 (2015).
Yamagishi, et al., "Single-Molecule Imaging of Beta-Actin mRNA s in the Cytoplasm of a Living Cell." *Exp Cell Res*, 315(7):1142-1147 (2009).
Yoon, et al., "Glutamate-Induced RNA Localization and Translation in Neurons." *Proceedings of the National Academy of Sciences*, 113(44):E6877-E6886 (2016).
You, et al., "Imaging Metabolite Dynamics in Living Cells Using a Spinach-Based Riboswitch." *Proceedings of the National Academy of Sciences*, 112(21):E2756-E2765 (2015).
Zimyanin, et al., "In Vivo Imaging of Oskar mRNA Transport Reveals the Mechanism of Posterior Localization." *Cell*, 134(5):843-853 (2008).
Zurla, et al., "Characterizing mRNA Interactions with RNA Granules During Translation Initiation Inhibition." *PLoS One*, 6(5):e19727 (2011).
Braselmann, et al., "Development of a riboswitch-based platform for live cell imaging of RNAs in mammalian cells." BioRxiv. Posted Oct. 10, 2017.
Braselmann, et al., "Development of a riboswitch-based platform for live cell imaging of RNAs. in mammalian cells." Supplemental Figures and Tables. BioRxiv. Posted Oct. 10, 2017.
Braselmann, et al., Poster Board B182 titled: "Color Riboswitch-Based Platform for Imagining of mRNA and all non-coding RNA in live mammalian cells". Abstract, Biophysical Journal, vol. 114, issue 3, pp. 437a-438a, Feb. 2, 2018.
Braselmann, et al., "Riboglow: a multicolor riboswitch-based platform for live cell imaging of mRNA and small non-coding RNA in mammalian cells." BioRxiv. Apr. 9, 2018.
Braselmann, et al., "Detection and quantification of single mRNA dynamics with the Riboglow fluorescent RNA tag." BioRxiv. Jul. 13, 2019.
Braselmann, et al., "Detection and quantification of single mRNA dynamics with the Riboglow fluorescent RNA tag." BioRxiv. Supplemental information. Jul. 13, 2019.
Cioni, et al. "Late Endosomes Act as mRNA Translation Platforms and Sustain Mitochondria in Axons." Cell 176, 56-72 (2019).
Eliscovich & Singer, "RNP transport in cell biology: the long and winding road." Curr. Opin. Cell Biol. 45, 38-46 (2017).
Hoek, et al. "Single-Molecule Imaging Uncovers Rules Governing Nonsense-Mediated mRNA Decay." Mol. Cell 75, 1-16 (2019).
Lionnet, et al. "A transgenic mouse for in vivo detection of endogenous labeled mRNA." Nat. Methods 8, 165-70 (2011).
Lyon, et al. "Live-Cell Single RNA Imaging Reveals Bursts of Translational Frameshifting." Mol. Cell 75, 1-12 (2018).
Moon, et al. "Multicolour single-molecule tracking of mRNA interactions with RNP granules." Nat. Cell Biol. 21, (2019).

Fig. 1C – cont.
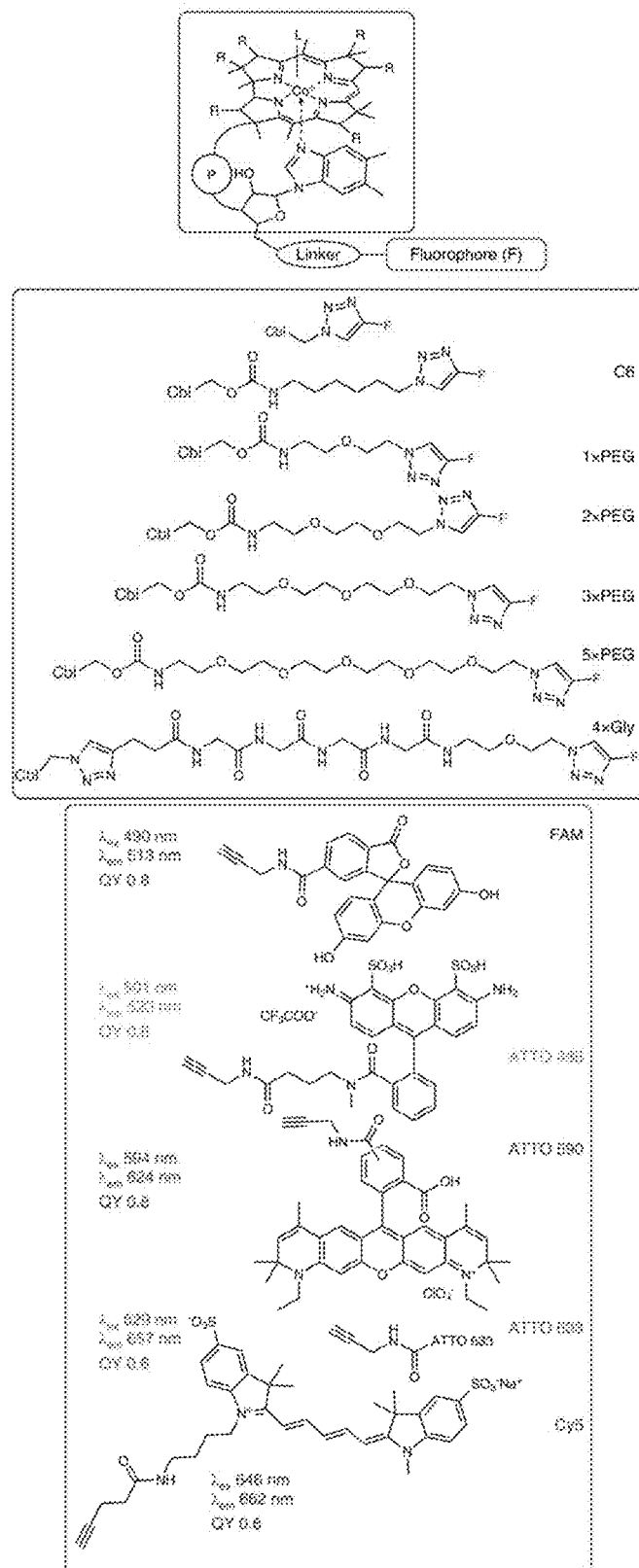

Fig. 6
SEQ ID NO: 1 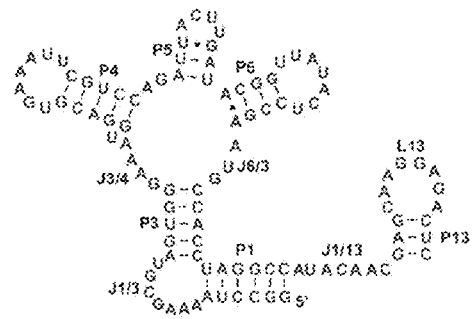 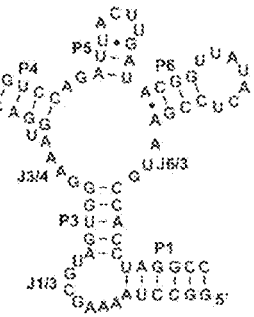 SEQ ID NO: 2
SEQ ID NO: 3 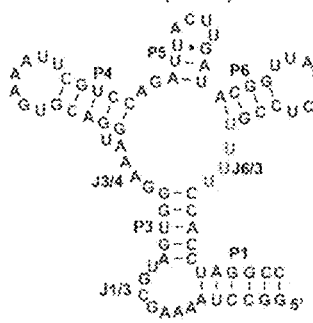 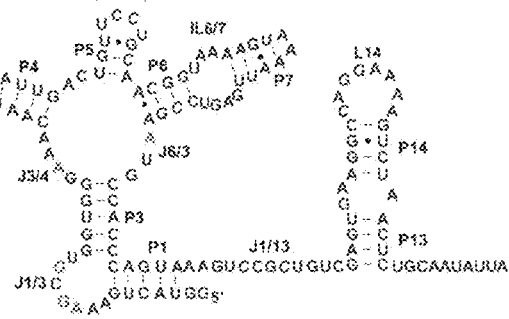 SEQ ID NO: 4
SEQ ID NO: 5 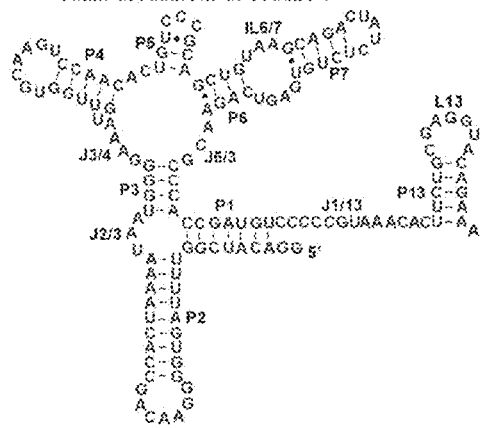 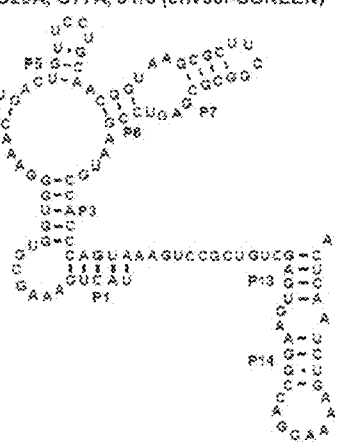 SEQ ID NO: 6

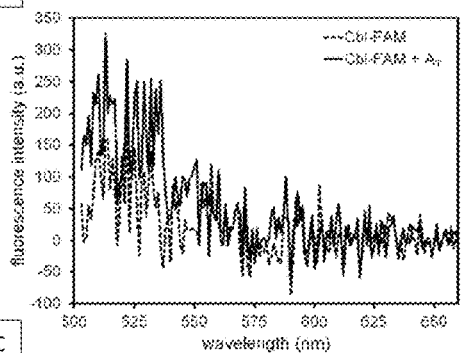
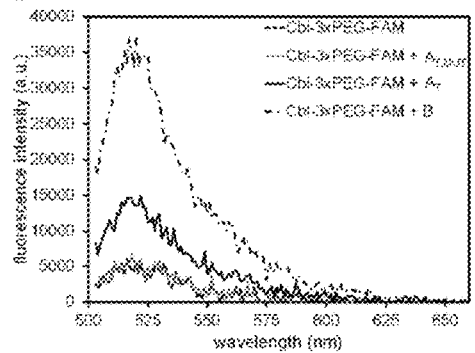
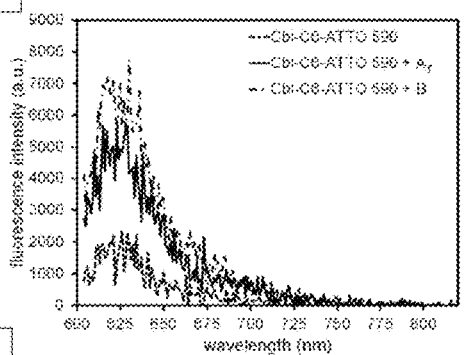
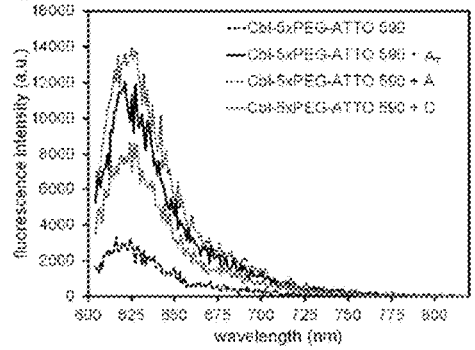
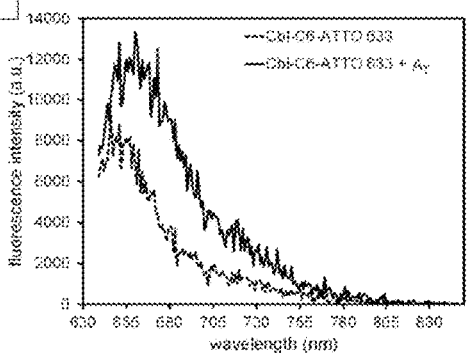
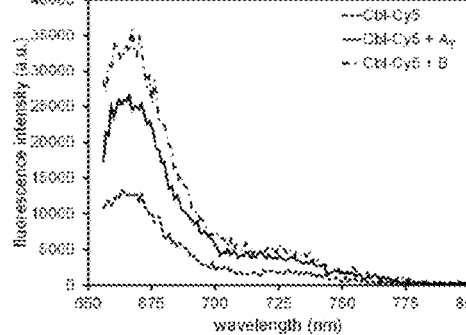

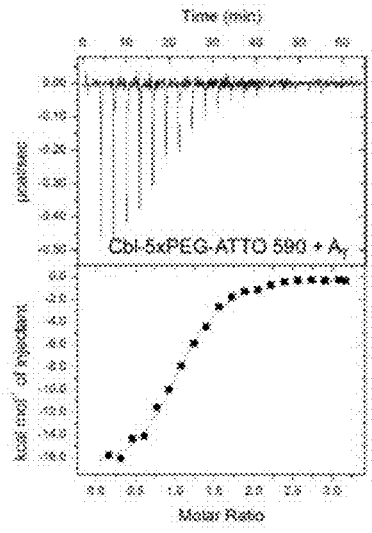 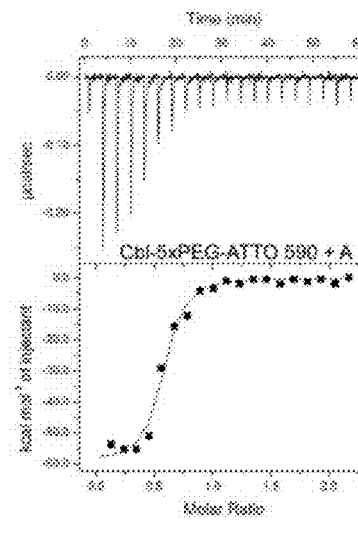 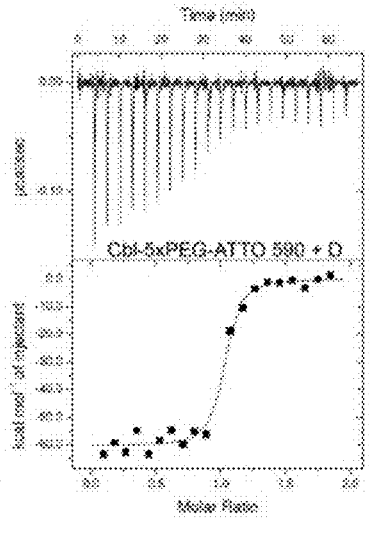

Cbl-Cy5
98% of cells (49/50)

Cbl-5xPEG-ATTO 590
98% of cells (127/129)

Cbl-5xGly-ATTO 590
99% of cells (156/158)

Cbl-Cy5
63% of cells (14/22)

Cbl-5xPEG-ATTO 590
89% of cells (39/44)

Cbl-5xPEG-ATTO 590
98% of cells (44/45)

Cbl-5xGly-ATTO 590
55% of cells (46/83)    45% of cells (37/83)

Fig. 34A
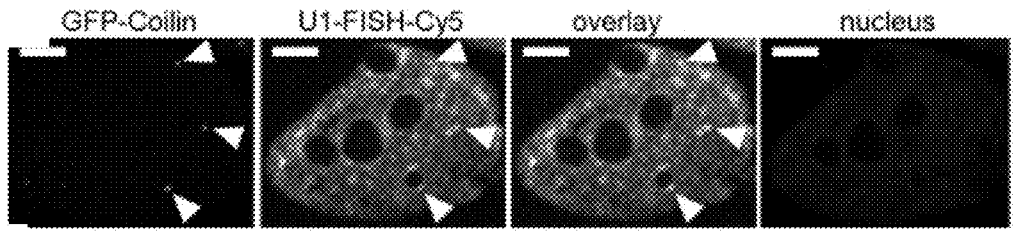
Fig. 34B
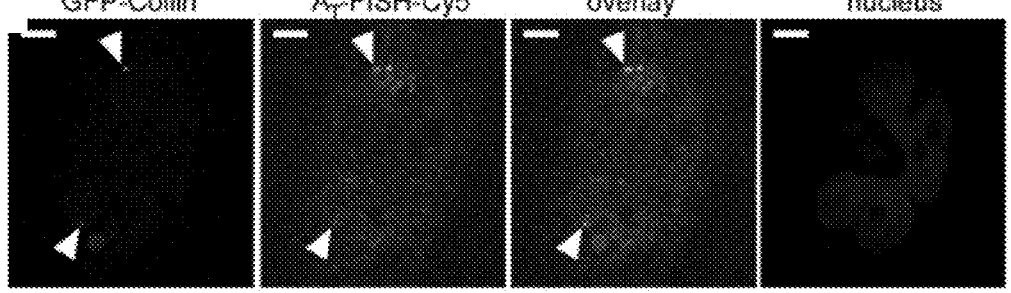
Fig. 34C
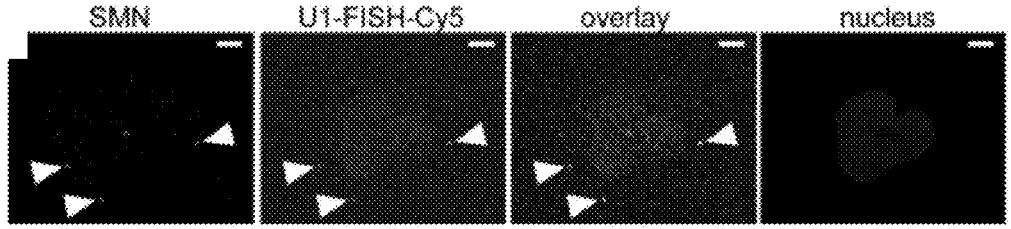
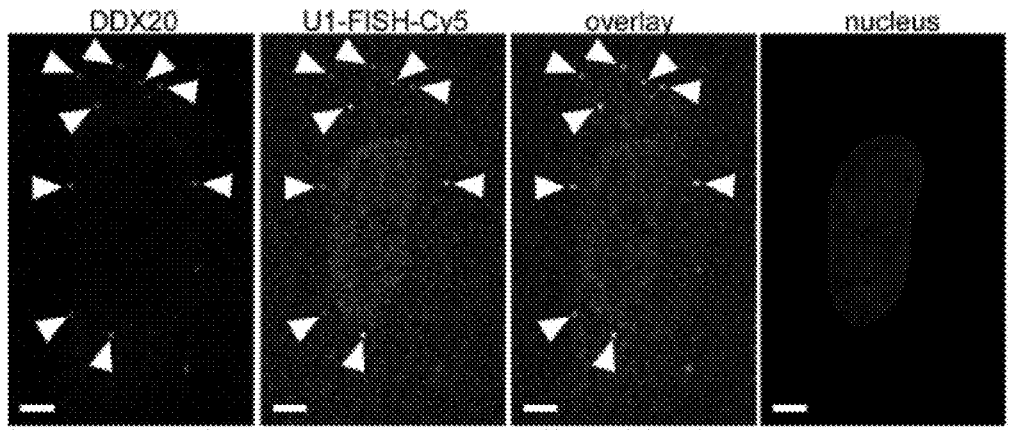

Fig. 38A
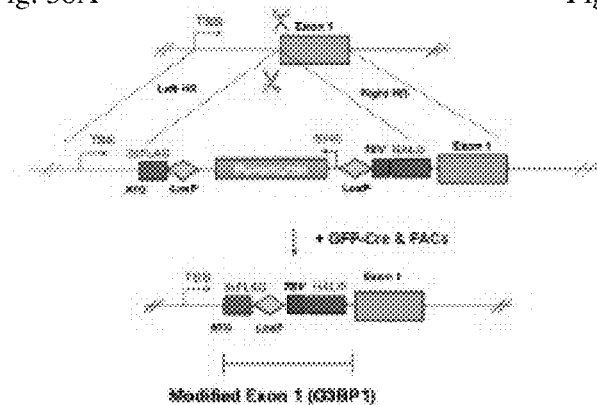
Fig. 38B
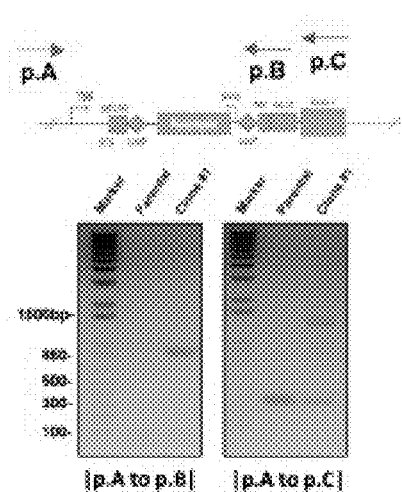
Fig. 38C
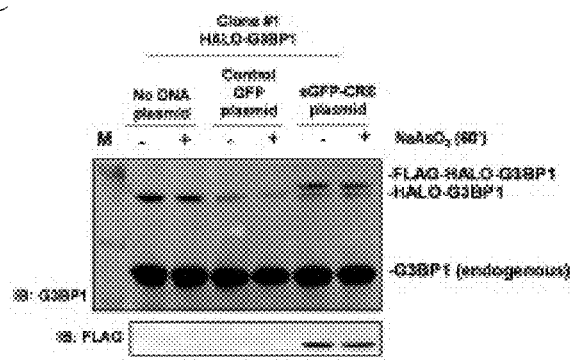
Fig. 38D
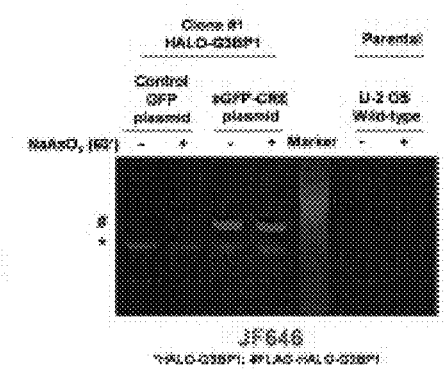
Fig. 38E
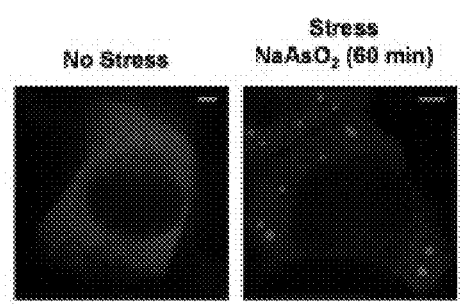
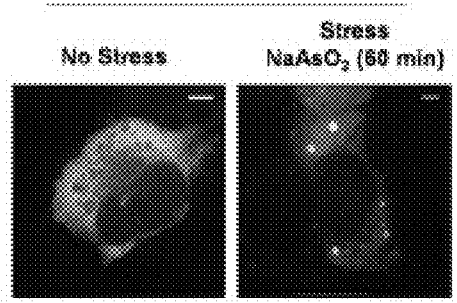

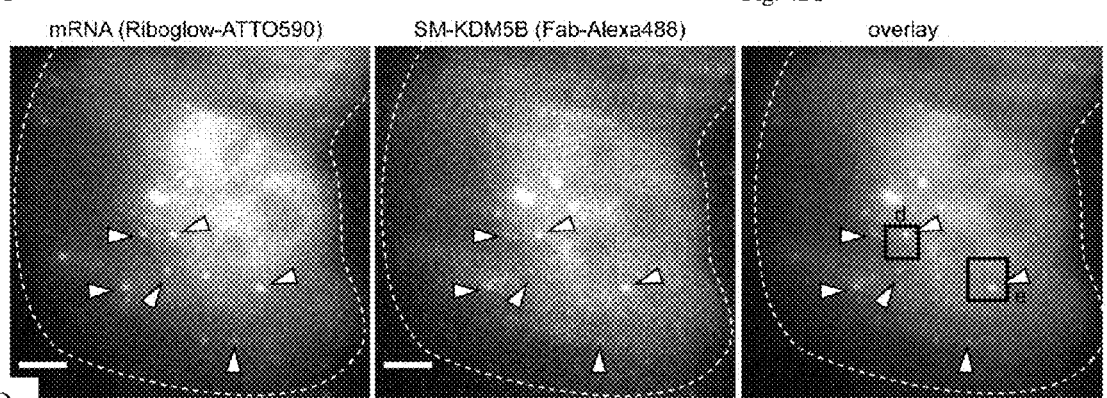

Fig. 43A
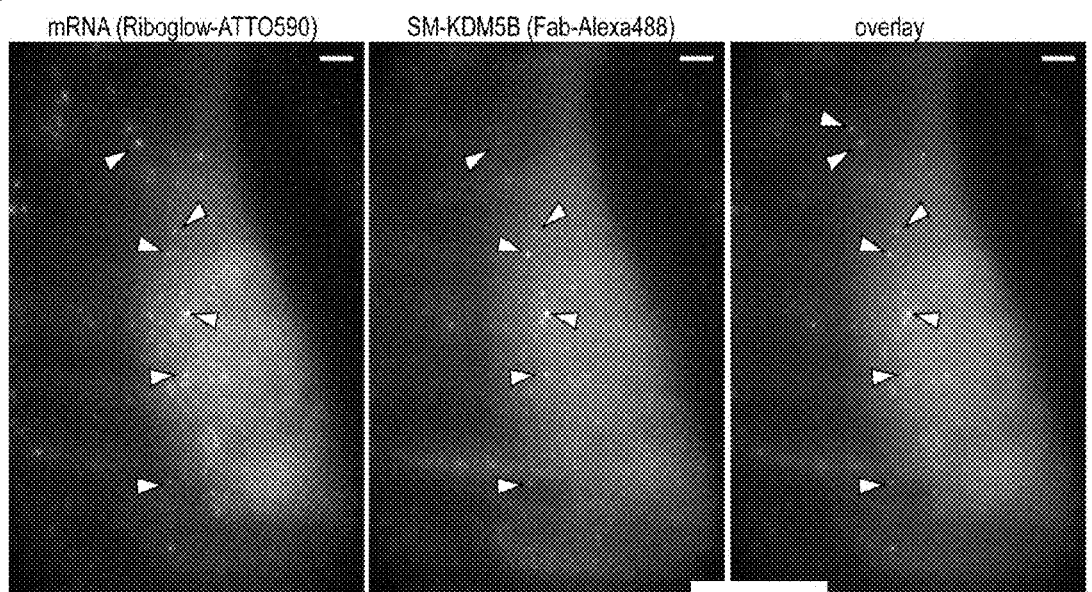
Fig. 43B
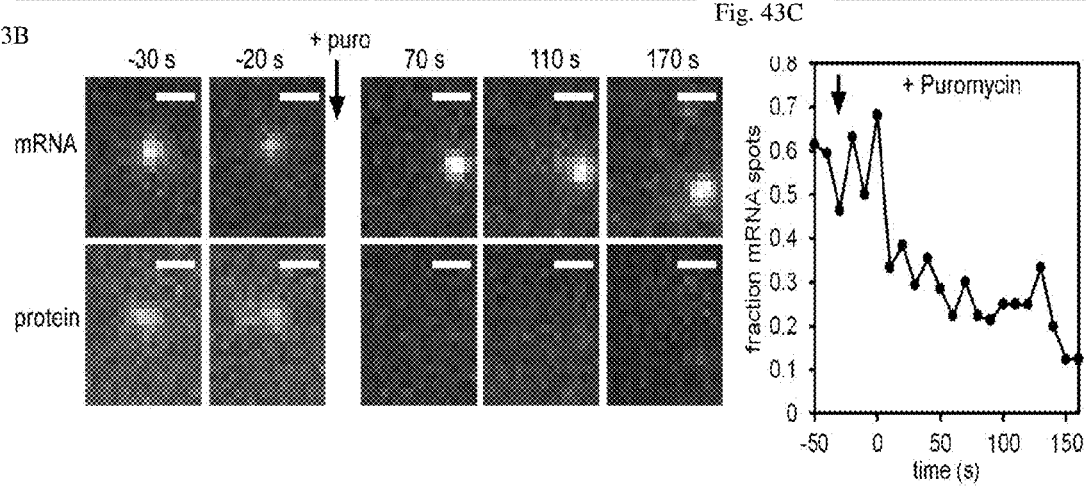
Fig. 43C

Fig. 49
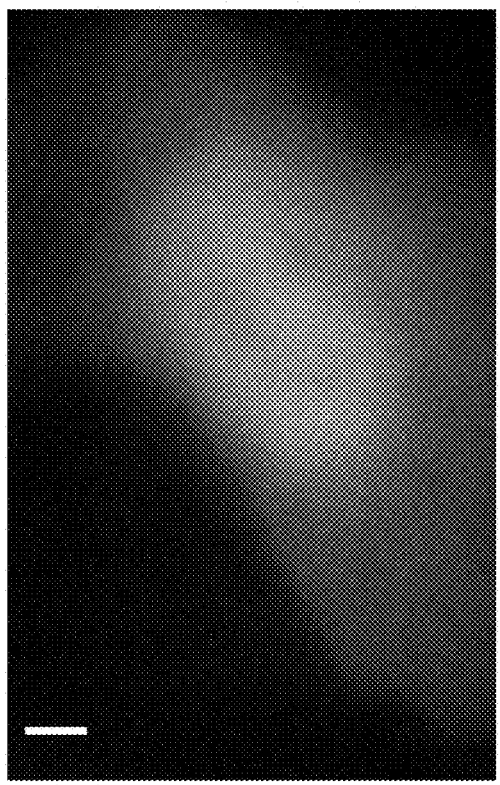
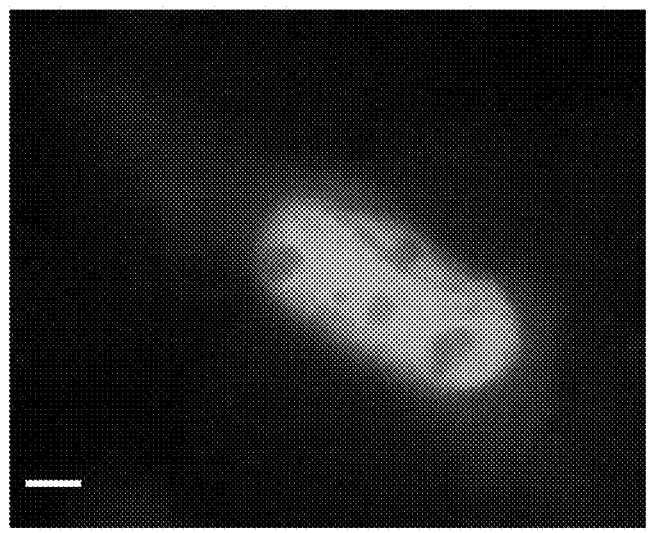
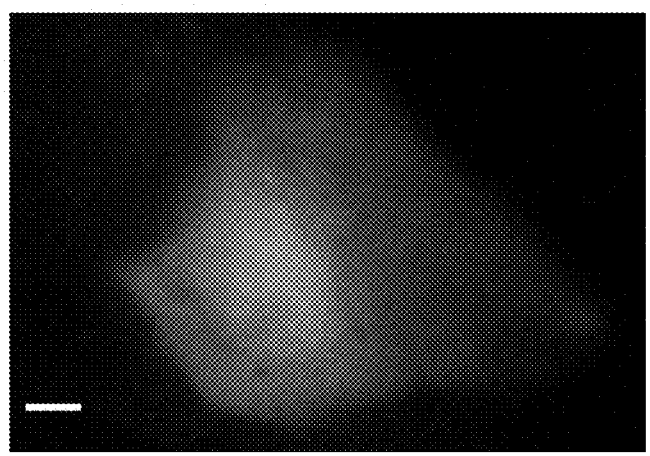

Fig. 50
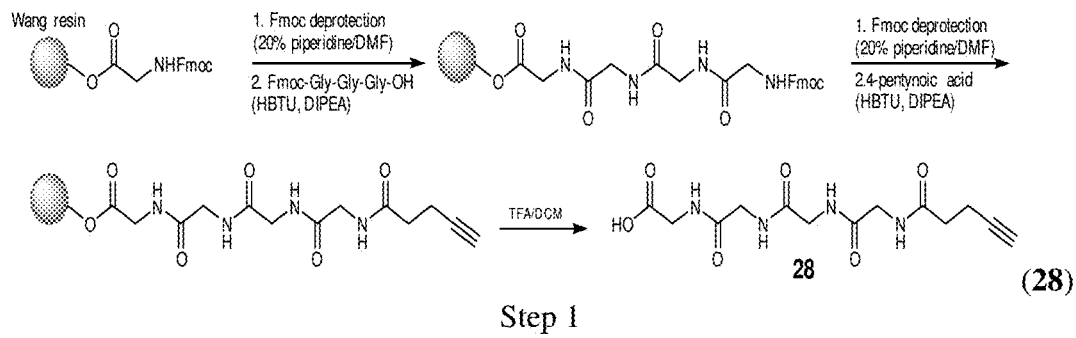
Step 1
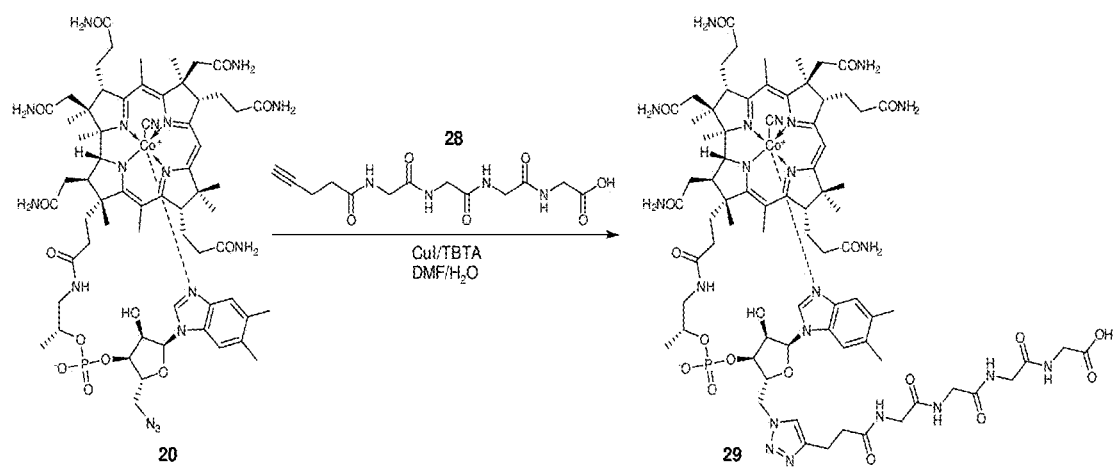
Step 2
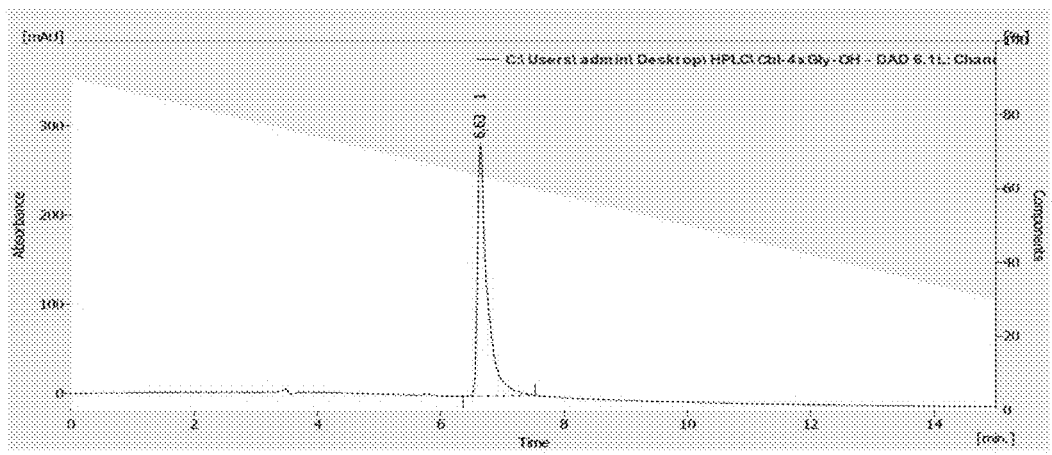

Fig. 50 (Cont)
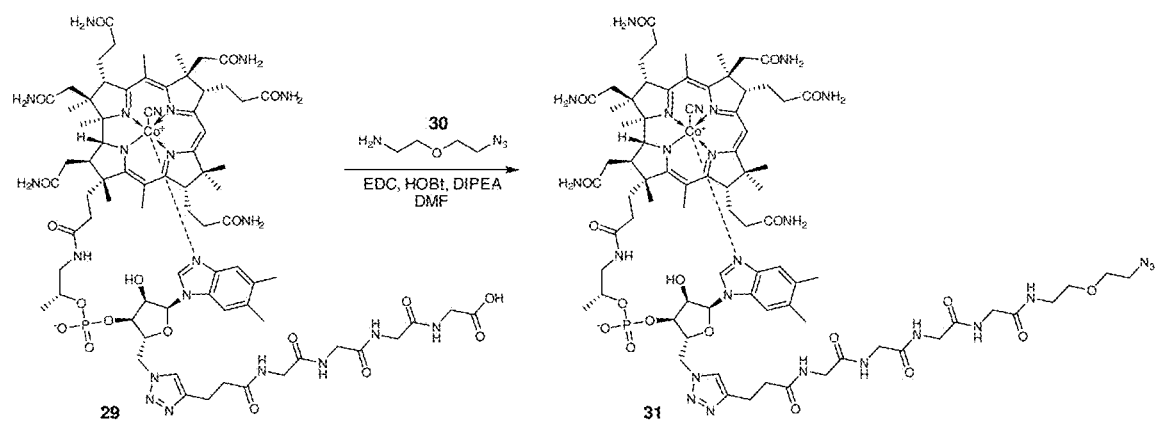
Step 3
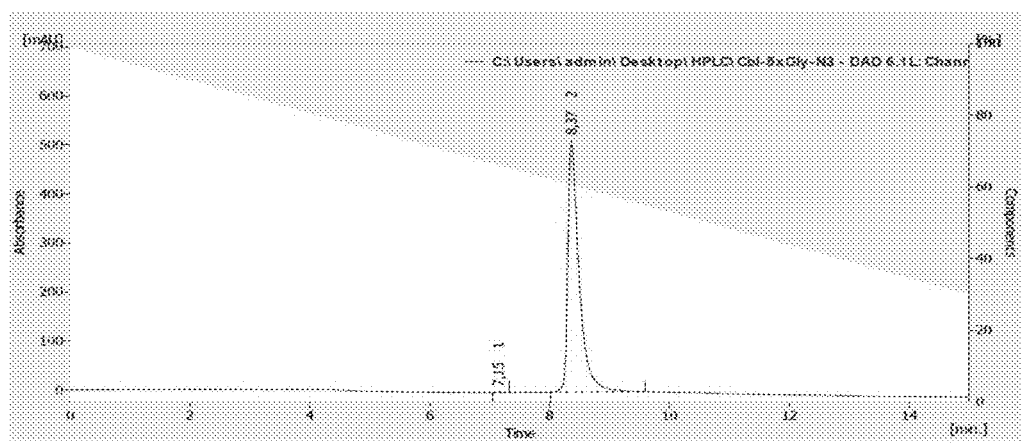

COMPOSITIONS AND METHODS FOR TAGGING RIBONUCLEIC ACIDS

This application claims priority to U.S. provisional application Ser. No. 62/712,832 filed 31 Jul. 2018, the contents of which are incorporated herein in their entirety.

A Sequence Listing has been submitted in an ASCII text file named "194151rg.txt" created on Jan. 29, 2020, consisting of 9,817 bytes, the entire content of which is herein incorporated by reference.

STATEMENT OF GOVERNMENT SUPPORT

This invention was made with government support under grant numbers GM119728; GM114863; GM073850; GM127752; and GM133184 awarded by National Institutes of Health. The government has certain rights in the invention.

FIELD OF THE INVENTION

This invention relates to the field of ribonucleic acid (RNA) regulation of intracellular activity. In particular, the invention relates to compositions and methods of identifying and tracking specific intracellular RNAs. For example, a fluorescently tagged RNA probe may be tracked by in vivo live imaging throughout its intracellular lifetime in order to determine its purpose and identify regulatory targets to modify its effects. Alternatively, an RNA probe may carry a therapeutic payload for treatment of a medical condition or disorder.

BACKGROUND

RNAs directly regulate a vast array of cellular processes. The complex spatiotemporal dynamics of messenger RNAs (mRNAs) and non-coding RNAs (ncRNAs) affect numerous aspects of cellular function. These RNAs associate with a large group of RNA binding proteins that dynamically modulate RNA localization and function [reference 1, 2]. Such interactions govern mRNA processing, export from the nucleus, and assembly into translationally competent messages, as well as association into large macromolecular granules that are not translationally active, including processing bodies (P-bodies) and stress granules (SGs) [reference 3-6].

Similarly, uridine-rich small nuclear RNAs ("U snRNAs", the RNA components of the spliceosome) [reference 7] dynamically associate with protein components to comprise the functional spliceosomal complex in the nucleus [reference 8]. During stress, such as nutrient deprivation or bacterial infection, U snRNAs along with the splicing machinery can be transiently sequestered in cytosolic foci called U-bodies [reference 7]. Given the intricate connection between RNA localization, dynamics and function, there has been interest in developing tools for visualization of RNA in live cells to elucidate mechanisms underlying dynamics of the mRNA and ncRNA life-cycle.

While there is a broad spectrum of tools to fluorescently tag proteins in live cells few tags are useful for live cell imaging of RNA in a variety of cell types. Moreover, there are no dye-binding aptamers, or other tags, being used to detect RNA polymerase-II dependent transcripts such as mRNAs, snRNAs, or microRNAs in live mammalian cells.

Therefore, there is a need for tools for identifying, tracking and in some cases perturbing, RNAs in living cells.

SUMMARY OF THE INVENTION

This invention relates to the field of ribonucleic acid (RNA) regulation of intracellular activity. In particular, the invention relates to compositions and methods of identifying and tracking specific intracellular RNAs. For example, a fluorescently tagged RNA probe may be tracked by in vivo live imaging throughout its intracellular lifetime in order to determine its purpose and identify regulatory targets to modify its effects. Alternatively, an RNA probe may carry a therapeutic payload for treatment of a medical condition or disorder.

In one embodiment, the present invention provides a composition comprising a riboswitch RNA fusion product and a plurality of cobalamin conjugates, wherein said riboswitch RNA fusion product has an RNA sequence of interest attached to a RNA tag comprising a cobalamin (Cbl)-binding aptamer and a riboswitch sequence. In one embodiment, said plurality of cobalamin conjugates are bound to said aptamer. In one embodiment, said RNA tag comprises 4 up to 15 copies of a cobalamin (Cbl)-binding aptamer. In one embodiment, said RNA tag comprises 8 up to 14 copies of a cobalamin (Cbl)-binding aptamer. In one embodiment, said RNA tag comprises 12 copies of a cobalamin (Cbl)-binding aptamer. In one embodiment, said conjugate is selected from the group consisting of a fluorophore conjugate and a therapeutic drug conjugate. In one embodiment, said RNA sequence of interest is a noncoding RNA. In one embodiment, said RNA sequence of interest is a mRNA. In one embodiment, said composition further comprises a fluorescently tagged protein expressed by said mRNA sequence of interest. In one embodiment, said therapeutic drug is selected from the group consisting of a small molecule, GSK2606414, one or more poly-ADP-ribose polymerase (PARP) inhibitors, one or more PARP activators, one or more PARP11 activators, and a therapeutic nucleotide molecule.

In one embodiment, the present invention contemplates a method for treating a neurodegenerative disease: a) providing; i) a patient exhibiting at least one symptom of a neurodegenerative disease, ii) a riboswitch RNA fusion product, wherein said riboswitch RNA fusion product has a RNA tag attached to a RNA sequence of interest, wherein said RNA tag comprises a cobalamin (Cbl)-binding aptamer and a riboswitch sequence, wherein said RNA sequence of interest is capable of binding to said at least one intraneuronal molecule that may be part of a stress granule; and iii) a plurality of Cbl RNA probes, wherein said probes are conjugates of Cbl-therapeutic drug; and b) administering said riboswitch RNA fusion products to said patient under conditions such that said tag RNA sequence binds to said at least one intraneuronal molecule that may be part of a stress granule; and c) delivering said plurality of Cbl RNA probes to said patient whereas said probes bind to said cobalamin (Cbl)-binding aptamer of said RNA tag such that said at least one symptom of a neurodegenerative disease is reduced. In one embodiment, said RNA tag comprises 4 up to 15 copies of a cobalamin (Cbl-binding aptamer. In one embodiment, said RNA tag comprises 8 up to 14 copies of a cobalamin (Cbl)-binding aptamer. In one embodiment, said RNA tag comprises 12 copies of a cobalamin (Cbl)-binding aptamer.

In one embodiment, the present invention contemplates a method for treating a neurodegenerative disease: a) providing; i) a patient exhibiting at least one symptom of a neurodegenerative disease, ii) a riboswitch RNA fusion product, wherein said riboswitch RNA fusion product has a RNA tag attached to a RNA sequence of interest, wherein said RNA tag comprises a cobalamin (Cbl)-binding aptamer and a riboswitch sequence, wherein said RNA sequence of interest is capable of trafficking to a stress granule; and iii) a plurality of Cbl RNA probes, wherein said probes are conjugates of Cbl-therapeutic drug; and b) administering said riboswitch RNA fusion products to said patient under conditions such that said tag RNA sequence is part of said stress granule; and c) delivering said plurality of Cbl RNA probes to said patient whereas said probes bind to said cobalamin (Cbl)-binding aptamer of said RNA tag such that said at least one symptom of a neurodegenerative disease is reduced. In one embodiment, said patient further comprises at least one intraneuronal stress granule. In one embodiment, said at least one intraneuronal stress granule comprises said at least one RNA molecule of interest. In one embodiment, said therapeutic drug disrupts said stress granule. In one embodiment, said therapeutic drug slows or inhibits progression of said neurodegenerative disease selected from the group consisting of amyotrophic lateral sclerosis (ALS), Alzheimer's disease, frontotemporal lobar degeneration (FTLD), repetitive head trauma, and other dementias. In one embodiment, said therapeutic agent is selected from the group consisting of a small molecule, GSK2606414, one or more poly-ADP-ribose polymerase (PARP) inhibitors, one or more PARP activators, one or more PARP11 activators, and A therapeutic nucleotide molecule. In one embodiment, said RNA tag comprises 4 up to 15 copies of a cobalamin (Cbl)-binding aptamer. In one embodiment, said RNA tag comprises 8 up to 14 copies of a cobalamin (Cbl)-binding aptamer. In one embodiment, said RNA tag comprises 12 copies of a cobalamin (Cbl)-binding aptamer.

In one embodiment, the present invention provides a method for identifying a therapeutic target in a cell derived from a disease: a) providing; i) a cell population derived from a patient at risk for or exhibiting at least one symptom of a degenerative disease, ii) a riboswitch RNA fusion product, wherein said riboswitch RNA fusion product has a RNA tag attached to a mRNA sequence of interest, wherein said RNA tag comprises a cobalamin (Cbl)-binding aptamer and a riboswitch sequence; and iii) a plurality of Cbl RNA probes, wherein said probes are conjugates of Cbl-fluorescent molecule; and iv) an fluorescent antibody tag for attaching to a protein expressed by said mRNA of interest; and b) delivery said riboswitch RNA fusion products and said antibody to said cells under conditions such that observations over time of said tagged mRNA and said fluorescent antibody tagged expressed protein show an abnormal accumulation of said protein for identifying a therapeutic target; and c) delivering a test therapeutic to said cells such that said abnormal accumulation of said protein is reduced.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A illustrates RNA-induced fluorescence turn-on for Cbl-fluorophore probes. Cbl (brown circle) acts as a quencher for the covalently attached fluorophore (red oval) due to proximity in space. Upon binding the RNA, Cbl is sterically separated from the fluorophore, resulting in de-quenching and fluorescence turn-on.

FIG. 1B illustrates a structure of the Cbl riboswitch RNA (variant A, see, FIG. 6) bound to Cbl [reference 30]. Loop P13 (teal) is at the 3'-end of the riboswitch. Cbl is shown in red spheres; '5'-position', e.g. 5'-hydroxyl residues, at the ribose moiety is shown in yellow. The four bases that were mutated to UUUU to abolish binding to Cbl are shown in magenta.

FIG. 1C illustrates synthetic Cbl-fluorophore probes used herein. The organic linker was attached at the 5'-hydroxyl of the ribose and conjugated to alkyne variants of commercially available fluorophores via click chemistry, resulting in the triazole linkage between the linker and fluorophore. Note that the structure of ATTO 633 is not completely shown because is proprietary.

FIG. 1D illustrates Spinach, Broccoli, and Mango type florescent probe molecules for comparison to one embodiment of a Riboglow RNA fusion molecule attached to a Cbl-conjugate probe.

FIG. 1E illustrates a MS2/PP7 system. References: Paige, et al., Science 2011; Shave-Tal, et al., Science, 2004; and Dolgosheina, et al., ACS Chem Bio, 2014.

FIG. 1F illustrates a Riboswitch fusion-construct system. Triangle=change.

FIG. 2A illustrates exemplary probes with fluorescence in the green wavelength range, FIG. 2B probes with fluorescence in the red wavelength range. FIG. 2C illustrates exemplary probes with fluorescence in the far-red wavelength range. Data are presented as mean for at least n=3 independent measurements (see Table 5 for a summary).

FIG. 3A shows an exemplary experimental strategy of labeling the Halo-tagged G3BP1 SG marker protein with the red fluorescent JF585 dye, followed by bead loading the Cbl-fluorophore probe, induction of SGs by arsenite for 30-45 min and live cell imaging.

FIG. 3B shows exemplary U2-OS cells producing Halo-G3BP1 were transfected with ACTB-(A)4x and the transfection marker TagBFP. Twenty-four (24) hour post transfection, cells were stained with the JF585 Halo dye. Shown are examples of representative live cells to assess colocalization of the SG marker protein Halo-G3BP1 and ACTB mRNA (3 experiments, 16 cells, 74 SGs). At least one SG was visible in total of 16 cells (100%) and 92% of SGs were detectable.

FIG. 3C shows exemplary data form using the same experimental design as in FIG. 3B) was performed, except that ACTB-(A)1x was transfected (3 experiments, 14 cells, 30 SGs). Two representative live cells are presented. In 43% of the cells at least one SG was detectable and 40% of total SGs were detected in the Cbl-Cy5 channel.

FIG. 3D The same experiment design as in FIG. 3b was performed, except that ACTB-(A)4x was not transfected (2 experiments, 39 cells, 100 SGs). Two representative examples of live cells are presented. In 38% of the cells at least one SG was detectable and 32% of total SGs were visible in the Cbl-Cy5 channel.

FIG. 3E presents a quantification of fluorescence signal accumulation in representative SGs. Scale bar=10 µm. One-way ANOVA (95% confidence limit), post hoc test (Tuskey HSD).

FIG. 3FA Monitoring ACTB mRNA localization to SGs via Cbl-fluorophore probe binding to the RNA $A_T$ tag.

FIG. 3FB shows exemplary Cbl-Cy5 probe colocalizing with SGs when ACTB mRNA is tagged with 4 copies of $A_T$. Cells stably expressing GFP-G38P1 were transfected with ACTB tagged with 1 or 4 $A_T$ copies. The probe was introduced and SGs were induced by treatment with 0.5 mM arsenite for 45 min before live microscopy.

FIG. 3FC shows exemplary Cbl-Cy5 accumulation in SGs was quantified via a line trace through each SG and calculating the ratio of signal in the SG over the average cytosol signal (FIG. 6). Robust fluorescence increase was only observed for ACTB mRNA tagged with 4 copies of $A_T$. Untransfected: 4 independent experiments, 37 cells, 63 SGs. ACTB-($A_T$)1x: 3 independent experiments, 20 cells, 63 SGs. ACTB-($A_T$)4x: 4 independent experiments, 45 cells, 105 SGs.

FIG. 4A shows ACTB-(2xdBroccoli) was transfected, the Broccoli probe DFHBI-1T was added and cells were assessed for SGs in the green channel (445 cells, 3 experiments). In 10% of total transfected cells, at least one SG was detected and 4% of total SGs were detected (1790 SGs in 445 cells).

FIG. 4B shows ACTB fused with two MS2 SL repeats transfected with the transfection marker into U2-OS Halo-G3BP1 cells that stably produced MS2-GFP (in 42% of total transfected cells at least one SG was detected and 17% of total SGs were detected; 162 SGs total in 53 cells).

FIG. 4C-4D shows ACTB tagged with four copies of the riboswitch tag A transfected with the transfection marker into U2-OS Halo-G3BP1 cells.

FIG. 4C shows Cbl-Cy5 loaded in cells (in 100% of total transfected cells at least one SG was detected in the Cy5 channel and 92% of total SGs were detected; 74 SGs total in 21 cells).

FIG. 4D shows Cbl-ATTO590 loaded in cells (in 64% of total transfected cells at least one SG was detected in the Cy5 channel and 58% of total SGs were detected; 59 SGs total in 22 cells). Scale bar=10 µm.

FIG. 5A shows post-transient transfection of $A_T$-U1, U-bodies were induced by Thapsigargin treatment followed by live cell microscopy.

FIG. 5B shows exemplary Cbl-5xPEG-ATTO590 localization to cytosolic puncta in Thapsigargin-treated HeLa cells is more likely when $A_T$-U1 was transfected ($A_T$-U1: mean from 4 independent experiments/326 cells; untransfected: mean from 4 independent experiments/677 cells). One-way ANOVA (95% confidence limit), post hoc test (Tuskey HSD).

FIG. 5C shows exemplary cytosolic puncta in Thapsigargin-treated cells expressing $A_T$-U1 co-localize to GFP-SMN U-bodies. 3 independent experiments, 10 cells. Scale bar=5 µm.

FIG. 6 illustrates exemplary secondary structures of RNAs used herein, see FIGS. 2A-C for examples, with certain structural regions denoted as P (paired), J (junction), L (loop), and IL (internal loop). Naturally derived sequences are shown with accompanying Rfam accession numbers, and the secondary structure of wild type env8 (variant A) is based on crystallographic data [reference 1]. Nucleotides that are colored red in variant $A_{T,MUT}$ represent point mutations made to the binding core of wild type env8 that abrogate cobalamin binding. Nucleotides that are colored red in variant B represent point mutations derived from wild type env8 that have been shown to increase the affinity of this RNA [reference 2] for forms of cobalamin similar to the conjugates used herein. Features that induce bulkiness of the RNA include P13 for variant A, P7, P13, P14 for variant B and P7, P2, P13 for variant C. Variant D is an LA and P7-optimized variant B that improved cobalamin affinity, see also FIG. 13A-C).

FIG. 10A-F shows representative fluorescence spectra of Cbl-fluorophore probes in the presence and absence of RNAs used herein (see also Table 1A-B for photophysical properties). Spectra show an increase in fluorescence intensity upon binding RNAs A, $A_T$, B, or C but not the non-binding variant $A_{T,MUT}$. Triplicates of spectra shown here were used to generate the bar graphs presented in FIG. 2A-C.

FIG. 14A shows an exemplary quantum yield for ATTO590 conjugates Cbl-5xPEG-ATTO590 and Cbl-5xGly-ATTO590 comprising 4xGly, in the presence and absence of variants A and D was measured using ATTO590 as a reference.

FIG. 14B shows an exemplary quantum yield for Cbl-Cy5 in the presence and absence of variants A and D was measured using Cy5 as a reference. The absorbance and integrated fluorescence sample was measured for samples of a dilution series of the indicated samples. See Table 9 for a summary of quantum yield results.

FIG. 10A-B shows exemplary measurements of fluorescence lifetime of Cbl-fluorophore probes in the presence and absence of RNA.

FIG. 15A shows an exemplary fluorescence lifetime of 0.5 µM Cbl-5xGly-ATTO590 comprising 4xGly, and Cbl-5xPEG-ATTO590 in the presence and absence of 5 µM of RNA variants A or D was measured in comparison to 0.5 µM free ATTO590.

FIG. 15B shows an exemplary fluorescence lifetime of 0.5 µM Cbl-Cy5 in the presence and absence of 5 µM of RNA variant A or D was measured in comparison to 0.5 µM free Cy5. See Table 10 for a summary of lifetime results.

FIG. 17A illustrates exemplary ligated DNA sequences comprising in operable combination, an operational CMV promoter region, at least a fragment of a human B-actin gene, at least one RNA riboswitch aptamer tag (e.g. A), poly A region, encoding an RNA tagged fusion product comprising an RNA riboswitch aptamer. Additionally, embodiments illustrating exemplary ligated DNA sequences comprising in operable combination, an operational CMV promoter region, mCherry or mNeonGreen, a RNA riboswitch aptamer tag (e.g. A, B, $A_T$, etc.), a poly A region, encoding an RNA tagged fusion product comprising an RNA riboswitch aptamer are shown.

FIG. 17B illustrates exemplary ligated DNA sequences comprising in operable combination, a U1 promoter (including enhancer regions), a RNA riboswitch aptamer tag (e.g. A), at least a fragment of a U1 gene, a U1 terminator region, encoding an RNA tagged fusion product comprising an RNA riboswitch aptamer.

FIG. 17C illustrates exemplary ligated DNA sequences comprising in operable combination, an operational CMV promoter region, at least a fragment of a human B-actin gene, at least one F30 region, at least one dBroc, region, a poly A region, encoding an RNA fusion product comprising Broccoli (top construct). Additionally, in lower constructs, FIG. 17C illustrates exemplary ligated DNA sequences comprising in operable combination, an operational CMV promoter region, at least a fragment of a human B-actin gene, at least one MS2-SL region, a poly A region, encoding an RNA tagged fusion product comprising MS2-SL.

FIG. 18A shows an exemplary total RNA was separated by agarose gel electrophoresis. The 28S and 18S rRNA bands across samples serve as loading controls and indicate that no unwanted RNA processing occurred during RNA preparation. Non-consecutive lanes of the same gel are indicated by vertical lines. Contrast settings were identical for the entire gel. A contrast enhanced version of the lane with the RNA ladder is shown as a reference.

FIG. 18B shows an exemplary Northern blot probed against $A_T$ (top panel) indicates that the full length mRNA (open triangle) is processed when produced with the tRNA folding scaffold (filled triangle). The blot was stripped and probed for GAPDH mRNA (star in bottom panel). Non-consecutive lanes of the same blot are indicated by vertical lines. No changes were made to contrast settings after cropping lanes. Table 11. Shows an exemplary properties of oligonucleotides from FIG. 18B (purchased as DNA oligos from IDT).

FIG. 19A shows an exemplary bead loading of Cbl-Cy5 in U2-OS Halo-G3BP1 cells results in diffuse cytosolic and nuclear probe localization with negligible probe aggregation (1 experiment, 50 cells).

FIG. 19B shows an exemplary Cbl-5xPEG-ATTO590 loaded in U2-OS Halo-G3BP1 cells that localizes diffusely in the cytosol and nucleus (I experiment, 129 cells).

FIG. 19C shows an exemplary Cbl-5xGly-ATTO590 comprising 4xGly, that localizes diffusely in the cytosol and nucleus of U2-OS Halo-G3BP1 cells (1 experiment, 158 cells).

FIG. 19D shows an exemplary bead loading of Cbl-Cy5 in HeLa cells that results in substantial localization of the Cbl-Cy5 probe in puncta (63% of cells, 1 experiment, 22 cells).

FIG. 19E shows an exemplary Cbl-5xPEG-ATTO590 loaded into HeLa cells that is largely localized diffusely in the nucleus and cytosol (89% of cells, 1 experiment, n=44 cells).

FIG. 19F shows exemplary HeLa cells loaded with Cbl-5xGly-ATTO590 comprising 4xGly (about half of the cells) where the probe localized in puncta in the cytosol (45% of cells, 1 experiment, 83 cells).

FIG. 19G shows exemplary results from increasing the concentration of Cbl-5xPEG-ATTO590 when loading HeLa cells that does not alter diffuse cytosolic and nuclear localization of the probe (1 experiment, 45 cells). Comparing localization of loading 50 µM probe in FIG. 14G versus 0.5 µM probe in FIG. 14E. Scale bar=S µm.

FIG. 21A shows exemplary transfection with ACTB-(A)4x (1 experiment, 15 cells) (FISH probe: $A_T$-FISH-Cy5).

FIG. 21B transfection with ACTB-(MS2-SL)24x (1 experiment, 8 cells) (FISH probe: MS2SL-FISH-Cy5); FIG. 21AC transfection with ACTB-2xdBroccoli (1 experiment, 13 cells) (FISH probe: Broccoli-FISH-Cy5). Scale bar=10 μm.

FIG. 25A exemplary SGs were identified in the Halo-G3BP1 channel via labeling of G3BP1 with JF585 and a line trace was drawn through the SG including cytosolic fluorescence near the SG. The same signal trace was recorded in the probe fluorescence channel (shown here for Cbl-Cy5).

FIG. 25B exemplary results after background subtraction, the Cbl-fluorophore probe fluorescence trace as well as the control Halo-G3BP1 trace were plotted. The maximum fluorescence signal for the Cbl-fluorophore probe was determined and divided by the average probe fluorescence in the cytosol.

FIG. 27A U2-OS cells producing Halo-G3BP1 were transfected with ACTB-(A)4x and the transfection marker TagBFP. 24 h post transfection, cells were stained with the JF646 Halo dye. The probe Cbl-5xGly-ATTO590 comprising 4xGly, was introduced into cells by bead loading, SG formation was induced by treatment with 0.5 mM arsenite for 45 min, followed by live cell microscopy (2 experiments, 22 cells, 59 SGs). In 64% of the cells at least one SG was detectable and 58% of total SGs were detected in the Cbl-5xGly-ATTO590 comprising 4xGly, channel.

FIG. 27B The same experiment as in FIG. 27A was performed, except that ACTB-(A)4x was not transfected (2 experiments, 37 cells, 92 SGs). In 0% of the cells at least one SG was detectable and 0% of total SGs were detected in the Cbl-5xGly-ATTO590, comprising 4xGly, channel.

FIG. 27C Fluorescence increase for Cbl-5xGly-ATTO590 comprising 4xGly, in SGs was quantified by collecting a line trace through each SG (identified in the JF646 channel) and calculating the ratio of the highest signal in the SG over the average signal in the cytosol for datasets from panels FIG. 27A and FIG. 27B (see FIG. 30 for details, presented are the individual data points and the mean). One-way ANOVA (95% confidence limit), post hoc test (Tuskey HSD), scale bar 10 μm.

FIG. 28A shows exemplary fluorescence of Cbl-Cy5 co-localized with SGs.

FIG. 28B shows exemplary results after fixation, localization of the $A_T$ tag to SGs was directly assessed by a red fluorescent (Alexa546) FISH probe ($A_T$, FISH-Alexa546) (2 experiments, 4 cells). Scale bar 5 μm.

FIG. 29A shows exemplary use of pAV5S-F30-2xdBroccoli (2 experiments, 14 cells).

FIG. 29B shows exemplary use of pAVU6+27-F30-2xd-Broccoli. Shown are two representative phenotypes where green fluorescence was either observed diffusely throughout the cell (top) or localized to cytosolic puncta (bottom) (2 experiments, 23 cells).

FIG. 29C shows exemplary results from a nontransfected control (2 experiments, 32 cells). The brightness and contrast was adjusted to be constant for these images shown. Scale bar=5 μm.

FIG. 32A shows exemplary ACTB-(MS2-SL)1x transfection (in 28% of total transfected cells at least one SG was detected in the green channel; 38/149 SGs).

FIG. 32B shows exemplary ACTB-(MS2-SL)2x transfection (in 42% of total transfected cells at least one SG was detected in the green channel; 28/162 SGs).

FIG. 32C shows exemplary ACTB-(MS2-SL)4x transfection (in 45% of total transfected cells at least one SG was detected in the green channel; 46/163 SGs).

FIG. 32D shows exemplary ACTB-(MS2-SL)24x transfection (in 86% of total transfected cells at least one SG was detected in the green channel; 109/144 SGs). Representative SGs were visualized by MS2-GFP as indicated by white arrows. Scale bar=10 μm.

FIG. 33A shows exemplary staining for Halo-G3BP1 (red). FIG. 33B shows exemplary staining for MS2-GFP (green). FIG. 33C shows exemplary staining for NLS-TagBFP (blue). U2-OS cells that stably produce Halo-G3BP1 and MS2-GFP were cotransfected with plasmid encoding for NLS-TagBFP and ACTB(MS2-SL)24x. 24 h post transfection, G3BP1 was labeled by the red JF585 fluorophore. Cells positive for the NLS-TagBFP transfection marker are indicated by white dashed lines. Untransfected cells as well as some NLS-TagBFP positive cells displayed nuclear MS2-GFP (see for example oval shaped cell in the middle of the field of view). In other cases, MS2-GFP was localized to the cytosol (see cells marked with white stars), FIG. 33B. Occasionally, stress granules were observed in the red JF585 channel in transfected cells (white arrow), FIG. 33A. Scale bar=10 μm.

FIG. 34A-C Supplementary FIG. 29A-C shows exemplary localization phenotypes of U1 snRNA in normal and Thapsigargin-stressed HeLa cells.

FIG. 34A shows exemplary endogenous U1 snRNA colocalized with nuclear Coilin-containing foci. HeLa cells were transiently transfected with a plasmid to produce GFP-Coilin, fixed and permeabilized. U1 snRNA was visualized via a probe against the U1 snRNA coding sequence (1 experiment, 6 cells).

FIG. 34B shows exemplary $A_T$-U1 RNA localized to Coilin-containing nuclear foci. HeLa cells were transiently transfected with two plasmids to produce GFP-Coilin and $A_T$-U1 snRNA, fixed and permeabilized. $A_T$-U1 snRNA was visualized via a probe against the $A_T$ aptamer (2 experiments, 3 cells).

FIG. 34C shows exemplary endogenous U1 snRNA colocalizes with two marker proteins for U-bodies, endogenous SMN (1 experiment, 5 cells) and endogenous DDX20 (I experiment, 9 cells), upon Thapsigargin treatment. HeLa cells were fixed and permeabilized. U1 snRNA was visualized via a probe against U1, and DDX20 and SMN were visualized by immunofluorescence. Scale bar 5 μm.

FIG. 35A shows exemplary $A_T$-U1 snRNA colocalized with the U-body marker protein DDX20 after treatment of cells with Thapsigargin. $A_T$-U1 snRNA was visualized via an $A_T$ aptamer specific probe and endogenous DDX20 was detected by immunofluorescence (1 experiment, 12 cells).

FIG. 35B shows exemplary $A_T$-U1 snRNA colocalized with the U-body marker protein SMN after treatment of cells with Thapsigargin. $A_T$-U1 snRNA was visualized via an $A_T$-Specific probe and endogenous SMN was detected by immunofluorescence (1 experiment, 8 cells).

FIG. 35C shows exemplary $A_T$-U1 snRNA colocalized with transiently transfected GFP-SMN after treatment of cells with Thapsigargin. $A_T$-U1 snRNA was visualized via an $A_T$-specific probe and SMN was detected by GFP fluorescence (1 experiment, 57 cells). Scale bar=5 μm.

FIG. 38A-E shows exemplary generation of endogenous Halo-G3BP1 cell line.

FIG. 38A shows an exemplary schematic for CRIPSR/Cas9-mediated 3xFlag-HALO-tag knockin into endogenous G3BP1 locus.

FIG. 38B shows exemplary genotyping results reveals proper integration in mixed U2-OS population.

FIG. 38C shows exemplary transient transfection of eGFP-Cre, but not control plasmids, in edited cell reveals correct expression of 3xFlag-HALO-tagged G3BP1 resolved by Western blotting.

FIG. 38D Same as FIG. 33C except shows exemplary 3xFlag-Halo-tag integration at the G3BP1 locus resolved by fluorescent imaging of protein gels.

FIG. 38E shows exemplary 3xFlag-Halo-tagged G3BP1, as resolved by different fluorescent dyes, redistributes from the cytoplasm to concentrate into stress granules during sodium arsenite stress. Scale bar=5 µm.

FIG. 39A shows exemplary U2-OS cells transfected with a plasmid encoding ACTB mRNA, tagged with 12 copies of Riboglow. Twenty-four hours after transfection, 4xGly-ATTO 590 was bead loaded and cells were imaged live. Fluorescent puncta were readily detected in the ATTO 590 fluorescence channel. Scale bar=5 µm.

FIG. 39B shows exemplary zoomed in view of areas indicated by white boxes in FIG. 39A. Scale bar=1 µm. Black circles indicate particles detected with the FIJI tracking plugin TrackMate (Tinevez, et al. "TrackMate: An open and extensible platform for single-particle tracking." *Methods,* 115:80-90 (2017)).

FIG. 39C shows exemplary intensity distribution of the mean puncta intensity for particles detected for the entire image acquisition for select ROIs. Data shown here were fit using a single Gaussian distribution. n=2764 puncta, R=0.98.

FIG. 40A-E: shows exemplary quantification of single mRNA dynamics with Riboglow-ATTO 590. U2-OS cells were transfected with a plasmid encoding twelve Riboglow-tagged ACTB mRNA, bead loaded with Cbl-4xGly-ATTO 590 and imaged live.

FIG. 40A shows exemplary traces of single mRNA particles were generated using the FIJI Trackmate plugin (Tinevez, et al. "TrackMate: An open and extensible platform for single-particle tracking." *Methods,* 115:80-90 (2017)). Shown are representative traces that were classified as "directed" (red, left) and "subdiffusion" (blue, right) with the TraJClassifier (Wagner, et al. "Classification and segmentation of nanoparticle diffusion trajectories in cellular micro environments." *PLoS One,* 12:1-20 (2017)). The movie was acquired with 30 ms exposure and a frame rate of 33.3 frames per second. Scale bar=1 µm.

FIG. 40B shows exemplary distribution of particle classifications using the FIJI TraJClassifier (Wagner, et al. "Classification and segmentation of nanoparticle diffusion trajectories in cellular micro environments." *PLoS One,* 12:1-20 (2017)) for the entire ACTB-12xRiboglow dataset (error bars are STD from three independent experiments).

FIG. 40C shows exemplary distribution of velocity for particles classified as moving by "directed movement" (Wagner, et al. "Classification and segmentation of nanoparticle diffusion trajectories in cellular micro environments." *PLoS One,* 12:1-20 (2017)).

FIG. 40D shows exemplary distribution of diffusion coefficients for particle movements classified as "diffusion" or "subdiffusion" using the FIJI TraJClassifier (Wagner, et al. "Classification and segmentation of nanoparticle diffusion trajectories in cellular micro environments." *PLoS One,* 12:1-20 (2017)).

FIG. 40E shows exemplary distribution of trace length for particles detected and tracked (113 tracks, mean length=67.6 frames, corresponding to 2.0 s at a frame rate of 33.3 frames per second). Data from three independent experiments, 6 cells' 18 ROIs across all experiments.

Figure 41A:
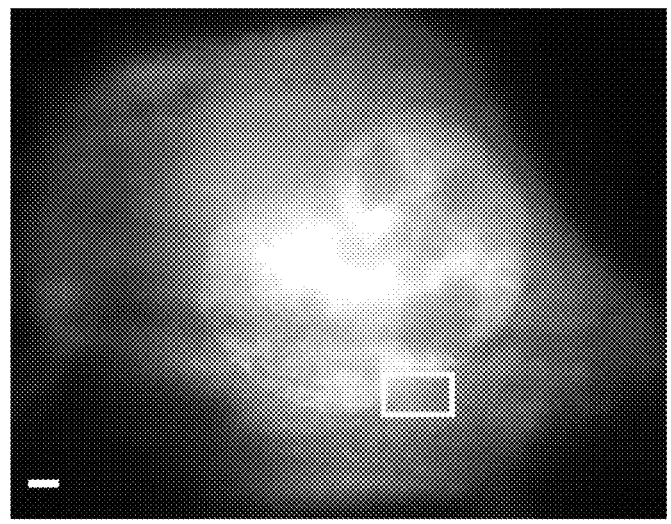
Figure 41B:
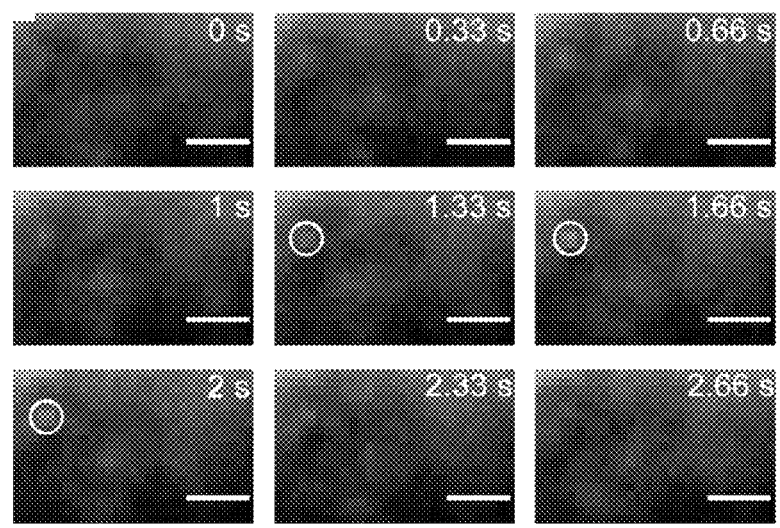

FIG. 41A-B: shows exemplary single particle tracking using 8 or more copies of Riboglow. A plasmid encoding ACTB tagged with 8 copies of the Riboglow tag "A" was transfected in U2-OS cells together with a transfection marker. The probe Cbl-4xGly-ATTO590 was bead loaded into cells 24 h post transfection.

FIG. 41A shows exemplary cells that were positive for the transfection marker and bead loading were interrogated further. No distinct puncta are visible. Scale bar=2 µm.

FIG. 41B shows exemplary insert with a white box in (A) shown for several consecutive frames. Rarely, distinct puncta are visible and detectable with the Trackmate (Tinevez, et al. "TrackMate: An open and extensible platform for single-particle tracking." *Methods,* 115:80-90 (2017)) algorithm (shown as white circles). Puncta could not be tracked across time points, as illustrated here where a puncta was detected in only 3 consecutive frames (representative example from 2 experiments, 7 cells). Scale bar=1 µm.

FIG. 42A-E: shows exemplary visualization of mRNA translation with Riboglow-tagged mRNA. U2-OS cells were bead loaded with a plasmid encoding the KDM5B translation assay reporter, together with the 4xGly-ATTO590 Riboglow probe to label mRNA and Fab-Alexa488 to label the nascent protein. Cells were visualized 6 h after bead loading. Cytosolic spots were detected in both the Riboglow-ATTO590 channel FIG. 42A and Fab-Alexa488 channel FIG. 42B, and these spots co-localize (white arrows).

FIG. 42C shows an exemplary Riboglow-ATTO590 signal in magenta, Fab-Alexa488 in green. FIG. 42D, FIG. 42E) Tracking of Riboglow-ATTO 590 tagged mRNA and Fab-Alexa488 tagged nascent protein over time (overlay: mRNA in magenta, protein in green). Spots tracked are indicated by black boxes in FIG. 42C. Maximal intensity projection of six z-stacks (0.5 µm distance per step in z), scale bar=5 µm.

FIG. 42A shows a Fab-Alexa488 channel FIG. 42B shows a Riboglow-ATTO 590 channel, FIG. 42C shows an overlay with Riboglow-ATTO590 signal is shown in magenta, Fab-Alexa488 is shown in cyan. Maximal intensity projection of six z-stacks (0.5 µm distance per step in z), scale bar=5 µm. 0.7 s frame rate, movie acquisition for 11 slices in z, 18 frames total (30 s).

FIG. 43A-C FIG. 5A-C: shows exemplary Puromycin-treatment releases the nascent polypeptide from translation sites.
One embodiment of a translation assay plasmid DNA encoding for SM-KDM5B was bead loaded together with the 4xGly-ATTO 590 probe and the green Fab fragment in U2-OS cells. Six hours later, cells positive for Riboglow (4xGly-ATTO 590 bound to the tagged mRNA) and SM-KDM5B (where the N-terminal SM was labeled with green fluorescent Fab) were visualized.

FIG. 43A shows exemplary fluorescence from Riboglow-ATTO 590, green Fab and an overlay of both is shown where Riboglow-ATTO590 is magenta and Fab is green (colocalization corresponds to white). Several spots where mRNA (labeled with Riboglow-ATTO 590) and nascent protein (labeled with Fab-Alexa 488) colocalize are marked with white arrows, before Puromycin treatment. Maximal intensity projection of 9 z-stacks (0.5 µm distance per step in z), scale bar=5 µm. Image collection every 10 s.

FIG. 43B shows exemplary representative translation spot in the Riboglow-ATTO590 channel (top) and SM-KDM5B channel (bottom) illustrates loss of the SM-KDM5B protein signal from the translation spot upon Puromycin addition. Maximal intensity projection of 9 z-stacks (0.5 µm distance per step in z), scale bar=1 m.

FIG. 43C shows exemplary quantification of mRNA colocalization with nascent protein. Spots in red (Riboglow-ATTO 590, labeling mRNA) for the cell shown in FIG. 43A were counted in each frame, and spots in green (Fab-Alexa 488, labeling nascent protein) were also counted. The fraction of red spots that also display green fluorescence is plotted over time for the cell shown in FIG. 43A).

Figure 44A:
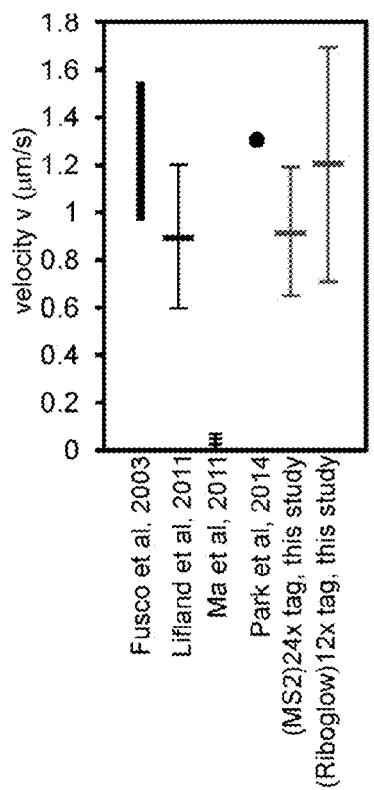
Figure 44B:
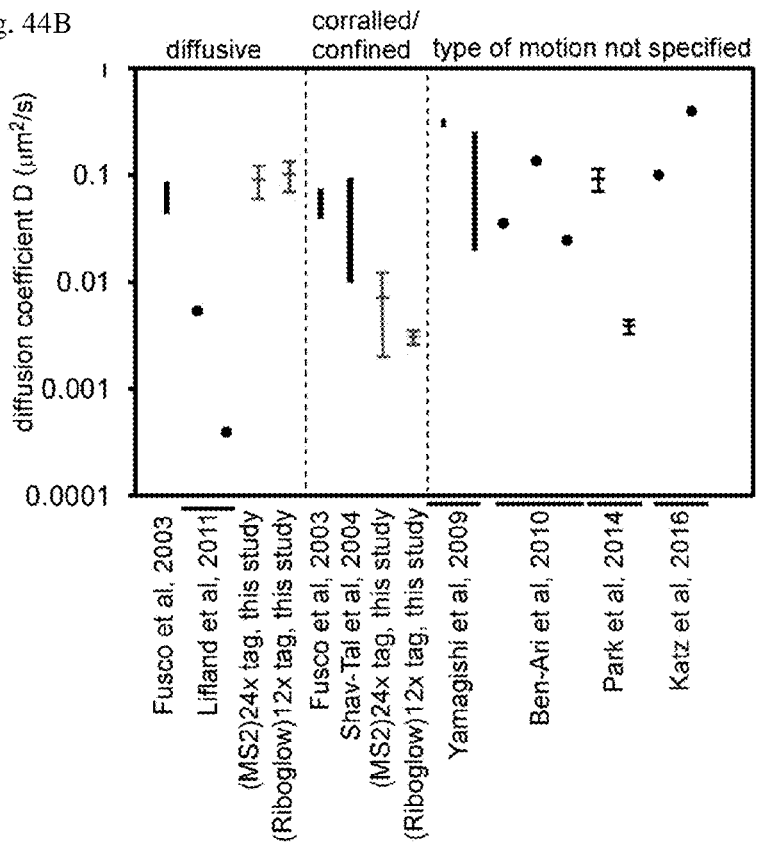

FIG. 44A-B: shows an exemplary comparison of literature values to values obtained using RNA tags, described and developed herein, for mRNA movement. A summary of literature values for single mRNA movement in live cells demonstrates: FIG. 44A shows a comparison of velocity (v) reported for directed movement, and FIG. 44B shows a comparison of diffusion coefficient D reported for non-directed movement. The type of motion is indicated at the top of the plot, if specified. Black bar indicates range of values reported. See also Table 14 for more details of literature studies. Error bars for data reported from this study represent the standard error.

FIG. 45A-D shows exemplary plasmid maps used on this study (not drawn to scale) (see also Table 16 for tag sequences).

Figure 45A:
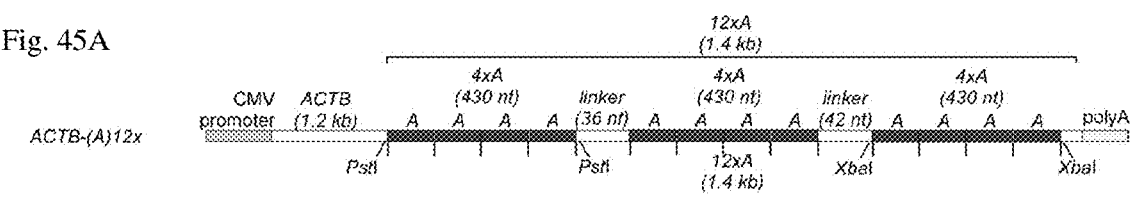

FIG. 45A In one embodiment, 12 copies of the Riboglow RNA-tag referred to as "A", as described herein, were fused to the ACTB gene, resulting in construct ACTB-(A)12x.

Figure 45B:
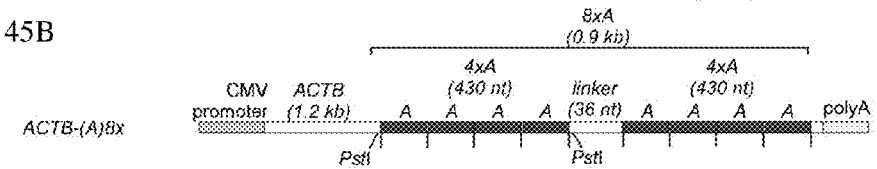

FIG. 45B shows in one embodiment, 8 copies of the Riboglow-RNA tag referred to as "A" were fused to the ACTB gene, resulting in construct ACTB-(A)8x.

Figure 45C:
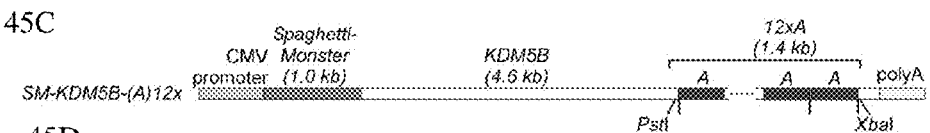

FIG. 45C shows one embodiment of a KDM5B gene N-terminally tagged with the 10xFlag-tag marker termed spaghetti-monster in: Viswanathan, et al. "High-performance probes for light and electron microscopy." *Nat. Methods* 12:68-576 (2015), and tagged with 12× Riboglow as in (A) in the 3'UTR.

Figure 45D:
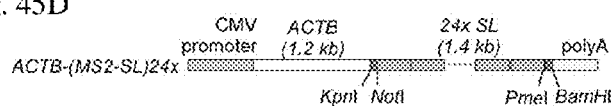

FIG. 45D shows one embodiment of an ACTB gene was tagged with 24 copies of the MS2SL sequence as described herein.

Figure 46:
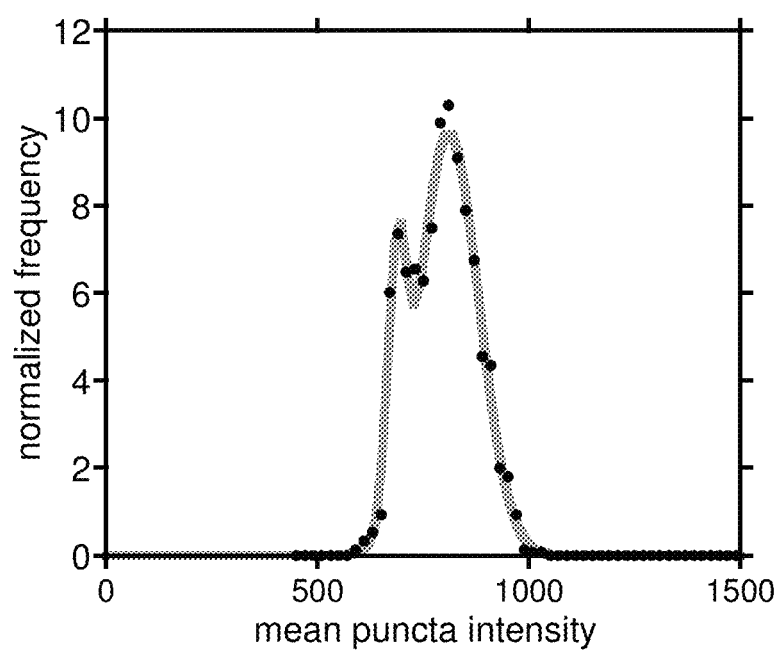

FIG. 46 shows exemplary particle intensity distribution in movie with ACTB mRNA tagged with 12 copies of Riboglow for region of interest (ROI) fit with two Gaussian distributions. Some regions of interest (ROI) in movies where fluorescent particles are tracked display particle intensity distributions that can be described with a multiple Gaussian fit. N=1496 puncta, R=1.0.

FIG. 47A-G shows exemplary detection of single ACTB mRNA with the MS2 system. U2-OS cells that stably produce NLS-MS2-GFP were transiently transfected with a plasmid producing ACTB mRNA tagged with 24 copies of the MS2 stem loop (SL) sequence and imaged 24 h later.

Figure 47A:
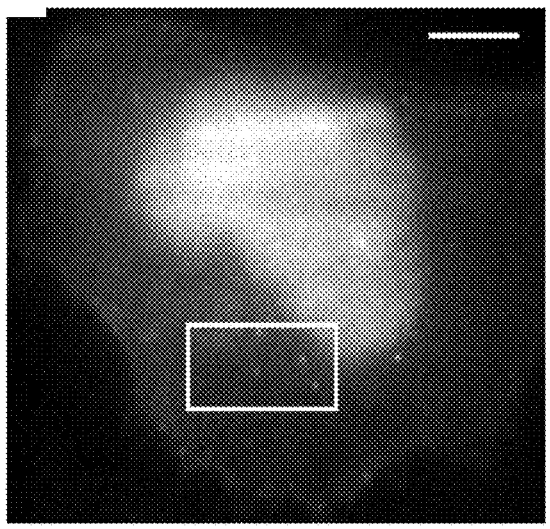

FIG. 47A shows an exemplary representative cell where distinct particles were detected in the green fluorescence channel, representing single mRNAs. Scale bar=5 µm. White box: panel FIG. 47B) zoom in.

Figure 47B:
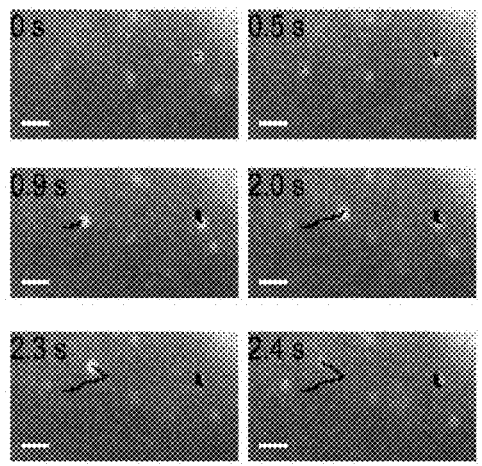

FIG. 47B shows exemplary time frames of zoomed in region (white box in panel (a)) reveal dynamics of mRNA movement. Movies were acquired at a frame rate of 33.3 frames per second, and select frames are shown. Particles were detected and tracked using the FIJI tracking plugin TrackMate (Tinevez, et al. "TrackMate: An open and extensible platform for single-particle tracking." *Methods,* 115: 80-90 (2017)). Shown are two tracked particles; the black lines represent traces over time.

Figure 47C:
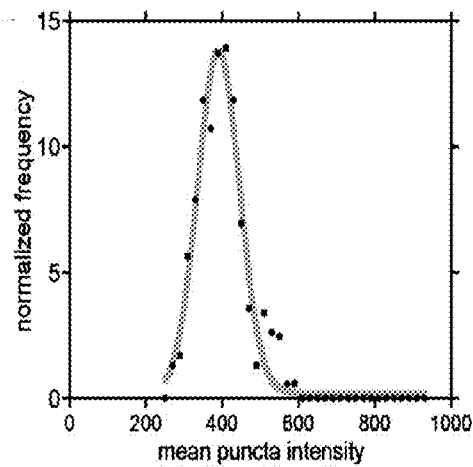

FIG. 47C shows exemplary particles detected using TrackMate have fluorescence intensities that follow a Gaussian distribution. Shown are all particles detected in a representative region of interest (ROI) used for tracking analysis over time (n=532 particles). The intensity distribution was fit with a Gaussian distribution (R 0.98). The type of movement for each tracked particle from the TrackMate analysis was classified using the FIJI TraJClassifier (Wagner, T., Kroll, A., Haramagatti, C. R., Lipinski, H. G. & Wiemann, M. Classification and segmentation of nanoparticle diffusion trajectories in cellular micro environments. *PLoS One* 12, 1-20 (2017)).

Figure 47D:
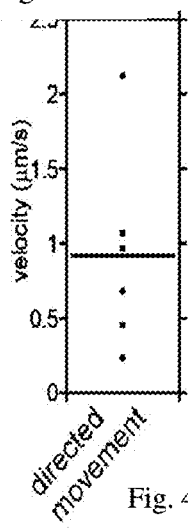

FIG. 47D shows exemplary distribution of velocity for particles classified as moving by "directed movement" (Wagner, T., Kroll, A., Haramagatti, C. R., Lipinski, H. G. & Wiemann, M. Classification and segmentation of nanoparticle diffusion trajectories in cellular micro environments. *PLoS One* 12, 1-20 (2017)).

Figure 47E:
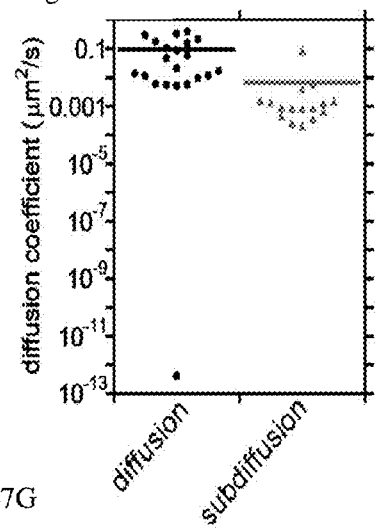

FIG. 47E shows exemplary distribution of diffusion coefficients for particle movements classified as "diffusion" or "subdiffusion" using the FIJI TraJClassifier (Wagner, T., Kroll, A., Haramagatti, C. R., Lipinski, H. G. & Wiemann, M. Classification and segmentation of nanoparticle diffusion trajectories in cellular micro environments. *PLoS One* 12, 1-20 (2017)).

Figure 47F:
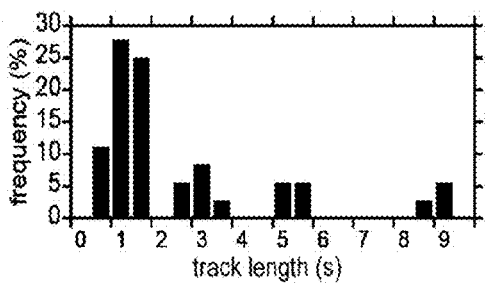

FIG. 47F shows exemplary length distribution of tracked particle traces (36 traces total, mean: 2.75 s 190.58 frames at a frame rate of 33.3 frames per second).

Figure 47G:
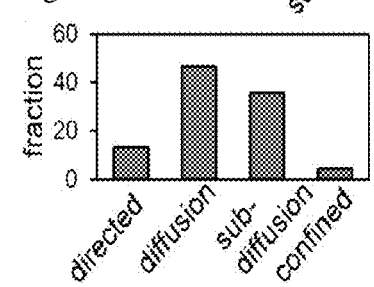

FIG. 47G shows exemplary distribution of particle classifications using the FIJI TraJClassifier (Wagner, T., Kroll, A., Haramagatti, C. R., Lipinski, H. G. & Wiemann, M. Classification and segmentation of nanoparticle diffusion trajectories in cellular micro environments. *PLoS One* 12, 1-20 (2017)) for the entire ACTB-24xMS2-SL dataset. Data from two experiments, three cells, 5 ROIs.

FIG. 48 A-B shows exemplary particle size estimates for spot detection. Estimate of diameter for spots detected by TrackMate.

Figure 48A:
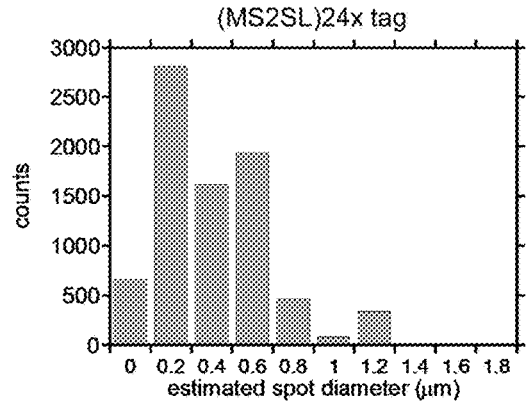

FIG. 48A shows exemplary distribution of estimated diameter for all spots for analysis of (MS2)24x-tagged ACTB mRNA (7935 spots total).

Figure 48B:
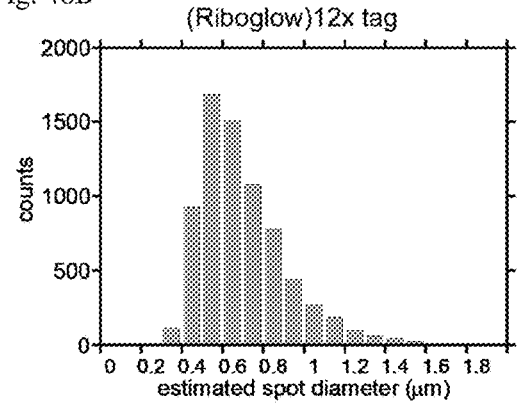

FIG. 48B shows exemplary representative distribution of estimated diameter for spots of (Riboglow)12x-tagged ACTB mRNA (7242 spots total).

FIG. 49 shows an exemplary KDM5B in the translation reporter construct localizing to the nucleus. U2-OS cells were bead loaded with a mix of the SM-KDM5B translation reporter plasmid DNA and a green fluorescent Fab fragment to label the N-terminus of the resulting SM-KDM5B protein. Cells were imaged 7 h post bead loading of DNA, Fab fragment, and Riboglow probe (cells from 2 separate experiments are shown). Scale bar=5 μm.

FIG. 50 shows exemplary structures and HPLC chromatographs during exemplary synthesis of one embodiment of a Cbl conjugate.

DEFINITIONS

As used herein, "RNA tag" refers to any "tag" molecule (sequence) attached (e.g. fused, covalently bonded, ligated, etc.) to a RNA of interest, i.e. "tagged RNA", "tagged RNA sequence", etc. As one example, the gene encoding mNeonGreen is fused with RNA tag A, ACTB mRNA tagged with 4 copies of aptamer A, etc. "RNA tag sequence" refers to both the expressed RNA tag sequence and the DNA sequence encoding the RNA tag sequence (two separate molecules, i.e. RNA or DNA). "RNA tagged sequence" refers to both the expressed RNA tag sequence attached to a RNA of interest sequence (as one molecule) and the DNA encoding the RNA tag sequence attached to the DNA sequence encoding the RNA tag sequence and the DNA sequence encoding the RNA of interest (two separate molecules, i.e. RNA or DNA).

A "riboswitch RNA tag" refers to a RNA tag, comprising or derived from a riboswitch sequence comprising an aptamer binding domain, artificially created from or using an isolated DNA sequence as a template, such as DNA encoding riboswitch RNA that is isolated from a bacterial cell that endogenously produces a riboswitch RNA.

As used herein, "riboswitch tag" or "riboswitch aptamer tag" in reference to a RNA tag developed as described herein, refers to a RNA tag comprising a Cbl aptamer (i.e. Cbl-binding sequence, Cbl-binding domain) derived from a riboswitch sequence. Whereas "existing RNA tags" refers to tags such as Broccoli, Spinach, MS2, etc. published by others.

As used herein, "aptamer" and "aptamer binding domain" or "binding domain" in reference to an aptamer, refers to an oligonucleotide molecule or peptide molecule that binds to a specific target small molecule, in addition to a gene (DNA sequence) encoding the aptamer. One example of a RNA tag is an aptamer, e.g. a Cbl-binding domain, an aptamer that is part of a full-length riboswitch sequence, such as a full-length bacterial riboswitch sequence, a full-length cobalamin riboswitch sequence, etc. Thus, a RNA tag may be a full-length riboswitch sequence and variants of a riboswitch sequence and/or a shorter aptamer domain, e.g. a fragment of a riboswitch sequence, a variant of a riboswitch sequence, a truncated RNA tag, etc. As used herein, a RNA tag does not directly bind to a fluorophore molecule while a RNA tag may bind directly to a small molecule that in turn is attached to a fluorophore molecule.

The term, "RNA aptamer" in reference to a riboswitch, refers to that portion of a riboswitch sequence that contains RNA nucleotides that are capable of contributing to or binding to a small molecule, e.g. a bacterial sequence that binds metabolites, or more specifically a sequence comprising a Cbl-aptamer for binding to Cbl, for regulating the expression of attached genes. As an example, RNA nucleotides contributing to binding a small molecule may be a combination of adjacent and nonadjacent RNA nucleotides, within the aptamer sequence such that when the sequence is folded in a certain manner these RNA nucleotides are capable of contributing to the binding of the aptamer to the small molecule. An aptamer may be derived from a riboswitch sequence comprising an aptamer region. An aptamer may be used as a riboswitch aptamer tag, i.e. RNA tag. An aptamer may be a "cobalamin (Cbl)-binding aptamer" or "Cbl-binding sequence", for example derived from a Cbl-riboswitch sequence, e.g. a truncated cobalamin-binding aptamer, a mutated cobalamin-binding aptamer, a multimer (multiple copies) of a cobalamin-binding aptamer, etc.

As used herein, "cobalamin aptamer" or "cobalamin-binding domain" refers to a RNA sequence comprising RNA nucleotides contributing to binding cobalamin (Cbl) and to an encoding DNA sequence.

As used herein, "riboswitch" in general refers to a regulatory segment, i.e. sequence that may be attached to a messenger (m)RNA molecule, that may be encoded naturally in vivo in cells comprising an aptamer and a riboswitch regulatory region. When a riboswitch is folded during or after translation, e.g. as a combination of a one-dimensional, 2-dimensional and/or 3-dimensional structure, at least part of the folded sequence is capable of undergoing a conformational change in structure after binding to the small molecule. In some embodiments, this "riboswitch regulatory region" or "riboswitch sequence" through conformational changes of the folded riboswitch sequence, controls production of protein(s), e.g. translation of a protein(s)) encoded by an attached mRNA sequence.

However, as used herein, in some embodiments, when the riboswitch comprises both aptamer and a "riboswitch regulatory region", the change in structure induced by the binding of a small molecule conjugate to the aptamer controls the distance between the small molecule and the conjugate instead of controlling translation of an attached mRNA.

Thus, a "riboswitch" in general may also refer to an in vitro isolated or artificially produced regulatory sequence that may or may not have a naturally found sequence, e.g. a riboswitch may be an artificially mutated riboswitch, i.e. for altering small molecule binding by the folded nucleotide sequence, for changing the interaction between the small molecule and a linked cargo (such as fluorophore or therapeutic), a fragment of a riboswitch, a truncated riboswitch, e.g. cobalamin riboswitch $A_T$, etc.

Therefore, a "full-length riboswitch" refers to a RNA sequence (or DNA encoding this sequence) comprising an aptamer binding domain and a "regulatory switch".

As used herein, "regulatory switch" and "riboswitch sequence" refers to the portion or fragment of nucleotides capable of undergoing a conformation (structural) change induced by the binding of a small molecule to an aptamer attached to the regulatory switch.

As used herein, "expression platform" refers to a sequence in operable combination comprising promoters and expressed sequences, e.g. mRNA, ncRNAs, such as snRNA U1, etc. In one embodiment, an expression platform comprising a riboswitch is under control of the conformation of a riboswitch sequence, e.g. Cbl riboswitch. In another embodiment, an expression platform is not under control of the attached riboswitch sequence whereas the presence of a riboswitch sequence is merely for sterically separating Cbl or the Cbl quencher from a covalently coupled molecule, such as a fluorophore or therapeutic, e.g. Cbl riboswitch as described herein.

As used herein, "cobalamin riboswitch" or "B12-element" refers to an RNA (or encoding DNA) which binds different variants or derivatives of cobalamin, e.g. molecules such as adenosylcobalamin (a coenzyme form of vitamin B12); aquocobalamin, synthetically modified variants of cobalamin, etc.

As used herein, "variant" in reference to a riboswitch sequence refers to altered riboswitches including natural variants, where sequences found naturally in cells are altered, such as truncated, i.e. AT, containing the aptamer domain of riboswitch A with linker region J1/3 and stem-loop P/L13 deleted, and engineered variants, such as riboswitch D derived from a naturally occurring riboswitch.

As used herein, "RNA imaging platform" refers to a Cobalamin (Cbl) riboswitch as an RNA aptamer and a series of probes containing Cbl as a fluorescent quencher linked to a range of fluorophores.

As used herein, "operable combination" "in operable combination", "in operable order" and "operably linked" refer to the linkage of nucleic acid sequence fragments in one DNA molecule, such as a promoter, mRNA, RNA tag, etc., in such a manner that one RNA molecule is produced (transcribed) comprising these gene fragments. The term also refers to the linkage of nucleic acid sequence fragments in one DNA molecule resulting in the linkage of amino acid sequences in such a manner so that a functional protein is produced (translated).

As used herein, "fold" in reference to a nucleotide sequence (molecule) refers to a sequence having at least one area that is nonlinear, e.g. having a bend in the sequence, including but not limited to having at least one section of the nucleotide sequence as a double stranded nucleotide sequence, i.e. at least one section having a hybridized nucleotide within the same molecule. Such a "folded" nucleotide sequence (molecule) results in a secondary and/or tertiary structure, i.e. 3-dimensional structure. A folded nucleotide sequence (molecule) may contain a combination of secondary and tertiary structures along with at least one or more areas, i.e. at least 2, up to 3, up to 4, up to 5, up to 6, up to 8, up to 10, or more areas having a section of hybridized nucleotides.

As used herein, "nucleotide" refers to a compound comprising a nitrogenous base (a purine nucleoside or a pyrimidine nucleoside) attached to a five-carbon sugar (ribose for RNA) or deoxyribose for DNA)), and at least one phosphate group, where the nucleoside is linked to the phosphate group. Four nitrogenous bases in DNA are purines: deoxyadenosine (A), deoxyguanosine (G), and pyrimidines: deoxycytidine (cytosine) (C) and thymidine (T). RNA contains riboseadenine/adenosine (A) ribosecytosine/cytidine (C), riboseguanine/guanosine (G), and uracil (U), instead of thymine/thymidine. As used herein, the nucleoside designation, such as G, refers to guanosine. When the nucleoside, such a G, is located in a DNA sequence (molecule) it refers to deoxyguanosine. When the nucleoside, such a G, is located in a RNA sequence (molecule) it refers to riboguanosine.

As used herein, "hybridization" or "hybridized" refers to hydrogen bonds between nucleotide base pairs (typically a purine nucleoside with hydrogen bonds to a pyrimidine nucleoside): A-T and C-G in DNA, A-U, G-U and C-G in RNA, i.e., the two nucleotide sequences (strands) or complementary nucleotides in two different sections within the same nucleotide sequence (strand) are complementary to each other to those base pair positions. The hybridization of two nucleic acid molecules or two nucleic acid compounds is affected by a number of conditions and parameters known to those of skill in the art. For example, the salt concentrations, pH, and temperature of the reaction all affect whether two nucleic acid molecules or nucleic acid compounds will hybridize. The use of the term "RNA" refers to an RNA sequence while the use of the term DNA refers to a DNA sequence. The use of the term "RNA A", "RNA B" and "RNA C" and the like, refers to variants of Cbl-binding riboswitch sequences. Such terms may refer to both DNA encoding these variants as well as the RNA molecule of the variant.

As used herein, "hydrogen bond" refers to an electrostatic attraction between two compounds resulting from between a proton attached to an electronegative atom in one compound and an electronegative atom in the other compound, where at least one compound is attached to a hydrogen (H) atom.

An "isolated" polypeptide or an "isolated" polynucleotide is one that is removed from its original environment. For example, a naturally occurring polypeptide or polynucleotide is isolated if it is separated from some or all of the coexisting materials in the natural system. Optionally, isolated polypeptides or isolated nucleotides can also be purified, e.g., are at least about 90% pure, more preferably at least about 95% pure and most preferably at least about 99% pure.

As used herein, "expression vector" or "expression construct" refers to a plasmid or virus designed for expression of a DNA construct in host cells, for translation into a RNA construct), typically containing a promoter sequence operable within the host cell.

As used herein, "promoter" refers to a region of DNA that initiates transcription of a particular DNA sequence. Promoters are located near the transcription start sites of, towards the 5' region of the sense strand. Promoters may be constitutive promoters, such as cytomegalovirus (CMV) promoters in mammalian cells, or inducible promoters, such as tetracycline-inducible promoters in mammalian cells.

As used herein, "transfection" refers to introducing nucleic acids into host cells, for example, a plasmid expression construct, inserted into or taken up by a host cell. Transfection may be transient, such that the nucleic acids introduced into the transfected host cell are not permanently incorporated into the cellular genome, or transfection may be carried out in a way such that the nucleic acids introduced are permanently incorporated into the genome.

As used herein, "host" in reference to a cell refers to a cell harboring a construct.

As used herein, "conjugate" refers to a covalently attachment of at least two compounds, for example, a cobalamin molecule and a fluorophore. In some embodiments, a conjugate further includes a linker molecular.

As used herein, "fusion" refers to an expressed product of an engineered construct i.e. a combination of several ligated sequences expressed as one molecule.

As used herein, "construct" refers to an engineered molecule, e.g. at least one fragment of DNA (DNA sequence) attached to another fragment of DNA (DNA sequence) as a DNA construct, and at least one fragment of RNA (RNA sequence) attached to another fragment of RNA (RNA sequence) as a RNA construct.

As used herein, "4xGly" and "5xGly" in reference to a linker refer to one embodiment of a Cbl conjugate linker region synthesized using substrates collectively providing 4 Glycine molecules to said linker, i.e. 4xGly, as described herein.

DETAILED DESCRIPTION OF INVENTION

This invention relates to the field of ribonucleic acid (RNA) regulation of intracellular activity. In particular, the invention relates to compositions and methods of identifying and tracking specific intracellular RNAs. For example, a fluorescently tagged RNA probe may be tracked by in vivo live imaging throughout its intracellular lifetime in order to determine its purpose and identify regulatory targets to modify its effects. Alternatively, an RNA probe may carry a therapeutic payload for treatment of a medical condition or disorder.

In one embodiment, the present invention relates to a modular RNA localization platform comprising a riboswitch RNA fusion construct resulting from an operably ligated and expressed engineered DNA, comprising an RNA sequence tagged with an RNA tag, i.e. a riboswitch sequence and a Cobalamin (Cbl)-binding domain (aptamer); and a Cobalamin conjugate probe comprising a Cbl molecule. In some embodiments, a fusion construct is used with a Cbl-fluorophore conjugate, wherein the Cbl binds to the RNA fusion molecule that turns on the fluorophore.

Figure 3A:
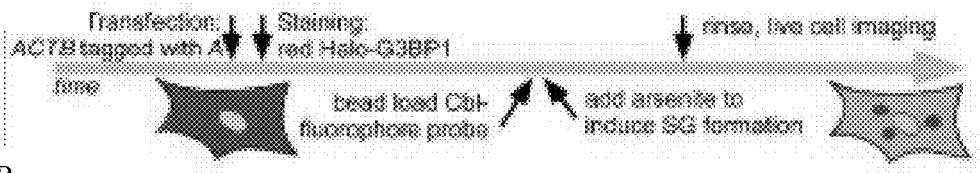
FIG. 3A-E shows exemplary monitoring ACTB mRNA localization to stress granules (SG) via Cbl-fluorophore probe binding to the RNA tag A.
Figure 3B:
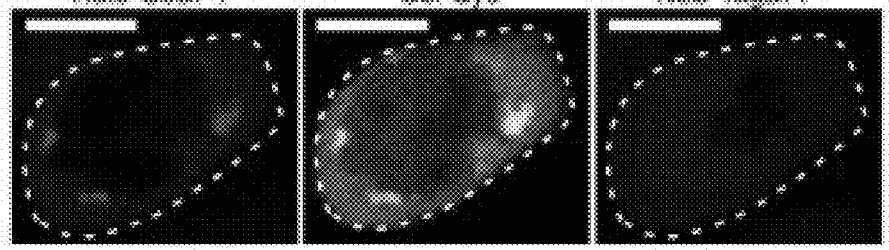
Figure 3C:
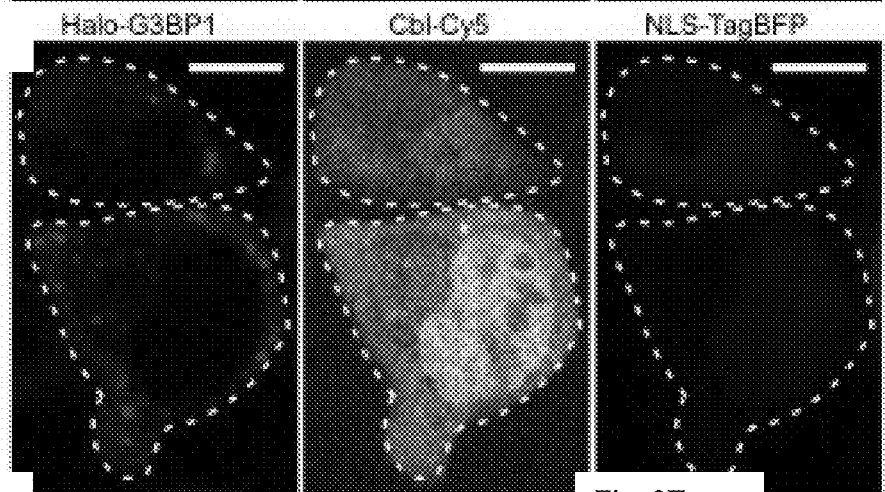
Figure 3D:
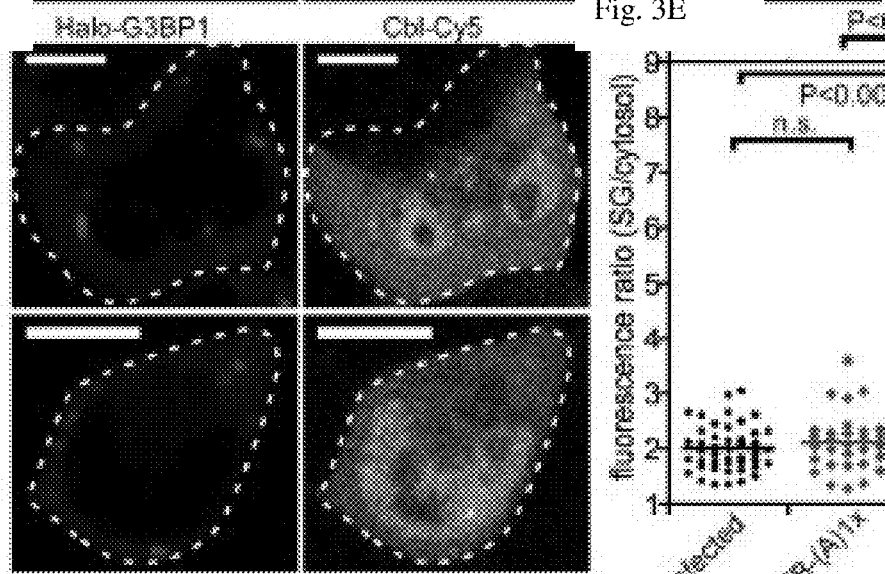
Figure 3E:
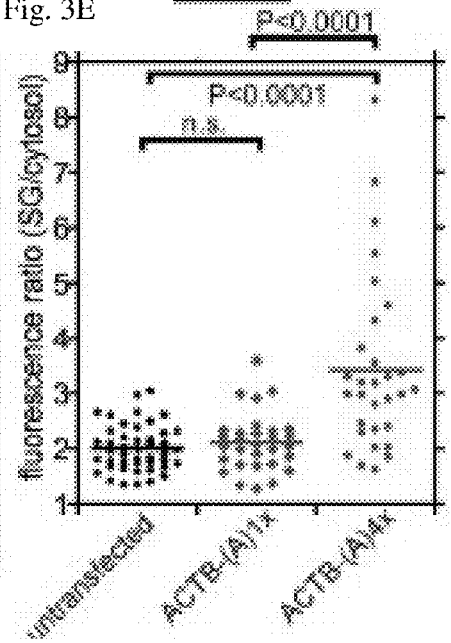
Figure 3F:
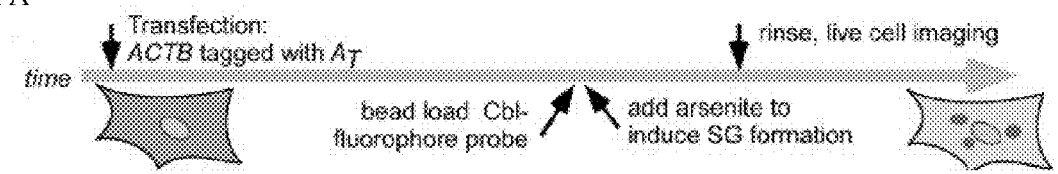
FIG. 3FA-3FC shows live cell visualization of mammalian RNAs via binding of the Cbl-fluorophore probes to the genetically encoded RNA $A_T$ tag.
Figure 3F:
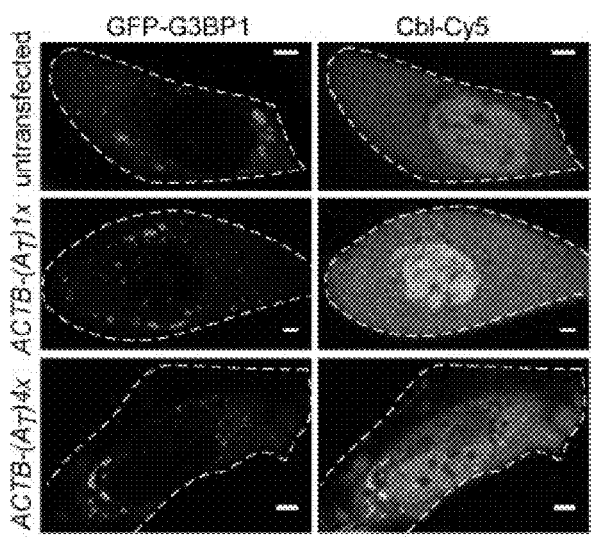
Figure 3F:
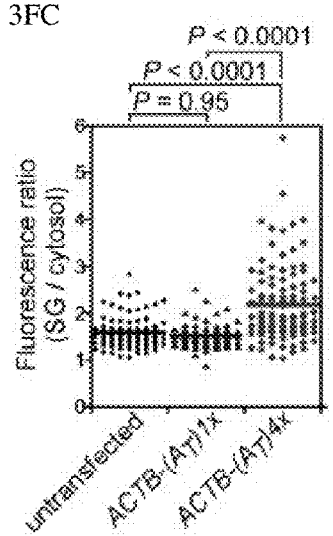

FIG. 3FA-3FC shows live cell visualization of mammalian RNAs via binding of the Cbl-fluorophore probes to the genetically encoded RNA $A_T$ tag.

FIG. 3FA Monitoring ACTB mRNA localization to stress granules (SGs) via Cbl-fluorophore probe binding to the RNA $A_T$ tag.

FIG. 3FB shows exemplary Cbl-Cy5 probe colocalizing with SGs when ACTB mRNA is tagged with 4 copies of $A_T$. Cells stably expressing GFP-G3BP1 were transfected with ACTB tagged with 1 or 4 $A_T$ copies. The probe was introduced and SGs were induced by treatment with 0.5 mM arsenite for 45 min before live microscopy.

FIG. 3FC shows exemplary Cbl-Cy5 accumulation in SGs was quantified via a line trace through each SG and calculating the ratio of signal in the SG over the average cytosol signal (FIG. 6). Robust fluorescence increase was only observed for ACTB mRNA tagged with 4 copies of $A_T$. Untransfected: 4 independent experiments, 37 cells, 63 SGs. ACTB-$(A_T)$1x: 3 independent experiments, 20 cells, 63 SGs. ACTB-$(A_T)$4x: 4 independent experiments, 45 cells, 105 SGs.

Thus, in some embodiments, these constructs and conjugates are used as a live cell imaging system for identifying particulate structures comprising the tagged RNA sequence of interest. In some embodiments, Riboswitch RNA fusion constructs are used with Cbl-therapeutic drug conjugates for disrupting RNA containing particulate structures, such as stress granules, for treating a neurodegenerative disease.

Figure 1A:
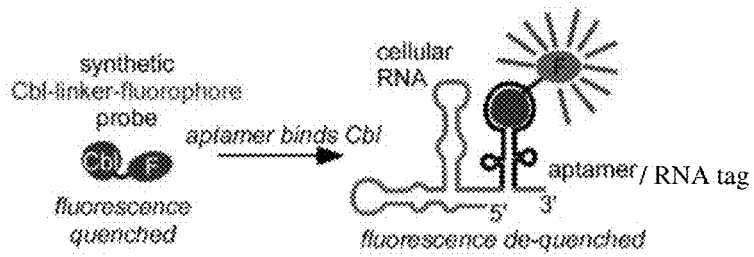
FIG. 1A-C illustrates that covalent attachment of different fluorophores to Cobalamin (Cbl) results in fluorescence quenching, allowing for a fluorescence turn-on of the probe upon binding to a riboswitch RNA.

As described herein, methods and materials for developing a fluorescent tagging system resulted in a system for identifying RNA in live cells using a "biological aptamer" or biological small-molecule binding RNAs", such as a bacterial riboswitch, e.g. Cbl aptamer, as the RNA tag and a series of small molecular riboswitch probes, e.g. Cbl probes, that increase in fluorescence upon binding the RNA tag. The folding capabilities of bacterial riboswitches in a variety of different genetic contexts in cells provided advantages [reference 28, 29], while exploiting specific binding of the riboswitch RNA to its natural ligand, cobalamin (Cbl) [reference 30, 31]. Cbl functions as an efficient fluorescence quencher when covalently coupled to a synthetic fluorophore [reference 32-34]. It was hypothesized that binding of Cbl to an RNA riboswitch would sterically separate the Cbl quencher and covalently coupled fluorophore resulting in fluorescence turn-on of a Cbl-fluorophore probe (FIG. 1A).

More specifically, described herein is a two-part composition for locating RNAs, e.g. by tagging RNA in a live cell, including but not limited to mammalian cells. RNAs designated for tagging include but are not limited to mRNA, small RNAs, such as non-coding RNAs, e.g. approximately 80-105 nucleotides; and large non-coding RNAs greater than 200 nucleotides, and greater than 300 nucleotides up to and ranging from 1,000-10,000), etc. Such small RNA visualization may be enhanced as RNAs begin clustering in structures that contain multiple RNAs and proteins, e.g stress granules and/or Cajal bodies, U-bodies, etc. A first portion of the composition termed a "riboswitch RNA construct" comprising, in operable combination, a RNA sequence of interest and an RNA tag, such as a Cbl aptamer attached to a regulatory domain. In some embodiments, the "riboswitch RNA construct" is encoded within an expression plasmid that is transfected into a host cell wherein upon expression the RNA of interest is transcribed attached to the RNA tag. The RNA tag functions as a riboswitch such that upon binding to at least one Cbl-fluorophore conjugate, the riboswitch region undergoes a conformation change which further separates the quenching Cbl molecule from the fluorophore thus allowing a significant increase in florescence, depending upon other modifying factors, as described herein. In some embodiments, the RNA sequence of interest is located before (5' of) the RNA tag. In some embodiments, the RNA sequence of interest is located after (3' of) the RNA tag. In some embodiments, the RNA tag can be placed in the middle of the RNA sequence of interest. In some embodiments, the RNA sequence attached to the RNA tag is the RNA intended for monitoring, such as RNA transcribed into a plus strand of RNA that encodes human B-actin. In some embodiments, the tagged RNA sequence is expressed as a minus strand for hybridizing to the B-actin sequence expressed from the cell's genome, for identifying human B-actin mRNA in the cell. In other words, a tagged RNA may be complementary to, and hybridize with, a small RNA target sequence. It is not meant to limit the tagged RNA to human B-actin, indeed small RNAs, such as U1 RNA, and other types of small RNAs, messenger RNAs and non-coding RNAs may be tagged as described herein.

A second portion of this composition is a cobalamin molecule covalently bonded (either with or without a linker) to either a fluorescent molecule or a therapeutic drug through a Cbl 5'-hydroxyl group. This Cbl-conjugate then binds with the riboswitch aptamer to form the functional Cbl-conjugate riboswitch RNA probe. Thus, in one embodiment, the fluorescent molecule or drug is conjugated through the Cbl 5'-position. However, it is not meant to limit the type of chemical group used at the Cbl 5'-position. In fact, other types of chemical groups may present at the Cbl 5'-position for use in attaching the fluorescent molecule or drug. Nor is it meant to limit the position for attaching a chemical group, or a fluorescent molecule or a therapeutic drug to Cbl. Thus, in other embodiments, the fluorescent molecule or a therapeutic drug (either with or without a linker) may be attached directly to the cobalt at another position. As nonlimiting examples, other positions include an axial position of cobalt, or at additional positions such as the meso, b-, c-, d-, or e-positions around the corrin ring.

Further, it is not intended to limit the molecules contemplated for attachment to a Cbl. In fact, as described herein, other types of molecules may be attached.

It is not intended to limit the composition of the linker molecule, in a Cbl construct. In some embodiments, a linker comprises Gly polymer regions, as described and shown herein. Thus, in some preferred embodiments, a "5xGly" linker comprises 4 Gly polymers, i.e. 4xGly, as described herein. However, it is not meant to limit the number of Glycine molecules used in a Cbl conjugate Glycine linker region, e.g. in some embodiments, a Glycine linker comprises at least one Glycine group during synthesis, in some embodiments, a Glycine linker comprises at least two or more Glycine groups, in some embodiments, a Glycine linker comprises three or more Glycine groups, in some embodiments, a Glycine linker comprises four or more Glycine groups, in some embodiments, a Glycine linker comprises five or more Glycine groups up to 8 Glycine groups, or more depending upon the components of a Cbl conjugate molecule.

In one embodiment, this Riboglow system is modular such that a variety of Cbl conjugates may be provided with any fluorescent molecule that may have an emission color ranging from green, red and far-red, examples include but are not limited to, ATTO 488, ATTO-590 and Cy5, respectively. In one contemplated embodiment, imaging agents other than fluorophores could be conjugated to cobalamin to expand the imaging modality, for example: $^{18}F$ agents for positron emission tomography, MRI contrast agents such as gadolinium agents for MRI, or ultrasound contrast agents for optical coherence tomography. In an additional envisioned embodiment, the cobalamin could be attached to biotin to enable pull-down of the tagged RNA via biotin-streptavidin affinity purification.

The Cbl-conjugate probe has and maintains a close proximity of the florescent probe and the cobalamin molecule, which quenches fluorescence. However, when the Cbl-conjugate probe binds to a RNA tag attached to an RNA target by directly binding to the RNA tag comprising an aptamer the cobalamin and the fluorescent probe separate thereby "turning-on" fluorescence. In some embodiments, the Cbl-conjugate probe-RNA tag attached to a target RNA composition where the target RNA in turn hybridizes with endogenous RNA, thus the "turned-on" fluorescence also identifies endogenous RNA. In some embodiments, such target RNA is transcribed as a minus strand for identifying plus strand endogenous mRNA. In other words, binding of Cbl-conjugate probe with the RNA tag-RNA target triggers the riboswitch sequence to change conformation thereby sterically separating the cobalamin from the fluorescent molecule allowing fluorescence. In other embodiments, where the conjugate comprises a drug, the conformational change may result in delivering a therapeutic drug to the RNA target and/or a structure attached to the RNA target. Linker regions of various types and lengths were also tested in vitro and in vivo for baseline fluorescence and then optimal fluorescence after the fluorescent probe (i.e. Cbl-conjugate, binds to the RNA tag.

As one example of a method for live cell labeling, cells were transfected with a plasmid expressing the riboswitch RNA probe, followed by contact with beads coated with the cobalamin-fluorescence conjugates as a means to enter the cell. Cells were also treated with arsinite in order to visualize the fluorescing labeled short RNA molecules, such as polymerase 11-dependent transcripts (mRNA and snRNA) to RNP-granules, including U1 snRNA, a small non-coding RNAs.

However, it is not meant to limit live cell labeling methods to the use of an aggregation agent or clustering agent for inducing "particle aggregation" such as arsenite. In fact, as described herein, RNA may be tagged and visualized without the use of such agents.

Moreover, several copies of the RNA aptamer tag can be fused genetically to a RNA of interest to achieve detection of single RNAs with Cbl-fluorophore probes as described herein. When 12 copies of the RNA tag are attached to a RNA of interest, up to 12 molecules of the Cbl-fluorophore probe 4xGly-ATTO 590 bind the RNA. Thus, single messenger RNAs (mRNAs) can be detected as distinct spots. Thus, in one application, dynamics of the RNA within a cell can be monitored. The diffusion coefficient and velocity can be quantified, and values can be compared to those reported for RNAs labeled with other tags. Mobility of RNAs that were previously not characterized on the single molecule level can now be quantified using a Riboglow RNA tag as described herein.

In one embodiment, use of such Riboglow RNA tags include quantification of mobility for mRNAs which have mutations that are indicative of genetic diseases or cancers. Thus, when mRNAs associated with diseases display distinct mobility values, this single molecule tracking assay, e.g. using a 12 copy RNA tag, may be used to screen pharmacological treatments that aim to reverse mRNA movement to the healthy phenotype. In another embodiment, mobility of RNAs relative to other fluorescent markers can be quantified. In this method, an mRNA is labeled with Riboglow, while the translated protein is labeled with a fluorescent antibody. Translation of the mRNA into the nascent protein is visualized as co-localizing and co-moving spots, and the translation rate can be extracted from this data. Disease mutations that alter protein translation can be characterized, and pharmacological treatment to reverse changes in translation can be screened with this assay. Examples of such diseases having mutations for altering translation include but are not limited to protein misfolding and degenerative diseases, e.g. where accumulation of misfolded proteins may cause disease, e.g. amyloid diseases, such as Alzheimer's, Parkinson's, Amyotrophic lateral sclerosis (ALS), Huntington's, and other diseases such as type 2 diabetes, inherited cataracts, some forms of atherosclerosis, hemodialysis-related disorders, short-chain amyloidosis, etc.

It is not intended to limit a Riboglow tag to 4, or even 12 copies of an RNA tag, for binding up to 12 cbl conjugates. In fact, a Riboglow tag may be used from 1 up to 5 copies, up to 6 copies, up to 7 copies, up to 10 copies, up to 12 copies or more, such as up to 14 copies, up to 18 copies, and up to 20 copies.

As described herein, the ability of at least two different Riboglow probes was demonstrated to track mRNA and small non-coding U RNA in live mammalian cells. A direct side-by-side comparison revealed that Riboglow outperformed the dye binding aptamer Broccoli and performed on par with the current gold standard RNA imaging system, the MS2-fluorescent protein system. Some advantages are described in Section III below, of using the Riboglow system described herein.

Further, the disclosed system and methods for visualizing clustered RNAs in live cells provide improvements and have numerous advantages over current constructs and methods used for visualizing clustered RNA within cells. In fact, comparative results to systems, i.e. Broccoli and MS2 system, indicated a number of advantages including improved labeling, increased photostability and increased sensitivity, in particular, when each RNA was comparatively labeled with 4 fluorescent molecules.

I. Medical Applications for a RNA Construct and Cbl-Probe.

In one embodiment, the present invention contemplates methods for using a RNA construct and Cbl-probe as described herein, for targeting specific types of forming or previously formed stress granules in mammalian cells. Thus, as used herein, the term "Riboglow" may also refer to a system/platform based upon a Cbl conjugate using a non-florescent molecule.

For example, in vitro, stress granules (SGs) form, then over time dissolve, as a cellular response to a stress trigger, such as hypoxia, heat-shock, arsenite, etc. However, in vivo, chronic stress or another stimulus, might induce formation of persistent, or induce larger numbers of stress granules, and thus contribute to pathological SGs associated with some neurodegenerative diseases, including but not limited to amyotrophic lateral sclerosis (ALS), frontotemporal lobar degeneration (FTLD), Huntington's chorea, Creutzfeld-Jacob disease. Therefore, use of a construct described herein, such as a RNA fusion product comprising a RNA tagged human β-actin for targeting a Cbl therapeutic to disrupt stress granules is contemplated for use. Thus, in some embodiments, RNA constructs are used with Cbl-therapeutic drug conjugates for manipulating intracellular RNA containing particulate structures, such as granules containing certain types of RNA, for treating a neurodegenerative disease.

For comparisons, the following references are described herein. WO2005025512, "Cobalamin conjugates for anti-tumor therapy." Published Mar. 24, 2005, herein incorporated by reference in its entirety, describes a cobalamin-drug conjugate suitable for the treatment of tumor related diseases. Cobalamin is covalently bound to an antitumor drug via a cleavable linker or optional spacers. Cobalamin is covalently bound to a first spacer or the cleavable linker via the 5'-OH of the cobalamin ribose ring. The drug is bound to a second spacer of the cleavable linker via an existing or added functional group on the drug. After administration, the conjugate forms a complex with transcobalamin (or any of its isoforms). The complex then binds to a receptor on a cell membrane and is taken up into the cell. Once in the cell, an intracellular enzyme cleaves the conjugate thereby releasing the drug. Due to the high demand for cobalamin in growing cells, tumor cells typically take up a higher percentage of the conjugate than do normal non-growing cells. Types of neuronal cells include, but are not limited to, neuroblastoma, neuroepithelioma, neurofibroma, and/or neuroma. Moreover, this reference describes and further references a fluorescent moiety linked to the cobalamin preferably via the corrin ring or the 5' —OH group. Imaging of tumors is mentioned but not described in detail. Additionally, numerous types of cobalamin-drug conjugates are mentioned and referenced. However, this reference does not mention a riboswitch RNA probe as described herein, for use with targeting a cobalamin-drug conjugate to a stress granule or applied to a neurodegenerative disorder.

U.S. Pat. No. 8,313,901, "Methods and compositions related to the modulation of riboswitches." Issued Nov. 2, 2012, herein incorporated by reference in its entirety, describes RNA riboswitches, derived from a naturally-occurring adenosylcobalamin-responsive riboswitch, operably linked to an aptamer for binding to a naturally occurring ligand. Binding of a trigger molecule can, depending on the nature of the riboswitch, reduce or prevent expression of the RNA molecule or promote or increase expression of the RNA molecule, apparently in bacteria cells. The fluorescent labels are positioned on the nucleic acid such that when an RNA stem structure forms a quenching moiety until the stem is disrupted (such as when a riboswitch containing the label is activated), the quenching moiety is no longer in proximity to the fluorescent label and fluorescence increases. Fluorescent molecules include 6-carboxyfluorescein (6-FAM), FITC (490 nm; 520 nm), Cy5 (652 nm: 672 nm) and other dyes offered by Molecular Probes, Eugene, Oreg. This reference does not mention a cobalamin-fluorophoretherapeutic drug conjugate bound to a riboswitch sequence, or describe a tag RNA sequence designed to bind to an intracellular small RNA molecule in mammalian cells.

Figure 11A:
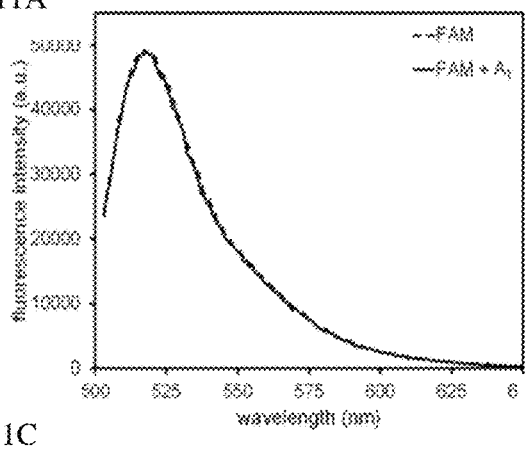
FIG. 11A-E shows representative fluorescence spectra of free fluorophores used herein in the presence and absence of RNA variant $A_T$. Spectra reveal no change in fluorescence intensity of free fluorophores in the presence of $A_T$. Triplicates of spectra shown here were used to generate the bar graphs presented in FIG. 1H.
Figure 11B:
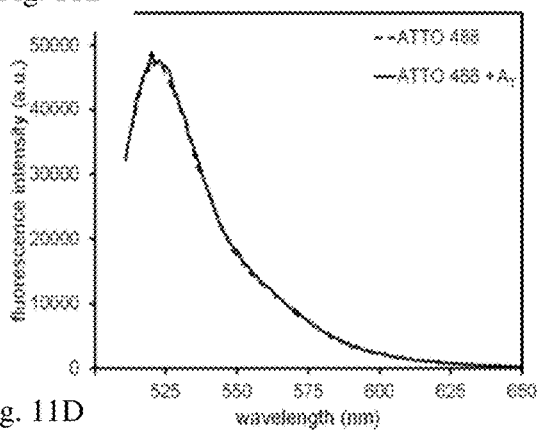
Figure 11C:
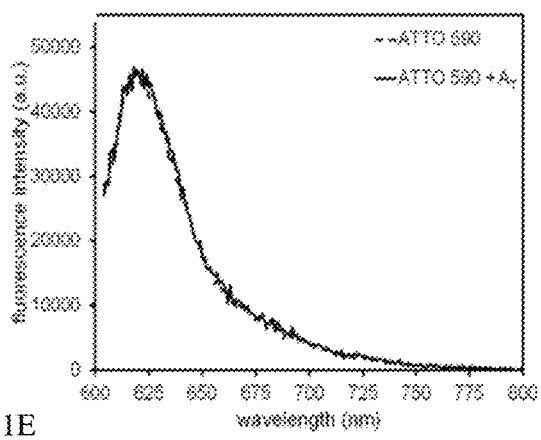
Figure 11D:
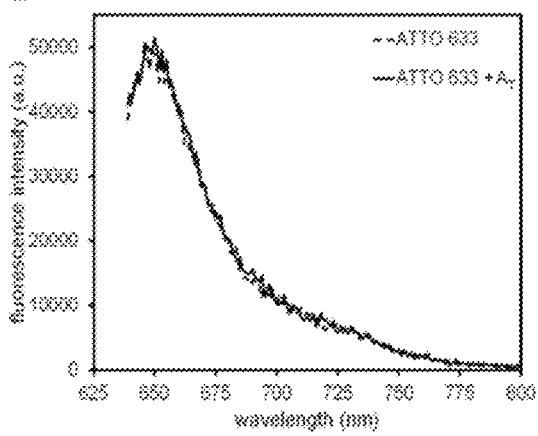
Figure 11E:
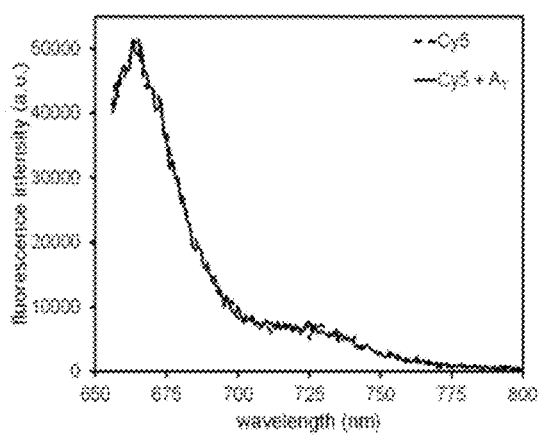
Figure 12A:
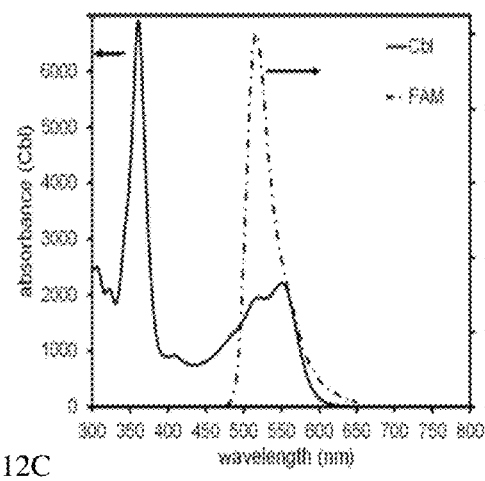
FIG. 12A-E shows exemplary Cbl absorbance spectra and fluorescence emission spectra of fluorophores to calculate the overlap integral J(λ). Arrows assign y-axis for the indicated spectra.
Figure 12B:
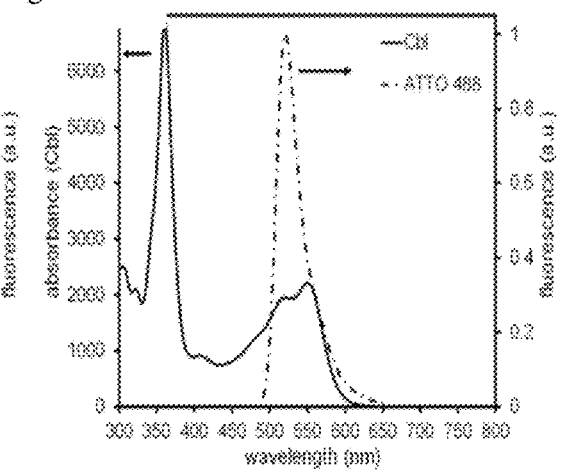
Figure 12C:
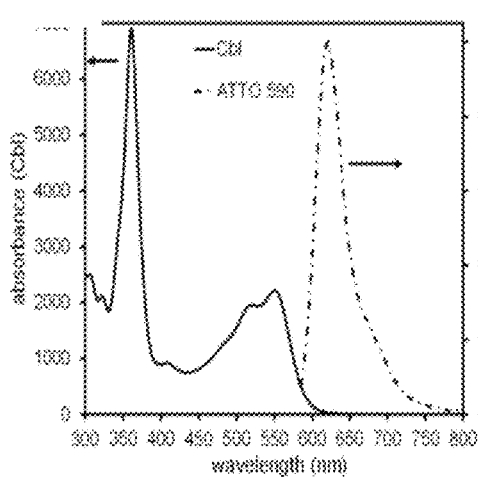
Figure 12D:
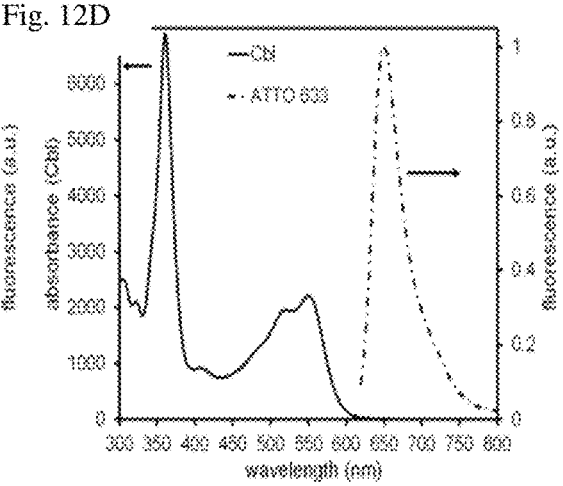
Figure 12E:
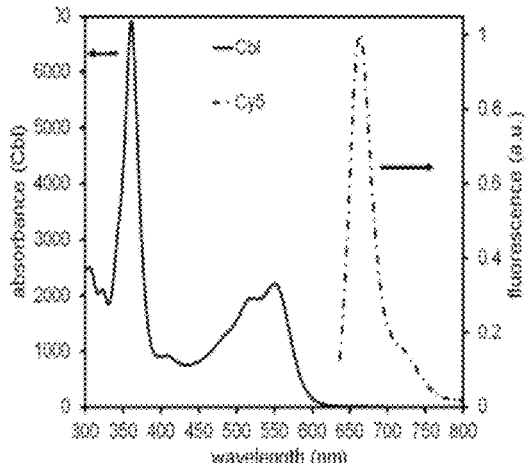

US Patent Application Publication No. US20110151471, "Riboswitches, methods for their use, and compositions for use with riboswitches", herein incorporated by reference in its entirety, describes and provides coenzyme $B_{12}$ (AdoCbl) riboswitches with applications to living biosensors and in advanced forms of gene therapy treatments. In fact, a coenzyme B12 aptamer consensus riboswitch RNA structure for binding to AdoCbl (B12) is shown in FIG. 11A of US20110151471. A fluorescent signal can also be generated by riboswitch-mediated triggering of a molecular beacon. Thus, riboswitch conformational changes cause a folded molecular beacon tagged with both a fluorphore and a quencher to unfold and force the fluorphore away from the quencher by forming a helix with the riboswitch. Further, the small molecule ligands of riboswitches are described as having useful sites for derivatization to produce drug candidates. However, this reference does not mention a cobalamin construct or describe a riboswitch RNA probe as described herein.

Lee, et al., "Therapeutic Applications of Aptamer-Based Riboswitches." Nucleic Acid Ther. 26(1):44-51. Epub 2015, herein incorporated by reference in its entirety, describes a summary of a recently developed and engineered aptamer-based riboswitches focusing on their therapeutic availability and further discusses their clinical potential in disease affected cells. However, this reference does not mention a cobalamin construct or describe a riboswitch RNA probe as described in Claim 1, stress granule or neurodegenerative disorder.

Batey, "Basis Of Gene Regulation By Purine And Cobalamin Riboswitches." 2R01GM073850-10. Project start date: 1 Apr. 2005. Downloaded Apr. 17, 2018, abstract only, herein incorporated by reference in its entirety. This abstract describes cobalamin-binding riboswitches as model systems. In some medically relevant pathogens such as *S. aureus, P. aeruginosa*, and *C. difficile* regulatory elements control expression of genes for survival or virulence, suggesting new targets for antimicrobial agents. It describes studies that will yield new insights into how to target RNA as a small-molecule therapeutic through structure-based drug design. However, this reference does not mention a cobalamin construct or describe a riboswitch RNA probe as described in Claim 1, stress granule or neurodegenerative disorder.

You, et al., "Imaging metabolite dynamics in living cells using a Spinach-based riboswitch." PNAS. Published online 2015, herein incorporated by reference in its entirety, describes an engineered Spinach riboswitch, used for RNA live imaging systems used in studies on neuronal cell line. However, this reference does not mention a cobalamin construct or describe a riboswitch RNA probe as described in Claim 1, stress granule or neurodegenerative disorder.

Filnov, et al. "RNA Imaging with Dimeric Broccoli in Live Bacterial and Mammalian Cells." Curr Protoc Chem Biol., 8(1): 1-28. (2016), herein incorporated by reference in its entirety, describes Broccoli (including dimeric dBroccoli) as an RNA aptamer for imaging RNA in live mammalian cells. Broccoli comprises an F30 scaffold based on the highly stable viral (φ29 three-way junction RNA motif where an RNA of interest can be appended on either 5' or 3' end. Upon binding to an RNA, the conformation of the one construct shifts allowing the binding of DFHBI, or DFHBI-1T (3,5-difluoro-4-hydroxybenzylidene 1-trifluoroethyl-imidazolinone), which is a modified version of DFHBI, both fluorescing in the green range. Broccoli is used to image high abundance RNAs in live cells, such as transcribed off Pol III-dependent promoters in mammalian cells, dBroccoli is an aptamer containing two Broccoli units in one stem-loop twice as bright as a single Broccoli aptamer. However, this reference does not mention a cobalamin construct or describe a riboswitch RNA probe as described in Claim 1, stress granule or neurodegenerative disorder.

Trausch and Batey, Chapter Three "Design of Modular "Plug-and-Play" Expression Platforms Derived from Natural Riboswitches for Engineering Novel Genetically Encodable RNA Regulatory Devices." In, Methods in Enzymology, Volume 550, Pages 41-71, 2015. Abstract only, herein incorporated by reference in its entirety, described expression platforms that regulate transcription through a secondary structural switch that can host a variety of different aptamers, including those derived through in vitro selection methods, to create novel chimeric riboswitches. These synthetic switches are capable of a highly specific regulatory response both in vitro and in vivo. There is no mention of using Cbl riboswitch aptamers for turning on a fluorophore after binding to an RNA fusion construct in a live mammalian cell.

As discovered and shown herein, Riboswitch RNA fusion constructs, combined with Cbl probes, have advantages over other types of RNA live imaging systems.

II. Cobalamin (Cbl) Conjugate Probes: Design of Cbl Probes with Fluorescence Quenching Properties.

In one embodiment, the present invention contemplates at least two parameters that modulate quenching efficiency of Cbl: the type of fluorophores and linker properties and type of RNA tag. Thus, in some embodiments, fluorophores have emittance ranging in red to far-red fluorescent molecules. In some embodiments, PEG Linkers range from 1.0 Å up to 3.5 Å, up to 10.5 Å, up to 17.5 Å in length. In some embodiments, linker distances between a corrin ring and click linkage to a fluorophore (or therapeutic), range from 1.0 Å, up to 9 Å, up to 12.5 Å, up to 16 Å, up to 26.5 Å, up to 30.4 Å in distance.

Fluorophore Colors and Quenching.

Figure 7:
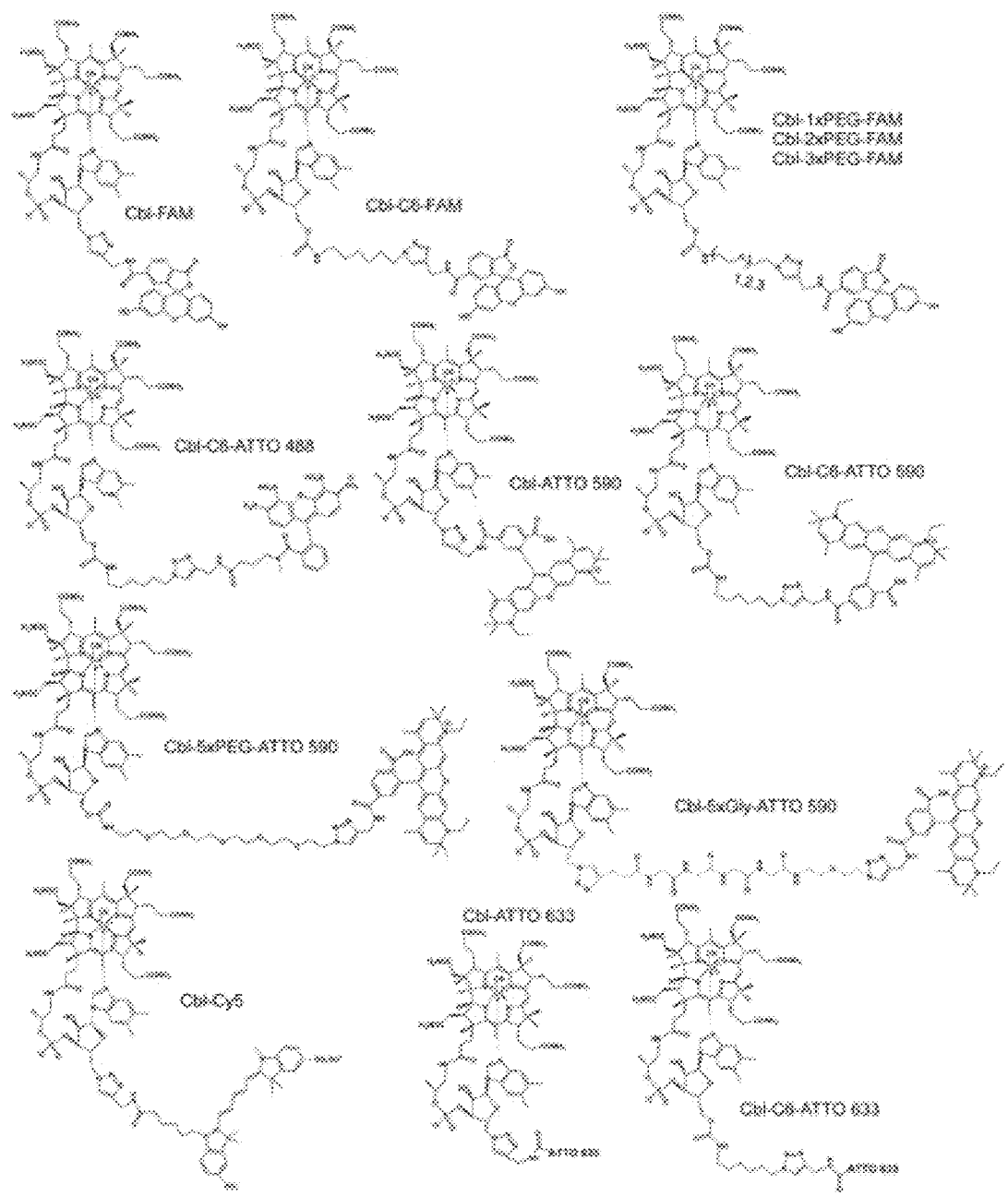
FIG. 7 illustrates exemplary embodiments of chemical structures of probes used herein. Note that the chemical structure of the ATTO 633 dye is proprietary and unknown.
Figure 7:
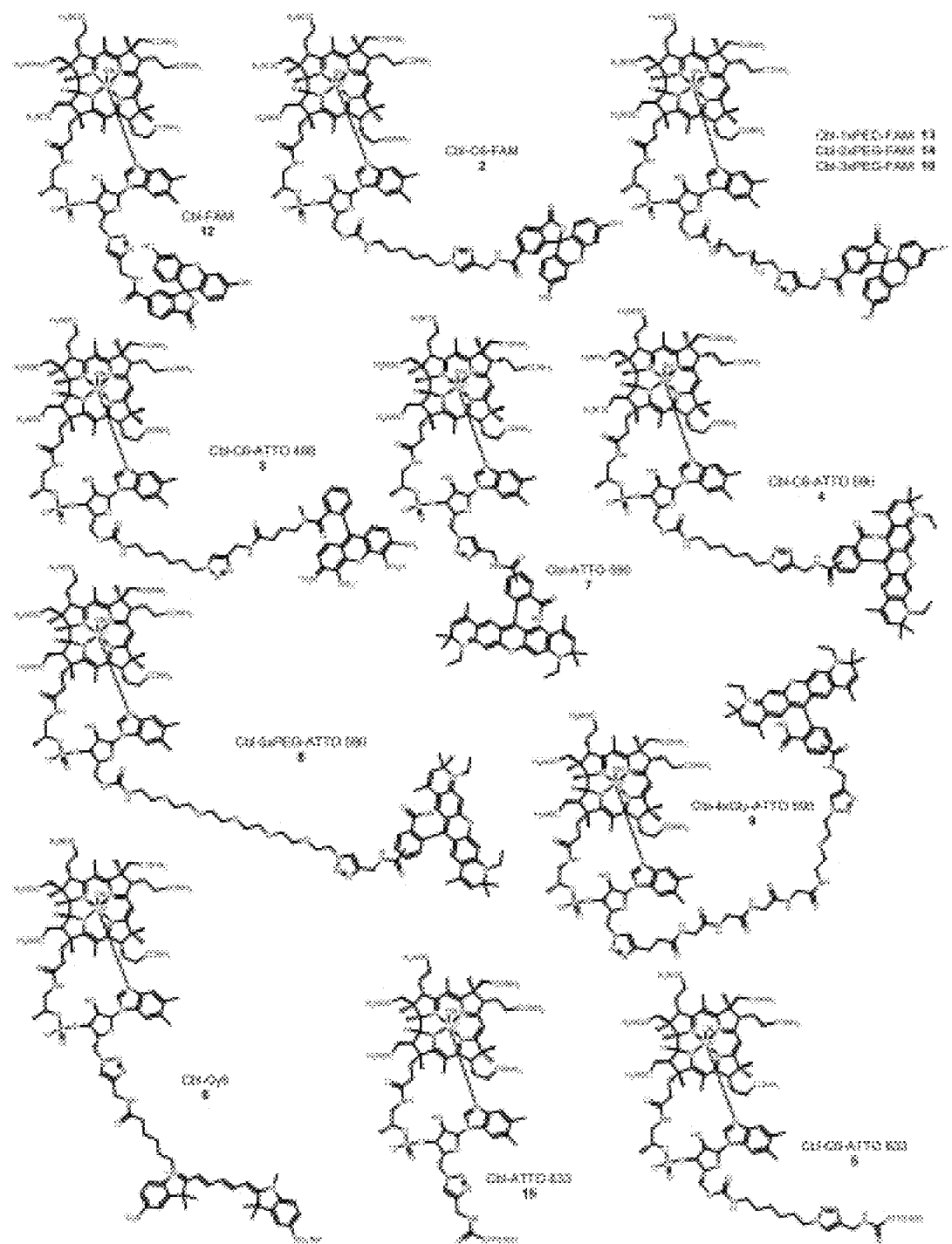
Figure 8A:
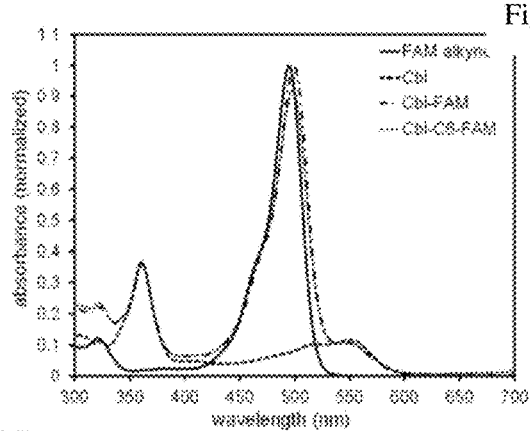
FIG. 8A-E shows exemplary absorbance spectra of representative Cbl-fluorophore probes in comparison to the spectra of free Cbl and each fluorophore. The absorbance intensities were normalized to the maximum absorbance peak of Cbl at 361 nm to allow for evaluation of changes in absorbance peak shapes.
Figure 8B:
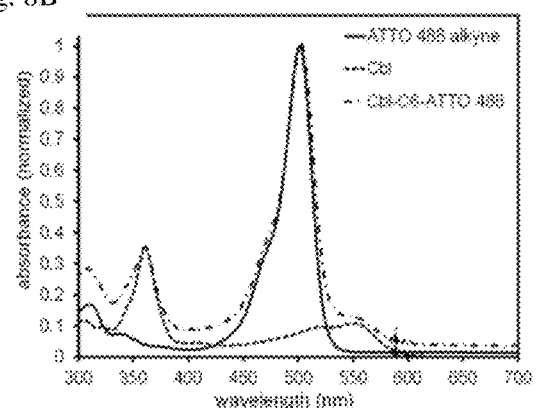
Figure 8C:
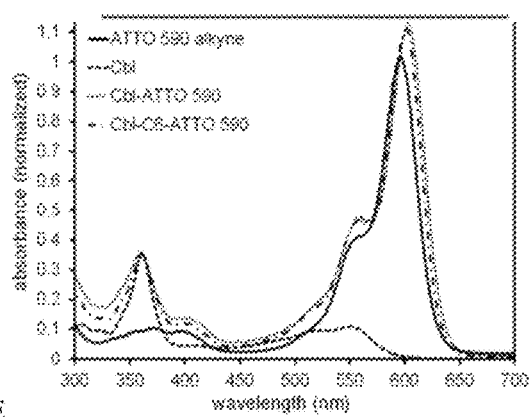
Figure 8D:
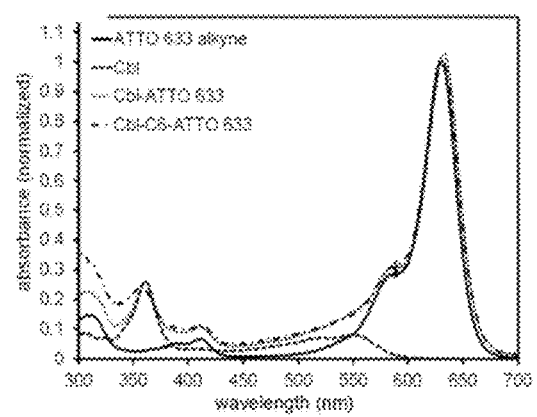
Figure 8E:
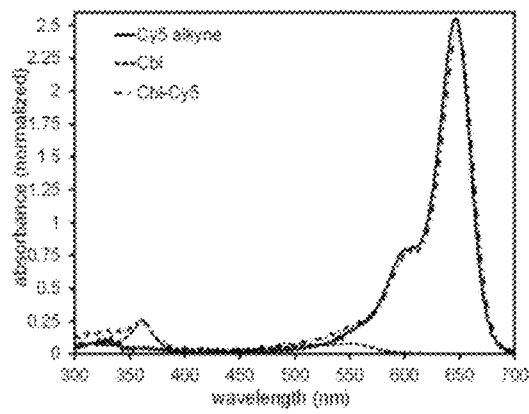

To assess how different fluorophores affect quenching, a series of probes with different fluorophores conjugated to Cbl via a 6-carbon chain (C6) were synthesized. See, FIG. 7 for examples). As shown in FIG. 7, "4xGly" and "5xGly" are used in names of molecules comprising a Gly linker comprising 4 glycine amino acid molecules, i.e. 4xGly, as described herein.

The fluorescence of each probe was measured and compared to that of the free fluorophore (FIG. 1G, FIG. 8A-E). Cbl-C6-FAM and Cbl-C6-ATTO488 retained only 0.5% and 2.5% fluorescence respectively, indicating that quenching, defined as reduction of the fluorescence signal, was highly efficient for probes with fluorophores in the green wavelength regime ($\lambda_{em}$ approximately 520 nm).

Figure 1B:
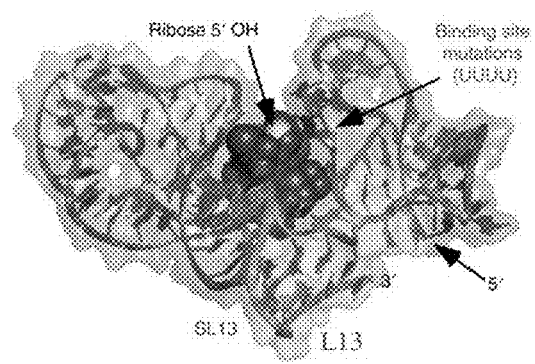
Figure 1C:
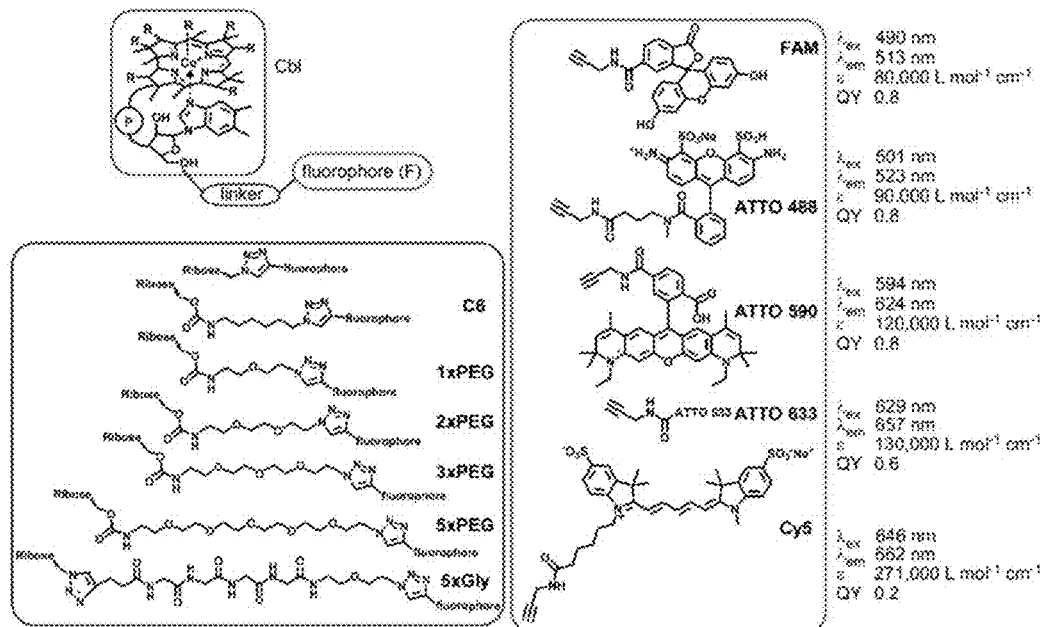
Figures 1D, 1E, 1F:
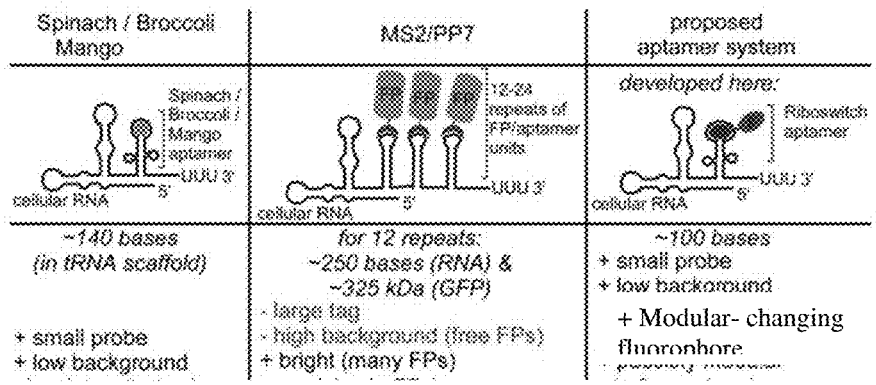
FIG. 1D-F illustrates some differences between compositions of vegetable/fruit systems vs. a Riboglow system.
Figure 1G:
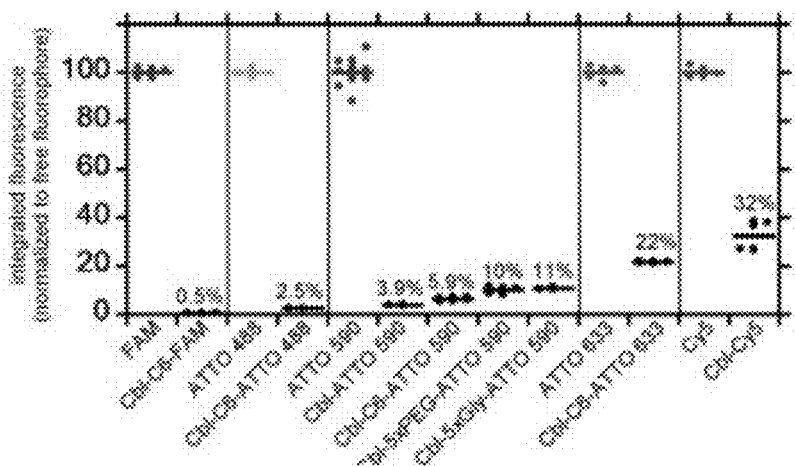
FIG. 1G shows an exemplary comparison of the fluorescence intensity of fluorophore vs. Cbl-[linker]-fluorophore probes. Cbl functions as an efficient quencher when covalently attached to fluorophores.
Figure 1H:
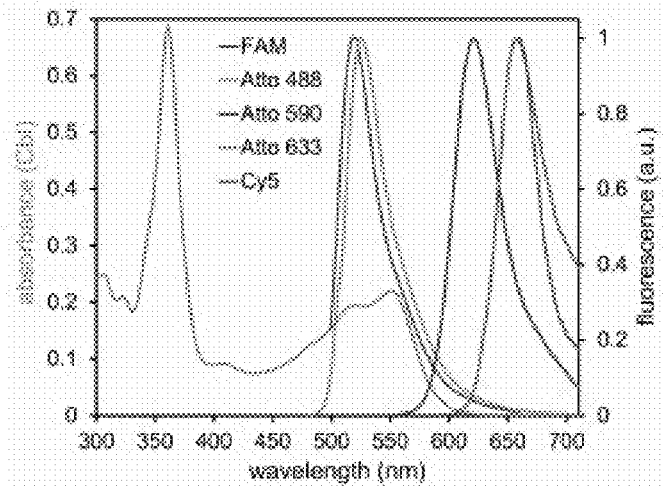
FIG. 1H shows a range of fluorescent wavelength emittance of fluorophores.

In contrast, probes with emission in the far-red range ($\lambda_{em}$ approximately 660 nm) retained around 25% fluorescence (22% for Cbl-C6-ATTO 633 and 32% fluorescence for Cbl-Cy5), corresponding to weaker quenching (FIG. 1H).

Cbl-C6-ATTO590 emits in the red range ($\lambda_{em}$ approximately 624 nm) and resulted in moderate quenching (5.9% residual fluorescence).

Together, the results revealed a correlation between quenching efficiency and the excitation/emission wavelengths of the fluorophore, where quenching was the least efficient in the far-red and most efficient in the green wavelength range.

Figure 2A:
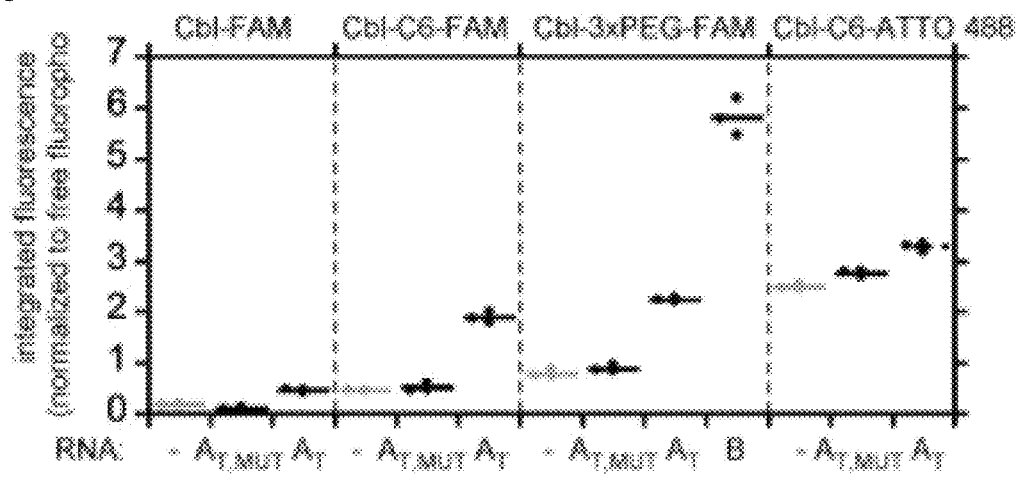
FIG. 2A-C shows exemplary Cbl riboswitch RNAs induce fluorescence turn-on in Cbl-fluorophore probes in vitro. The fluorescence intensity of Cbl-fluorophore probes in the presence or absence of different RNAs was quantified as in FIG. 1H and normalized relative to the intensity of the free fluorophore. The RNAs A, B, C and D are variants of Cbl-binding riboswitch sequences, where $A_T$ refers to a truncated version of A with linker region J1/3 and stem-loop P/L13 deleted, see FIG. 6. The subscript MUT in $A_{T,MUT}$ refers to four point mutations in the Cbl-binding site (see, FIG. 6 for the position of these residues).

The observation that spectral properties of the fluorophore impacted the extent of quenching and fluorescence turn-on (see herein) upon riboswitch binding, i.e. aptamer binding to Cbl, suggests that Förster resonance energy transfer (FRET) may contribute to quenching, a hypothesis evaluated by calculating the Förster radius ($R_0$) and estimating the distance between the fluorophore and quencher for each of the probes (Tables 3, 4, 6). The estimated distance between quencher and fluorophore for probes in the green wavelength range (FAM and ATTO488 fluorophores) is significantly below the calculated values for $R_0$, consistent with efficient quenching (<3% residual fluorescence, FIG. 1H, FIG. 2A). In line with this model, even the bulkiest aptamers tested induced fluorescence turn-on that resulted in approximately 5% or less fluorescence compared with the free fluorophore (FIG. 2A).

Probes with the ATTO590 fluorophore have a Forster distance ($R_0$=20 Å) close to the estimated distance between corrin ring and fluorophore (Table 6), suggesting that ATTO590 probes are particularly susceptible to large changes in fluorescence intensity for small distance changes.

While theoretical estimates are consistent with a model where FRET contributes to quenching, it was observed that conjugates in the far-red wavelength regime ($\lambda_m$ approximately 660 nm) lack spectral overlap with the Cbl absorbance spectrum (FIG. 12A-E), yet moderate fluorescence quenching was still observed, suggesting that non-FRET mechanisms such as contact quenching or electron transfer may also contribute to fluorescence quenching. Together, theoretical estimates calculated herein are consistent with a model where FRET contributes to quenching of the attached fluorophore.

Choosing Fluorophores for Use with Cbl-Fluorophore Probes.

Cbl-fluorophore probes with red and far-red fluorescent properties were chosen for further characterization for the following reasons. Red and far-red fluorescent molecules conjugated to probes are desirable for live-cell imaging due to decreased cellular autofluorescence in this wavelength regime. While probes in the green wavelength range (for example Cbl-3xPEG-FAM, FIG. 2A) display efficient quenching and reasonable fluorescence turn-on (up to 7.4× fluorescence turn-on for Cbl-3xPEG-FAM with aptamer B, FIG. 2A-C, Table 3), the fluorescence signal after turn-on was low (only approximately 5% of fluorescence of free FAM in the presence of the best aptamer), raising concerns about the signal and contrast that would be achievable in live cell microscopy applications. Since during the development of the present inventions, it was discovered that FRET is likely a contributing factor to quenching in Cbl-ATTO488 and Cbl-FAM probes, higher fold turn-on is contemplated to require a linker longer than the Förster radius of 35 Å (Table 3). Thus, in one embodiment, a linker is longer than the longest linker in this study (5xPEG, 21.4 Å, see, Table 4), for allowing quenching and turn-on florescence for use in Cbl probes. Therefore, red and far-red fluorescent molecules conjugated to probes (Cbl-5xPEG-ATTO590, Cbl-5xGly-ATTO590 comprising 4xGly. and Cbl-Cy5, as nonlimiting examples of fluorescent probes) were chosen since upon RNA binding, they exhibited bight turn-on and fluorescence closer to the free dye (FIG. 2B, 2C).

Figure 2B:
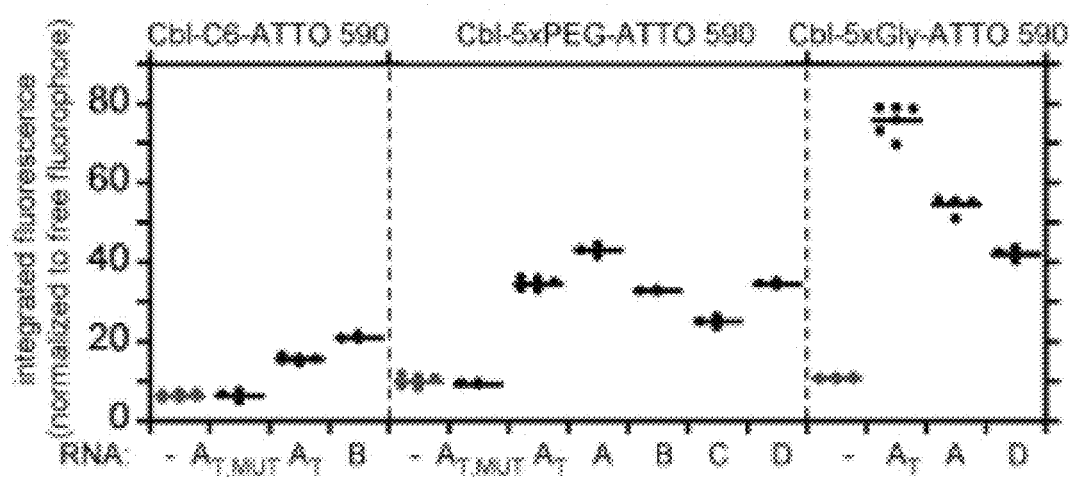
Figure 2C:
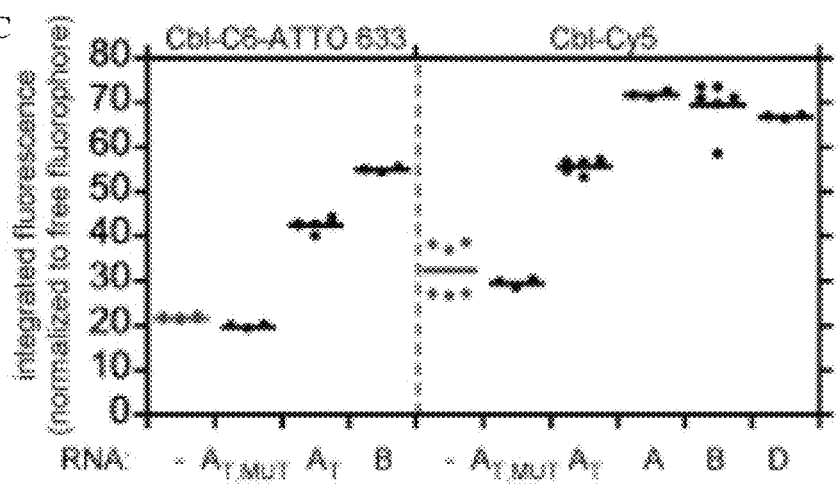

FIG. 2A-C shows exemplary Cbl riboswitch RNA fusion molecules, i.e. riboswitch RNAs, induce fluorescence turn-on from attached Cbl-fluorophore probes in vitro. The fluorescence intensity of Cbl-fluorophore probes in the presence or absence of different RNAs in the fusion construct was quantified as in FIG. 1G and normalized relative to the intensity of the free fluorophore. RNAs A, B, C and D are variants of Cbl-binding riboswitch sequences, where $A_T$ refers to a truncated version of A with linker region J1/3 and stem-loop P/L13 deleted, see FIG. 6. The subscript MUT in $A_{T,MUT}$ refers to having four point mutations in the Cbl-binding site that abolishes binding to Cbl (see, FIG. 6 for position of these residues) FIG. 2A illustrates exemplary probes with fluorescence in the green wavelength range.

FIG. 2B illustrates exemplary probes with fluorescence in the red wavelength range.

FIG. 2C illustrates exemplary probes with fluorescence in the far-red wavelength range. Data are presented as mean for n=3 independent measurements (see Table 3 for a summary).

Linker Properties.

A systematic assessment of how the length of the chemical linker affects quenching found that increasing the linker length reduces quenching efficiency (FIG. 1G). As one example, addition of a C6 linker (approximately 10.5 Å, Table 4) between Cbl and ATTO590 resulted in higher residual fluorescence (5.9% for Cbl-C6-ATTO590 vs. 3.9% for Cbl-ATTO590) (FIG. 1G).

In line with this trend, increasing the linker length further to five polyethylene glycol (PEG) units (approximately 17.5 Å, Table 4) or a 5x glycine linker comprising 4xGly, (approximately 21.4 Å, Table 4) increased the residual fluorescence to 10% and 11%, respectively. Similar trends were observed when changing the linker length for probes with FAM as the fluorophore (FIG. 8A-E), confirming that quenching is most efficient when the fluorophore is closer to Cbl.

In other embodiments, linker properties may be altered and tested based upon biochemical properties and/or structures (e.g. polarity, charge, rigidity, etc.) in order to alter properties, such as quenching and dequenching properties; altering interactions with the RNA riboswitch, etc.

III. Variation of RNA Aptamer Tag Properties Modulates Fluorescence Turn-on, De-Quenching, Upon Probe Binding to a Cbl Binding Portion (Aptamer) of a RNA Tag.

In one embodiment, RNA aptamers upon binding to a Cbl probe induced de-quenching of probe fluorescent molecules, thus de-quenching and fluorescence turn-on occurs when RNA aptamers bind to the Cbl portion of the probes.

Figure 9:
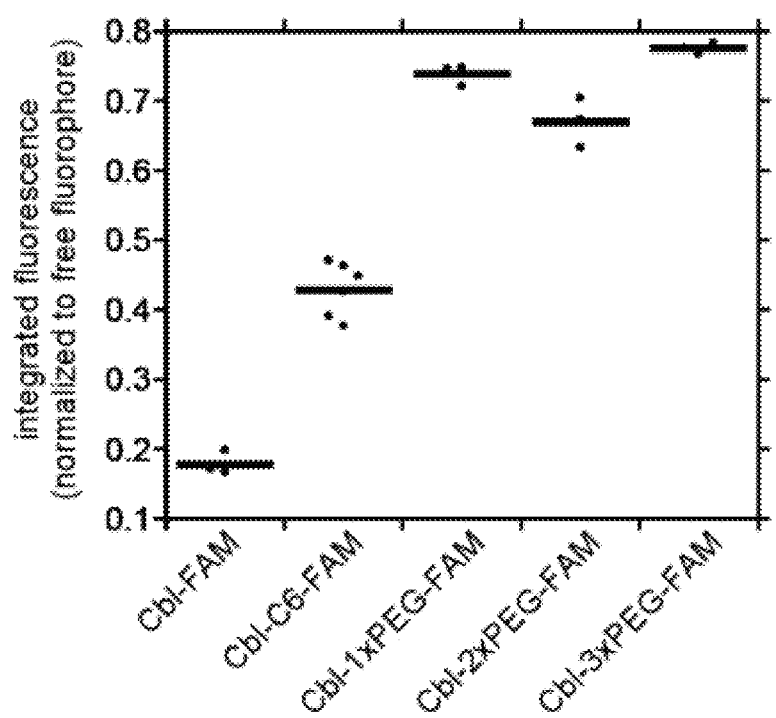
FIG. 9 shows exemplary comparison of residual fluorescence for Cbl-FAM probes with varied linkers. The fluorescence was quantified and compared to the signal of the free fluorophore at the same concentration as in FIG. 1H. The mean for at least n=3 independent measurements is shown.

It was hypothesized that binding of an RNA aptamer to the Cbl moiety of probes would sterically separate fluorophore and quencher and thereby reduce quenching, resulting in an increase in fluorescence (FIG. 1A). To test this, the fluorescence signal of several probes in the presence and absence of a minimal truncated aptamer ($A_T$) was compared. Also included was a control aptamer that has four point mutations to abolish binding to Cbl ($A_{T,MUT}$) (FIG. 9).

Upon binding, fluorescence increase was observed for probes binding to $A_T$ (FIG. 2A, 2B, FIG. 10A-F, see, Table 6 for a summary of fold turn-on results). The signal was not significantly changed in the presence of the negative control aptamer RNA $A_{T,MUT}$ (FIGS. 2A, 2B), and RNA $A_T$ did not affect the fluorescence signal of the free fluorophore (FIG. 11A-F). Together, these observations indicate that fluorescence turn-on is specifically induced when the aptamer $A_T$ binds the Cbl portion of the probe.

FIG. 2A-C shows exemplary Cbl riboswitch RNAs induce fluorescence turn-on in Cbl-fluorophore probes in vitro. The fluorescence intensity of Cbl-fluorophore probes in the presence or absence of different RNAs was quantified as in FIG. 1G and normalized relative to the intensity of the free fluorophore. The RNAs A, B, C and variant D are s of Cbl-binding riboswitch sequences, where $A_T$ refers to a truncated version containing the aptamer domain of riboswitch A with linker region J1/3 and stem-loop P/L13 deleted, see also FIG. 1G. The subscript MUT in $A_{T,MUT}$ refers to four point mutations in the Cbl-binding site (see, FIG. 6 for exemplary positions of these residues). FIG. 2A illustrates exemplary probes with fluorescence in the green wavelength range, FIG. 2B illustrates exemplary probes with fluorescence in the red wavelength range, FIG. 2C illustrates exemplary probes with fluorescence in the far-red wavelength range. Data are presented as mean for n=3 independent measurements (see, Table 5 for a summary).

FIG. 6 illustrates exemplary secondary structures of RNAs used herein with structural regions denoted as P (paired), J (junction), L (loop), and IL (internal loop). Naturally derived sequences are shown with accompanying Rfam accession numbers, and the secondary structure of wild type env8 (variant A) is based on crystallographic data [reference 1]. Nucleotides that are colored red in variant $A_{T,MUT}$ represent point mutations made to the binding core of wild type env8 that abrogate cobalamin binding. Nucleotides that are colored red in variant B represent point mutations derived from wild type env8 that have been shown to increase the affinity of this RNA [reference 2] for forms of cobalamin similar to the conjugates used herein. Features that induce bulkiness of the RNA include P13 for variant A, P7, P13, P14 for variant B and P7, P2, P13 for variant C. Variant D is an L4 and P7-optimized variant B that improved cobalamin affinity, see also see also FIG. 13A-C. Together, these observations indicate that fluorescence turn-on is specifically induced when the aptamer $A_T$ binds the Cbl portion of the probe.

A. Biophysical Characterization of RNA/Probe Complexes.

After further characterizing Cbl-5xPEG-ATTO590 and the aptamer $A_T$ biophysically, it was found that the affinity for Cbl was within the same order of magnitude in the context of the probe (0.29 µM vs. 1.3 µM, FIG. 9 and quantum yield measurements were consistent with plate reader fluorescence assay used herein (FIG. 13A-C, FIG. 2B).

Figure 13A:
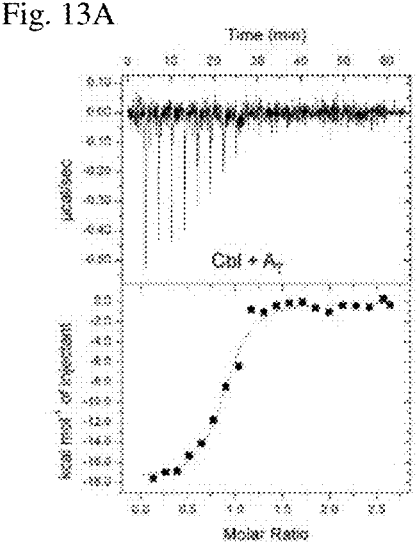
FIG. 13A-C RNA variants A and D (FIG. 13B and FIG. 13C), but not $A_T$ (FIG. 13A), bind to the probe Cbl-5xPEG-ATTO 590 with a dissociation constant (KD) in the nM range. Representative isothermal titration calorimetry thermograms of the RNA binding to Cbl (top) and Cbl-5xPEG-ATTO 590 (bottom) are presented. KD values as the mean of 3 independent experiments+/−STDEV are listed in Table 7.
Figure 13B:
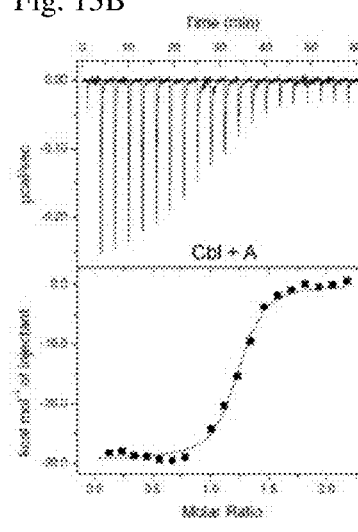
Figure 13C:
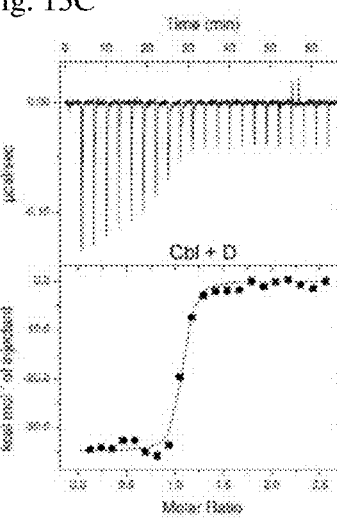

More specifically, RNA and Cbl-fluorophore probes were identified with a preferred photophysical behavior for cellular imaging and characterized for their biophysical properties. It was hypothesized that shorter RNA tags would be less disruptive in RNA fusions. Therefore, RNAs A and $A_T$ were chosen for their small size (103 and 81 nucleotides, respectively) and induction of strong fluorescence turn-on in vitro (for example, 4.9× turn-on for A with Cbl-5xPEG-ATTO590 and 7.3× turn-on for $A_T$ with Cbl-5xGly-ATTO590 comprising 4xGly, FIG. 2A-C, Table 5). Also included was aptamer D (130 nucleotides) for further in vitro characterization, since preliminary studies indicated high binding affinity to Cbl. Indeed, RNA tags A and D bind Cbl-5x-PEG-ATTO590 tightly with a dissociation constant (KD) of 34 nM and 3 nM, respectively, comparable to the KD for Cbl alone (FIG. 13A-C, Table 7). The truncated riboswitch, $A_T$, bound Cbl-5xPEG-ATTO590 with a lower affinity with a KD of 1.3 µM.

Quantum Yield of Exemplary Probes.

Figure 14A:
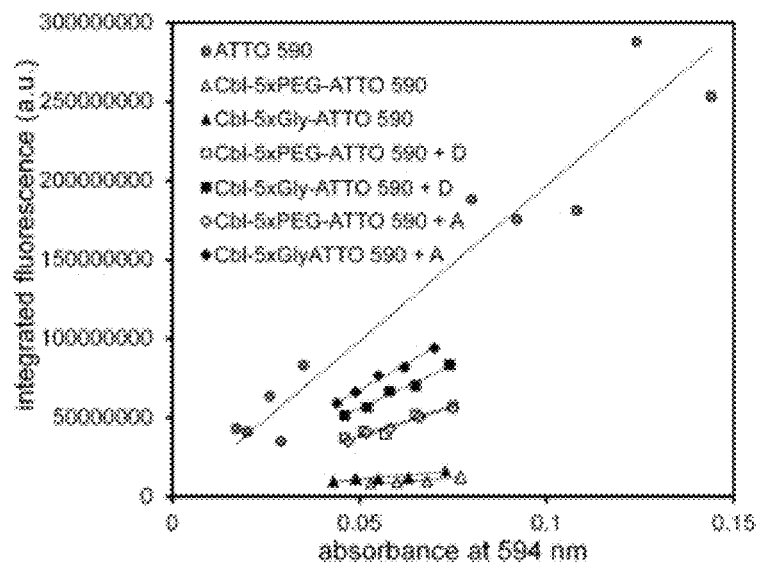
FIG. 14A-B shows exemplary determination of the quantum yield for different Cbl-fluorophore probes in the presence and absence of various RNAs.
Figure 14B:
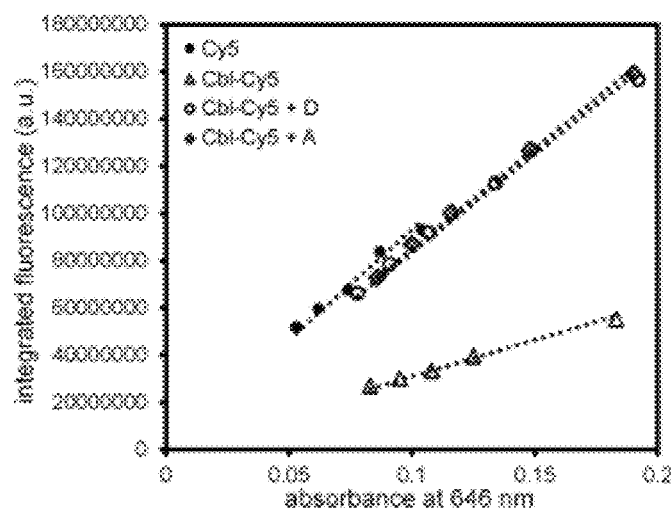
Figure 15A:
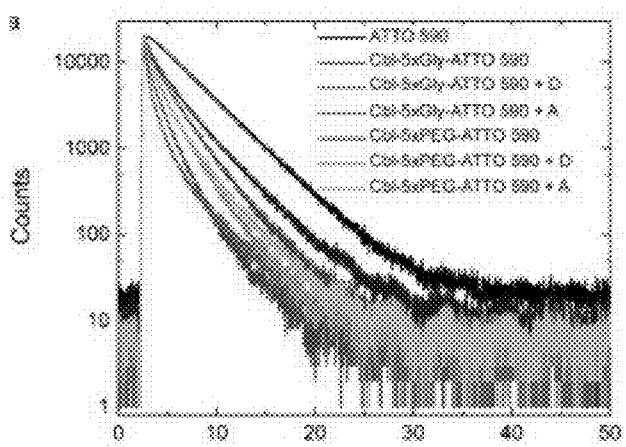
FIG. 15A-B Supplementary
Figure 15B:
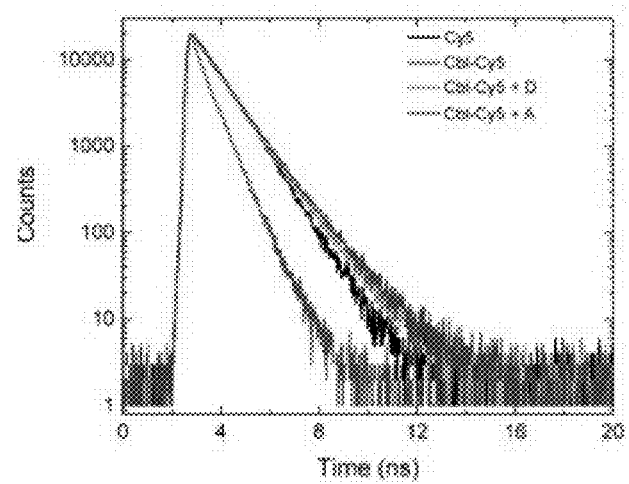
Figure 16:
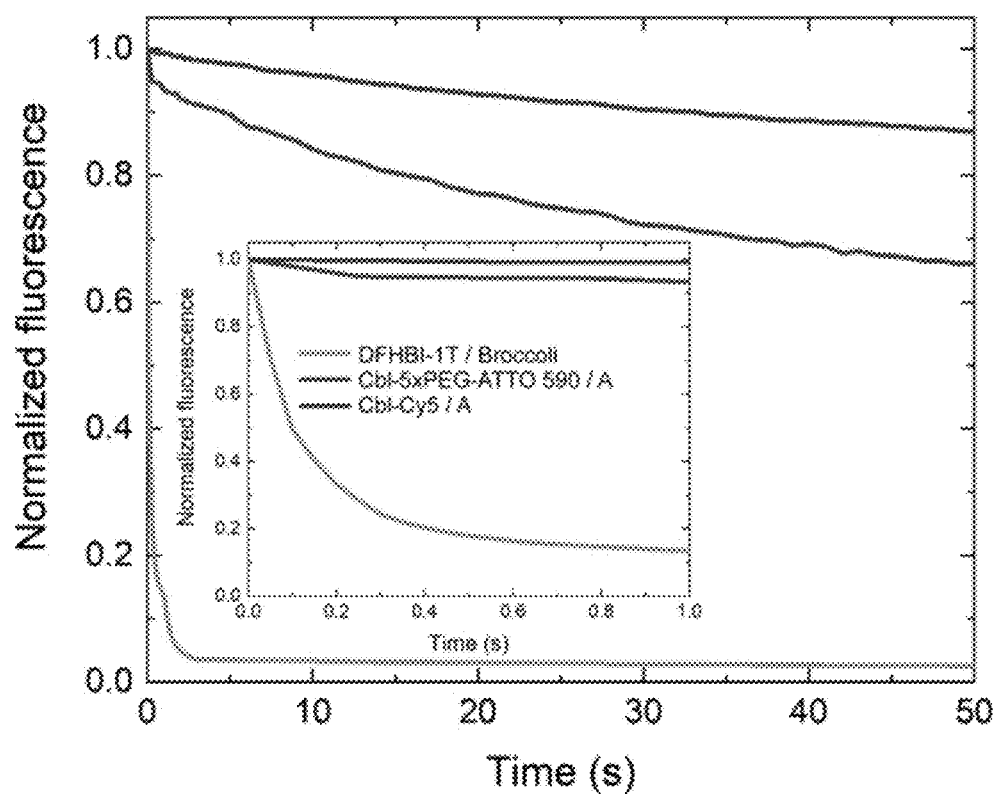
FIG. 16 shows exemplary photobleaching of RNA/probe complexes. Droplets containing the indicated RNA/probe complexes were constantly illuminated on a wide field microscope. The excitation rate (the number of absorbed excitation photons, determined from the extinction coefficient) were the same for each sample (see Table 10 for a summary of experimental conditions). Representative background subtracted and normalized fluorescence decay curves for each sample are reported. Inset: Photobleaching for the first 1 second.

The quantum yield of probes Cbl-5xPEG-ATTO590, Cbl-5xGly-ATTO590 comprising 4xGly, and Cbl-Cy5 was determined in the presence and absence of A and D (FIG. 14A-B. Table 8). A decrease in quantum yield was observed for Cbl-fluorophore probes vs. free fluorophores and an increase in the presence of RNA, consistent with results from a plate reader fluorescence assay (FIG. 2B, 2C). In line with the changes in quantum yield, the fluorescence lifetime was reduced for Cbl-fluorophore probes vs. their free fluorophore counterparts and fluorescence lifetime increased in the presence of the RNA (FIG. 15A-B, Table 9). Then, photostability of the red Cbl-5xPEG-ATTO590 and the far-red Cbl-Cy5 bound to RNA A was assessed in vitro under constant illumination. As seen by others [reference 27], the most widely used dye-binding RNA aptamer platform, DFHBI-1T-Broccoli, photobleaches to <20% fluorescence within a second. In contrast, Cbl-Cy5 bound to A retained >80% fluorescence even after 50 seconds (s) constant illumination (>60% fluorescence after 50 s for Cbl-5xPEG-ATTO590 bound to A) (FIG. 16). Together, tight binding of probes to the riboswitch variants A and D resulting in a high increase in quantum yield upon RNA binding, as well as substantially slower photobleaching compared with the dye-binding aptamer Broccoli, show beneficial properties for cellular imaging applications.

Steric Bulk of the Aptamers.

It was predicted that increasing the steric bulk of the RNA aptamer tag would promote greater separation between Cbl and fluorophore upon binding, leading to a larger fluorescence turn-on. To test this hypothesis, fluorescence turn-on was compared for Cbl-5xPEG-ATTO590 in the presence of $A_T$ vs. the full-length aptamer A that contains an additional structural element to increase 'bulkiness' (FIG. 9) Binding of Cbl-5xPEG-ATTO590 to A compared to $A_T$ resulted in a modest increase in fluorescence (35% vs. 43%, FIG. 2B, see also Table 5 for a summary of fluorescence turn-on results). To further test the influence of RNA structure, three additional riboswitch aptamer variants B, C and D were synthesized, FIG. 9) derived from other members of the Cbl riboswitch family.

The three variants B, C and D include bulky features that could potentially introduce steric constraints when binding the probe (FIG. 9). Variants B, C and D resulted in similar fluorescence turn-on compared with variant A for most probes tested (FIG. 2A, 2B). Variant B results in a modest improvement in fluorescence turn-on compared with variant $A_T$ for most probes tested (FIG. 2A, 2B). However, variant C did not increase fluorescence turn-on of Cbl-5xPEG-ATTO590 compared to variant $A_{T,MUT}$ (FIG. 2B). Together, while bulky features appended to the aptamer modestly improve fluorescence turn-on, i.e. no significant increase was observed (Table 5). Still, in other embodiments of the RNA tag, modifying the steric bulk of the RNA tag generating tags with different cobalamin riboswitch-derived sequences contemplated for enhancing the changes that occur when the Cbl conjugate binds the RNA tag.

B. Discovery of Functional RNA Tagging within Cells with RNA Tag Constructs Lacking a tRNA Folding Scaffold.

Other types of fluorophore-quencher systems are used for RNA tagging in vitro and in bacteria [reference 18, 19]. In vitro developed dye-binding aptamers often contain a G-quadruplex fold [reference 37, 38] which was shown to complicate RNA folding in mammalian cells [reference 39]. Furthermore, ligands for evolved aptamers with the G-quadruplex fold may bind other RNAs with G-quadruplex folds [reference 39], have been shown to bind nucleic acids non-specifically [reference 25] and G-quadruplex structures may be disrupted by dedicated helicases [reference 40]. Thus, to improve folding and stabilize against RNA degradation in cells, such aptamers often include a folding scaffold when fused to mammalian RNAs [reference 25-27, 41]. Two possible concerns of using a folding scaffold are that it further increases the size of the RNA tag, and certain scaffolds increase undesired RNA processing in mammalian cells [reference 42].

Indeed, initial designs of aptamers for use with the present inventions included a folding scaffold. In fact, the use of such a folding scaffold improved brightness of Spinach 2 [Strack, el al., "A superfolding Spinach2 reveals the dynamic nature of trinucleotide repeat-containing RNA." Nat. Methods 10, 1219-24 (2013)] in mammalian RNAs, however this can lead to unwanted processing of the RNA.

Figure 18A:
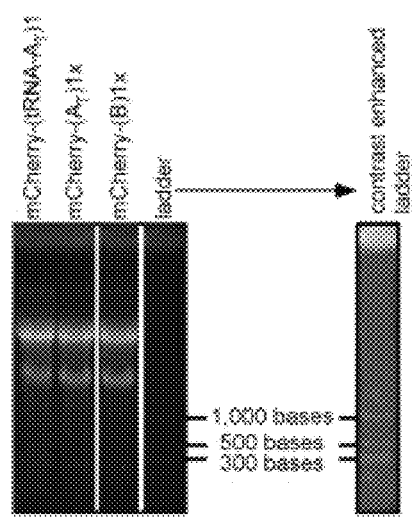
FIG. 18A-B shows exemplary mRNA that can be tagged with RNA variant $A_T$ without unwanted processing. 293T cells were transiently transfected with plasmid DNA where the $A_T$ or B tag was genetically fused to a reporter mRNA (encoding mCherry). The tag $A_T$ was produced with or without the tRNA folding scaffold. The tRNA processing phenotype was reproducible for two independent experiments.

Conversely, when tests were made as described herein, using an $A_T$ aptamer with and without a scaffold, it was discovered that the $A_T$ aptamer did not need the tRNA folding scaffold [reference 34]. Further, exclusion of the scaffold prevented unwanted processing, prompting the design and use of aptamers that did not include this scaffold (FIG. 16). Thus, some of the RNA tags described herein do not contain a tRNA folding scaffold [reference 43]. Further, it was discovered that exclusion of the scaffold from a RNA riboswitch-aptamer prevented unwanted processing (FIGS. 18A-B and Table 11) and exclusion of the folding scaffold resulted in reducing the overall tag size. Thus, the tRNA scaffold was not present in the RNA riboswitch-aptamer constructs used in live cell experiments described herein.

IV. Riboswitch RNA Fusion Constructs.

In one embodiment, the present invention contemplates, a Cbl riboswitch construct comprising an aptamer (Cbl-binding domain), a riboswitch sequence and an expression platform, i.e. a promoter in operable combination with an RNA intended for expression. Variants of both the full-length riboswitch sequence and the shorter aptamer domain were used (FIG. 6), collectively referred to as the 'riboswitch RNA tag'. The crystal structure of Cbl bound to the aptamer revealed that the Cbl 5'-hydroxyl group is accessible even in the RNA-bound state [reference 30] (FIG. 1B). In one embodiment, this position is used for conjugation with fluorophores via the copper catalyzed alkyne-azide cycloaddition reaction [reference 35, 36] to explore different conformational and photochemical properties of the probe (FIG. 1C). In other embodiments, the fluorophore could be conjugated to the Cbl at a different position, see example described herein.

In one embodiment, the present invention contemplates at least one parameter of the RNA tag to modulate fluorescence turn-on. Thus, in some embodiments, an RNA tag may range from 81-103 nucleotides per individual RNA tag.

V. Riboswitch-Based RNA Imaging Platform Used in Live Mammalian Cells.

The riboswitch-based tagging system described herein was found to have features prompting design and testing of this imaging platform while contemplating broad applicability in live mammalian cell applications.

Visualization of mRNA Dynamics in Live Mammalian Cells.

At least two different types of applications, including single molecule imaging for tracking of individual RNA molecules; use of Riboglow to track mRNA molecules that are translated into nascent polypeptide chains, etc., were developed and tested, as described herein, for live mammalian cells included visualizing recruitment of β-actin mRNA (ACTB) to SGs in U2-OS cells and sequestration of the non-coding U1 snRNA in U-bodies in HeLa cells.

Figure 19A:
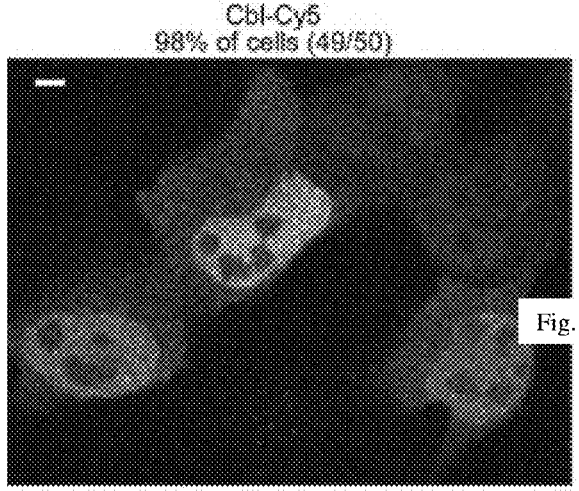
FIG. 19A-G shows exemplary residual fluorescence of Cbl-fluorophore probes reports on probe localization in live cells upon bead loading.
Figure 19B:
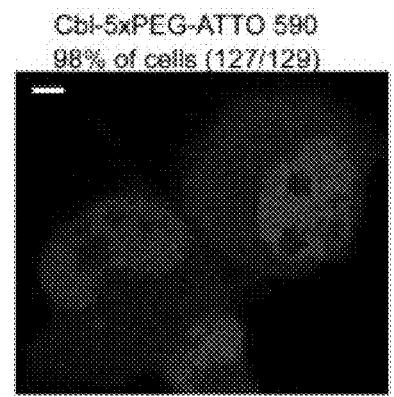
Figure 19C:
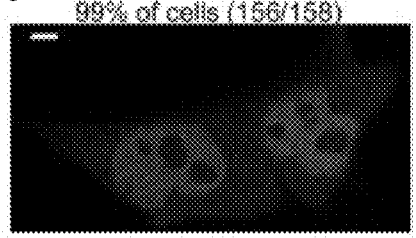
Figure 19D:
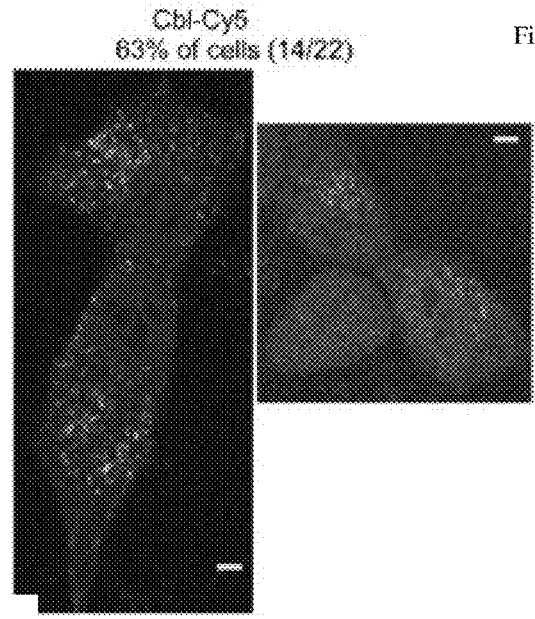
Figure 19E:
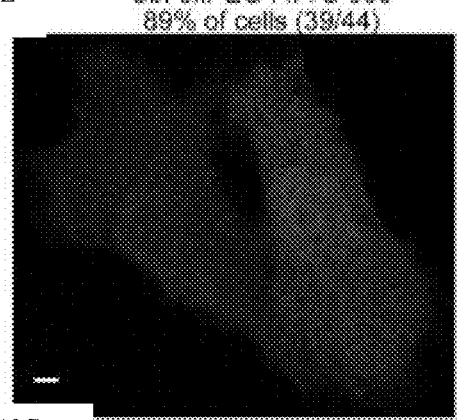
Figure 19G:
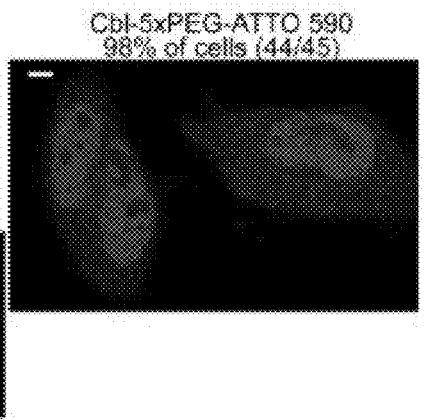
Figure 19F:
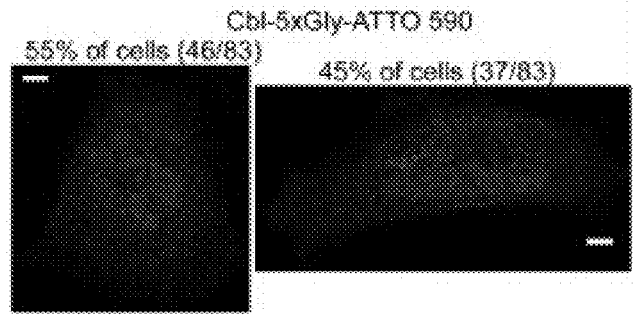

Moreover, residual unquenched fluorescence of three exemplary Cbl-fluorophore probes used in cellular studies (Cbl-5xPEG-ATTO590, Cbl-5xGly-ATTO590 comprising 4xGly, Cbl-Cy5) revealed that in the absence of the riboswitch RNA, bead loading the probes in U2-OS cells [reference 44-46] gave rise to diffuse cytosolic and nuclear localization (FIG. 19A-C). At least two of these Cbl-fluorophore probes were chosen for live imaging (Cbl-5xPEG-ATTO590 and Cbl-Cy5) because they exhibited the highest fluorescence upon binding the aptamer.

Figure 20:
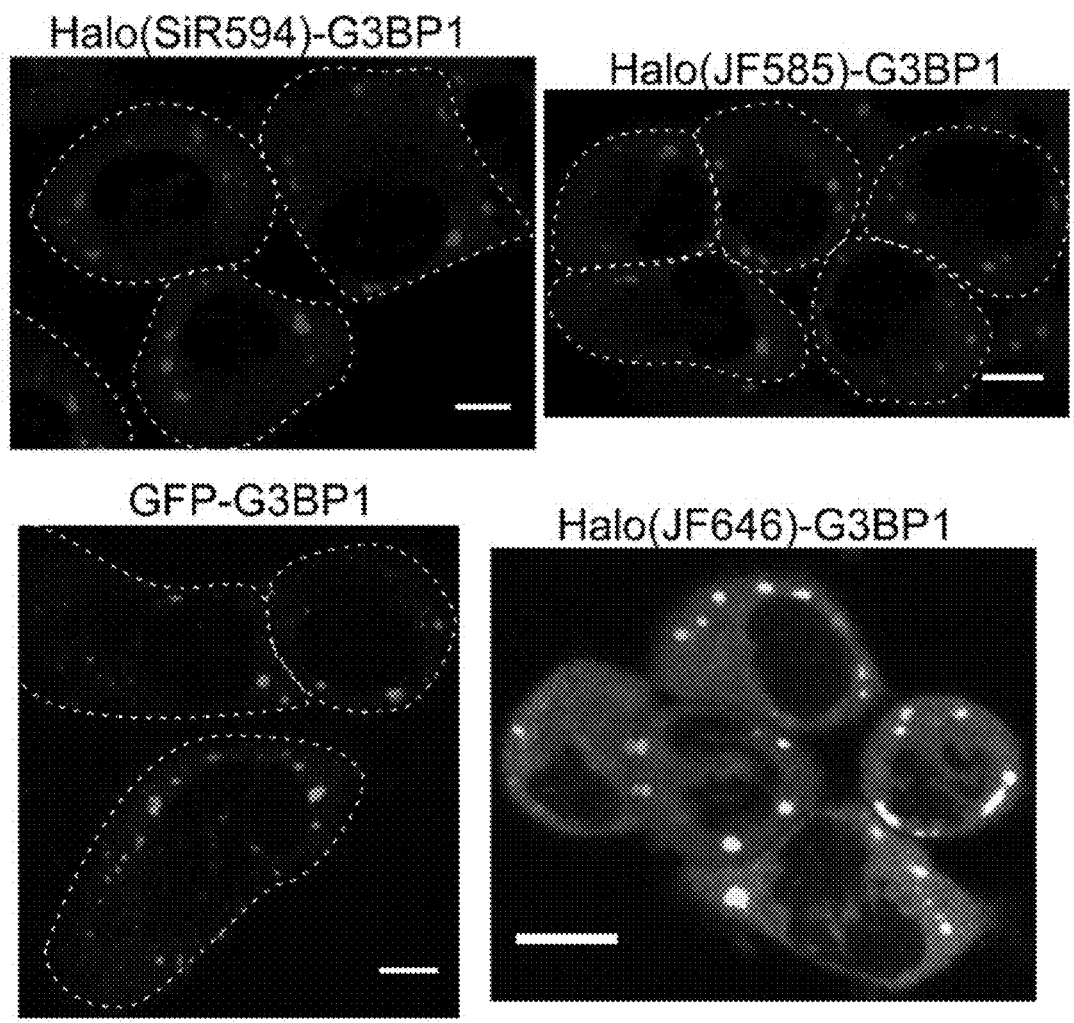
FIG. 20 shows exemplary stress granule (SG) visualization by Halo-tag or GFP in U2-OS cells. Top panel: U2-OS cells producing Halo-tagged G3BP1 from the chromosome were treated with two different red fluorescent Halo dyes (SiR594 and JF585). Arsenite stress induced recruitment of Halo-G3BP1 to SGs. Bottom panel, left: U2-OS cells stably producing GFP-G3BP1 were treated with arsenite to induce SGs. Bottom panel, right: U2-OS cells producing Halo-tagged G3BP1 from the chromosome were treated with a far-red fluorescent Halo dye (JF646). Scale bar=10 μm.

Treatment of U2-OS cells with arsenite induced formation of SGs that contain a marker protein G3BP1 [as described herein-49], which can be tagged with GFP or the Halo-tag and subsequently labeled with red or far-red fluorophores JF585, SiR594 or JF646 [reference 50] (FIG. 20). Thus, stress granules may be induced in order to visualize concentrations of Cbl-fluorophore probes within living cells. Further, stress granules may be induced in order to visualize the RNA of interested tagged with the riboswitch aptamer bound to Cbl-fluorophore probes within living cells.

A. Aptamer-Tagged Human ACTB.

Figure 21A:
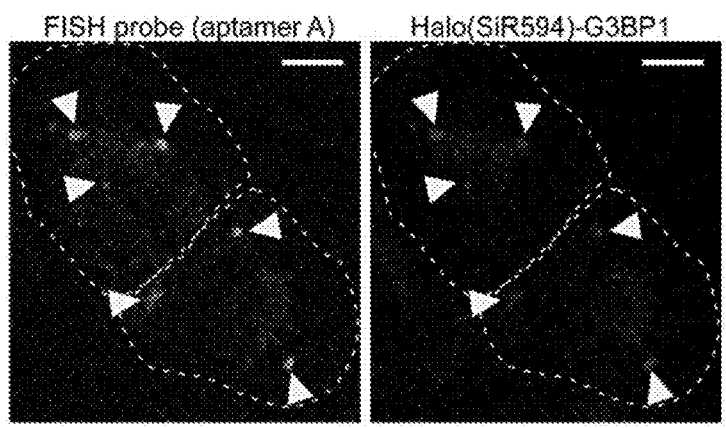
FIG. 21A-C shows exemplary ACTB mRNA fused with different RNA visualization tags localized to stress granules (SG). Plasmids encoding for ACTB tagged with RNA visualization tags at the 3' end were transfected in U2-OS Halo-G3BP1 cells. G3BP1 was labeled with red fluorescent SiR594 dye 24 h post transfection and SGs were induced by treatment with arsenite for 30-45 min. Cells were fixed, permeabilized and the RNA tag was probed with Cy5-fluorescently labeled oligos against the indicated RNA tag.

In fact, recruitment of ACTB mRNA tagged with the riboswitch RNA and colocalization with the fluorescently labeled marker protein G3BP1 was used to quantitatively validate the RNA imaging platform in live cells. Further, ACTB mRNA [as described herein, 48] tagged with riboswitch variant A localized to G3BP1-positive SGs via fluorescence in situ hybridization (FISH) in fixed cells (FIG. 21A-C), similar to endogenous ACTB mRNA (FIG. 22). Together, tagging ACTB mRNA with an RNA tag and expression of the fusion construct by an expression plasmid in transiently transfected cells, adding a quenched Cbl-florescent probe, and then visualizing recruitment to SGs is a system is one exemplary method for assessing an imaging platform in live mammalian cells.

B. Visualizing ACTB mRNA in Live Cells Via Bound Cbl-Aptamer.

Figure 23:
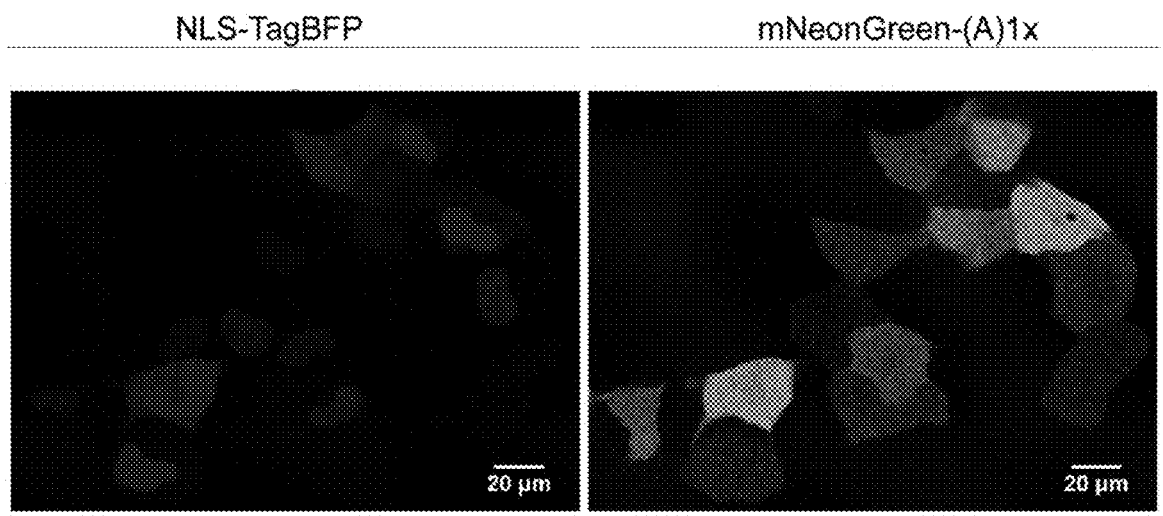
FIG. 23 shows exemplary transfecting U2-OS cells with the plasmid NLS-TagBFP serves as a transfection marker for mRNA-tagged plasmids. U2-OS cells were transfected with a 1:1 mixture of NLS-TagBFP and mNeonGreen-(A)1x and the fluorescence signal was analyzed 24 h post transfection. Each cell harboring the blue NLS-TagBFP transfection marker was assessed for presence of green fluorescence as a measure for successful transfection of mNeonGreen mRNA tagged with riboswitch variant A. 94% of cells with NLS-TagBFP also have mNeonGreen signal (2 independent experiments, 561 cells).

In one embodiment, an A-tagged ACTB mRNA was used in combination with a Cbl-Cy5 probe, see FIG. 3A. To identify cells that produce the ACTB mRNA tagged with riboswitch variant A after transient transfection, a plasmid encoding for a blue nuclear NLS-TagBFP marker as a cotransfection marker was used and it was found that >90% of cells positive for NLS-TagBFP also produce the cotransfected mRNA (in this case mNeonGreen fused with RNA tag A, FIG. 23).

Figure 26:
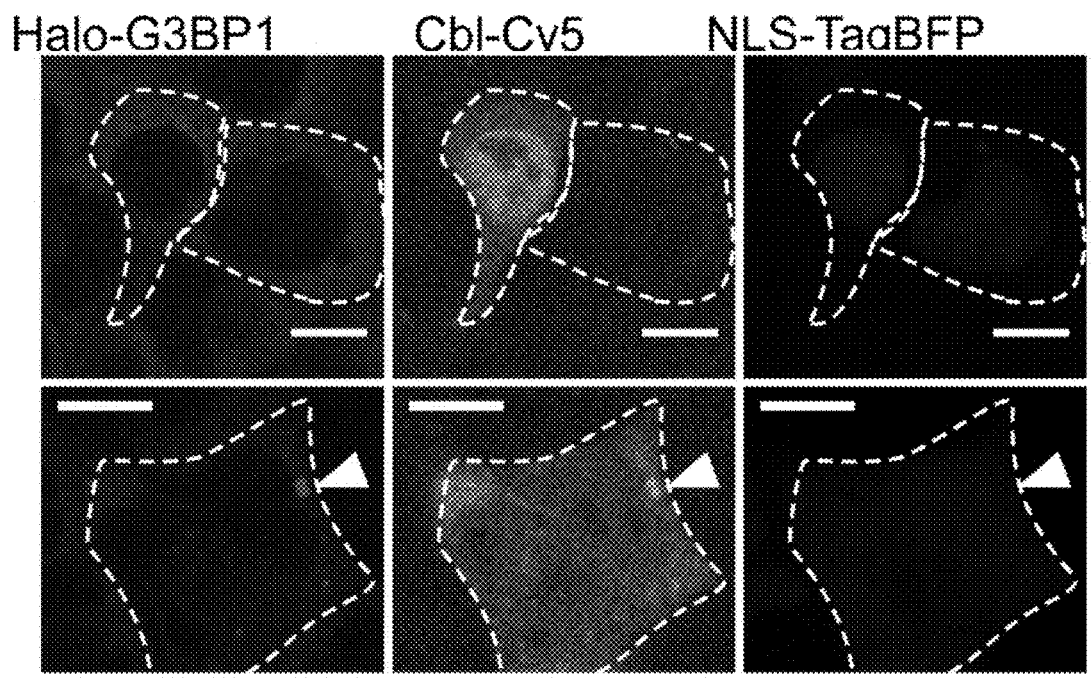
FIG. 26 shows exemplary localization phenotypes for U2-OS cells transfected with tagged mRNA and loaded with Cbl-Cy5 probe in the absence of arsenite stress. U2-OS cells producing Halo-G3BP1 from the genome were transfected with the plasmid ACTB-(A)4x and the transfection marker plasmid NLS-TagBFP as in FIG. 3A-F. Halo-G3BP1 was labeled with JF585 24 h post transfection and Cbl-Cy5 was bead loaded. Shown are representative cells demonstrating two different phenotypes. Top panel: Halo-G3BP1 was diffusely localized in the cytosol and Cbl-Cy5 displayed nuclear and cytosolic localization as in the untransfected control FIG. 3C). Bottom panel: In some cells, stress granules (SGs) formed in the absence of arsenite treatment, as indicated by the signal in the red Halo-G3BP1 channel. The process of transfection has been shown to lead to formation of SGs in a small number of cells. In the cell shown here, Cbl-Cy5 fluorescence co-localized with SGs (white arrow), as expected due to recruitment of ACTB tagged with the RNA tag variant A to SGs. Two experiments, 20 cells positive for Cbl-Cy5 and NLS-TagBFP (12 cells without SGs in red channel, 8 cells with SGs in red channel). Scale bar=10 μm.
Figure 27A:
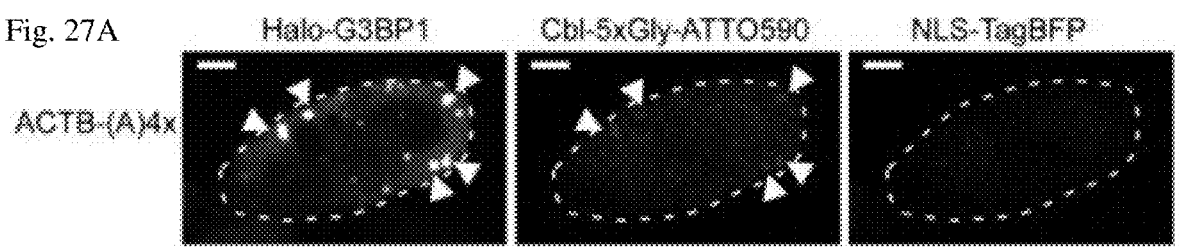
FIG. 27A-C shows exemplary Cbl-5xGly-ATTO590 comprising 4xGly, fluorescence signal increased in SGs in cells that were transiently transfected with ACTB-(A)4x.
Figure 27B:
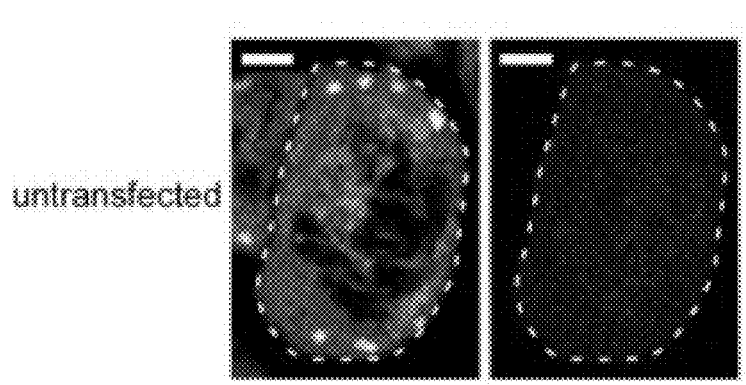
Figure 27C:
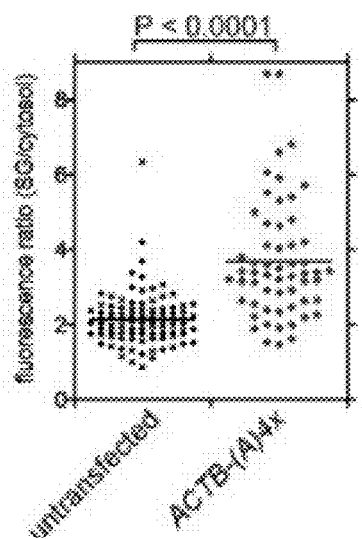

As one control, Cbl-Cy5 probes were added (via beads) to untransfected cells. The Cbl-Cy5 fluorescence signal remained diffuse throughout the cytosol in these untransfected cells even when G3BP1-labeled SGs were induced by arsenite stress (FIG. 3C, 3D), indicating that Cbl-Cy5 specifically binds to the A aptamer. Additionally, in the absence of arsenite stress, the Halo-G3BP1 fluorescence signal (where G3BP1 would label SGs) was diffusely localized throughout the cytosol, and a smaller fraction of cells showed SG formation, in which case Cbl-Cy5 fluorescence localized to these rare SGs (FIG. 26). In this case, the rare SGs result from the process of transfection, which has been shown to induce SGs occasionally [reference 51].

Also visualized were ACTB mRNA tagged with 4 copies of the aptamer A and used with the probe Cbl-5xGly-ATTO590 comprising 4xGly, and similar results were observed (FIG. 27A-C, FIG. 4D).

Thus, to visualize A-tagged ACTB mRNA using the combination of RNA construct and Cbl probe, cells were transfected with a plasmid to produce the A-tagged ACTB mRNA, then the Cbl-Cy5 probe was loaded in live cells before inducing SGs by arsenite (FIG. 3A). High accumulation of Cbl-Cy5 fluorescence in SGs upon arsenite treatment was observed when 4 copies of A were used, but not when one copy was used (FIG. 3B, 3D, FIG. 25A-B).

Figure 24:
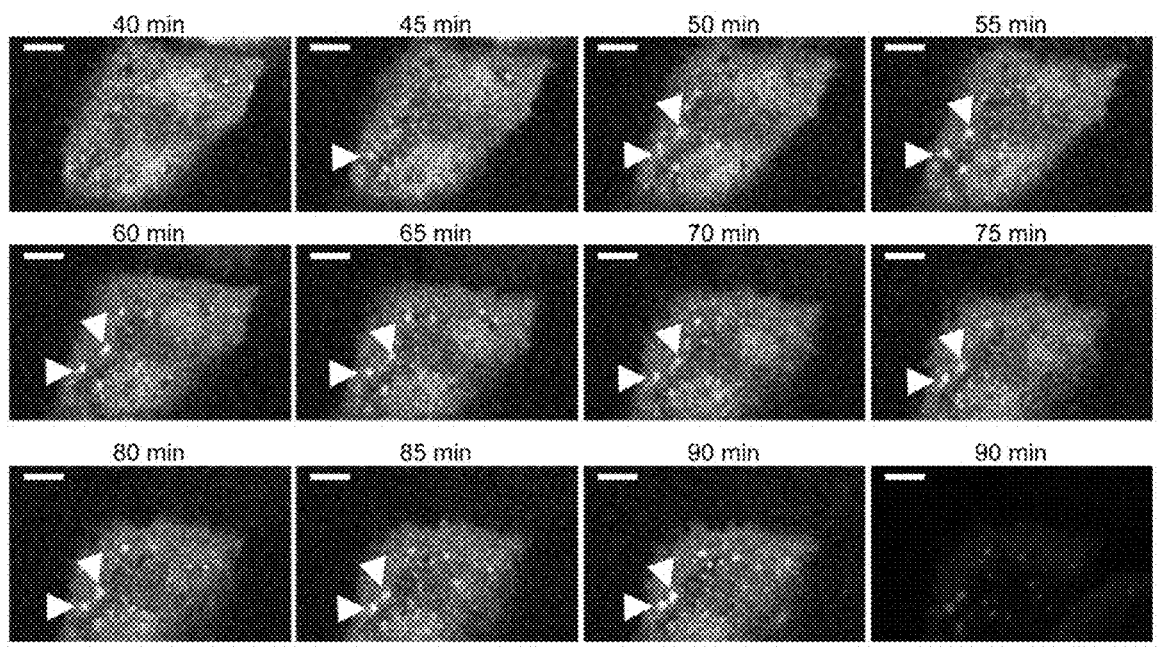
FIG. 24 shows an exemplary time course of ACTB mRNA recruitment to stress granules (SG) and dynamics of SGs. U2-OS cells constitutively producing Halo-G3BP1 were transfected with a plasmid to produce ACTB-(A)4x mRNA and a transfection marker (NLS-TagBFP) as in FIG. 3A-F. 24 hours (hr) post transfection, cells were stained with the JF585 Halo dye, bead loaded with Cbl-Cy5 and treated with 0.5 mM arsenite to induce SGs. Shown are fluorescence images in the Cbl-Cy5 channel (collected in 5 min intervals). Cbl-Cy5 labels ACTB-(A)4x mRNA and formation of SGs is visible at about 45 min post arsenite treatment (white arrows). SGs move throughout the cell and are closer together by 90 min post arsenite treatment (white arrows). Red panel: 90 min time point collected in the red fluorescence channel to visualize Halo-G3BP1 via the JF585 dye. Scale bar=5 μm.
Figure 25A:
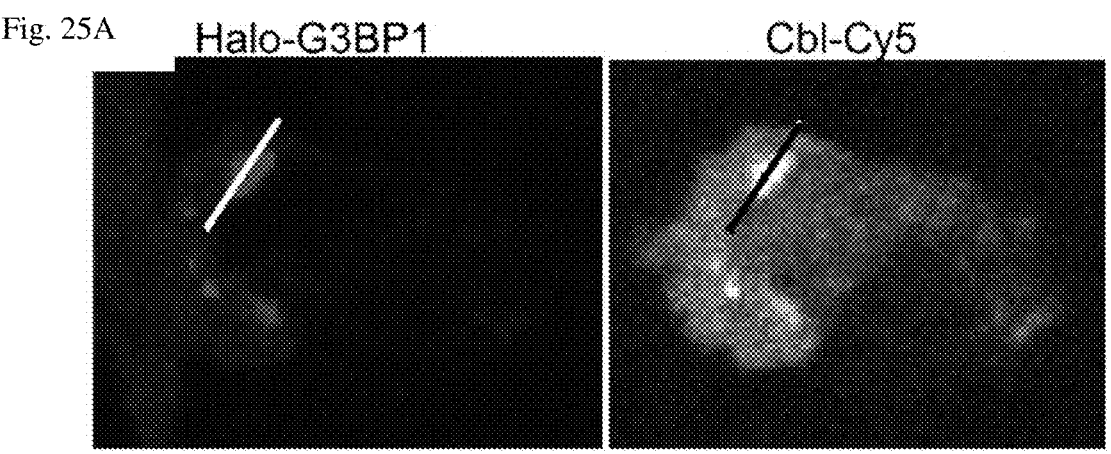
FIG. 25A-B shows exemplary analysis of live U2-OS cells to quantify Cbl-fluorophore probe fluorescence in stress granules (SG).
Figure 25B:
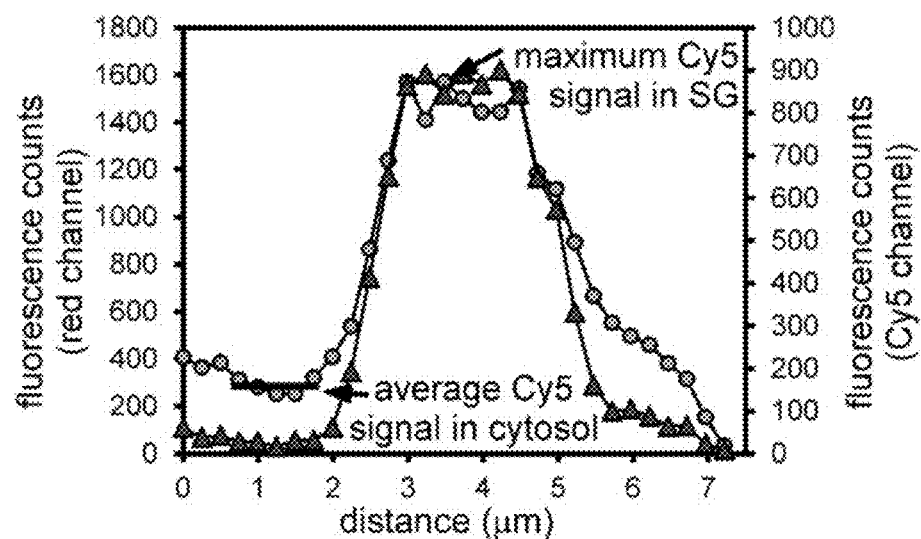

When Cbl-Cy5 fluorescence was monitored over time upon arsenite treatment in cells containing ACTB-(A)4x mRNA, formation of ACTB-(A)4x mRNA-containing SGs was detected and dynamics of SGs were monitored for approximately 50 min (FIG. 24). Together, the SG visualization experiments demonstrate that ACTB mRNA recruitment to SGs and mRNA dynamics over time can be visualized via the Riboglow platform (RNA tag plus Cbl conjugate).

Figure 28A:
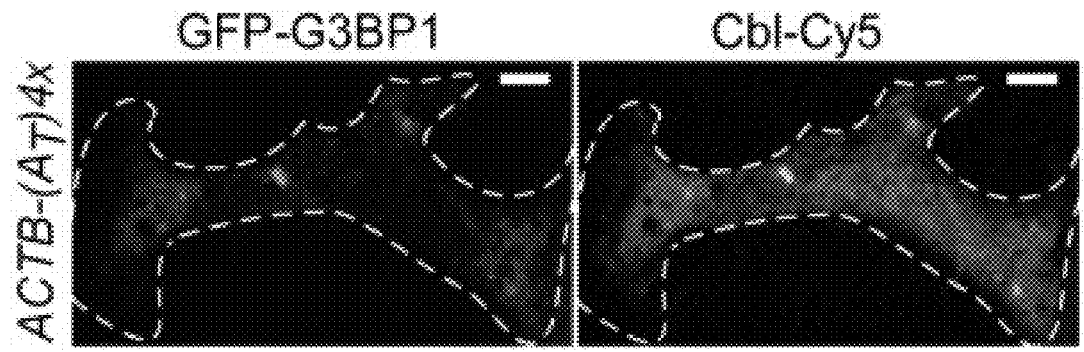
FIG. 28A-B shows exemplary correlative fluorescence microscopy of live FIG. 28A and fixed cells FIG. 28B confirming co-localization of ACTB mRNA to SGs. U2-OS cells that stably produce GFP-G3BP1 were transfected with a plasmid encoding for ACTB-($A_T$)4x. 24 hours post transfection, the probe Cbl-Cy5 was loaded and SGs were induced by arsenite treatment. After live imaging, cells were fixed, permeabilized and probed with a FISH probe against the $A_T$ tag.
Figure 28B:
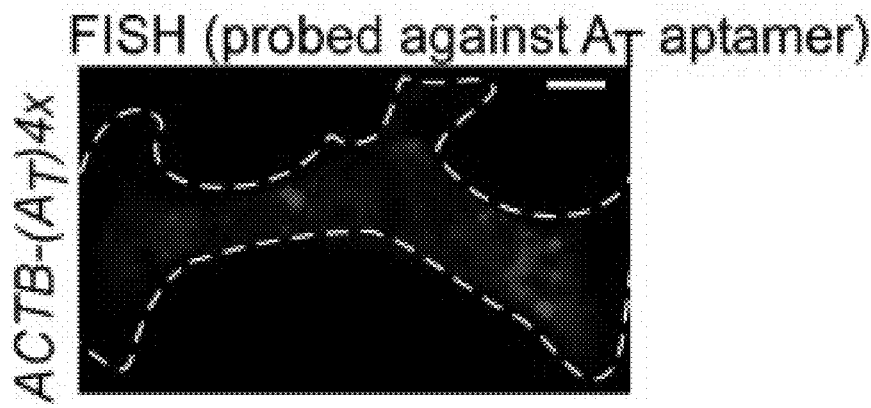

It was observed that the expression level of mRNA fusions and probe uptake efficiency (FIG. 19A-G) are heterogeneous processes, which may explain the broad distribution of Cbl-Cy5 fluorescence increase in SGs (FIG. 3D). To directly confirm that Cbl-Cy5 fluorescence accumulation in SGs is due to the presence of tagged ACTB mRNA in SGs, the formation of SGs in live cells was measured via colocalization with the GFP-tagged G3BP1 marker protein and subsequently fixed cells and confirmed RNA tag colocalization with SGs by FISH (FIG. 28A-B).

In summary, it was demonstrated recruitment of ACTB mRNA to SGs in live cells using one embodiment of the RNA-riboswitch/Cbl probe tagging system, enabled visualization of 100% of cells containing at least 1 SG and 92% of total SGs, with the additional benefit of allowing visualization with two orthogonal colors (ATTO590 and Cy5). Together, the present data confirms that localization of ACTB mRNA to SGs can be readily visualized in live cells using one embodiment of the RNA-riboswitch/Cbl probe tagging system, with the additional benefit of allowing visualization with two orthogonal colors (ATTO590 and Cy5) while keeping the size of the tag below 350 nucleotides (for 4 copies of the $A_T$ aptamer).

C. Aptamer-Tagged U1 snRNA.

In one embodiment, the present invention contemplates that the small size of a truncated RNA tag (81 nt for one copy of $A_T$) would allow for tagging of ncRNAs such as snRNA U1 in live cells. Proper processing of U snRNA was found to depend on its length with an overall size limit of 200-300 nucleotides (nt) [reference 54], limiting the size of any U1 fusion tag to approximately 100 nt.

To keep the RNA tag size as short as possible, an $A_T$ variant (81 nt, Table 1A-B) was chosen and introduced near the 5' end of the U1 coding sequence (FIG. 6 and FIG. 17A-C), a position that was previously shown to be compatible with short RNA tags [reference 55].

U snRNAs localize to nuclear Cajal bodies [reference 56] and U1 tagged with $A_T$ can also localize to the Cajal body marker protein Coilin in HeLa cells (FIG. 34A, FIG. 2B). Treatment of HeLa cells with Thapsigargin induced sequestration of the endogenous U1 snRNA and $A_T$-tagged U1 in cytosolic U-bodies that contained the marker proteins DEAD-Box Helicase 20 (DDX20) and survival motor neuron (SMN) (FIG. 34C, FIG. 35A-C). U snRNAs localize to nuclear Cajal bodies. U1 tagged with $A_T$ can also localize to the Cajal body marker protein Coilin in HeLa cells.

Figure 5A:
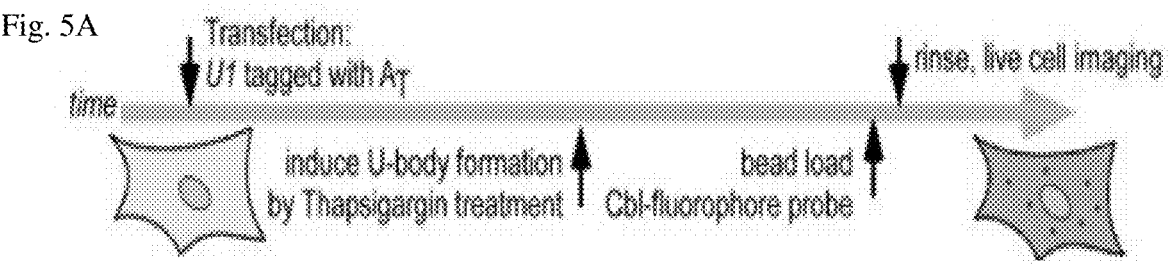
FIG. 5A-C shows exemplary monitoring cytosolic U-bodies via $A_T$-tagged U1.
Figure 5B:
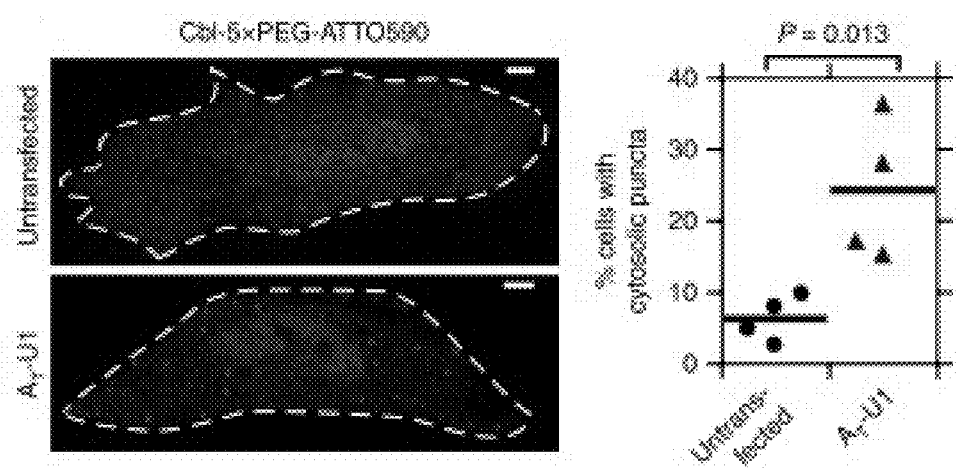
Figure 36:
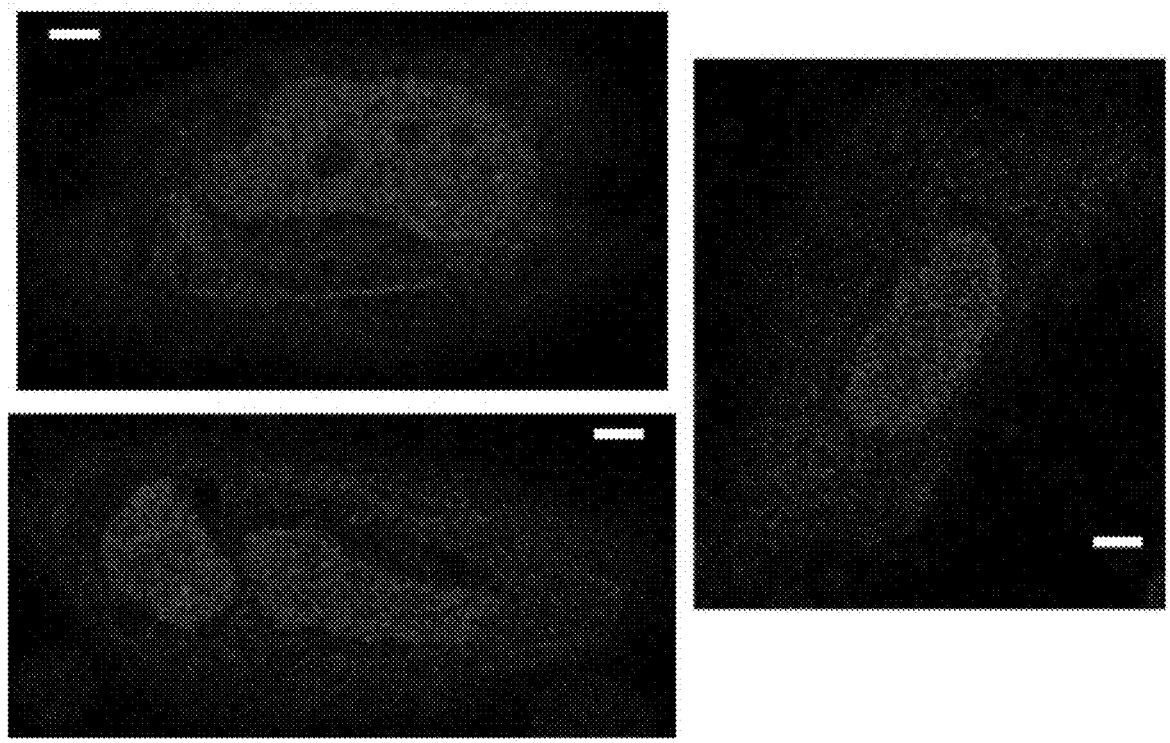
FIG. 36 shows exemplary results in the absence of Thapsigargin-treatment, such that HeLa cells transfected with $A_T$-U1 and bead loaded with Cbl-5xPEG-ATTO590 do not display cytosolic granules resembling U-bodies. HeLa cells were transfected with $A_7$-U1, bead loaded with Cbl-5xPEG-ATTO590 24 h later and live microscopy was performed as described in FIGS. 5A-C, except that no prior treatment with Thapsigargin was done. Out of 86 cells (1 experiment), 2 cells (2%) displayed cytosolic puncta. Scale bar=5 µm.

When loading Cbl-fluorophore probes into live HeLa cells, non-specific puncta formation was observed for Cbl-Cy5 and for Cbl-5xGly-ATTO590 comprising 4xGly, but not for Cbl-5xPEG-ATTO590, even at elevated probe concentrations (FIG. 19D-G), leading to selection of Cbl-5xPEG-ATTO590 for live U1 snRNA visualization. After Thapsigargin-treatment of cells transiently transfected with the $A_7$-tagged U1, 24±10% of cells contained cytosolic puncta resembling U-bodies, whereas such puncta were only observed in 6±3% of untransfected cells (FIG. 5B). These results are in line with reports in the literature, where approximately 25% of HeLa cells were reported to contain U-bodies upon Thapsigargin-treatment [reference 7]. Similarly, no cytosolic puncta were observed in the absence of Thapsigargin-treatment (FIG. 36).

Figure 5C:
Figure 37:
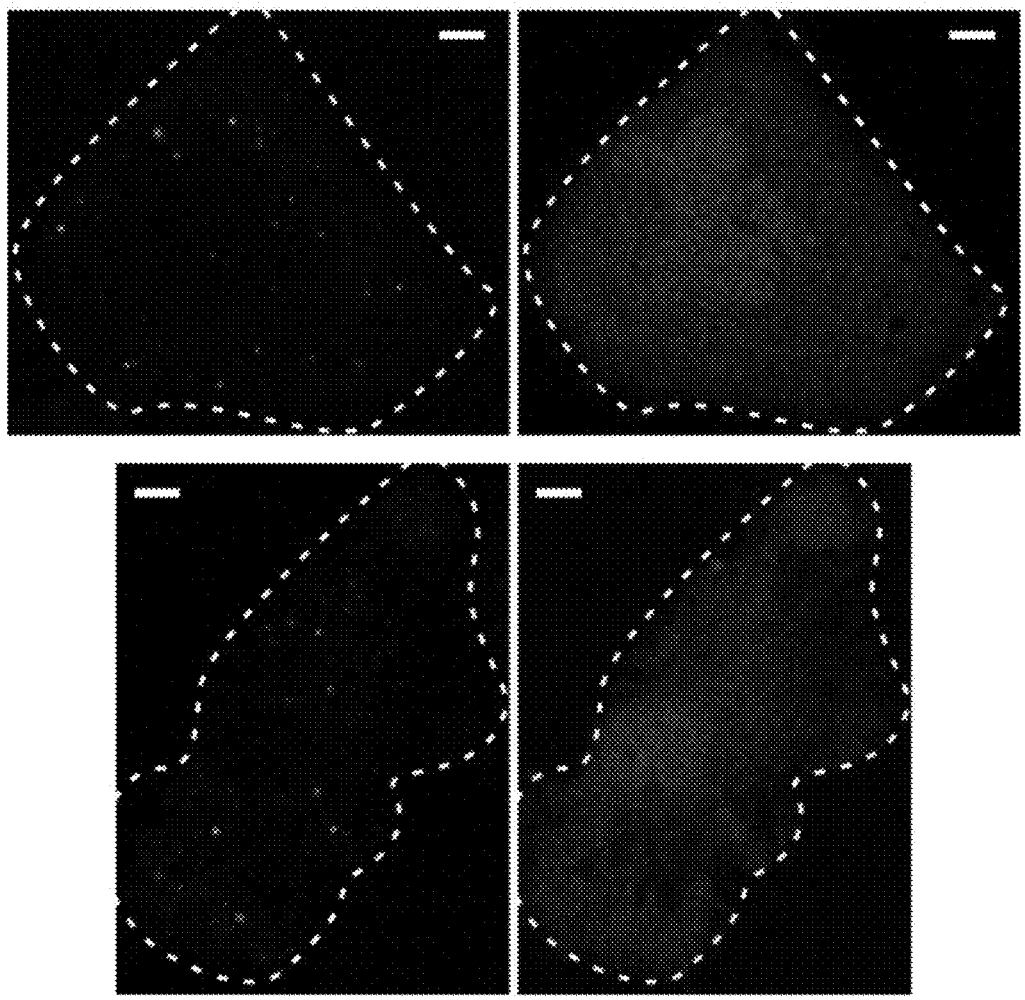
FIG. 37 shows exemplary Cbl-5xPEG-ATTO590 that does not co-localize to GFP-SMN puncta in the absence of $A_7$-U1 snRNA. HeLa cells were transiently transfected with a plasmid to produce GFP-SMN, treated with Thapsigargin and loaded with Cbl-5xPEG-ATTO590. In the absence of a co-transfected plasmid to produce $A_7$-U1 snRNA, the probe does not accumulate in the puncta marked with GFP (compare with FIG. 5C) (3 experiments, 6 cells). Scale bar=5 µm.

To confirm that the cytosolic puncta constitute U1 snRNA containing U-bodies, the GFP-tagged U-body marker protein SMN was transiently transfected together with the $A_7$-tagged U1 and colocalization was observed (FIG. 5C, FIG. 37. Together, it was concluded that the presently disclosed riboswitch-based imaging system allows for live cell visualization of small non-coding RNAs such as the snRNA U1.

Thus, the parameter-space of Cbl-fluorophore probes was assessed with different organic linkers and fluorophores, and identified quenching and de-quenching trends that guided the creation of constructs and probes used herein. Furthermore, these discoveries are contemplated for use in future development of this system. The fact that Cbl riboswitches represent a diverse family of sequences and may further be subjected to modifications through in vitro evolution (SELEX) may be explored for multiplexing of this system in the future. Thus, the present data demonstrates a proof-of principle application of the Cbl-riboswitch based aptamer imaging system in live mammalian cells by visualizing two distinct RNAs, including the small non-coding U1 snRNA.

The riboswitch-based RNA imaging system presented here includes several unique features that promise broad applicability to visualize diverse RNAs in live cells. By utilizing binding of the aptamer to its native binding partner Cbl, binding specificity between aptamer tag and the probe is ensured. Because the RNA does not bind to the fluorophore directly, the presently disclosed system enables flexibility to include synthetic fluorophores with different spectral properties (Cbl-5xPEG-ATTO590 and Cbl-Cy5).

VI. Some Advantages of Using a Riboglow System.

To compare the performance of Riboglow to existing RNA imaging platforms that may be adapted for use in live mammalian cells, recruitment of mRNA to SGs in live cells was used for comparison.

Other dye-binding systems that may be used in mammalian cells include (Spinach [reference 22], Broccoli [reference 23] and Mango [reference 24,25]). A two-fold repeat of dimer-Broccoli was used as a point of comparison because it is the brightest of the Spinach/Broccoli family of dye-binding aptamers. The Mango system, which was published recently, appears to exhibit properties similar to Broccoli and the dye is not commercially available, making it challenging to test.

A. Assessing Performance of a Riboswitch Tag Versus Existing RNA Tags for Live Mammalian Cell Imaging.

Performance of the presently disclosed riboswitch-based RNA tag for RNA imaging was assessed in live cells vs. commonly used RNA imaging platforms, namely the dye binding aptamer Broccoli [reference 22, 26] and the MS2 system [reference 9, 10]. Recruitment of tagged ACTB mRNA to SGs was used as a model system for this comparison as it represents a well-established mRNA localization phenotype [as described herein, 48].

1. Broccoli and MS2.

Figure 17A:
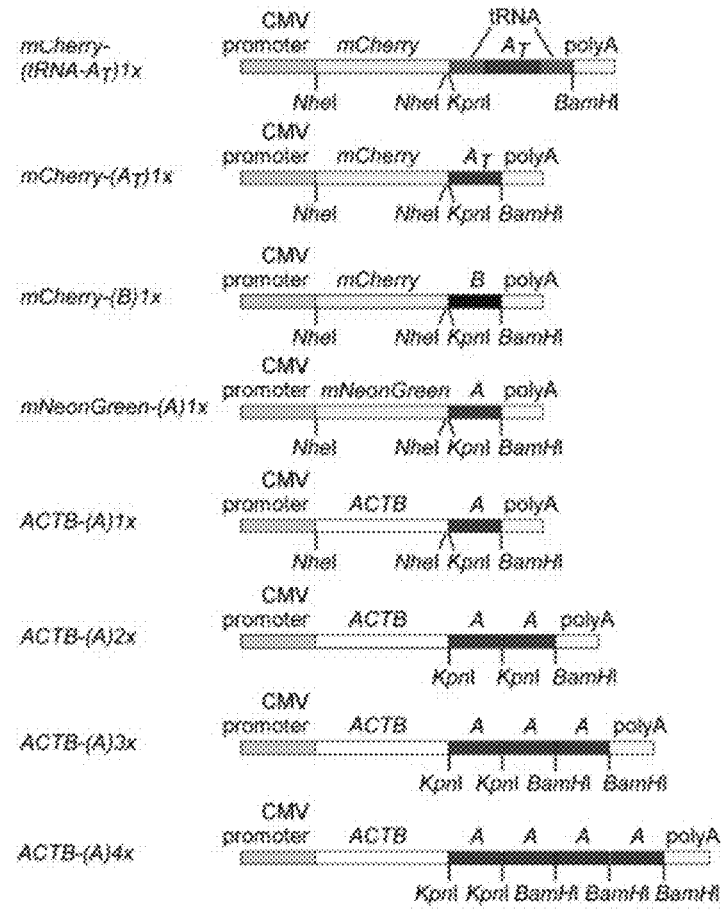
FIG. 17A-C shows exemplary plasmid maps of RNA fusion constructs used herein illustrating exemplary constructs that were inserted into expression plasmids with some annotated restriction sites.
Figure 17B:
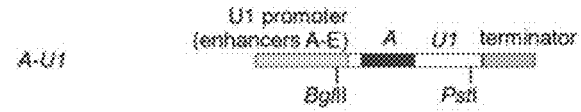
Figure 17C:
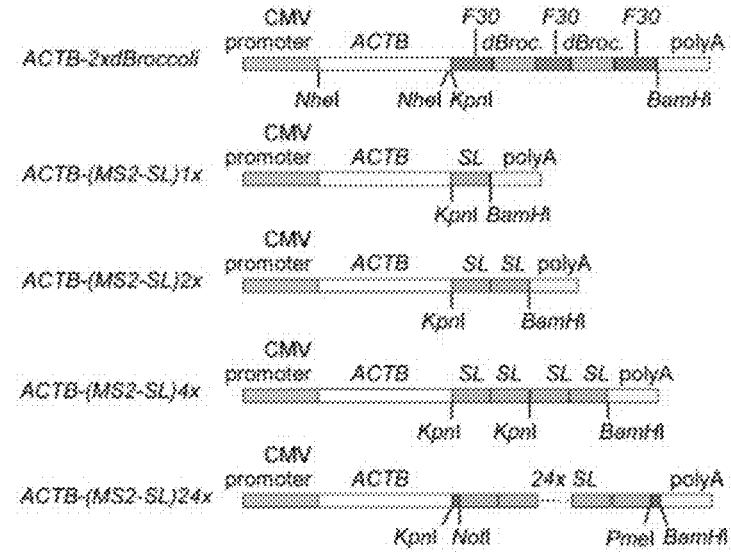

ACTB mRNA was tagged with the brightest known Broccoli tag developed to date where a dimer of Broccoli dimers is integrated in the F30 folding scaffold [reference 26], such that each tag binds four fluorogens (called 2xdBroccoli, FIG. 17A-C, Table 1A-B). Also, a series of mRNA tags with the MS2 stem-loop repeats were generated, where 1, 2, 4 or 24 copies of the hairpin stem-loop were added (FIG. 17A-C, Table 1A-B). Dimers of MS2-GFP bind to each MS2 stem-loop [reference 52], such that mRNA with two copies of the MS2 stem-loop recruits a total of four GFP molecules per mRNA, leading to selection of ACTB-(MS2-SL)2x as a fair comparison with one embodiment of the RNA-riboswitch/Cbl probe tagging system where four copies of the RNA tag were used (Table 1A-B).

Figure 21B:
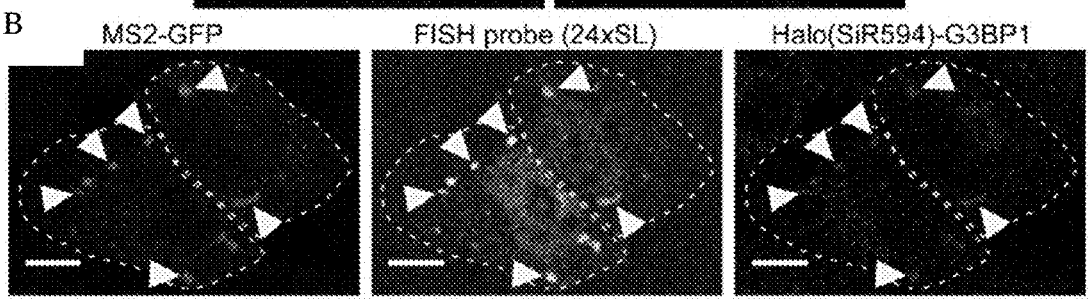
Figure 21C:
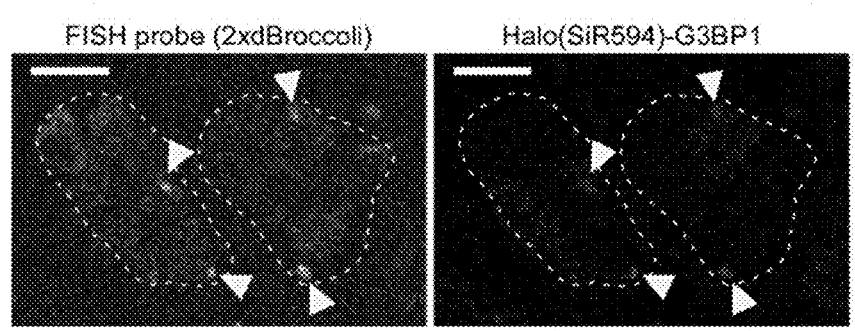
Figure 22:
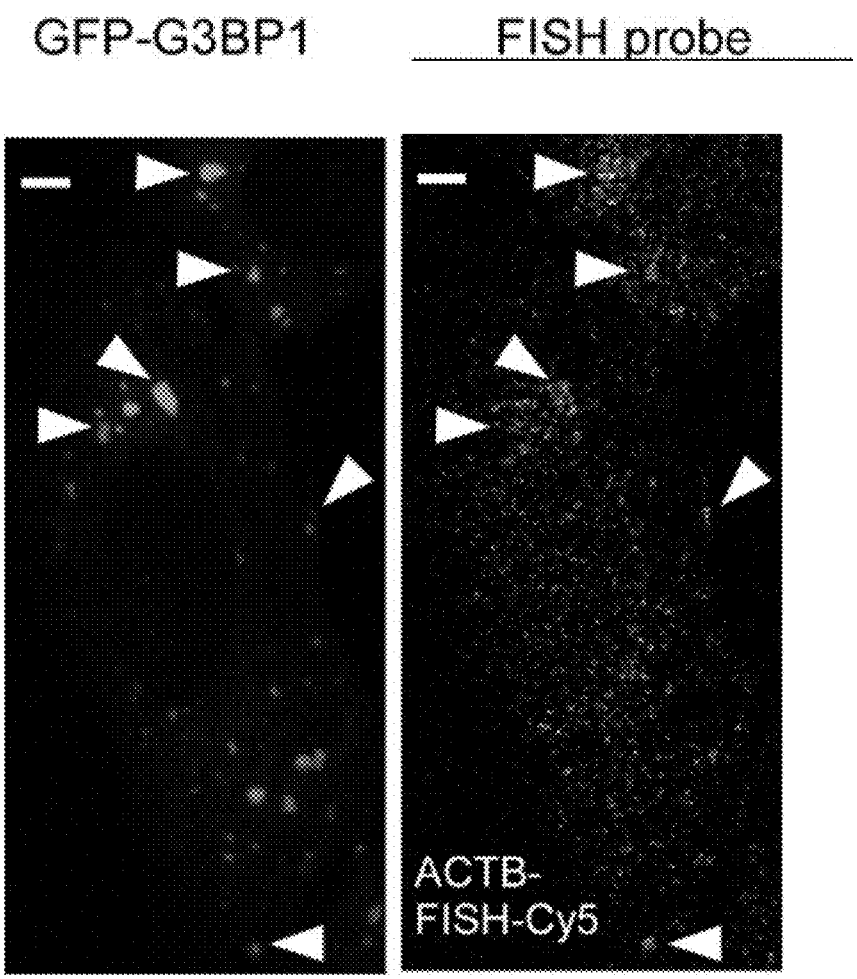
FIG. 22 shows exemplary endogenous ACTB mRNA colocalized with GFP-G3BP1, a marker protein for SGs in U2-OS cells. Detection of endogenous ACTB mRNA in U2-OS cells that stably produce GFP-G3BP1, a SG marker protein. Cells were fixed, permeabilized and ACTB fusion mRNA was visualized by FISH using a Cy5-conjugated probe. Representative cells show localization of ACTB mRNA to SGs (1 experiment, 15 cells). Scale bar=5 μm.

Tagging of ACTB mRNA with 2xdBroccoli or with up to 24 copies of the MS2 stem-loop did not affect mRNA localization to SGs (FIG. 21B, 21C. Therefore, these Broccoli and MS2 constructs were used to test live mRNA recruitment to SGs.

Figure 4A:
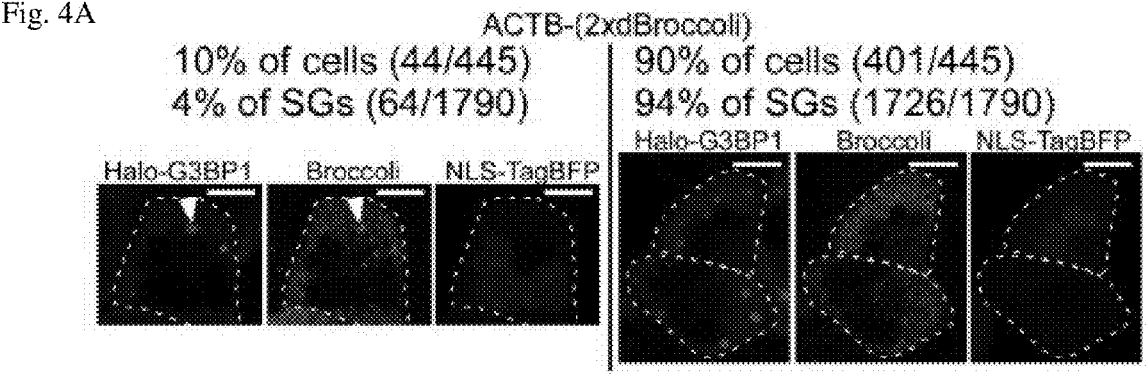
FIG. 4A-D shows an exemplary comparison of ACTB mRNA imaging in stress granules (SG) by RNA tagging systems with four fluorophores per RNA. A plasmid encoding for tagged ACTB was transfected in U2-OS Halo-G3BP1 cells and with the NLS-TagBFP transfection marker. Halo-G3BP1 was labeled with a Halo dye for SG identification and SGs were induced by arsenite.
Figure 4B:
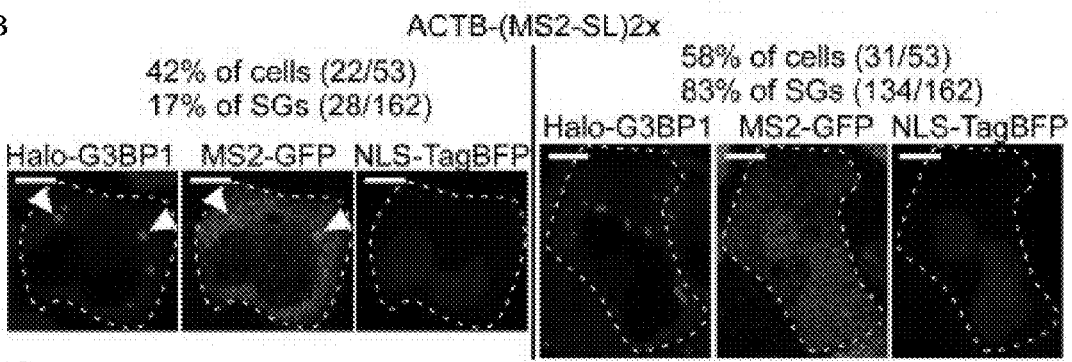
Figure 4C:
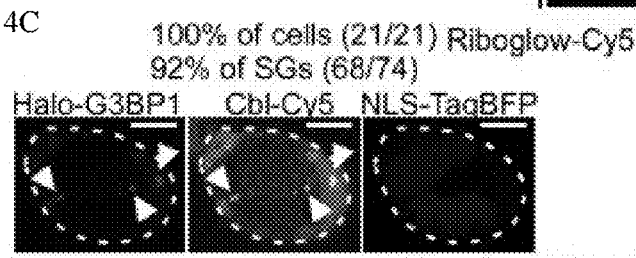
Figure 4D:
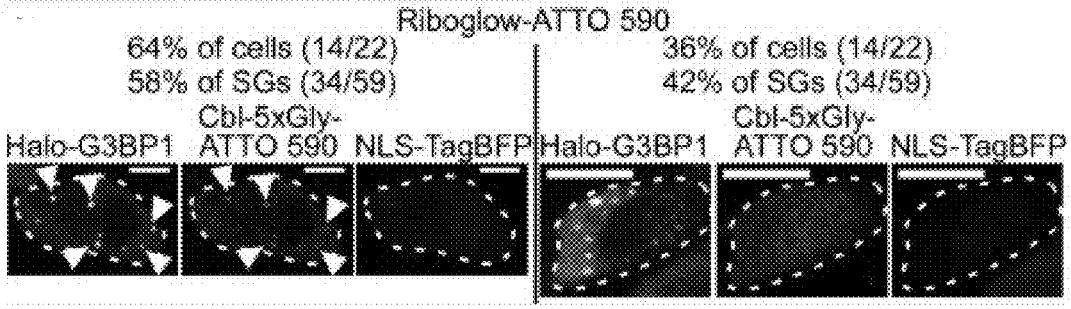
Figure 29A:
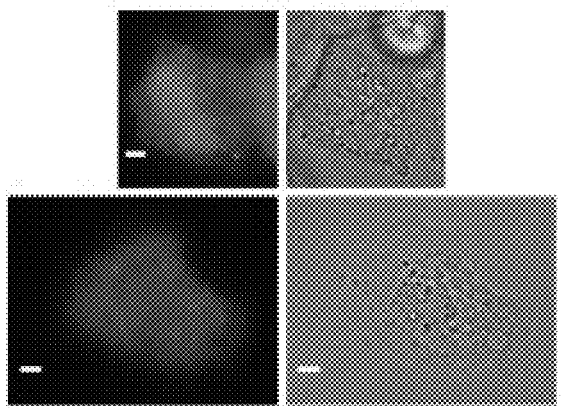
FIG. 29A-C shows exemplary visualization of Broccoli RNA in HEK293T cells using published expression platforms and published imaging conditions. Plasmids pAVU6+27-F30-2xdBroccoli and pAV5S-F30-2xdBroccoli [reference 3] were transfected in HEK293T cells and split into imaging dishes 48 h post transfection following published protocols [reference 3]. 24 h later, DFHBI-1T was added at a final concentration of 40 μM and cells were imaged under wide field illumination conditions as recommended [reference 3].
Figure 29B:
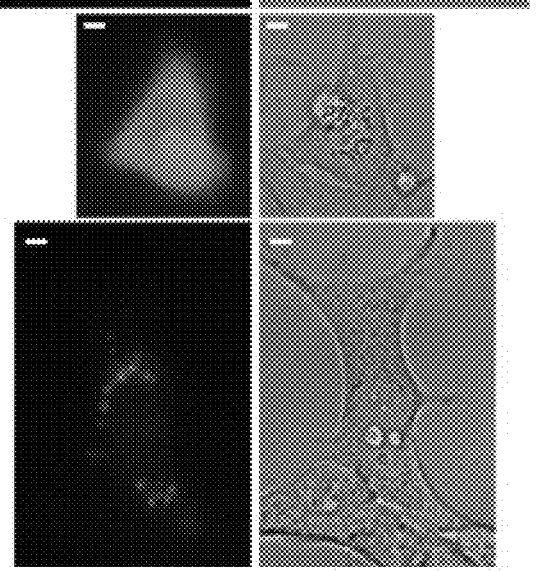
Figure 29C:
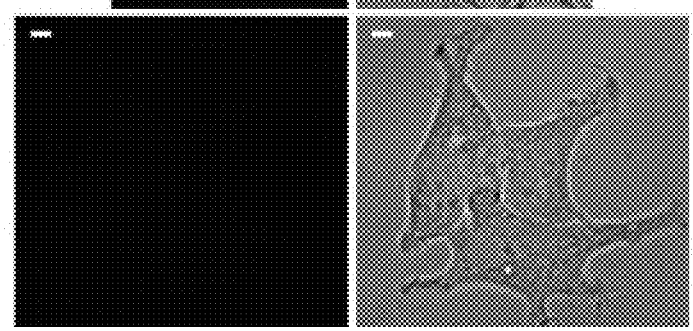
Figure 30:
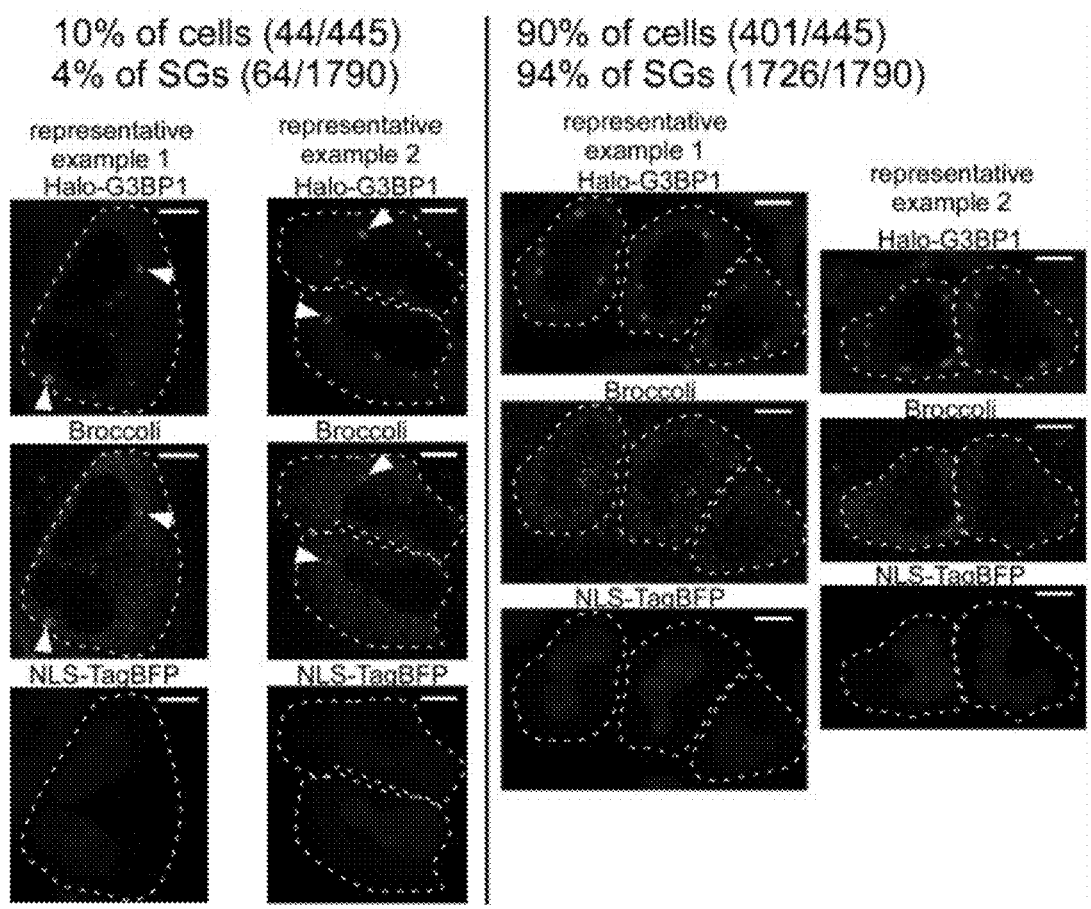
FIG. 30 shows exemplary visualization of ACTB mRNA in stress granules (SG) by RNA tagging with Broccoli. ACTB-(2xdBroccoli) was transfected in U2-OS Halo-G3BP1 cells together with the NLS-TagBFP transfection marker. Halo-G3BP1 was labeled with the red fluorescent JF585 dye and SGs were induced by incubation with arsenite for 30-45 min. SGs were identified via the red fluorescent JF585 signal. After addition of the Broccoli probe DFHBI-1T, cells positive for the blue transfection marker (445 cells, 3 experiments), were assessed for visible SGs in the green Broccoli channel. In 10% of total cells with TagBFP signal, at least one SG was detected in the green channel and overall, 4% of total SGs identified in red were also detected in the green Broccoli channel (1790 SGs total in total of 445 cells). Representative SGs visualized by Broccoli are indicated with white arrows. Scale bar=10 μm.

ACTB mRNA recruitment to SGs was assessed by using the 2xdBroccoli tag (FIG. 4A). It was first confirmed that Broccoli RNA could be visualized when tagging 5S and U6 RNA using recommended experimental procedures [reference 26] (FIG. 29A-C). A plasmid was then transfected encoding for 2xdBroccoli-tagged ACTB mRNA and the NLS-TagBFP transfection marker in U2-OS cells that chromosomally produce Halo-G3BP1, SGs were induced at 24 h post transfection and the DFHBI-1T probe was added to assess visualization of Broccoli-labeled SGs in the green fluorescence channel. In 90% of cells with the blue transfection marker that have Halo-G3BP1 labeled SGs in the red fluorescent channel, no corresponding SGs in the green Broccoli channel were detectable (401/445 cells, FIG. 4A, FIG. 30, right panel).

Figures 31A, 31B, 31C:
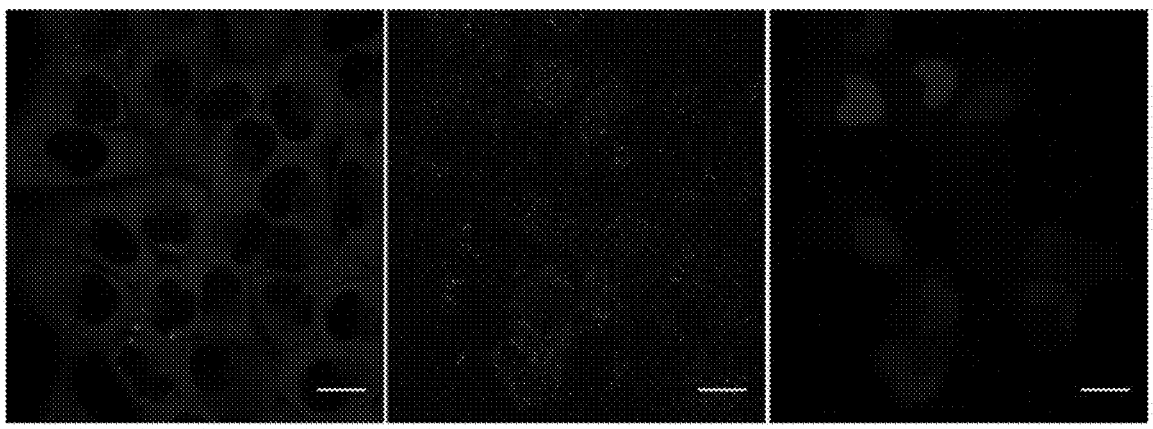
FIG. 31A-C shows exemplary visualization of Broccoli-tagged ACTB mRNA in the absence of arsenite treatment. Plasmids encoding for ACTB-(2xdBroccoli) FIG. 31B and the transfection marker NLS-TagBFP FIG. 31C were transfected in U2-OS cells. 24 h after transfection, G3BP1 was labeled with the red fluorophore JF585 FIG. 31A and the Broccoli dye DFHBI-1T FIG. 31B was added. Shown are representative cells. Scale bar=20 μm.
Figure 32A:
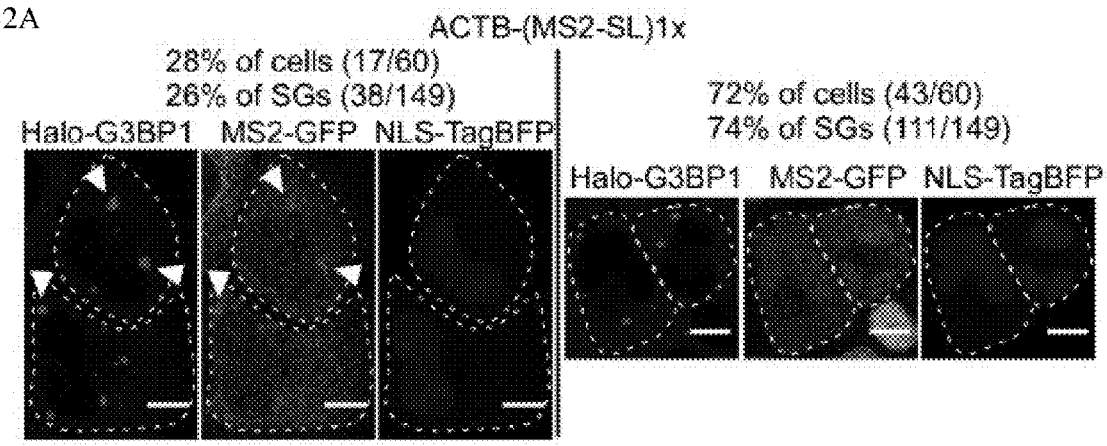
FIG. 32A-D shows exemplary visualization of ACTB mRNA in stress granules (SG) by RNA tagging with MS2 stem-loop (SL) repeats. A plasmid encoding for ACTB tagged with MS2 SL repeats was transfected in U2-OS Halo-G3BP1 cells that stably produce MS2-GFP with the NLS-TagBFP transfection marker. Halo-G3BP1 was labeled with the red fluorescent JF585 dye for SG identification and SGs were induced by arsenite.
Figure 32B:
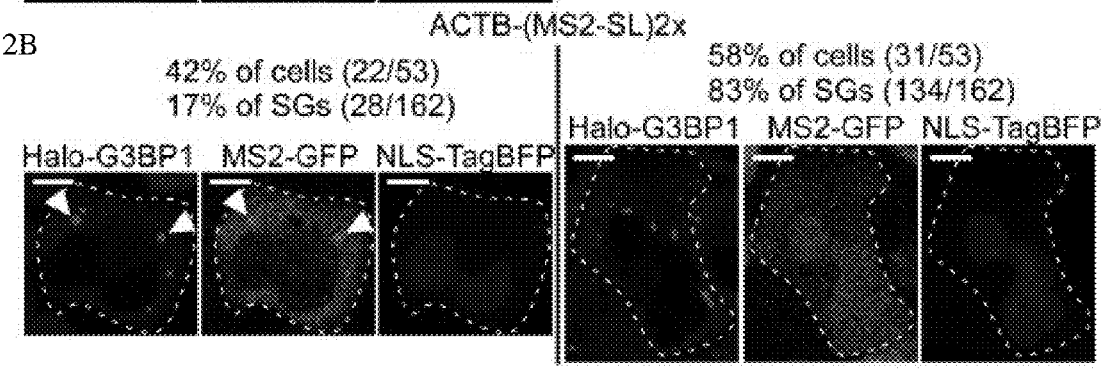
Figure 32C:
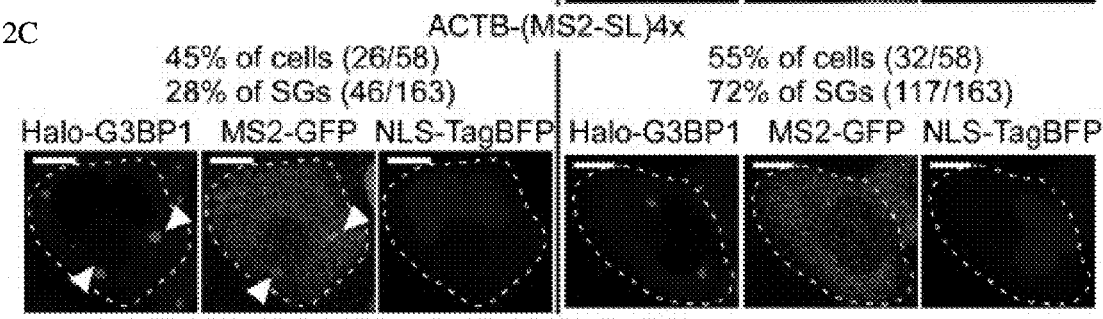
Figure 32D:
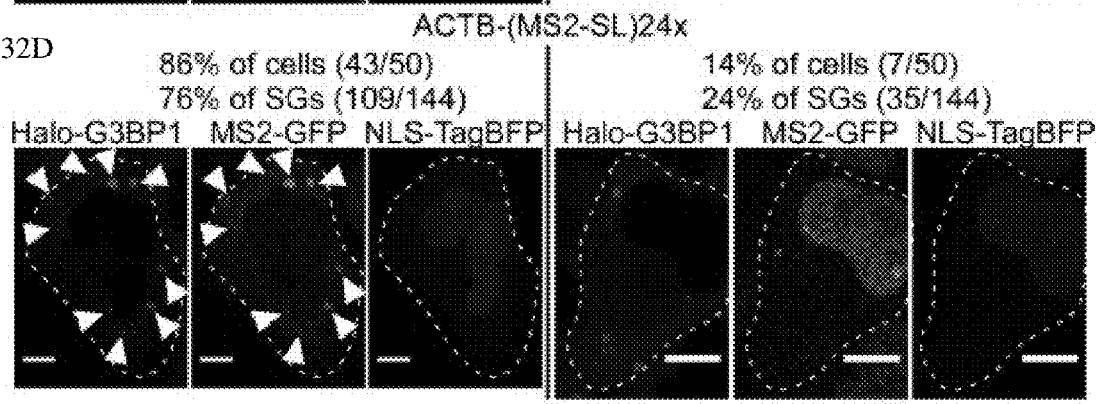

In the remaining 10% of cells, green puncta corresponding to SGs (judged by colocalization with Halo-G3BP1 granules) were detectable (FIG. 30, left panel), but only a minor fraction of total SGs were detected (4% of SG, 64/1790 SGs total). As seen for tagging with the riboswitch, transient transfection of the 2xdBroccoli-tagged ACTB mRNA in U2-OS cells alone occasionally induced G3BP1-positive SGs even in the absence of arsenite treatment (FIG. 31A-C).

Figures 33A, 33B, 33C:
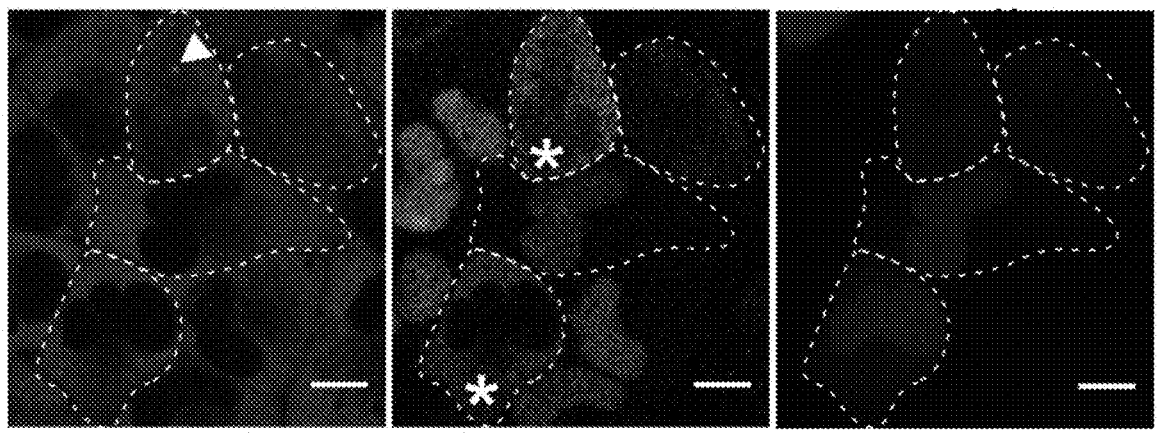
FIG. 33A-C shows exemplary cotransfection of NLS-TagBFP and ACTB-(MS2-SL)24x in U2-OS induces different phenotypes.
Figure 35A:
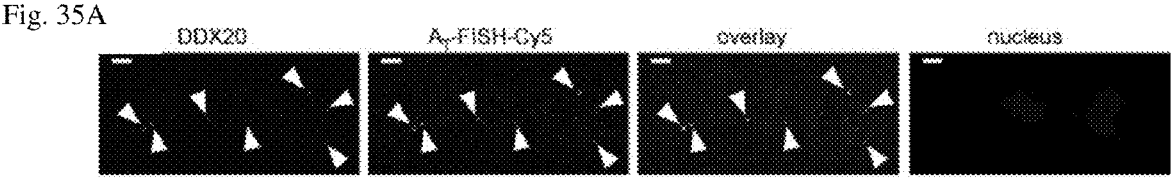
FIG. 35A-C shows exemplary transiently transfected U1 snRNA tagged with $A_T$ that localized to U-body marker proteins DDX20 and SMN.
Figure 35B:
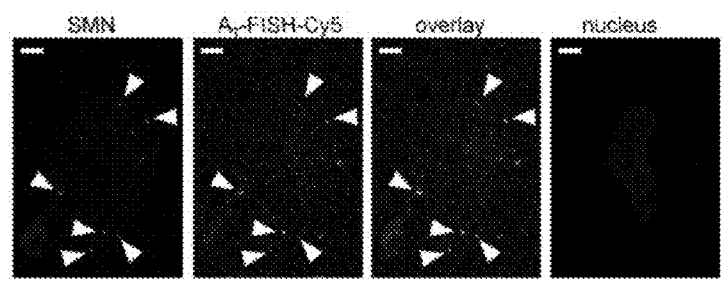
Figure 35C:
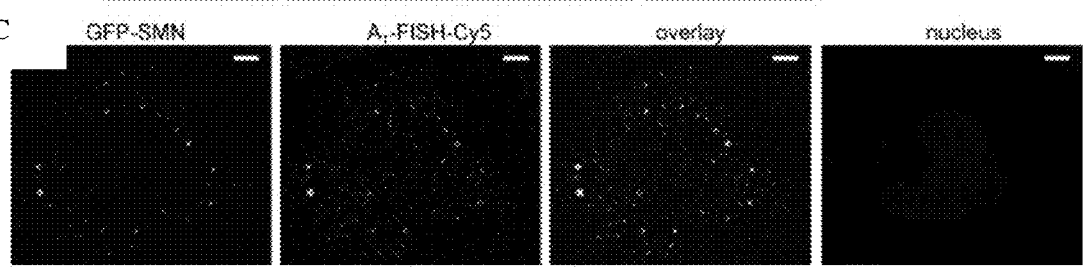

While rapid photobleaching of Broccoli is a well-established complication of using the Spinach and Broccoli system [reference 27, 53] (FIG. 16), the laser scanning confocal microscopy used here was a modality that resembles pulsed illumination. Pulsed illumination was shown to be ideal for Spinach and Broccoli imaging [reference 53], however, there was a lack of brightly visualized recruitment of ACTB mRNA tagged with a total of four Broccoli copies to SGs found here. ACTB mRNA recruitment to SGs via tagging was then assessed with one, two, four or 24 copies of the MS2 stem-loop (FIG. 32A-D, FIG. 4B). A plasmid producing NLS-TagBFP was used as a transfection marker and SGs were induced 24 h post transfection for assessment of mRNA localization to Halo-G3BP1 labeled SGs. These experiments were performed in a variant of the U2-OS Halo-G3BP1 where NLS-MS2-GFP was also stably produced from the chromosome such that MS2-GFP remains nuclear in the absence of mRNA fused to MS2 stem-loops (FIG. 33A-C). As expected, localization of mRNA tagged with 24 copies of the MS2 stem loop to SGs was readily visualized via MS2-GFP recruitment to SGs in a large majority of cells that contained Halo-G3BP1 labeled SGs and that were also positive for the NLS-TagBFP transfection marker (86%, 43/50 cells, FIG. 32D).

When one, two or four copies of the MS2 stem-loop were used, visualization of ACTB mRNA localization to SGs was less efficient (28% of cells, 26% of total SGs for 1× MS2 SL tag; 42% of cells, 17% of total SGs for 2× MS2 SL tag; 45% of cells, 28% of total SGs for 4× MS2 SL tag, FIG. 4B, FIG. 32A-D). The fluorescence contrast for SGs over cytosolic background signal was markedly reduced when one, two or four copies of the MS2 stem-loop were used vs. 24 copies of the MS2 stem-loop, FIG. 32A-D). In summary, one embodiment of the RNA-riboswitch/Cbl probe tagging system performed similarly to the 24x MS2 system with respect to reliably detecting localization of a candidate mRNA (ACTB) to SGs, while the platform outperformed both the Broccoli and MS2 system on a fluorophore by fluorophore basis (where four fluorophores per RNA are used in MS2, FIG. 4A-D).

Compared to Riboglow (92% of SGs for Riboglow-Cy5, FIG. 3A-E, 58% of SGs for Riboglow-ATTO590, FIG. 27A-B), a small minority of SGs were detected via the Broccoli-labeled mRNA (4% of SGs, FIG. 28A-B). This may be because dye-binding aptamers have not yet been used to detect RNA polymerase-II transcripts, such as mRNA.

Instead, in previous experiments these systems were applied to RNA polymerase-III transcripts [reference 25, 27] which are expressed at much higher levels, particularly in HEK 293 cells. One embodiment of the RNA-riboswitch/Cbl probe tagging system displayed much weaker fold fluorescence turn-on in vitro than the approximately 1,000-fold in vitro fluorescence enhancement for both Broccoli [reference 23] and Mango [reference 24, 25] (FIG. 2A-C). However, cellular contrast defined as fluorescence signal in RNA-granules vs. cytosolic background was comparable for one embodiment of the RNA-riboswitch/Cbl probe tagging platform (approximately 3-4-fold, FIG. 3D) and Mango-tagged 5S-RNA and U6-RNA foci (approximately 2-3-fold fluorescence turn-on in fixed mammalian cells [reference 25]). The in vitro-evolved dye-binding uptamers feature G-quadruplex RNA folds [reference 38, 39], and it was shown that the dyes bind other G-quadruplex RNAs non-specifically in cells [reference 39], possibly contributing to diminished cellular contrast. Other factors besides in vitro enhancement may contribute to cellular contrast, including high folding capabilities of the RNA tag in the cellular environment, temperature-dependent and salt-dependent stability of the RNA-probe complex, and probe photo-bleaching properties. Indeed, Broccoli is less photostable than the RNA-riboswitch/Cbl probe that is contemplated to be at least part of its poor performance in live cell studies.

Thus, poor performance of Broccoli (including a low level of fluorescence) was observed even though pulsed illumination modalities such as the laser scanning confocal setup was used, whose use in previous publications markedly improve microscopy image acquisition for Spinach [reference 53].

2. MS2/PP7 System.

The MS2/PP7 system is the gold standard for detection of mRNA dynamics in mammalian cells [reference 9-11]. Indeed, it was found that 1×, 2×, 4×, and 24× copies of the stem-loop permitted visualization of mRNA recruitment to SGs. The 24x tag yielded the strongest fluorescence contrast and led to detection of the greatest number of SGs (86% of cells with at least 1 SG were detected, 76% of total SGs were detected, FIG. 32D).

The data show that the presently disclosed Riboglow platform outperformed the MS2 system in a fluorophore by fluorophore comparison where four GFP molecules were bound to each RNA and the Riboglow platform used four fluorophore-binding RNA tags (Table 1A-B, FIG. 4A-D). Riboglow even compared favorably with the 24x MS2 system, yielding bright detection of SGs in transfected cells (92% of SGs for Riboglow-Cy5, 58% of SGs for Riboglow-ATTO590) and bright fluorescence contrast of labeled mRNA in SGs (on average 3-4-fold, FIG. 3D).

There are some properties of Riboglow that are different when compared to other RNA-tagging systems. While the Broccoli probe DFHBI-1T and Mango probe TO1-Biotin are cell-permeable, bead loading was used for cellular Cbl-fluorophore probe uptake. Although it was found bead loading to be a bright and simple procedure that is routinely used in other live cell-imaging applications [reference 44, 45], this process added an additional step to the imaging process. Utilization of the natural cobalamin uptake route is contemplated as an alternative route of loading cells with Cbl-probes [reference 58, 59].

3. Summary.

Overall, the Riboglow platform compares favorably in a direct side-by-side comparison with existing RNA imaging platforms and presents an orthogonal approach for live cell RNA imaging applications. The highly modular nature of the Riboglow platform currently allows for multicolor imaging and detection of mRNAs as well as small non-coding RNAs, while presenting a system that is ideally set up for straightforward future customization to include desired features for RNA imaging.

B. Additional Advantages of Using a Riboswitch-Based RNA Imaging Platform 'Riboglow'.

Additional advantages of using a riboswitch-based RNA imaging platform 'Riboglow' as described herein is characterized by several features that distinguish it from other RNA-detection systems. Distinguishing features include but are not limited to, a small RNA tag that has a selective and high affinity (dissociation constant in nM range) binding between a riboswitch aptamer and its ligand, Cbl; Because the RNA tag binds the fluorescence quencher, Cbl, the system is compatible with a wide range of synthetic fluorophores spanning the green to far-red spectral range; The Riboglow-ATTO590 and Riboglow-Cy5 probes used for live cell studies retain favorable photophysical properties, including slow photobleaching, of the parent dyes when bound to RNA. Indeed, tagged mRNA was visualized over 50 min without detectable photobleaching (FIG. 24); the presently disclosed RNA tag was not subjected to undesired processing and hence does not require the tRNA-like scaffold used for other dye-binding aptamers. Cobalamin riboswitches include a large family of RNA sequences that total bind Cbl [reference 57] that are contemplated for use in optimization and customization of the Riboglow platform; the fluorescence lifetime of ATTO590 and Cy5 in the context of the Cbl probes varies when the RNA binds (FIG. 15A-B), thus using this system is contemplated for fluorescence lifetime imaging; and recruitment was visualized of RNA polymerase II-dependent transcripts (mRNA and snRNA) becoming incorporated into RNP-granules, where the short size of the RNA tag (approximately 80 nts for RNA tag AT) enabled tagging and visualization of U1 snRNA in live cells.

TABLE 1A

Comparison of length and fluorophore properties for RNA tags used for live cell RNA fluorescence microscopy as described herein.

| Name of tag | Length of RNA tag (nucleotides) | Number of dye/FP molecules per tag | Molecular weight (kDa) of fluorophore |
|---|---|---|---|
| $(A_T)1x$ | 81 | 1 | 2.3 (Cbl-5xPEG-ATTO590) |
| (A)1x | 103 | 1 | 2.3 (Cbl-5xPEG-ATTO590) |

TABLE 1A-continued

Comparison of length and fluorophore properties for RNA tags used for live cell RNA fluorescence microscopy as described herein.

| Name of tag | Length of RNA tag (nucleotides) | Number of dye/FP molecules per tag | Molecular weight (kDa) of fluorophore |
|---|---|---|---|
| (A)2x | 212 | 2 | 2.3 (Cbl-5xPEG-ATTO590) |
| (A)3x | 321 | 3 | 2.3 (Cbl-5xPEG-ATTO590) |
| (A)4x | 430 | 4 | 2.3 (Cbl-5xPEG-ATTO590) |
| 1x MS2 SL | 61 | 2 | Approximately 88 (MS2-GFP homo-dimer) |
| 2x MS2 SL | 102 | 4 | Approximately 176 |
| 4x MS2 SL | 210 | 8 | Approximately 352 |
| 24x MS2 SL | 1354 | 48 | Approximately 2,112 |
| 2xd Broccoli | 234 | 4 | 0.3 (DFHBI-1T) |

TABLE 1B

Photophysical properties of fluorophore, probes and Cbl.

| Name | Extinction coefficient ε [L mol$^{-1}$ cm$^{-1}$] (source) | Excitation λ | Emission range | |
|---|---|---|---|---|
| FAM | 80,000 (490 nm) (Lumiprobe) | 488 nm | 503 | 660 nm |
| Cbl-FAM | 80,000 (490 nm) (Lumiprobe) | 488 nm | 503 | 660 nm |
| Cbl-C6-FAM | 80,000 (490 nm) (Lumiprobe) | 488 nm | 503 | 660 nm |
| Cbl-1xPEG-FAM | 80,000 (490 nm) (Lumiprobe) | 488 nm | 503 | 660 nm |
| Cbl-2xPEG-FAM | 80,000 (490 nm) (Lumiprobe) | 488 nm | 503 | 660 nm |
| Cbl-3xPEG-FAM | 80,000 (490 nm) (Lumiprobe) | 488 nm | 503 | 660 nm |
| ATTO 488 | 90,000 (501 nm) (Atto tec) | 501 nm | 511 | 700 nm |
| Cbl-C6-ATTO488 | 90,000 (501 nm) (Atto tec) | 501 nm | 511 | 700 nm |
| ATTO590 | 120,000 (594 nm) (Atto tec) | 594 nm | 604 | 820 nm |
| Cbl-ATTO590 | 120,000 (594 nm) (Atto tec) | 594 nm | 604 | 820 nm |
| Cbl-C6-ATTO590 | 120,000 (594 nm) (Atto tec) | 594 nm | 604 | 820 nm |
| Cbl-5xPEG-ATTO590 | 120,000 (594 nm) (Atto tec) | 594 nm | 604 | 820 nm |
| Cbl-5xGly-ATTO590 comprising 4xGly | 120,000 (594 nm) (Atto tec) | 594 nm | 604 | 820 nm |
| ATTO 633 | 130,000 (629 nm) (Atto tec) | 629 nm | 639 | 850 nm |
| Cbl-ATTO 633 | 130,000 (629 nm) (Atto tec) | 629 nm | 639 | 850 nm |
| Cbl-C6-ATTO 633 | 130,000 (629 nm) (Atto tec) | 629 nm | 639 | 850 nm |
| Cy5 | 271,000 (646 nm) (Lumiprobe) | 646 nm | 656 | 800 nm |
| Cbl-Cy5 | 271,000 (646 nm) (Lumiprobe) | 646 nm | 656 | 800 nm |
| Cbl | 27,64216 (361 nm) | — | — | — |

TABLE 2

Sequences of riboswitch RNA tags used in this study. Listed are the RNA sequences that were purified for in vitro work (see also FIG. 6).

| Name | SEQ ID NOS: | Sequence |
|---|---|---|
| A | 1 | 5'-GGC CUA AAA GCG UAG UGG GAA AGU GAC GUG AAA UUC GUC CAG AUU ACU UGA UAC GGU UAU ACU CCG AAU GCC ACC UAG GCC AUA CAA CGA GCA AGG AGA CUC |
| AT | 2 | 5'-GGC CUA AAA GCG UAG UGG GAA AGU GAC GUG AAA UUC GUC CAG AUU ACU UGA UAC GGU UAU ACU CCG AAU GCC ACC UAG GCC |
| AT,MUT | 3 | 5'-GGC CUA AAA GCG UAG UGG GAA AGU GAC GUG AAA UUC GUC CAG AUU ACU UGA UAC GGU UAU ACU CCG UUU UCC ACC UAG GCC |
| B | 4 | 5'-GGU ACU GAA AGC GUG GUG GGA AAC AAU GUG AAA UUC AUU GAG UGU UCC UGC AAC GGU AAA AGU AAA AUU GAG UCC GAA UGC CAC CCA GUA AAG UCC GCU GUC GAG UGA AGG CCA GGA AAA GUC UAA CUC UGC AAU AUU AAA |
| C | 5 | 5'-GGA CAU CGG UUU UAG UGG GGA ACA GCC ACU AAA AUA AUG GGG AAA GUU UGG UGC AAG UCC AAC ACU GUC CCG CAG CUG UAA GCA GAC UAU CUC UGU GAG UCA GAA CGC CCA CCG AUG UCC CCC GUA AAC ACU UCU GCG AGG UAC AGA AA |
| D | 6 | 5'-UAC UGA AAG CGU GGU GGG AAA CAA UGU GAA AGU CAU UGA CUG UUC CUG CAA CGG UAA GCG CUU CGG CGC GAG UCC GAA UGC CAC CCA GUA AAG UCC GCU GUC GAG UGA AGG CCA GGA AAA GUC UAA CUC A |

TABLE 3

Theoretical estimates of parameters for energy transfer between Cbl absorbance and fluorescence emission of each fluorophore.

| Fluorophore | Overlap integral J(λ) between fluorescence emission and Cbl absorbance | Quantum yield Q of fluorophore (source) | Forster distance $R_0$ |
|---|---|---|---|
| FAM | $1.374 \times 10^{14}$ nm$^4$ M$^{-1}$ cm$^{-1}$ | 0.93 (Lumiprobe) | 35 Å |
| ATTO488 | $1.424 \times 10^{14}$ nm$^4$ M$^{-1}$ cm$^{-1}$ | 0.80 (Atto tec) | 35 Å |
| ATTO590 | $5.266 \times 10^{12}$ nm$^4$ M$^{-1}$ cm$^{-1}$ | 0.80 (Atto tec) | 20 Å |

TABLE 3-continued

Theoretical estimates of parameters for energy transfer between Cbl absorbance and fluorescence emission of each fluorophore.

| Fluorophore | Overlap integral $J(\lambda)$ between fluorescence emission and Cbl absorbance | Quantum yield Q of fluorophore (source) | Forster distance $R_0$ |
|---|---|---|---|
| ATTO633 | $1.026 \times 10^{12}$ nm$^4$ M$^{-1}$ cm$^{-1}$ | 0.64 (Atto tec) | 15 Å |
| Cy5 | $7.638 \times 10^{11}$ nm$^4$ M$^{-1}$ cm$^{-1}$ | 0.28 (Lumiprobe) | 12 Å |

TABLE 4

Estimates of linker lengths in Cbl-fluorophore probes.

| Name of linker | Estimated length (values for PEG linkers published by ThermoFisher Scientific) |
|---|---|
| C6 | 10.5 Å |
|  | (estimated to be similar to 3xPEG) |
| 1xPEG | 3.5 Å |
| 2xPEG | 7.0 Å |
| 3xPEG | 10.5 Å |
| 5xPEG | 17.5 Å |
| "5xGly" comprising 4xGly | 21.4 Å (Berg, Tymoczko & Stryer, Biochemistry, 2002) |

TABLE 5

Summary of fold on turn-on for Cbl fluorophore probes in the presence of aptamers (FIG. 2A-C).

| Name of Cbl-fluorophore probe | Name of aptamer | Fold fluorescence turn-on |
|---|---|---|
| Cbl-FAM | $A_{T,MUT}$ | 0.5x |
|  | $A_T$ | 2.5x |
| Cbl-C6-FAM | $A_{T,MDT}$ | 1.1x |
|  | $A_T$ | 4.1x |
| Cbl-3xPEG-FAM | $A_{T,MUT}$ | 1.1x |
|  | $A_T$ | 2.8x |
|  | B | 7.4x |
| Cbl-C6-ATTO488 | $A_{T,MUT}$ | 1.1x |
|  | $A_T$ | 1.3x |
| Cbl-C6-ATTO590 | $A_{T,MDT}$ | 1.2x |
|  | $A_T$ | 2.9x |
|  | B | 3.9x |
| Cbl-5xPEG-ATTO590 | $A_{T,MUT}$ | 1.1x |
|  | $A_T$ | 4.0x |
|  | A | 4.9x |
|  | B | 3.7x |
|  | C | 4.0x |
|  | D | 2.9x |
| Cbl-C6-ATTO590 comprising 4xGly | $A_T$ | 7.3x |
|  | A | 5.0x |
|  | D | 3.9x |
| Cbl-C6-ATT0633 | $A_{T,MDT}$ | 0.9x |
|  | $A_T$ | 1.9x |
|  | B | 2.5x |
| Cbl-Cy5 | $A_{T,MDT}$ | 1.1x |
|  | $A_T$ | 2.1x |
|  | A | 2.7x |
|  | B | 2.5x |
|  | D | 2.5x |

TABLE 6

Comparison of maximal distance between the corrin ring in Cbl and the fluorophore in probes. Values are based on structural estimates and the Förster distance $R_0$ estimated from spectral properties.

| Name | Distance estimate between corrin ring and click linkage to fluorophore | Forster distance $R_0$ |
|---|---|---|
| Cbl-FAM | 9 Å | 35 Å |
| Cbl-C6-FAM | 12.5 Å |  |
| Cbl-1xPEG-FAM | 12.5 Å |  |
| Cbl-2xPEG-FAM | 16 Å |  |
| Cbl-3xPEG-FAM | 19.5 Å |  |
| Cbl-C6-ATT0488 | 12.5 Å | 35 Å |
| Cbl-ATTO590 | 9 Å | 20 Å |
| Cbl-C6-ATTO590 | 12.5 Å |  |
| Cbl-5xPEG-ATTO590 | 26.5 Å |  |
| Cbl-5xGly-ATTO590 comprising 4xGly | 30.4 Å |  |
| Cbl-ATTO633 | 9 Å | 15 Å |
| Cbl-C6-ATTO633 | 12.5 Å |  |
| Cbl-Cy5 | 9 Å | 12 Å |

TABLE 7

Summary of ITC titrations for different aptamers in the presence of Cbl or the Cbl-5xPEG-ATTO590 probe.

| Name of aptamer | Name of conjugate | $K_D$ |
|---|---|---|
| A | Cbl | 37 ± 1 nM |
| A | Cbl-5xPEG-ATTO590 | 34 ± 9 nM |
| $A_T$ | Cbl | 290 ± 100 nM |
| $A_T$ | Cbl-5xPEG-ATTO590 | 1.3 ± 0.56 μM |
| D | Cbl | 2.2 ± 1.6 nM |
| D | Cbl-5xPEG-ATTO590 | 3.0 ± 0.6 nM |

TABLE 8

Quantum yield of probes in the presence and absence of different aptamers.

| Name | Quantum yield (QY) |
|---|---|
| Cy5 | 0.28 (Lumiprobe) |
| Cbl-Cy5 | 0.09 |
| Cbl-Cy5 + A | 0.26 |
| Cbl-Cy5 + D | 0.25 |
| ATTO590 | 0.8 (Atto Tec) |
| Cbl-5xPEG-ATTO590 | 0.06 |
| Cbl-5xPEG-ATTO590 + A | 0.31 |
| Cbl-5xPEG-ATTO590 + D | 0.31 |
| Cbl-5xGly-ATTO590 comprising 4xGly | 0.09 |
| Cbl-5xGly-ATTO590 comprising 4xGly + A | 0.55 |
| Cbl-5xGly-ATTO590 comprising 4xGly + D | 0.45 |

TABLE 9

Summary of fluorescence lifetime measurements for Cbl-fluorophore probes in the presence and absence of indicated aptamers. The lifetime decay data presented in FIG. 15A-B was fit and exponential components and their weight are indicated together with the overall fluorescence lifetime.

| | $t_i$ (ns) | $t_i$ % | $t_2$ (ns) | $t_2$ % | $t_3$ (ns) | $t_3$ % | lifetime (ns) |
|---|---|---|---|---|---|---|---|
| Cy5 | 1.04 | 100 | — | — | — | — | 1.04 |
| Cbl-Cy5 | 0.33 | 25 | 0.7 | 75 | — | — | 0.61 |

TABLE 9-continued

Summary of fluorescence lifetime measurements for Cbl-fluorophore probes in the presence and absence of indicated aptamers. The lifetime decay data presented in FIG. 15A-B was fit and exponential components and their weight are indicated together with the overall fluorescence lifetime.

| | $t_1$ (ns) | $t_1$ % | $t_2$ (ns) | $t_2$ % | $t_3$ (ns) | $t_3$ % | lifetime (ns) |
|---|---|---|---|---|---|---|---|
| Cbl-Cy5 + D | 1 | 100 | — | — | — | — | 1 |
| Cbl-Cy5 + A | 1.05 | 100 | — | — | — | — | 1.05 |
| ATTO590 | 3.99 | 100 | — | — | — | — | 3.99 |
| Cbl-5xGly-ATTO590 comprising 4xGly | 0.2 | 9 | 0.89 | 32 | 1.94 | 59 | 1.44 |
| Cbl-5xGly-ATTO590 comprising 4xGly + D | 0.4 | 6 | 1.75 | 46 | 3.3 | 48 | 2.42 |
| Cbl-5xGly-ATTO590 comprising 4xGly + A | 0.43 | 5 | 1.84 | 33 | 3.79 | 62 | 2.98 |
| Cbl-5xPEG-ATTO590 | 0.25 | 28 | 1.56 | 72 | — | — | 1.19 |
| Cbl-5xPEG-ATTO590 + D | 0.4 | 12 | 1.61 | 60 | 3.22 | 28 | 1.93 |
| Cbl-5xPEG-ATTO590 + A | 0.41 | 13 | 1.42 | 43 | 3.34 | 44 | 2.14 |

TABLE 10

Experimental conditions for RNA/probe photobleaching experiments.

| Probe | RNA | Excitation wavelength (nm) | Irradiance (W/cm$^2$) |
|---|---|---|---|
| 55 μM Cbl-Cy5 | 550 μM A | 640 | 0.27 |
| 48 μM Cbl-5xPEG-ATTO590 | 480 μM A | 555 | 1.31 |
| 7 μM DFHBI-1T | 80 μM Broccoli | 470 | 3.16 |

TABLE 11

Sequence and properties of DNA oligos used in FISH. Microscope settings for live and fixed fluorescence microscopy. Images were integrated once unless otherwise noted below.

| Experiment | Pinhole | Laser settings | Notes |
|---|---|---|---|
| Live imaging of A-tagged mRNA, Cbl-Cy5 probe (U2-OS cells) | 67.7 μm | DAPI: 1.0 (HV = 100) TRITC: 0.4 (HV = 20) Cy5: 12.0 (HV = 100) | 4x integration for all channels |
| Live imaging of A-tagged mRNA, Cbl-5xGly-ATTO590 comprising 4xGly probe (U2-OS cells, | 67.7 μm | DAPI: 1.0 (HV = 100) TRITC: 1.0 (HV = 80) Cy5: 5.0 (HV = 100) | N/A |
| Correlative imaging (U2-OS cells, live) | 67.7 μm | GFP: 1.0 (HV = 40) Cy5: 7.0 (HV = 110) | |
| Correlative imaging (fixed) | 26.8 μm | GFP: 2.0 (HV = 40) TRITC: 1.0 (HV = 40) | 40x Plan Apo Air objective, Nyquist sampling at 0.16 μm per pixel |
| Live imaging of 2xdBroccoli-tagged mRNA (U2-OS cells) | 67.7 μm | DAPI: 5.0 (HV = 110) GFP: 1.0 (HV = 110) TRITC : 1.0 (HV = 40) | N/A |
| FISH on fixed cells, exogenously produced RNA | 63.9 μm | GFP: 1.5 (HV = 80) TRITC: 2.0 (HV = 110) Cy5: 6.0 (HV = 110) | N/A |
| FISH on fixed cells, endogenous ACTB mRNA | 58.7 μm | GFP: 0.4 (HV = 40) Cy5: 12.0 (HV = 120) | 16x integration for Cy5 channel |
| Immunofluorescence/FISH on fixed cells, endogenous SMN/ DDX20 and U1 RNA | 49.8 μm | DAPI: 2.0 (HV = 90) TRITC: 0.3 (HV = 40) for SMN/1.0 (HV = 40) for DDX20 Cy5: 10.0 (HV = 120) | N/A |
| Immunofluorescence/FISH on fixed cells, cotransfected GFP-SMN and $A_T$-U1 RNA | 49.8 μm | GFP: 0.3 (HV = 25) Cy5: 10.0 (HV = 120) | N/A |
| Immunofluorescence/FISH on fixed cells, transfected EGFP-Coilin and U1 RNA | 0.8 AU | DAPI: 1.0 (HV = 100) GFP: 2.0 (HV = 40) Cy5: 4.0 (HV = 110) | N/A |
| Live imaging of $A_T$-tagged U1 RNA, (HeLa cells) | 5.1 μm | GFP: 0.5 (HV = 50) TRITC: 2-5 (HV = 50-80) | TRITC settings adjusted for optimal contrast without detector saturation |
| Live imaging of GFP-SMN, with our without cotransfected A T-tagged U1 RNA, (HeLa cells) | 51.1 μm | GFP: 0.5 (HV = 30-50) TRITC: 2 (HV = 50) | GFP settings adjusted for optimal contrast without detector saturation |

TABLE 12

Sequence and properties of DNA oligos used in FISH.

| Name | SEQ ID NOS: | Sequence | Melting temperature (IDT) | Amount per cover slip |
|---|---|---|---|---|
| ACTB-FISH-Cy5 | 7 | 5'-Cy5-CAC AGC TTC TCC TTA ATG TCA CGC ACG ATT TCC CGC TCG GCC GTG-3' | 71.rc | 300 ng |
| A$_r$-FISH-Cy5 | 8 | 5'-Cy5-CCT AGG TGG CAT TCG GAG TAT AAC CGT ATC AAG TAA TCT G-3' | 63.3° C. | 200-300 ng |
| A$_r$-FISH-Alexa546 | 9 | 5'-Alexa546-CCT AGG TGG CAT TCG GAG TAT AAC CGT ATC AAG TAA TCT G-3' | 63.3° C. | 300 ng |
| Broccoli-FISH-Cy5 | 10 | 5'-Cy5-TTG CCA TGA ATG ATC CAG CCC ACA CTC-3' | 62.8° C. | 300 ng |
| MS2SL-FISH-Cy5 | 11 | 5'-Cy5-GTT TAA ACG AAT TCG CCC TTA GAT CTG AGT AAC CCT GG-3' | 63.5° C. | 300 ng |
| U1-FISH-Cy5 | 12 | 5'-Cy5-TCA GCA CAT CCG GAG TGC AAT GGA TAA GCC TCG CCC TGG GAA AA-3" | 71.3° C. | 200-300 ng |

TABLE 13

Figure 18B:
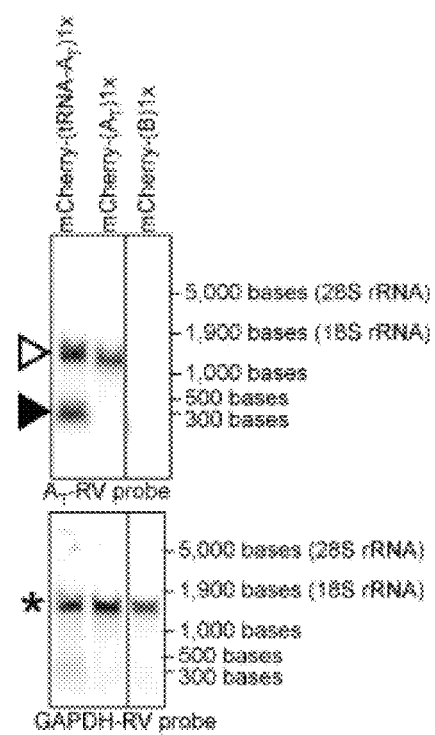

Properties of oligonucleotides used in FIG. 18B were purchased as DNA oligos from Integrated DNA Technologies, Inc. (IDT)).

| Name | SEQ ID NOS: | Sequence | Melting temperature (IDT) | Amount per cover slip |
|---|---|---|---|---|
| ACTB-FISH-Cy5 | 7 | 5'-Cy5-CAC AGC TTC TCC TTA ATG TCA CGC ACG ATT TCC CGC TCG GCC GTG-3' | 71.rc | 300 ng |
| A$_r$-FISH-CY5 | 8 | 5'-Cy5-CCT AGG TGG CAT TCG GAG TAT AAC CGT ATC AAG TAA TCT G-3' | 63.3° C. | 200-300 ng |
| A$_r$-FISH-Alexa546 | 9 | 5'-Alexa546-CCT AGG TGG CAT TCG GAG TAT AAC CGT ATC AAG TAA TCT G-3' | 63.3° C. | 300 ng |
| Broccoli-FISH-Cy5 | 10 | 5'-Cy5-TTG CCA TGA ATG ATC CAG CCC ACA CTC-3' | 62.8° C. | 300 ng |
| MS2SL-FISH-Cy5 | 11 | 5'-Cy5-GTT TAA ACG AAT TCG CCC TTA GAT CTG AGT AAC CCT GG-3' | 63.5° C. | 300 ng |
| U1-FISH-Cy5 | 12 | 5'-Cy5-TCA GCA CAT CCG GAG TGC AAT GGA TAA GCC TCG CCC TGG GAA AA-3" | 71.3° C. | 200-300 ng |

REFERENCES FOR TABLES, HEREIN INCORPORATED BY REFERENCE IN THEIR ENTIRETY

1. Johnson, J. E., Reyes, F. E., Polaski, J. T. & Batey, R. T. B12 cofactors directly stabilize an mRNA regulatory switch. Nature 492, 133-7 (2012).
2. Polaski, J. T., Webster, S. M., Johnson, J. E. & Batey, R. T. Cobalamin Riboswitches Exhibit a Broad Range of Ability to Discriminate between Methylcobalamin and Adenosylcobalamin. J. Biol. Chem. 292, 11650-11658 (2017).
3. Filonov, G. S. & Jaffrey, S. R. RNA Imaging with Dimeric Broccoli in Live Bacterial and Mammalian Cells. Current protocols in chemical biology 8, (2016).

REFERENCES, HEREIN INCORPORATED BY REFERENCE IN THEIR ENTIRETY

1. Müller-McNicoll, M. & Neugebauer, K. M. How cells get the message: dynamic assembly and function of mRNA-protein complexes. Nat. Rev. Genet. 14, 275-287 (2013).
2. Gerstberger, S., Hafner, M. & Tuschl, T. A census of human RNA-binding proteins. Nat. Rev. Genet. 15, 829-845 (2014).
3. Buchan, J. R. & Parker, R. Eukaryotic Stress Granules: The Ins and Outs of Translation. Mol. Cell 36, 932-941 (2009).
4. Decker, C. J. & Parker, R. P-Bodies and Stress Granules: Possible Roles in the Control of Translation and mRNA Degradation. Cold Spring Harb. Perspect. Biol. 4, a012286 (2012).
5. Mollet, S. et al. Translationally Repressed m RNA Transiently Cycles through Stress Granules during Stress. Mol. Biol. Cell 19, 4469-4479 (2008).
6. Balagopal, V. & Parker, R. Polysomes, P bodies and Stress granules: States and Fates of Eukaryotic mRNAs. Curr. Opin. Cell Biol. 21, 403-408 (2009).
7. Tsalikis, J. et al. Intracellular bacterial pathogens trigger the formation of U small nuclear RNA bodies (U bodies) through metabolic stress induction. J. Biol. Chem. 290, 20904-20918 (2015).
8. Matera, A. G. & Wang, Z. A day in the life of the spliceosome. Nat. Rev. Mol. Cell Biol. 15, 108-21 (2014).
9. Wu, B., Chao, J. A. & Singer, R. H. Fluorescence fluctuation spectroscopy enables quantitative imaging of single mRNAs in living cells. Biophys. J. 102, 2936-44 (2012).
10. Fusco, D. et al. Single mRNA molecules demonstrate probabilistic movement in living mammalian cells. Curr. Biol. 13, 161-7 (2003).
11. Wu, B., Chen, J. & Singer, R. H. Background free imaging of single mRNAs in live cells using split fluorescent proteins. Sci. Rep. 4, 3615 (2014).
12. Garcia, J. F. & Parker, R. MS2 coat protein bound to yeast mRNAs block 5' to 3' degradation and trap mRNA decay products: implications for the localization of mRNAs by MS2-MCP system. RNA 21, 1393-5 (2015).
13. Yoon, Y. J. et al. Glutamate-induced RNA localization and translation in neurons. Proc. Natl. Acad. Sci. 113, E6877-E6886 (2016).
14. Wu, B., Eliscovich, C., Yoon, Y. J. & Singer, R. H. Translation dynamics of single mRNAs in live cells and neurons. Science (80-). Vol. 352, Issue 6292, pp. 1430-1435. Published online 2016 May 5, aaf1084 (2016), doi:10.1126/science.aaf1084

15. Katz, Z. B. et al. Mapping translation 'hot-spots' in live cells by tracking single molecules of mRNA and ribosomes. Elife 5, 1-17 (2016).
16. Nguyen, D. H., DeFina, S. C., Fink, W. H. & Dieckmann, T. Binding to an RNA aptamer changes the charge distribution and conformation of malachite green. J. Am. Chem. Soc. 124, 15081-15084 (2002).
17. Babendure, J. R., Adams, S. R. & Tsien, R. Y. Aptamers Switch on Fluorescence of Triphenylmethane Dyes. J. Am. Chem. Soc. 125, 14716-14717 (2003).
18. Arora, A., Sunbul, M. & Jäschke, A. Dual-colour imaging of RNAs using quencher- and fluorophore-binding aptamers. Nucleic Acids Res. 43, e144 (2015).
19. Sunbul, M. & Jäschke, A. Contact-mediated quenching for RNA imaging in bacteria with a fluorophore-binding aptamer. Angew. Chem. Int. Ed. Engl. 52, 13401-4 (2013).
20. Tan, X. et al. Fluoromodules Consisting of a Promiscuous RNA Aptamer and Red or Blue Fluorogenic Cyanine Dyes: Selection, Characterization, and Bioimaging. J. Am. Chem. Soc. 139, 9001-9009 (2017).
21. Ouellet, J. RNA Fluorescence with Light-Up Aptamers. Front. Chem. 4, 1-12 (2016).
22. Paige, J. S., Wu, K. Y. & Jaffrey, S. R. RNA mimics of green fluorescent protein. Science 333, 642-6 (2011).
23. Filonov, G. S., Moon, J. D., Svensen, N. & Jaffrey, S. R. Broccoli: Rapid Selection of an RNA Mimic of Green Fluorescent Protein by Fluorescence-Based Selection and Directed Evolution. J. Am. Chem. Soc. 136, 16299-308 (2014).
24. Dolgosheina, E. V et al. RNA Mango Aptamer-Fluorophore: A Bright, High-Affinity Complex for RNA Labeling and Tracking. ACS Chem. Biol. 9, 2412-2420 (2014).
25. Autour, A. et al. Fluorogenic RNA Mango aptamers for imaging small non-coding RNAs in mammalian cells. Nat. Commun. 9, 656 (February, 2018).
26. Filonov, G. S. & Jaffrey, S. R. RNA Imaging with Dimeric Broccoli in Live Bacterial and Mammalian Cells. Current protocols in chemical biology 8, (2016).
27. Song, W. et al. Imaging RNA polymerase 111 transcription using a photostable RNA-fluorophore complex. Nat. Chem. Biol. 13, 1187-1194 (2017).
28. Ceres, P., Trausch, J. J. & Batey, R. T. Engineering modular 'ON' RNA switches using biological components. Nucleic Acids Res. 41, 10449-61 (2013).
29. Ceres, P., Garst, A. D., Marcano-Veliázquez, J. G. & Batey, R. T. Modularity of select riboswitch expression platforms enables facile engineering of novel genetic regulatory devices. ACS Synth. Biol. 2, 463-72 (2013).
30. Johnson, J. E., Reyes, F. E., Polaski, J. T. & Batey, R. T. B12 cofactors directly stabilize an mRNA regulatory switch. Nature 492, 133-7 (2012).
31. Polaski, J. T., Holmstrom, E. D., Nesbitt, D. J. & Batey, R. T. Mechanistic Insights into Cofactor-Dependent Coupling of RNA Folding and m RNA Transcription/Translation by a Cobalamin Riboswitch. Cell Rep. 15, 1100-1110 (2016).
32. Lee, M. & Grissom, C. B. Design, synthesis, and characterization of fluorescent cobalamin analogues with high quantum efficiencies. Org. Lett. 11, 2499-502 (2009).
33. Smeltzer, C. C. et al. Synthesis and characterization of fluorescent cobalamin (CobalaFluor) derivatives for imaging. Org. Lett. 3, 799-801 (2001).
34. Fedosov, S. N. et al. Application of a fluorescent cobalamin analogue for analysis of the binding kinetics. A study employing recombinant human transcobalamin and intrinsic factor. FEBS J. 273, 4742-53 (2006).
35. Chromiński, M. & Gryko, D. 'Clickable' vitamin B12 derivative. Chem. — A Eur. J. 19, 5141-8 (2013).
36. Loska, R., Janiga, A. & Gryko, D. Design and synthesis of protoporphyrin IX/vitamin B-12 molecular hybrids via CuAAC reaction. J. Porphyrins phtalocynines 17, 104-117 (2013). 37. Trachman, R. J. et al. Structural basis for high-affinity fluorophore binding and activation by RNA Mango. Nat. Chem. Biol. 13, 807-813 (2017).
38. Warner, K. D. et al. Structural basis for activity of highly efficient RNA mimics of green fluorescent protein. Nat. Struct. Mol. Biol. 8, 658-63 (2014).
39. Jeng, S. C. Y., Chan, H. H. Y., Booy, E. P., McKenna, S. A. & Unrau, P. J. Fluorophore ligand binding and complex stabilization of the RNA Mango and RNA Spinach aptamers. RNA 22, 1884-1892 (2016).
40. Sauer, M. & Paeschke, K. G-quadruplex unwinding helicases and their function in vivo. Biochem. Soc. Trans. BST20170097 (2017), doi:10.1042/BST20170097
41. Strack, R. L., Disney, M. D. & Jaffrey. S. R. A superfolding Spinach2 reveals the dynamic nature of trinucleotide repeat-containing RNA. Nat. Methods 10, 1219-24 (2013).
42. Filonov, G. S., Kam, C. W., Song, W. & Jaffrey, S. R. In-gel imaging of RNA processing using Broccoli reveals optimal aptamer expression strategies. Chem. Biol. 22, 649-660 (2015).
43. Ponchon, L. & Dardel, F. Recombinant RNA Technology: the tRNA scaffold. Nat. Methods 4, 571-576 (2007).
44. Morisaki, T. et al. Real-time quantification of single RNA Translation dynamics in living cells. Science 6392, 1425-1429 (2016).
45. Hayashi-Takanaka, Y. et al. Tracking epigenetic histone modifications in single cells using Fab-based live endogenous modification labeling. Nucleic Acids Res. 39, 6475-6488 (2011).
46. McNeil, P. L. & Warder, E. Glass beads load macromolecules into living cells. J. Cell Sci. 88, 669-678 (1987).
47. Nelles, D. A. et al. Programmable RNA Tracking in Live Cells with CRISPR/Cas9. Cell 165, 488-496 (2016).
48. Zurla, C., Lifland, A. W. & Santangelo, P. J. Characterizing mRNA interactions with RNA granules during translation initiation inhibition. PLoS ONE 6, e1 9727 (2011).
49. Jain, S. et al. ATPase-Modulated Stress Granules Contain a Diverse Proteome and Substructure. Cell 164, 487-498 (2016).
50. Grimm, J. B. et al. A general method to fine-tune fluorophores for live-cell and in vivo imaging. Nat. Methods 14, 987-994 (2017).
51. Kedersha, N., Tisdale, S., Hickman, T. & Anderson, P. Real-time and quantitative imaging of mammalian stress granules and processing bodies. Methods in enzymology 448, (Elsevier Inc., 2008).
52. Ni, C. Z. et al. Crystal structure of the MS2 coat protein dimer: implications for RNA binding and virus assembly. Structure 3, 255-263 (1995).
53. Han, K. Y., Leslie, B. J., Fei, J., Zhang, J. & Ha, T. Understanding the photophysics of the Spinach-DFHBI RNA aptamer-fluorogen complex to improve live-cell RNA imaging. J. Am. Chem. Soc. 135, 19033-19038 (2013).

54. McCloskey, A., Taniguchi, I., Shinmyozu, K. & Ohno, M. hnRNP C Tetramer Measures RNA Length to Classify RNA Polymerase II Transcripts for Export. Science 335, 1643-1646 (2012).
55. Ishikawa, H. et al. Identification of truncated forms of U1 snRNA reveals a novel RNA degradation pathway during snRNP biogenesis. Nucleic Acids Res. 42, 2708-2724 (2014).
56. Hutten, S., Chachami, G., Winter, U., Melchior, F. & Lamond, a. I. A role for the Cajal-body-associated SUMO isopeptidase USPL1 in sn RNA Transcription mediated by RNA polymerase II. J. Cell Sci. 127, 1065-1078 (2014).
57. Nahvi, A., Barrick, J. E. & Breaker, R. R. Coenzyme B12 riboswitches are widespread genetic control elements in prokaryotes. Nucleic Acids Res. 32, 143-50 (2004).
58. Fowler, R. et al. Uptake and transport of B12-conjugated nanoparticles in airway epithelium. J. Control. Release 172, 374-81 (2013).
59. Quadros, E. V & Sequeira, J. M. Cellular uptake of cobalamin: transcobalamin and the TCblR/CD320 receptor. Biochimie 95, 1008-18 (2013).
60. Edwards, A. L., Garst, A. D. & Batey, R. T. Determining Structures of RNA Aptamers and Riboswitches by X-Ray Crystallography. Methods Mol. Biol. 535, 135-63 (2009).
61. Gilbert, S. D. & Batey, R. T. Monitoring RNA-Ligand Interactions Using Isothermal Titration Calorimetry. Methods Mol. Biol. 540, 97-114 (2009).
62. Quenching of Fluorescence, in Principles of Fluorescence Spectroscopy (ed. Lakowicz, J. R.) 277-330 (Springer, 2006).
63. Beckley, S. a, Liu, P., Stover, M. L., Gunderson, S. I. & Rowe, D. W. Reduction of Target Gene Expression by a Modified U1 snRNA. Mol. Cell. Biol. 21, 2815-25 (2001).
64. Wheeler, J., Matheny, T., Jain, S., Abrisch, R. & Parker, R. Distinct stages in stress granule assembly and disassembly. Elife 5, 1-25 (2016).
65. Xi, L., Schmidt, J. C., Zaug, A. J., Ascarrunz, D. R. & Cech, T. R. A novel two-step genome editing strategy with CRISPR-Cas9 provides new insights into telomerase action and TERT gene expression. Genome Biol. 16, 1-17 (2015).
66. Shpargel, K. B. & Matera, A. G. Gemin proteins are required for efficient assembly of Sm-class ribonucleoproteins. Proc. Natl. Acad. Sci. U.S.A. 102, 17372-17377 (2005).
67. Shpargel, K. B. Control of Cajal body number is mediated by the coilin C-terminus. J. Cell Sci. 116, 303-312 (2003).

VII. Detection and Quantification of Single mRNA Dynamics with the Riboglow Fluorescent RNA Tag.

Riboglow, referring to a platform for tagging RNAs, has a short aptamer tag where in one embodiment, additionally binds to a small molecule for inducing a fluorescence increase of an attached fluorophore. As described herein, embodiments of a Riboglow tag were further developed that are capable of detecting and tracking single RNA molecules within living cells. Thus, in one embodiment, a Riboglow RNA tag detects a single RNA molecule within a living cell. In one embodiment, a Riboglow RNA tag tracks a single RNA molecule within a living cell.

A. Introduction.

Approaches to label and track cellular biomolecules using fluorescent tags have revolutionized the capability to investigate how their spatiotemporal dynamics relate to function in live cells [reference 1]. While tagging proteins with fluorescent markers offers a versatile repertoire of choices in terms of color, labeling modality and detection mode [reference 2], labeling RNAs with genetically encoded tags lagged behind this progress due to the absence of naturally occurring fluorescent RNAs. Seminal work by the Singer lab [references 3-4] established the MS2 system as a tool to interrogate dynamics of mRNAs in live cells. The MS2 system typically consists of 24 stem-loop (SL) repeats genetically fused to a gene of interest in the 3' untranslated region (UTR) [reference 3, 5, 6]. Each SL binds a dimer of the bacteriophage-derived MS2 coat protein, which is genetically fused to GFP [reference 3]. By tagging each RNA in vivo with 24 copies of the SL, up to 48 copies of MS2-GFP accumulate on each RNA molecule. The MS2 system was instrumental for elucidating mRNA dynamics, and is a RNA-tagging platform shown to enable single molecule RNA imaging in live mammalian cells. As described herein, Riboglow was developed as an alternative technique to label and track single RNAs in live cells in order to complement and broaden the scope of MS2-based single RNA tracking. In other words, Riboglow provides additional advantages over MS2 such as smaller size, the option of incorporating diverse small molecule fluorophores, the potential for improved contrast with reduced background fluorescence.

Visualizing mRNA with the MS2 system has enabled tracking of single mRNAs, characterization of their movement, and has revealed fundamental features of mRNA biology that cannot be studied without single molecule resolution. Tracking of single mRNAs revealed different types of movement (diffusive, corralled and directed) [reference 3] (see also Table 14, FIG. 44A-B, for a summary), and tracking β-actin mRNA (encoded by ACTB) emerged as a model mRNA for single particle studies [references 7-13]. mRNAs have "zipcode" sequences, often in their 3' UTR [reference 14]. Interactions of these zipcode sequences with RNA binding proteins enables directed movement along the cytoskeleton [reference 6]. Transport along the cytoskeleton, along with other mechanisms to distribute mRNA throughout the cell, results in distinct mRNA localization patterns in cells to ensure that the message is positioned close to where the translated protein is needed [reference 15]. Single mRNAs have been tracked in whole organisms, including in yeast [reference 4], *Escherichia coli* [reference 16], and *Drosophila melanogaster* [reference 17] and the creation of a transgenic mouse [reference 11, 18] allowed mRNA tracking in the whole mouse and in diverse primary cell types, including neurons [reference 19]. Interestingly, different cell types such as neurons with protrusions exceeding hundreds of μm, and compact cell types such as fibroblasts, utilize different mechanisms to distribute β-actin mRNA [reference 20]. The diversity of mRNA dynamics highlights the need to investigate mRNA movement in different cell types and interrogate the complex network of mRNA binding proteins and their role for distributing mRNAs within cells [reference 21].

Recently, the MS2 system was combined with antibody-based probes to gain insights in the mRNA life cycle. Translation of single mRNAs can be monitored by following the nascent peptide chain via a loaded affinity probe [reference 22] or the SunTag [reference 23-25]; these studies from different labs yielded comparable protein translation kinetics (see reference 26 for a comparison). Other aspects of the mRNA life cycle, such as interactions with stress granules and P bodies, association with the endoplasmic reticulum [reference 28], mRNA frame shifting and nonsense-mediated mRNA decay, were also characterized using a combination of MS2-based mRNA labeling and complementary fluorescent probes on the single molecule level. Further contemplated is mRNA tagging using a Riboglow tag having different fluorophores and using different labeling systems for combining different fluorescent probes and labeling systems are contemplated for use, as described herein.

While the MS2 system was used for single mRNA tracking, its large size, with a need for genetic incorporation of both the tag and the MS2-fluorescent fusion protein, and background signal from the unbound fluorescent protein represent limitations that sparked efforts to develop additional RNA tracking platforms. Advances of the MS2 platform itself include development of the orthogonal PP7 system [reference 31], a split fluorescent protein system [reference 32], use of HaloTag [reference 23] to reduce background fluorescence, and engineering efforts to avoid MS2-tag induced changes in mRNA degradation [reference 33]. More recently developed techniques to label RNA use smaller aptamer tags that bind small molecules, including the Spinach/Broccoli [reference 34-35] and Mango tags [reference 36-37], but single molecule detection in living cells has not yet been achieved with any small molecule-based approach. Entirely orthogonal tools have been developed in which fluorescent probes are delivered into cells to bind untagged RNA without the need to genetically add tags [reference 38-40], enabling in principle visualization of any endogenous RNA of any size, such as miRNA [reference 41, 42]. Finally, additional approaches for tracking RNAs include incorporation of fluorescent nucleotide analogs to study mRNAs encoding mitochondrial proteins translated on endosome-containing 'hotspots' in axons, molecular beacons for studying co-transcriptional vs. post-transcriptional alternative splicing [reference 44], and micro-injected fluorescent RNA probes to examine the miRNA life cycle [reference 41, 42]. While delivery of probes into cells may be technically challenging, advances to improve delivery routes of various fluorescent molecules in live cells have been explored [references 26, 45, 46]. Despite these advances, the growing field of RNA biology is in need of diverse and robust fluorescence tools to visualize RNAs with single molecule detection in live cells to gain insights in the complexity and regulation of RNA dynamics.

In one embodiment, Riboglow relies on the bacterial cobalamin riboswitch, which binds cobalamin. In preferred embodiments, a bacterial cobalamin riboswitch binds cobalamin within a nM $K_d$ range, where a bacterial cobalamin riboswitch is genetically fused to an RNA of interest. In preferred embodiments, cobalamin has fluorescence quenching properties. Thus, a suite of cobalamin-fluorophore probes were synthesized and validated where fluorescence is quenched relative to the free fluorophore. A RNA tag binds cobalamin, inducing a conformational change and hence an increase in fluorescence. This architecture allows observations for easily picking and choosing an organic probe moiety and thereby a color. Therefore, demonstrated herein is recruitment of mRNAs to stress granules and then tagging of the short non-coding U snRNA using this platform [as described herein]. During the development of the present inventions, this work was furthered for demonstrating tracking of single mRNAs with additional embodiments of a Riboglow tag. The Riboglow platform promises to be a powerful addition to the growing toolbox for live cell RNA imaging, especially for single molecule sensitivity.

Labeling and tracking biomolecules with fluorescent probes on the single molecule level enables quantitative insights into their dynamics in living cells. As discussed herein, Riboglow was developed as a platform to label RNAs in live mammalian cells, comprising a short RNA tag and a small organic probe that increases fluorescence upon binding RNA. Further, in this section, we demonstrate that Riboglow is capable of detecting and tracking single RNA molecules. RNA tracking was benchmarked by comparing results with the established MS2 RNA tagging system. To demonstrate versatility of Riboglow, we assayed translation on the single molecule level, where the translated mRNA is tagged with Riboglow and the nascent polypeptide is labeled with a fluorescent antibody.

B. Detecting and Tracking Single RNA Molecules within Living Cells.

For assessing whether single mRNAs can be detected and tracked with a Riboglow platform [as described herein] in live cells, in one embodiment a ACTB mRNA was tagged with 12 copies of the Riboglow RNA tag (FIG. 46A). ACTB mRNA was chosen to visualize as a test for a 12× Riboglow RNA tag because single ACTB mRNAs were detected and tracked with the MS2 system in a variety of cell types and experimental conditions [reference 3, 7-12 and 48]. Thus comparisons to published studies enabled benchmarking, i.e. comparing, detection sensitivity and results between Riboglow tagging to other means of RNA tagging (see Table 14 and FIG. 45A-B for an overview of literature data and experimental conditions).

In one embodiment, a 4xGly-ATTO 590 fluorescent probe for Riboglow was chosen for comparison, as this probe exhibits approximately a 5-fold fluorescence turn-on (increase) upon binding to the RNA tag with minimal photobleaching [as described herein]. Cells were imaged with highly inclined and laminated optical sheet (HILO) microscopy [reference 49-50], an image acquisition modality commonly used for single particle tracking in live cells that allows single particle detection throughout the cell volume while minimizing photo-bleaching [references 22, 42, 49, 51].

Figure 39A:
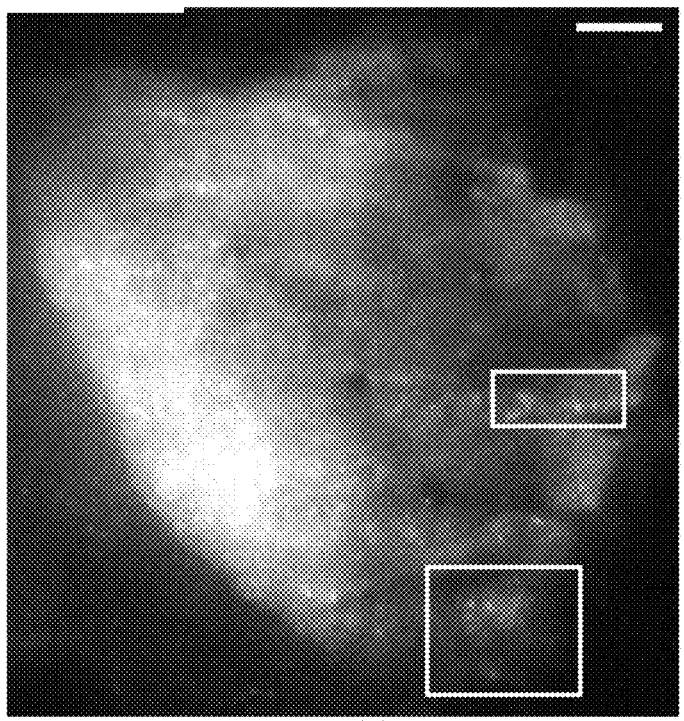
FIG. 39A-C: Detection of single mRNAs using the Riboglow platform.
Figure 39B:
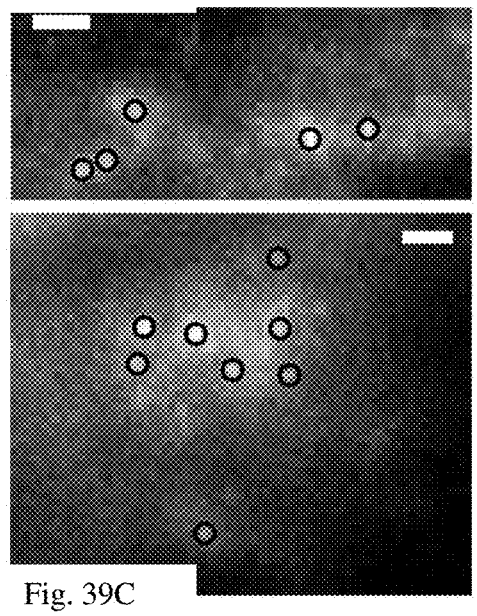

After using a method of labeling with a 12× Riboglow tag, as described herein, distinct puncta were readily detected in the ATTO 590 channel (FIG. 39A) that moved rapidly throughout the cell when a plasmid to produce the Riboglow-tagged ACTB was transfected. In movie 1, a plasmid encoding ACTB mRNA tagged with 12 copies of Riboglow was transfected in U2-OS cells, followed by bead loading of 4xGly-ATTO 590 24 h (hours) post transfection, as in FIG. 39A-B FIG. 1. Movies of live cells reveal rapid movement of red fluorescent puncta. The movie was acquired with 30 ms exposure and a frame rate of 33.3 frames per second. Scale bar=2 μm. See, still images representing Movie 1; FIGS. 39A-B. Fluorescent puncta were detected over background using the FIJI plugin Trackmate [reference 52] (FIG. 39B), enabling us to develop a detection and tracking pipeline for these particles, see Methods Section II, for parameters used for single particle detection.

Figure 39C:
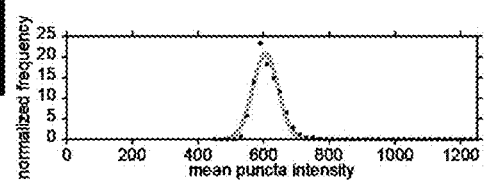

We determined that the observed puncta represent single mRNAs, based on the following observations: (i) When we compared cells with and without transfection of the Riboglow-tagged ACTB, no fluorescent puncta were seen in the untransfected control (Movie 2 vs. 3, representative still images shown in FIG. 39D and FIG. 39E, respectively, see additional information below); and (ii) The distribution of intensities of individual puncta in each region of interest (ROI) analyzed by Trackmate follows a Gaussian distribution (FIG. 39C), as others observed for tracking of single MS2-tagged ACTB mRNA [reference 7].

Figure 39D:
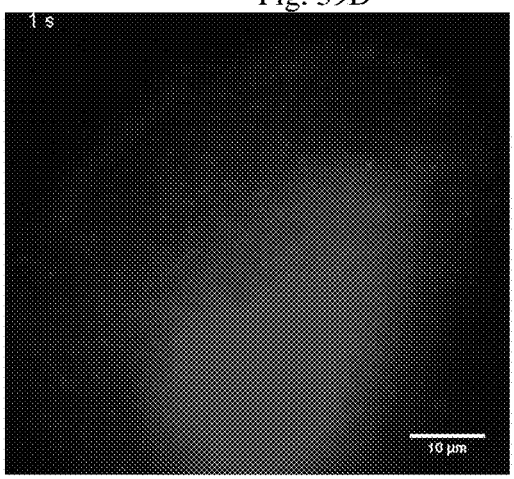
FIGS. 39D and 39E: Movie 2 and 3: shows exemplary comparison of U2-OS cells that were bead loaded with Cbl-4xGly-ATTO 590, with (FIG. 39D movie 2) or without (FIG. 39E movie 3) transfection of a plasmid encoding ACTB mRNA tagged with 12 copies of Riboglow 24 h prior. Red fluorescent puncta that rapidly move in cells are only detectable in cells that were transfected. Movies were acquired with 30 ms exposure and a frame rate of 13 frames per second. Scale bar=10 µm.
Figure 39E:
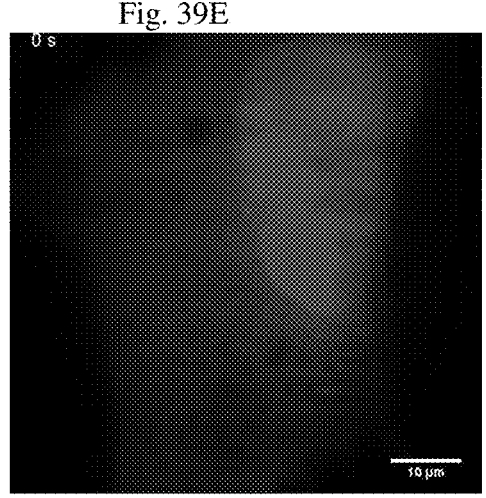

FIGS. 39D and 39E: Movie 2 and 3, respectively, shows exemplary comparison of U2-OS cells bead loaded with 4xGly-ATTO 590, with (FIG. 39D a still image representing movie 2) or without (FIG. 39E a still image representing movie 3) transfection of a plasmid encoding ACTB mRNA tagged with 12 copies of Riboglow 24 h prior. Red fluorescent puncta that rapidly move in cells are only detectable in cells that were transfected. Movies were acquired with 30 ms exposure and a frame rate of 13 frames per second. Scale bar=10 µm.

Figure 40A:
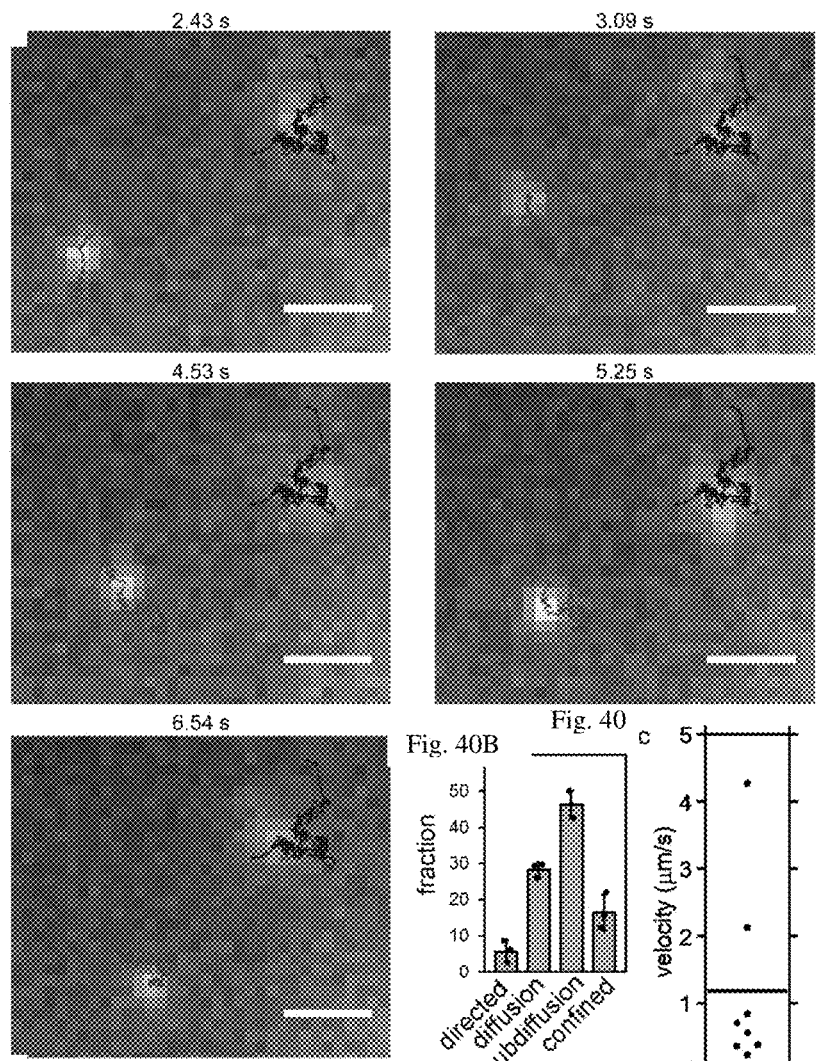

FIG. 40A shows a representative still image of this movie 4. In Movie 4: Example of single particle tracking for puncta detected in U2-OS cells that were transfected with 12× Riboglow-tagged ACTB and subsequently bead loaded with Cbl-4xGly-ATTO 590. Shown are traces that were classified as "directed" (red) and "subdiffusion" (blue). Select frames of movie 4 are shown in FIG. 40A. The movie was acquired with 30 ms exposure and a frame rate of 33.3 frames per second. Scale bar=1 µm.

FIG. 42A-C shows representative still images of Movie 6. In Movie 6: U2-OS cells were bead loaded with a plasmid encoding the SM-KDM5B translation assay reporter, together with the Cbl-4xGly-ATTO 590 Riboglow probe to label mRNA and Fab-Alexa488 to mark the nascent protein. Cells were visualized 6 h after bead loading.

We reasoned that a Gaussian distribution is indicative of a single species of molecules, as one would expect for single molecules. In some ROIs, we detected two populations across the entire movie (FIG. 46). To exclude potential artifacts, only ROIs with a single population were used for further analysis. (iii) We observed similar behavior for MS2-tagged ACTB mRNA in our hands, as follows. We transfected a construct producing ACTB tagged with 24 copies of the MS2-SL (FIG. 45D) into U2-OS cells that stably produce GFP-tagged MS2 with a nuclear localization sequence (NLS), as we have done previously [as described herein]. Distinct puncta representing single particles were readily detected in the cytosol (FIG. 47A). As with the Riboglow-tagged mRNA, the intensities of the puncta in an ROI follow a Gaussian distribution (FIG. 47C), indicating single MS2-GFP tagged ACTB mRNA [reference 7]. (iv) We did not observe appreciable variability in particle size for Riboglow-tagged ACTB FIG. 48B or ACTB tagged with 24xMS2-SL (FIG. 48B), a feature that would be indicative of fluorophore or particle aggregation. We concluded that we are able to detect single mRNAs when tagging the reporter ACTB mRNA with twelve copies of Riboglow.

We developed and validated a pipeline to quantify single ACTB mRNA tagged with 24 copies of the MS2-SL (FIGS. 47A-G) and took advantage of existing studies to validate our approach. Qualitative inspection of movies revealed different types of movement, as expected (FIG. 47A-G): the movement of the majority of particles was non-directional, resembling diffusion (FIG. 47B, right side of the field of view). A minority of particles appeared to move in a directional manner, sometimes rapidly changing direction (FIG. 47B, left side of the field of view). To classify and quantify particle motions systematically, we employed the FIJI TraJClassifier [reference 53]. Briefly, the TraJClassifier analyzes single particle trajectories as one of four motion types ("directed/active", "confined", "subdiffusion" and "normal diffusion", FIG. 47G). We analyzed MS2-tagged mRNA particles in this way yielding traces with a mean duration of 2.75 s (corresponding to 91 frames at a framerate of 33.3 frames per second, FIG. 47F). We observed several examples of "directed", "normal diffusion" and "subdiffusion" motion (FIG. 47D-E). As others have reported [reference 3, 11], we saw directed motion of ACTB mRNA only for a minority of traces (~15%, FIG. 47G). The particle velocity for directed motion was 0.92±0.27 µm/s (FIG. 47D), well within the range reported in the literature for directed motion of MS2-tagged mRNA [reference 3, 9-11] (FIG. 44A, Table 14). We further inspected non-directional movement classified as either "normal diffusion" or "subdiffusion" by the TraJClassifier [reference 53]. The diffusion coefficient we observed for normal diffusion was 0.09±0.03 µm²/s, comparable with values observed in the literature [reference 3, 7-9, 11, 12, 49] (FIG. 44B, Table 14). Traces labeled as "subdiffusion" by the TraJClassifier describe restricted movement [reference 53], resembling a behavior called "corralled" by Fusco et al[3]. Indeed, as Fusco et al [reference 3] (FIG. 44B), we observed "subdiffusion" behavior with a diffusion coefficient of 0.007±0.005 µm²/s, vs. faster normal diffusion (0.09±0.03 µm²/s, FIG. 47E). The strong resemblance of MS2-SL tagged ACTB mRNA dynamics in our hands vs. previous measurements validates our image acquisition, particle detection, tracking and classification approach to accurately detect and quantify movement of single mRNAs.

Figure 40B:
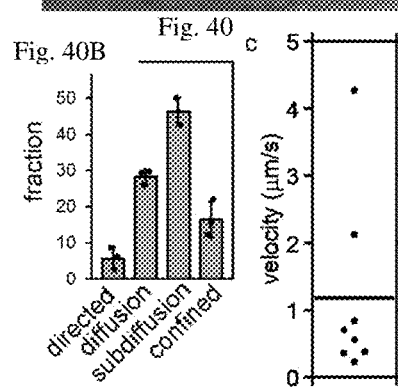
Figure 40D:
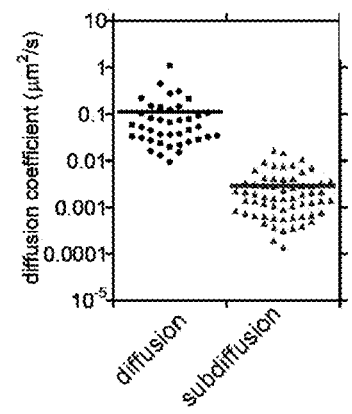
Figure 40E:
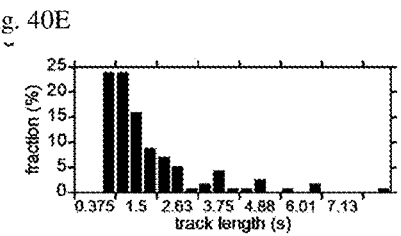

Having established a pipeline to detect and quantify movement of single ACTB mRNAs in our hands, we asked whether Riboglow-tagging is compatible with single mRNA detection. As for 24x MS2-SL-tagged mRNA, we tracked particles over several seconds and observed random movement resembling diffusion (FIG. 40A, blue trace), or movement in a directional manner with sudden changes in direction (FIG. 40A, red trace). With the constraint that the minimal track length was set as 30 frames, we detected tracks with a mean length of 68 frames (corresponding to 2.0 s), and the longest track was 281 frames (8.4 s, FIG. 40E). Tracks generated with Trackmate were categorized by the TraJClassifier [reference 53]. Directed movement was detected for a minority of traces (6±3%, average and standard deviation between independent experiments) (FIG. 40B). The mean velocity for "directed" tracks of 1.2±0.5 µm/s (FIG. 40C) was comparable with the number for 24x MS2-SL-tagged ACTB mRNA (0.92±0.27 µm/s, FIG. 46D) and values observed in the literature[3,7-9,11,12,48] (FIG. 44B, Table 14). Particles classified as "normal diffusion" moved with an apparent diffusion coefficient of 0.09±0.03 µm²/s (FIG. 2D), comparable with the value we observed for 24x MS2-SL-tagged ACTB (0.09±0.03 µm²/s, FIG. 9E). Similarly, the diffusion coefficient for traces classified as "subdiffusion" was reduced (0.0029±0.0004 µm²/s, FIG. 2D), as for 24x MS2-SL (0.007±0.005 µm²/s, FIG. 47E). These numbers and trends are consistent with observations in the literature [reference 3, 7-9, 11, 12, 48] (FIG. 44B, Table 14). We concluded that the Riboglow platform is capable of detecting single mRNAs in live cells and those mRNAs can be tracked over several seconds.

We sought to explore whether the size of the Riboglow tag can be shortened by reducing the number of tag repeats, as smaller tags are less likely to perturb function of tagged proteins and RNAs. While tagging ACTB mRNA with 12 copies of Riboglow only adds a maximum of 470 kDa to the mRNA, vs. approximately 2,500 kDa added when all 24 SLs are bound to a GFP-MS2 dimer in the 24xMS2-SL tag (Table 15), we wondered whether a further reduction in tag size may be possible without compromising single mRNA detection. We reduced the number of Riboglow repeats fused to ACTB mRNA to eight copies. As we have demonstrated before [as described herein], when two plasmids are co-transfected in our hands, the chances of double transfection (e.g. the cell receiving both plasmids) are >90%. We co-transfected a plasmid encoding ACTB tagged with eight copies of the Riboglow tag with a blue marker (NLS-TagBFP), and bead loaded the Cbl-4xGly-ATTO 590 probe.

When we only analyzed cells positive for the blue nuclear co-transfection marker, no distinct puncta were visible (Movie 5, compare with Movie 1). FIG. 41A-B shows representative still images of Movie 5. In Movie 5, A plasmid encoding ACTB mRNA tagged with 8 copies of Riboglow was transfected in U2-OS cells, followed by bead loading of Cbl-4xGly-ATTO 590 24 h post transfection, as in Movie 1, representative still images shown in FIGS. 39A-B. Transfected cells, as judged by the presence of the blue nuclear co-transfection marker protein, were chosen for analysis. A movie was acquired with 30 ms exposure and a frame rate of 33.3 frames per second. Scale bar=2 µm.

Likewise, puncta could not routinely be detected via the Trackmate [reference 52] algorithm (FIG. 41A). In a small subset of ROIs, occasional puncta were visible and could be detected with Trackmate using our constraints (a radius of 0.5 µm, etc, see Methods), but these puncta were not detectable in subsequent frames and hence we were unable to track them (FIG. 41B). We concluded that robust detection and tracking of single ACTB mRNA molecules with Riboglow occurs using 12 copies of Riboglow, although a reduction in tag length is likely feasible with improvement of features of the Riboglow platform, namely fluorescence contrast between the free and bound Cbl-fluorophore probe.

The recent rapid advances in visualizing and quantifying the mRNA lifecycle on the single molecule level using a combination of fluorescent tools prompted us to assess the possibility of monitoring mRNA translation with Riboglow-labeled mRNA. We adapted a translation assay previously developed in the Stasevich lab [reference 22], where a gene encoding KDM5B has an N-terminal 'spaghetti monster' (SM) tag that includes 10 FLAG tag copies to visualize the nascent protein, and the 3' end includes the MS2-SL mRNA tag. Our KDM5B reporter construct also has the N-terminal SM tag, and we used 12 copies of Riboglow instead of the MS2-tag in the 3' UTR for mRNA tagging (FIG. 45C). The design of this construct allows for detection of the nascent protein with an anti-FLAG antibody fragment (Fab), labeled with green fluorescent Alexa488, as established previously [reference 22-26]. Our reporter gene allows for correct protein translation, confirmed by accumulation of SM-KDM5B labeled with green Fab in cell nuclei (FIG. 49). When we loaded the green Fab together with the Riboglow probe Cbl-4xGly-ATTO590 and the SM-KDM5B reporter plasmid DNA, we observed diffraction limited spots where green fluorescence from the nascent protein tag and red fluorescence from the Riboglow-ATTO590 tagged mRNA colocalized in the cytosol (FIG. 42A-E). These spots are consistent with translation sites, for the following reasons. First, we detected co-localization spots around 6 hours post transfection, in line with the timing of translation detection in previous studies [reference 22]. Second, we observed co-movement of these spots, as expected for mRNA translation (Movie 6, FIG. 42D, 42E). At 6-8 hours post transfection, we detected 6±4 spots per cell (6 experiments, 16 cells, 94 total spots) that can be tracked together for at least five consecutive imaging frames (corresponding to >7 s tracking). Finally, when Puromycin was added to cells with co-moving translation spots, we observed rapid disappearance of the protein signal from the translation sites (FIG. 43B-D). Before Puromycin treatment, 64±14% mRNA spots co-localized with protein signal, vs. 30±12% mRNA spots colocalized with protein signal after Puromycin treatment (3 experiments, 47 mRNA spots total). Puromycin halts translation and releases the elongating polypeptide from the translation site, as used in similar translation assays [reference 22-23]. Together, we established Riboglow as a suitable addition to the growing toolbox of RNA probes to interrogate aspects of the mRNA lifecycle on the single molecule level, including protein translation.

C. Summary.

In this work we demonstrate Riboglow is a versatile tool capable of detecting and tracking single molecules of RNA in live mammalian cells. We readily detected single mRNA molecules when 12 copies of Riboglow were used and were able to track each mRNA for up to 6 s. Tracking allowed us to characterize and quantify the type of movement. We observed directed movement, diffusion, subdiffusion and confined movement, and quantified parameters for each type (velocity of 1.2±0.5 µm/s for directed tracks, diffusion coefficient of 0.09±0.03 µm$^2$/s for diffusive behavior). Our values are consistent with data for single mRNA tagged with 24 copies of MS2-SL, serving as a robust validation for our tool. To demonstrate the potential of Riboglow for multiplexing with other fluorescent reporters, we visualized single Riboglow-tagged mRNA molecules and labeled emerging nascent polypeptide chains at translation sites. Together, we present Riboglow as a robust tool to visualize single mRNAs, and demonstrate its usability for multi-color tracking applications.

Riboglow features several advantageous properties for live RNA labeling. First, Riboglow features organic dyes with photophysical properties ideal for single molecule imaging (high brightness and slow bleaching). Second, we have previously explored exchanging the fluorophore and hence color of Riboglow from red (ATTO 590) to far red (Cy5) [as described herein] without compromising function. This feature will be desirable for usage of Riboglow in multi-color applications. Third, the size of even a 12 copy tag of Riboglow (471 kDa) is significantly smaller than the conventional 24xMS2 tag (2,527 kDa, assuming 1:1 binding of RNA to dye, Table 15). Note that the more recently used MS2-Halo is even larger than MS2-GFP (Halo is 33 kDa, vs. 27 kDa for GFP). It is noteworthy that the smaller overall Riboglow tag vs. the larger 24xMS2 tag did not reveal detectable changes in mRNA dynamics in our hands (FIG. 47A-G vs. FIG. 40A-E).

These results indicate that ACTB mRNA mobility in this model system is not likely to be altered by large tags. Regardless, shortening tags for minimal perturbation of the tagged species is advantageous to minimize potential perturbation of the tagged RNA's function. Lastly, Riboglow is entirely orthogonal to MS2-based mRNA labeling systems, enabling simultaneous labeling of different parts of the same mRNA, or multiple different mRNAs in the same cell. Together, we envision Riboglow as a new member of the growing toolbox for labeling mRNA on the single molecule level.

D. Discussion.

As described herein, the development and use of a Riboglow system is a versatile tool capable of detecting and tracking single molecules of RNA in live mammalian cells. We readily detected single mRNA molecules when 12 copies of Riboglow were used and were able to track each mRNA for up to 6 seconds (s). Tracking allowed us to characterize and quantify the type of movement. We observed directed movement, diffusion, subdiffusion and confined movement, and quantified parameters for each type (velocity of 1.2±0.5 µm/s for directed tracks, diffusion coefficient of 0.09±0.03 µm$^2$/s for diffusive behavior). Our values are consistent with data for single mRNA tagged with 24 copies of MS2-SL, serving as a robust validation for our tool. To demonstrate the potential of Riboglow for multi plexing with other fluorescent reporters, we visualized single Riboglow-tagged mRNA molecules and labeled emerging nascent polypeptide chains at translation sites. Together, we present Riboglow as a robust tool to visualize single mRNAs, and demonstrate its usability for multi-color tracking applications.

Riboglow is entirely orthogonal to MS2-based mRNA labeling systems, enabling simultaneous labeling of different parts of the same mRNA, or multiple different mRNAs in the same cell. Together, we envision Riboglow as a new member of the growing toolbox for labeling mRNA on the single molecule level.

TABLE 14

Literature values for live mRNA dynamic measurements (relevant studies).

| Exemplary Experimental Conditions | Quantification Of Movement | Reference |
|---|---|---|
| lacZ tagged with 24x MS2-SL, in COS cells | Directed movement (2-5%): $v = 1 - 1.5$ μm/s; diffusional movement ($D = 0.08 - 0.045$ μm$^2$/s); corralled movement ($D = 0.07 - 0.0413$ μm$^2$/s) | 3 |
| YFP tagged with 24x MS2-SL, stably integrated in U2OS cells, tracking of nuclear movement | $D = 0.01 - 0.09$ μm$^2$/s (nucleus, SPT) (simple diffusion, corralled diffusion); $D = 0.09 \pm 0.0006$ μm$^2$/s (nucleus, FRAP) | 48 |
| Beta-actin tagged with 24x MS2-SL, in chicken embryo fibroblast (CEF) cells | $D = 0.32 - 0.29$ μm$^2$/s (lending edge of the cell); $D = 0.02 - 0.24$ μm$^2$/s (perinuclear region) | 7 |
| Chicken beta-actin (with its 3'UTR, zipcode), tagged with CFP (N-terminus) and 24x MS2-SL, stably integrated in U2OS cells | $D = 0.035$ μm$^2$/s (cytoplasm, SPT); $D = 0.13$ μm$^2$/s (cytoplasm, FRAP), $D = 0.024$ μm$^2$/s (nucleoplasm, SPT) | 8 |
| Endogenous beta-actin, labeled with MTRIPs (multiply-labeled tetravalent imaging probes), in A549 cells (epithelial cell line) and human dermal fibroblasts (primary) | SPT: active, processive motion ($v = 0.9 \pm 0.3$ μm$^2$/s) and passive, diffusive motion (0.0053 μm$^2$/s in A549 cells, 0.0004 μm$^2$/s in fibroblasts) | 9 |
| Beta-actin tagged with 24x MS2-SL, in primary rat cortical neurons | $v = 0.0294 +/- 0.0215$ μm/s | 10 |
| Beta-actin tagged with 24x MS2-SL, in mice. Imaging in primary cells from those mice. | SPT: In primary fibroblasts: $D = 0.09 \pm 0.02$ μm$^2$/s, ~1% directed movement; in primary neurons: $D = 3.8 (\pm 0.5) \times 10^{-3}$ μm$^2$/s, ~10% active transport ($v = 1.3$ μm/s) | 11 |
| Endogenous beta-actin tagged with 24x MS2-SL, fibroblast cells derived from transgenic mouse | $D = 0.1$ (slow) $- 0.4$ (fast) μm$^2$/s, shift to fast state upon puromycin treatment (ribosome release) | 12 |

D = diffusion coefficient; v = velocity; SPT = single particle tracking; FRAP = fluorescence recovery after photobleaching, MS2-SL = MS2 stem loop.

Riboglow features several advantageous properties for live RNA labeling. First, Riboglow features organic dyes with photophysical properties ideal for single molecule imaging (high brightness and slow bleaching). Second, we have previously explored exchanging the fluorophore and hence color of Riboglow from red (ATTO 590) to far red (Cy5) [as described herein] without compromising function. This feature will be desirable for usage of Riboglow in multi-color applications. Third, the size of even a 12 copy tag of Riboglow (471 kDa) is significantly smaller than the conventional 24xMS2 tag (2,527 kDa, assuming 1:1 binding of RNA to dye, Table 15). Note that the more recently used MS2-Halo is even larger than MS2-GFP (Halo is 33 kDa, vs. 27 kDa for GFP). It is noteworthy that the smaller overall Riboglow tag vs. the larger 24xMS2 tag did not reveal detectable changes in mRNA dynamics in our hands (FIG. 47A-G vs. FIG. 2). These results suggest that ACTB mRNA mobility in this model system is not likely to be altered by large tags. Regardless, shortening tags for minimal perturbation of the tagged species is advantageous to minimize potential perturbation of the tagged RNA's function. Lastly,

TABLE 15

Size comparison of RNA tags.

| Name of tag component | Size estimate (kDa) |
|---|---|
| 12x Riboglow RNA tag (A variant) | 442 kDa |
| 8x Riboglow RNA tag (A variant) | 290 kDa |
| Cbl-4xGly-ATTO590 | 2.4 kDa |
| 12x Riboglow RNA tag bound to 12 Cbl-4xGly-ATTO590 probes | 471 kDa |
| 8x Riboglow RNA tag bound to 8 Cbl-4xGly-ATTO590 probes | 309 kDa |
| 24x MS2-SL RNA tag | 415 kDa |
| MS2-GFP homo dimer | 88 kDa |
| 24x MS2-SL RNA tag bound to 24 MS2-GFP homo dimers | 2,527 kDa |

TABLE 16

Sequences for relevant plasmid regions.

| Name | SEQ ID NOS. | Sequence |
|---|---|---|
| Riboglow DNA sequence (1 copy, A [as described herein]) | 15 | 5'-CCT AAA AGC GTA GTG GGA AAG TGA CGT GAA ATT CGT CCA GAT TAC TTG ATA CGG TTA TAC TCC GAA TGC CAC CTA GGC CAT ACA ACG AGC AAG GAG ACT CA |
| 8 × Riboglow sequence (Riboglow sequence in italic, linkers in bold) | 16 | 5'-CCT AAA AGC GTA GTG GGA AAG TGA CGT GAA ATT CGT CCA GAT TAC TTG ATA CGG TTA TAC TCC GAA TGC CAC CTA GGC CAT ACA ACG AGC AAG GAG ACT CAG GTA CCG GCC TAA AAG CGT AGT GGG AAA GTG ACG TGA AAT TCG TCC AGA TTA CTT GAT ACG GTT ATA CTC CGA ATG CCA CCT AGG CCA TAC AAC GAG CAA GGA GAC TCA GGA TCC GGC CTA AAA GCG TAG TGG GAA AGT GAC GTG AAA TTC GTC CAG ATT ACT TGA TAC GGT TAT ACT CCG AAT GCC ACC TAG GCC ATA CAA CGA GCA AGG AGA CTC AGG ATC CGG CCT AAA AGC GTA GTG GGA AAG TGA CGT GAA ATT CGT CCA GAT TAC TTG ATA CGG TTA TAC TCC GAA TGC CAC CTA GGC CAT ACA ACG AGC AAG GAG ACT CAG GAT CCA CCG GAT CTA GCT GCA GTC GAC GGT AAC GGC CTA AAA GCG TAG TGG GAA AGT GAC GTG AAA TTC GTC CAG ATT ACT TGA TAC GGT TAT ACT CCG AAT GCC ACC TAG GCC ATA CAA CGA GCA AGG AGA CTC AGG TAC CGG CCT AAA AGC GTA GTG GGA AAG TGA CGT GAA ATT CGT CCA GAT TAC TTG ATA CGG TTA TAC TCC GAA TGC CAC CTA GGC CAT ACA ACG AGC AAG GAG ACT CAG GAT CCG GCC TAA AAG CGT AGT GGG AAA GTG ACG TGA AAT TCG TCC AGA TTA CTT GAT ACG GTT ATA CTC CGA ATG CCA CCT AGG CCA TAC AAC GAG CAA GGA GAC TCA GGA TCC GGC CTA AAA GCG TAG TGG GAA AGT GAC GTG AAA TTC GTC CAG ATT ACT TGA TAC GGT TAT ACT CCG AAT GCC ACC TAG GCC ATA CAA CGA GCA AGG AGA CTC AGG ATC C |
| 12 × Riboglow sequence (Riboglow sequence in italic, linkers in bold) | 17 | 5'-CCT AAA AGC GTA GTG GGA AAG TGA CGT GAA ATT CGT CCA GAT TAC TTG ATA CGG TTA TAC TCC GAA TGC CAC CTA GGC CAT ACA ACG AGC AAG GAG ACT CAG GTA CCG GCC TAA AAG CGT AGT GGG AAA GTG ACG TGA AAT TCG TCC AGA TTA CTT GAT ACG GTT ATA CTC CGA ATG CCA CCT AGG CCA TAC AAC GAG CAA GGA GAC TCA GGA TCC GGC CTA AAA GCG TAG TGG GAA AGT GAC GTG AAA TTC GTC CAG ATT ACT TGA TAC GGT TAT ACT CCG AAT GCC ACC TAG GCC ATA CAA CGA GCA AGG AGA CTC AGG ATC CGG CCT AAA AGC GTA GTG GGA AAG TGA CGT GAA ATT CGT CCA GAT TAC TTG ATA CGG TTA TAC TCC GAA TGC CAC CTA GGC CAT ACA ACG AGC AAG GAG ACT CAG GAT CCA CCG GAT CTA GCT GCA GTC GAC GGT AAC GGC CTA AAA GCG TAG TGG GAA AGT GAC GTG AAA TTC GTC CAG ATT ACT TGA TAC GGT TAT ACT CCG AAT GCC ACC TAG GCC ATA CAA CGA GCA AGG AGA CTC AGG TAC CGG CCT AAA AGC GTA GTG GGA AAG TGA CGT GAA ATT CGT CCA GAT TAC TTG ATA CGG TTA TAC TCC GAA TGC CAC CTA GGC CAT ACA ACG AGC AAG GAG ACT CAG GAT CCG GCC TAA AAG CGT AGT GGG AAA GTG ACG TGA AAT TCG TCC AGA TTA CTT GAT ACG GTT ATA CTC CGA ATG CCA CCT AGG CCA TAC AAC GAG CAA GGA GAC TCA GGA TCC GGC CTA AAA GCG TAG TGG GAA AGT GAC GTG AAA TTC GTC CAG ATT ACT TGA TAC GGT TAT ACT CCG AAT GCC ACC TAG GCC ATA CAA CGA GCA AGG AGA CTC AGG ATC CAC CGA GTC TAG AAG CAT GCA GTC GAC GGT ACG GCC TAA AAG CGT AGT GGG AAG TGA CGT GAA ATT CGT CCA GAT TAC TTG ATA CGG TTA TAC TCC GAA TGC CAC CTA GGC CAT ACA ACG AGC AAG GAG ACT CAG GTA CCG GCC TAA AAG CGT AGT GGG AAA GTG ACG TGA AAT TCG TCC AGA TTA CTT GAT ACG GTT ATA CTC CGA ATG CCA CCT AGG CCA TAC AAC GAG CAA GGA GAC TCA GGA TCC GGC CTA AAA GCG TAG TGG GAA AGT GAC GTG AAA TTC GTC CAG ATT ACT TGA TAC GGT TAT ACT CCG AAT GCC ACC TAG GCC ATA CAA CGA GCA AGG AGA CTC AGG ATC CGG CCT AAA AGC GTA GTG GGA AAG TGA CGT GAA ATT CGT CCA GAT TAC TTG ATA CGG TTA TAC TCC GAA TGC CAC ACA ACG AGC AAG GAG ACT CAG GAT CC |

TABLE 17

Image acquisition.

| Experiment | Image acquisition details |
|---|---|
| Live imaging of ACTB-(MS2-SL)24x mRNA | 30 ms exposure, no binning or 2 × 2 binning, 13.3 or 33.3 frames per second, movie length typically 300 frames, 488 nm laser (~15% power) |
| Live imaging of ACTB-(Riboglow)12x mRNA | 30 ms exposure, 2 × 2 binning, movie acquisition at 512 × 512 pixel and 600 frames (33.3 frames per second), 561 nm laser (50% power) |
| Live imaging of ACTB-(Riboglow)8x mRNA | 30 ms exposure, 2 × 2 binning, movie acquisition at 512 × 512 pixel and 600 frames (33.3 frames per second), 561 nm laser (50% power) |
| Live imaging of ACTB-(Riboglow)12x mRNA, translation assay | 31 ms exposure, no binning, 1 frame per 10 second, 561 nm laser (15% power), 488 nm laser (15% power), image acquired for 11 z stacks at 0.5 μm per stack |

REFERENCES FOR SECTION VII AND EXPERIMENTAL SECTION II, HEREIN INCORPORATED BY REFERENCE

1. Specht, et al., "A Critical and Comparative Review of Fluorescent Tools for Live Cell Imaging. *Annu. Rev. Physiol.* 79, 93-117 (2017).
2. Dean, et al., "Advances in fluorescence labeling strategies for dynamic cellular imaging. *Nat. Chem. Biol.* 10, 512-523 (2014).
3. Fusco, et al., "Single mRNA molecules demonstrate probabilistic movement in living mammalian cells. *Curr. Biol.* 13, 161-7 (2003).

4. Bertrand, et al., "Localization of ASH 1 mRNA Particles in Living Yeast. *Mol. Cell* 2, 437-445 (1998).
5. Querido, et al., "Using Fluorescent Proteins to Study mRNA Trafficking in Living Cells. *Methods Cell Biol.* 85, 273-292 (2008).
6. Buxbaum, et. al., "In the right place at the right time: visualizing and understanding mRNA localization. *Nat. Rev. Mol. Cell Biol.* 16, 95-109 (2014).
7. Yamagishi, et al., "Single-molecule imaging of R-actin mRNAs in the cytoplasm of a living cell. *Exp. Cell Res.* 315, 1142-1147 (2009).
8. Ben-Ari, et al., "The life of an mRNA in space and time. *J. Cell Sci.* 123, 1761-1774 (2010).
9. Lifland, et al., "Dynamics of native β-actin mRNA transport in the cytoplasm. *Traffic* 12, 1000-11 (2011).
10. Ma, et al., "Huntingtin mediates dendritic transport of beta-actin mRNA in rat neurons. *Sci. Rep.* 1, 1-1 (2011).
11. Park, el al., "Visualization of Dynamics of Single Endogenous mRNA Labeled in Live Mouse. *Science* 343, 422-424 (2014).
12. Katz, et al., "Mapping translation 'hot-spots' in live cells by tracking single molecules of mRNA and ribosomes. *Elife* 5, 1-17 (2016).
13. Buxbaum, et al., "Single β-Actin mRNA Detection in Neurons Reveals a Mechanism for Regulating Its Translatability. *Science* 343, 419-422 (2014).
14. Andreassi, et al., "To localize or not to localize: mRNA fate is in 3'UTR ends. *Trends Cell Biol.* 19, 465-474 (2009).
15. Condeelis, et al., "How and why does β-actin mRNA target? *Biol. Cell* 97, 97-110 (2005).
16. Golding, et al., "RNA dynamics in live *Escherichia coli* cells. *Proc. Natl. Acad. Sci.* U.S.A 101, 11310-5 (2004).
17. Zimyanin, et al., "In Vivo Imaging of oskar mRNA Transport Reveals the Mechanism of Posterior Localization. *Cell* 134, 843-853 (2008).
18. Lionnet, et al., "A transgenic mouse for in vivo detection of endogenous labeled mRNA. *Nat. Methods* 8, 165-70 (2011).
19. Yoon, et al., "Glutamate-induced RNA localization and translation in neurons. *Proc. Natl. Acad. Sci.* 113, E6877-E6886 (2016).
20. Song, et al., "Specific interaction of KIF11 with ZBP1 regulates the transport of—actin mRNA and cell motility. *J. Cell Sci.* 128, 1001-1010 (2015).
21. Eliscovich, et al., "RNP transport in cell biology: the long and winding road. Curr. *Opin. Cell Biol.* 45, 38-46 (2017).
22. Morisaki, et al., "Real-time quantification of single RNA translation dynamics in living cells. *Science* 6392, 1425-1429 (2016).
23. Wu, et al., "Translation dynamics of single mRNAs in live cells and neurons. *Science* 352, 1430-5 (2016).
24. Tanenbaum, et al., "A protein tagging system for signal amplification in gene expression and fluorescence imaging. *Cell* 159, 635-646 (2014).
25. Wang, et al., "Real-Time Imaging of Translation on Single mRNA Transcripts in Live Cells. *Cell* 165, 990-1001 (2016).
26. Lyon, et al., "Imaging Translational and Post-Translational Gene Regulatory Dynamics in Living Cells with Antibody-Based Probes. *Trends Genet.* 33, 322-335 (2017).
27.
28. Voigt, et al., "Single-Molecule Quantification of Translation-Dependent Association of mRNAs with the Endoplasmic Reticulum. *Cell Rep.* 21, 3740-3753 (2017).
29.
30.
31. Chao, J. a, Patskovsky, Y., Almo, S. C. & Singer, R. H. Structural basis for the coevolution of a viral RNA-protein complex. *Nat. Struct. Mol. Biol.* 15, 103-5 (2008).
32. Wu, et al., "Background free imaging of single mRNAs in live cells using split fluorescent proteins. *Sci. Rep.* 4, 3615 (2014).
33. Tutucci, et al., "An improved MS2 system for accurate reporting of the mRNA life cycle. *Nat. Methods* 15, 81-89 (2018); Published: 13 Nov. 2017.
34. Filonov, et al., "Broccoli: Rapid Selection of an RNA Mimic of Green Fluorescent Protein by Fluorescence-Based Selection and Directed Evolution. *J. Am. Chem. Soc.* 136, 16299-308 (2014).
35. Paige, el al., "RNA mimics of green fluorescent protein. *Science* 333, 642-6 (2011).
36. Dolgosheina, e al., "RNA Mango Aptamer-Fluorophore: A Bright, High-Affinity Complex for RNA Labeling and Tracking. *ACS Chem. Biol.* 9, 2412-2420 (2014).
37. Autour, et al., "Fluorogenic RNA Mango aptamers for imaging small non-coding RNAs in mammalian cells. *Nat. Commun.* 9, 656 (2018); Published: 13 Feb. 2018.
38. Vargas, et al., "Mechanism of mRNA transport in the nucleus. *Proc Natl Acad Sci* USA 102, (2005).
39. Santangelo, et al., "Single molecule-sensitive probes for imaging RNA in live cells. *Nat. Methods* 6, 10-14 (2009).
40. Custer, et al., "In vitro labeling strategies for in cellulo fluorescence microscopy of single ribonucleoprotein machines. *Protein Sci.* 26, 1363-1379 (2017).
41. Pitchiaya, et al., "Resolving Subcellular miRNA Trafficking and Turnover at Single-Molecule Resolution. CellReports 19, 630-642 (2017).
42. Pitchiaya, et al., "Intracellular single molecule microscopy reveals two kinetically distinct pathways for microRNA assembly. *EMBO Rep.* 13, 709-15 (2012).
43.
44. Vargas, et al., "Single-Molecule Imaging of Transcriptionally Coupled and Uncoupled Splicing. *Cell* 147, 1054-1065 (2011).
45. Teng, et al., "Delivery of Fluorescent Probes Using Streptolysin O for Fluorescence Microscopy of Living Cells. *Curr. Protoc. Protein Sci.* 93, 1-11 (2018); Epub 2018 Jul. 30.
46. Wieneke, et al., "Live-cell protein labelling with nanometre precision by cell squeezing. *Nat. Commun.* 1-8 (2016). doi:10.1038/ncomms10372
47. as described herein.
48. Shav-Tal, et al., "Dynamics of single mRNPs in nuclei of living cells. *Science* (80) 304, 1797-1800 (2004).
49. Tokunaga, et al., "Highly inclined thin illumination enables clear single-molecule imaging in cells. *Nat. Me* 5, 159-161 (2008).
50. Konopka, et al., "Variable-angle epifluorescence microscopy: a new way to look at protein dynamics in the plant cell cortex. *Plant J.* 53, 186-196 (2008).
51. Schmidt, et al., "Live Cell Imaging Reveals the Dynamics of Telomerase Recruitment to Telomeres. *Cell* 166, 1188-1197.e9 (2016).
52. Tinevez, et al., "TrackMate: An open and extensible platform for single-particle tracking. *Methods* 115, 80-90 (2017).
53. Wagner, et al., "Classification and segmentation of nanoparticle diffusion trajectories in cellular micro environments. *PLoS One* 12, 1-20 (2017).
54. McNeil, et al., "Glass beads load macromolecules into living cells. *J. Cell Sci.* 88, 669-678 (1987).

55. Viswanathan, et al., "High-performance probes for light and electron microscopy. *Nat. Methods* 12, 568-576 (2015).

Examples

The following examples are offered to illustrate various embodiments of the invention, but should not be viewed as limiting the scope of the invention.

I. Methods.

Synthesis of Fluorophore Probes.

In general, probes are derivatives of CN-Cbl. Exemplary structures of the probes used herein are shown in FIG. 6 while Table 3 provides a summary of their photophysical properties.

Commercially available reagents and solvents were used as received. 6-FAM alkyne and sulfo-Cyanine5 alkyne were purchased from Lumiprobe and ATTO propargylamide were obtained from ATTO-TEC. The structure of ATTO633 alkyne was not provided by the producer. As one example, synthesis of a Cbl-4xGly-$N_3$ (product 31) molecule for use in conjugating to a fluorescent probe, a therapeutic, etc., is described as follows.

STEP 1: HO-4xGly-alkyne (28) was synthesized manually by Fmoc chemistry on a 0.124 mmol scale of Fmoc-Gly attached to the Wang resin (Fmoc-Gly-Wang resin), 4-fold molar excess of the Fmoc-Gly-Gly-Gly-OH and 5-fold molar excess of 4-pentynoic acid. Fmoc deprotection was performed with 20% piperidine in DMF (1.5 mL, 1-2 h) and coupling with the use of HBTU (6 equiv.) and DIPEA (6 equiv.) in DMF (2 mL). After final coupling the resin was washed with DMF (5×1 mL), DCM (5×1 mL) and dried. Cleavage from the resin was carried with the use of a TFA/DCM (25%, v/v) with the catalytic amount of anisole for 2.5 h. Obtained product 28, comprising a 4xGly structure was precipitated with $Et_2O$ and centrifuged. LRMS (ESI) m/z $[M+Na]^+$ calcd (calculated) for $C_{13}H_{18}N_4O_6Na$ 349.12, found 349.20. See, FIG. 50.

STEP 2: Cbl-$N_3$ (20) (0.068 mmol, 94 mg) and HO-4xGly-alkyne (0.062 mmol, 20 mg) was dissolved in DMF/$H_2O$ mixture (5:3 v/v, Σ=4 mL). Catalyst—CuI (0.032 mmol, 6 mg) and TBTA (0.057 mmol, 30 mg) mixed in 2 mL of DMF for 20 min—was added and the resulting solution was stirred for 16 h at 40° C. The reaction mixture was diluted with MeOH (5 mL) and poured into $Et_2O$ (60 mL). The resulting precipitate was filtered through a cotton wool, washed with AcOEt (2×10 mL) and $Et_2O$ (2×10 mL). After drying, the resulting solid was dissolved in MeOH and concentrated in vacuo. The crude was dissolved in water and purified by RP column chromatography with a mixture of MeCN/$H_2O$ (10% v/v) as an eluent. The desired compound 29 was obtained as a red powder, yield: 59% (0.073 mmol, 124 mg). $^1$H NMR spectra were recorded for $D_2O$ at rt and at 80° C. but the signals were very broad and subtle structure of multipletes or integrations could not be fully distinguished (see part NMR spectra). $^{13}$C NMR (126 MHz, $D_2O$) δ 182.5, 181.4, 180.2, 180.0, 179.4, 179.4, 178.2, 178.1, 177.5, 177.2, 176.0, 175.1, 174.6, 174.2, 168.4, 167.8, 144.3, 139.0, 137.7, 135.2, 132.4, 119.0, 113.8, 110.0, 106.7, 97.4, 89.0, 87.6, 81.3, 77.3, 76.8, 75.6, 71.1, 61.6, 58.7, 58.2, 56.2, 53.9, 50.5, 49.7, 47.6, 45.4, 45.2, 45.1, 41.8, 41.5, 37.4, 37.0, 36.6, 34.4, 34.3, 34.7, 34.0, 33.8, 30.1, 28.9, 28.5, 28.4, 27.1, 26.9, 22.3, 21.9, 21.8, 21.7, 21.5, 21.5, 19.3, 18.3, 17.8, 17.7. UV/vis ($H_2O$) $\lambda_{max}$ (nm) (ε, L $mol^{-1}$ $cm^{-1}$) 549(5.8× $10^3$), 520 (5.2×$10^3$), 361 (1.8×$10^4$), 276 (1.0×$10^4$), 222 (3.5×$10^4$). HRMS (ESI) m/z $[M+Na]^+$ calcd for $C_{76}H_{105}N_{21}O_{19}PCoNa$ 1728.6863, found 1728.6897. See, FIG. 50.

TABLE 18

| HPLC Method. See. FIG. 50. | | | | |
|---|---|---|---|---|
| Time [min] | $H_2O$ + 0.2% TFA [%] | MeCN [%] | λ [nm] | $R_1$ [min] |
| Initial | 90 | 10 | 361 | 6.63 |
| 15 | 30 | 70 | | |

STEP 3: Cbl-4xGly-OH (29) (80 mg, 0.047 mmol) and 2-(2-azidoethoxy)ethanamine (30) (300 μL) was dissolved in DMF (5 mL). EDC (90 mg, 0.470 mmol), HOBt (127 mg, 0.940 mmol) and DIPEA (0.470, 82 μL) were added. The resulting solution was stirred at rt for 1 h. Desired product, the product lacking CN ligand and the unreacted substrate were present in the reaction mixture in the approx. ratio 2.3:2.5:1 (according to RP-HPLC). The reaction mixture was diluted with MeOH (5 mL) and poured into $Et_2O$ (60 mL). The resulting precipitate was filtered through a cotton wool, washed with AcOEt (2×10 mL) and $Et_2O$ (2×10 mL). After drying, the resulting solid was dissolved in MeOH and concentrated in vacuo. Desired compound was purified by RP column chromatography with a mixture of MeCN/$H_2O$ (gradually from 8% to 40% v/v). Order of elution: substrate, desired product, product lacking CN ligand. The solvent was concentrated in vacuo and the product was obtained as a red solid. Yield of desired product 31 (with CN ligand): 41% (0.019 mmol, 35 mg), yield of product 31 without CN ligand (L=$H_2O$): 14% (0.007 mmol, 12 mg). $^1$H NMR (500 MHz, $CD_3OD$) δ 8.18 (s, 1H), 7.19 (s, 1H), 7.15 (s, 1H), 6.56 (s, 1H), 6.06 (s, 1H), 5.90 (d, J=2.9 Hz, 1H), 5.02 (dd, J=14.7, 3.5 Hz, 1H), 4.86-4.82 (m, 1H), 4.54 (td, J=8.4, 4.0 Hz, 1H), 4.49 (d, J=8.7 Hz, 1H), 4.44-4.33 (m, 2H), 4.13 (d, J=11.3 Hz, 1H), 4.09-4.04 (m, 1H), 4.02-3.81 (m, 8H), 3.69 (d, J=13.9 Hz, H), 3.66-3.60 (m, 3H), 3.55 (t, J=5.7 Hz, 2H), 3.38-3.34 (m, 4H), 3.25 (d, J=10.5 Hz, 1H), 3.09-3.06 (m, 2H), 2.90-2.85 (m, 2H), 2.73-2.31 (m, 19H), 2.27 (s, 3H), 2.24 (s, 3H), 2.22-1.97 (m, 5H), 1.96-1.80 (m, 3H), 1.89 (s, 3H), 1.77-1.68 (m, 1H), 1.49 (s, 3H), 1.380 (s, 3H), 1.375 (s, 3H), 1.32-1.24 (m, 1H), 1.28 (d, J=6.2 Hz, 3H), 1.20 (s, 3H), 1.15-1.07 (m, 1H), 0.44 (s, 3H), $^{13}$C NMR (126 MHz, $CD_3OD$) δ181.6, 180.1, 177.5, 177.3, 177.2, 176.6, 176.0, 175.6, 175.5, 175.3, 174.6, 174.2, 173.0, 172.7, 172.2, 171.7, 167.8, 166.9, 147.3, 143.3, 138.2, 135.8, 134.0, 131.3, 126.0, 117.8, 112.6, 108.8, 105.2, 95.8, 87.9, 86.4, 80.9, 80.7, 76.4, 75.0, 73.7, 73.6, 70.9, 70.4, 70.3, 66.9, 60.3, 57.7, 57.0, 55.5, 52.6, 51.8, 50.6, 46.8, 44.3, 44.0, 43.9, 43.5, 43.1, 40.4, 40.1, 36.2, 35.9, 35.4, 33.4, 32.9, 32.8, 32.6, 32.4, 32.3, 29.5, 27.4, 22.4, 20.9, 20.5, 20.4, 20.3, 19.9, 17.5, 17.1, 16.4, 16.1, 15.4.UV/vis ($H_2O$)$\lambda_{max}$(nm) (ε, L $mol^{-1}$ $cm^{-1}$) 548 (8.0×$10^3$), 520 (7.0×$10^3$), 361 (2.5×$10^4$), 279 (1.3×$10^4$), 222 (4.5×$10^4$). HRMS (ESI) m/z $[M+Na]^+$ calcd for $C_{80}H_{113}N_{25}O_{19}PCoNa$ 1840.7612, found 1840.7611. See, FIG. 50.

Because the resulting product 31 on its face appears to include a 5 Glycine polymer, e.g. "5xGly", it may be referred to herein using the term "5xGly". However, because during synthesis of on embodiment of a Glycine linker region (product 31) using 4 Gly groups, i.e. a "4xGly" polymer, there was an addition of an extra C=O and N—H from chemical reactants to the end of the 4 Gly polymer, resulting in the appearance of a $5^{th}$ Glycine group. Therefore, molecules containing product 31, see, FIG. 50, and related structures, may also be referred to as "4xGly" in addition to "5xGly", e.g. fluorescent Cbl constructs referred to as Cbl-4xGly and Cbl-5xGly, e.g. Cbl-5xGly comprising 4xGly; Cbl-5xGly-Fluorescent molecule comprising 4xGly, etc.

TABLE 19

HPLC Method. See. FIG. 50.

| Time [min] | H$_2$O + 0.2% TFA [%] | MeCN [%] | λ [nm] | R$_1$ [min] |
|---|---|---|---|---|
| Initial | 90 | 10 | 361 | 8.37 |
| 15 | 30 | 70 | | |

$^1$H and $^{13}$C NMR spectra were recorded on a Bruker 500 MHz or Varian 500 MHz spectrometer with the residual solvent peak used as an internal standard. Data are reported as follows: chemical shift [ppm], multiplicity (s=singlet, bs=broad singlet, d=doublet, t=triplet, q=quartet, m=multiplet), coupling constant and integration. HRMS spectra were recorded on a spectrometer with TOF mass analyzer.

The scale of the reactions with ATTO and Cyanine dyes did not provide sufficient amount of products for NMR analyses thus the HPLC and MS analyses were performed to characterize those compounds. During the synthesis of Cbl conjugates, the conversion of a substrate to a product was estimated based on a dye as the vitamin B 12 derivative was used in excess and was calculated using the integration of a signal coming from the dye in RP-HPLC analysis. Reactions used during the development of the present inventions, proceeded with the conversion >99% (on the HPLC chromatograms signals corresponding to the desired conjugate and the remaining azide were mainly observed. For Cbl-1xPEG-FAM, Cbl-2xPEG-FAM and Cbl-3xPEG-FAM signals in 1H NMR spectra recorded in CH$_3$OD were much broader comparing to Cbl-FAM and Cbl-C6-FAM and subtle structure of multiplates or integrations could not be fully distinguished.

Preparative chromatography was performed using LiChroprep® RP-18 gel (Merck) with redistilled water and HPLC grade MeCN as eluents. Progress of the reactions was monitored using RP-HPLC techniques. HPLC measurement conditions: column, Eurospher II 100-5, C18, 250 mm=4.6 mm with a precolumn or Kromasil C18 5 µm 250 mm×4.0 mm; detection, UV/vis; pressure, 10 MPa; temperature, 30'C; flow rate, 1 mL/min; wavelengths and HPLC methods are listed for each compound. Abbreviations: CDT—1,1'-Carbonyl-di-(1,2,4-triazole); RP HPLC—Reverse-phase high-performance liquid chromatography; TBTA—Tris[(1-benzyl-1H-1,2,3-triazol-4yl)methyl]amine; TEA—Triethylamine.

RNA Synthesis and Preparation

For in vitro experiments, DNA templates were amplified using recursive PCR and transcribed by T7 RNA polymerase using established methods. [reference 60]. Transcription reactions were purified using the appropriate percentage denaturing polyacrylamide gel (8 M urea, 29:1 acrylamide:bisacrylamide) based on RNA length. Transcripts were visualized by UV shadowing, excised from the gel and soaked overnight in 0.5×TE buffer (10 mM Tris-HCl, pH 8.0, 1 mM EDTA) at 4° C. RNAs were buffer exchanged into 0.5× TE and concentrated using centrifugal concentrators (Amicon) with the appropriate molecular weight cutoff. RNA concentration was determined using the absorbance at 260 nm and molar extinction coefficients calculated as the summation of the individual bases. Sequences and secondary structures of exemplary riboswitch RNAs used herein are shown in FIG. 6 and the published sequence for the Broccoli sequence was used (5'-GGA GCG CGG AGA CGG TCG GGT CCA GAT ATT CGT ATC TGT CGA GTA GAG TGT GGG CTC CGC GC)(SEQ ID NO: 18) [reference 26].

Absorbance Measurements and Quantum Yield Determination.

Absorbance spectra were collected using a Cary 500 UV-VIS-NIR spectrophotometer and buffer subtracted and measurements were reproducible compared with literature data. The quantum yield (Q) of probes was determined by comparison with the published quantum yield of ATTO590 (0.80, Atto tec) or the published quantum yield of Cy5 (0.28, Lumiprobe). Experiments were conducted in RNA buffer (100 mM KCl, 10 mM NaCl, 1 mM MgCl$_2$, 50 mM HEPES, pH 8.0). First, absorbance was determined at the excitation wavelength (Table 1B) for a dilution series of free fluorophore and the indicated Cbl-fluorophore probes in the presence and absence of different RNAs. To ensure saturation of binding, the concentration was chosen such that the final concentration of RNA was above 5 µM in the most diluted sample. The fluorescence spectrum at the emission range indicated in Table 1B for each sample was then recorded using a PTI-fluorimeter (1 nm steps, 1 s integration time, 2 nm slits for the excitation and 4 nm slits for detector). After subtracting the buffer background signal, the fluorescence signal for each sample was integrated and plotted vs. the absorption. The steepness of the resulting linear plot for each dilution series reports on the quantum yield relative to the reference of the free fluorophore (Table 8). These measurements were done once for the Q determination, and spectra were comparable with absorbance/fluorescence measurements done for fold fluorescence measurements.

Fluorescence Lifetime Measurements.

The fluorescence lifetime of Cbl-fluorophore probes in the presence and absence of RNA (see, Table 9) was measured in RNA buffer (100 mM KCl, 10 mM NaCl, 1 mM MgCl$_2$, 50 mM HEPES, pH 8.0) using Time-Correlated Single Photon Counting (TCSPC). A PicoQuant FluoTime 100 fluorescence spectrometer and PicoQuant Picosecond Pulsed Diode Laser Heads with wavelengths 561 nm (LDH-D-TA-560) and 640 nm (LDH-P-C-640B) were used in this measurement. Data were iteratively reconvoluted from the Instrument Response Function with one to three exponential decay functions, and the intensity weighted average lifetime values are reported.

Photobleaching Measurements.

For photobleaching experiments, indicated probes and RNA (Table 10) were mixed before about 3 to 4× of microscope immersion oil (Olympus immersion oil type-F) was added and the solution was emulsified to generate droplets. Samples were prepared in RNA buffer for Cbl-fluorophore samples (100 mM KCl, 10 mM NaCl, 1 mM MgCl$_2$, 50 mM HEPES, pH 8.0) and in Broccoli buffer (40 mM HEPES pH 7.4, 100 mM KCl, 1 mM MgCl$_2$) for the DFHBI-1T/Broccoli sample. The droplets were sandwiched between a glass slide and a coverslip. The sample was placed on the sample stage of a Nikon Ti-E HCA widefield fluorescence microscope with the coverslip facing a 20× objective lens. Samples were continuously illuminated throughout the experiment at the irradiance reported in Table 10. Photostability was assessed in part by fixing the excitation rate, i.e. the number of absorbed excitation photons were the same for Cbl-fluorophore/RNA samples and the DFHBI-1T/Broccoli sample. The high irradiance for the DFHBI-1T Broccoli sample is a result of its low extinction coefficient.

Images were acquired every 50 ms for DFHBI-1T/Broccoli and every 250 ms for others for 3 seconds, then every second for 47 seconds or longer, and the exposure time of each image was 15 ms for DFHBI-1T/Broccoli and 40 ms for others. A total of 6 to 15 droplets were analyzed for each sample.

In Vitro Fluorescence Measurements.

The concentration of Cbl-fluorophore probes, free fluorophores and free Cbl was determined using extinction coefficients listed in Table 1B. In vitro experiments were conducted in RNA buffer (100 mM KCl, 10 mM NaCl, 1 mM MgCl2, 50 mM HEPES, pH 8.0). For the Cbl-fluorophore probes, the extinction coefficient of the fluorophores was used to determine the concentration. The shape of the absorption spectra did not change significantly for the conjugated probes compared with the sum of spectra for free fluorophores and free Cbl (FIG. 7). The fluorescence intensity of each probe was measured in the presence or absence of RNA in RNA buffer as technical triplicates in a Tecan Safire-II fluorescence plate. The concentration of the probe was 0.25 µM or 0.5 µM and the RNA concentration was at least 5 µM, significantly above the dissociation constant (KD) of the RNAs tested [reference 30, 31]. Samples were incubated for at least 20 minutes (min) at room temperature in the dark to allow for Cbl-binding of the RNA prior to data collection. The excitation wavelength for each probe is listed in Table 1B and the emission spectrum was collected in 1 nm increments for the range listed in Table 1B. Each emission spectrum was buffer subtracted, integrated and normalized to the signal of the free fluorophore at the same concentration. Resulting % fluorescence measurements were reproducible for measurements on different days. Representative fluorescence spectra of probes in the presence and absence of RNA are shown in FIG. 10A-F.

Isothermal Titration Calorimetry (ITC)

ITC experiments were performed using protocols previously established and described [reference 30, 31]. Briefly, the RNA was dialyzed overnight at 4° C. into RNA buffer (100 mM KCl, 10 mM NaCl, 1 mM MgCl$_2$, 50 mM HEPES, pH 8.0) using 6-8000 Dalton molecular weight cutoff dialysis tubing (Spectra/Por). The dialysis buffer was used to dissolve Cbl and Cbl-5xPEG-ATTO590, and to dilute RNA To the desired concentration. The concentration of Cbl and Cbl-fluorophore probe was determined using the extinction coefficients listed in Table 1B. Titrations were performed at 25° C. using a MicroCal ITC 200 microcalorimeter (GE Healthcare) and data were fit using the Origin software suite as previously described [reference 61].

Estimation of Theoretical Photophysical Properties and Distances in Probes

The overlap integral J(1) of each fluorophore with Cbl absorbance was calculated from equation (1) [reference 62]

$$J(\lambda)=\int_0^\infty F_0(\lambda)\varepsilon_A(\lambda)\lambda^4 d\lambda \quad (1)$$

where $F_D$ is the emission spectrum of the fluorophore normalized to unity and e A is the extinction coefficient of the acceptor (Cbl) in M-1 cm-1 using a MATLAB script (ale—UV-Vis-IR Spectral Software 1.2, FluorTools, www.fluortools.com). To include the entire fluorescence emission spectrum of each fluorophore (FIG. 11A-E), fluorophores were excited 10 nm (nanometer) below the typical (Table 1B) excitation 1 and emission was collected 10 nm above the excitation 1 using a PTI-fluorimeter (1 nm steps, 1 s integration time, 2 nm slits for the excitation and 4 nm slits for detector). Cbl absorbance and fluorophore emission spectra (shown in FIG. 12 A-E) and were converted in units of $M^{-1}$ $cm^{-1}$ (for absorbance of Cbl) and to unity (for emission of fluorophores) to calculate J(1). The Förster distance R 0 was calculated from equation (2) [reference 62]

$$R_0=0.211(\kappa^2 n^{-4} Q_D J(\lambda))^{1/6} \quad (2)$$

where $\kappa^2$ is a factor describing the relative orientations of the transition dipoles and was assumed as $\kappa^2=2/3$ [reference 62] and the refractive index n was assumed to be 1.4 for aqueous solutions. The quantum yield Q of each donor fluorophore is available from the manufactures of the fluorophores and is listed in Table 3.

The maximal distance between quencher and fluorophore in each probe was estimated as the length of the chemical linker (listed in Table 4) plus the distance between the 5' hydroxyl moiety of Cbl (where the linker is attached) and the corrin ring in the structure of Cbl 30, assuming that this region of Cbl harbors quenching properties. The distance between 5' hydroxyl moiety and the corrin ring was estimated to be 9 Å from the Cbl crystal structure [reference 30]. This distance was added to each linker lengths, resulting in the distances listed in Table 6.

Construction of Plasmids for Mammalian Expression of RNA Tag Variants

Plasmids to produce RNA tags fused with RNA of interest in mammalian cells were constructed by standard molecular cloning techniques (see, FIG. 6 and exemplary plasmid constructs FIG. 17A-C, for additional constructs, for exemplary RNA aptamer sequences and see herein for exemplary RNA sequences for use as tagged RNA fusion constructs.

To construct mRNA fusions, a commercially available vector pmCherry-Cl (Clontech) was used as a starting point, since it harbors the CMV promoter for strong expression in mammalian cells. A NheI restriction site was introduced immediately following the stop codon by site directed mutagenesis. Different RNA sequences were inserted between the stop codon and the polyA site using existing KpnI and BrnHI restrictions sites. Inserts encoding for RNA tags were purchased as g-blocks or ultramers depending on sequence length with the appropriate restriction site overhangs from IDT. Exemplary sequences for RNA tags are shown in FIG. 6. The tRNA scaffold previously used in Spinach constructs [reference 22] was used in constructs and tested but as described herein, was not used in constructs for live cell imaging.

For ACTB mRNA fusions, the coding sequence of mCherry was replaced with the ACTB coding sequence. The ACTB coding sequence was PCR amplified from a plasmid producing a mNeonGreen-actin fusion (sequence was verified to be identical with *Homo sapiens* beta actin (ACTB), NCBI Reference Sequence NM_001101.3) by standard restriction based cloning using NheI restriction sites flanking the coding sequence of the mCherry gene.

NM_001101.3 *Homo sapiens* actin beta (ACTB), mRNA, of which at least a portion was used (SEQ ID NO: 19):

```
accgccgaga  ccgcgtccgc  cccgcgagca  cagagcctcg cctttgccga  tccgccgc    ccgtccacacc  gccgccagct caccatggat  gatgatatcg  ccgcgctcgt  cgtcgacaac ggctccggca  tgtgcaaggc  cggcttcgcg  ggcgacgatg ccccccgggc  cgtcttcccc  tccatcgtgg  ggcgccccag gcaccagggc  gtgatggtgg  gcatgggtca  gaaggattcc tatgtgggcg  acgaggacca  gagcaagaga  ggcatcctca
```

-continued

```
ccctgaagta ccccatcgag cacggcatcg tcaccaactg ggacgacatg gagaaaatct ggcaccacac cttctacaat gagctgcgtg tggctcccga ggagcaccc  gtgctgctga ccgaggcccc cctgaacccc aaggccaacc gcgagaagat gacccagatc atgtttgaga ccttcaacac cccagccatg tacgttgcta tccaggctgt gctatccctg tacgcctctg gccgtaccac tggcatcgtg atggactccg gtgacggggt cacccacact gtgcccatct acgaggggta tgccctcccc catgccatcc tgcgtctgga cctggctggc cgggacctga ctgactacct catgaagatc ctcaccgagc gcggctacag cttcaccacc acggccgagc gggaaatcgt gcgtgacatt aaggagaagc tgtgctacgt cgccctggac ttcgagcaag agatggccac ggctgcttcc agctcctccc tggagaagag ctacgagctg cctgacggcc aggtcatcac cattggcaat gagcggttcc gctgccctga ggcactcttc cagccttcct tcctgggcat ggagtcctgt ggcatccacg aaactacctt caactccatc atgaagtgtg acgtggacat ccgcaaagac ctgtacgcca acacagtgct gtctggcggc accaccatgt accctggcat tgccgacagg atgcagaagg agatcactgc cctggcaccc agcacaatga agatcaagat cattgctcct cctgagcgca agtactccgt gtggatcggc ggctccatcc tggcctcgct gtccaccttc cagcagatgt ggatcagcaa gcaggagtat gacgagtccg gcccctccat cgtccaccgc aaatgcttct aggcggacta tgacttagtt gcgttacacc ctttcttgac aaaacctaac ttgcgcagaa aacaagatga gattggactg gctttatttg tttttttgt  tttgttttgg tttttttttt tttttggct  tgactcagga tttaaaaact ggaacggtga aggtgacagc agtcggttgg agcgagcatc ccccaaagtt cacaatgtgg ccgaggactt tgattgcaca ttgttgtttt tttaatagtc attccaaata tgagatgcgt tgttacagga agtcccttgc catcctaaaa gccaccccac ttctctctaa ggagaatggc ccagtcctct cccaagtcca cacaggggag gtgatagcat tgctttcgtg taaattatgt aatgcaaaat tttttaatc  ttcgccttaa tacttttta ttttgtttta ttttgaatga tgagccttcg tgccccccct tccccctttt ttgtccccca acttgagatg tatgaaggct tttggtctcc ctgggagtgg gtggaggcag ccagggctta cctgtacact gacttgagac cagttgaata aaagtgcaca ccttaaaaat gaaaaaaaa  aaaaaaaaa  aaaaaaaaa aaaaaaaaaa aa
```

For mCherry fusions, DNA encoding RNA tags were purchased as ultramers or gblocks from IDT (Integrated DNA Technologies, Inc. 8180 N. McCormick Blvd. Skokie, Ill. 60076, USA) then added by standard restriction based cloning using existing KpnI and BamHI sites. The monomeric tags were introduced by ligating the first g-block into the plasmid with KpnI/BamHI restriction sites resulting in ACTB-(A)1x. Additional copies were introduced sequentially, where the second and third copy was encoded on a g-block with KpnI/KpnI and BamHI/BamHI restriction sites, respectively, resulting in ACTB-(A)2x and ACTB-(A)3x. ACTB-(A)4x was the result of the third ligation step, where colonies were screened for insertion of more than one copy of A. ACTB-(AT) 4x was constructed using the same strategy.

The 2xdBroccoli sequence [reference 26] to generate ACTB-2xdBroccoli was purchased as a g-block with KpnI and BamHI overhangs and ligated downstream of the ACTB sequence analogous to riboswitch RNA tags described above. Plasmids pAV5S-F30-2xdBroccoli and pAVU6+27-F30-2xdBroccoli [reference 42] (Addgene plasmid #66845 and #66842). The 1x and 2x copies of MS2 stem-loop (SL) sequences were purchased as g-blocks with KpnI and BamHI overhangs and ligated downstream of the ACTB sequence analogous to riboswitch RNA tags described above. The 4x MS2 SL sequence was generated by ligating another 2x MS2 SL g-block sequence with KpnI restriction sites on both ends in the ACTB-(MS2-SL)2x plasmid.

The 24xMS2 SL tag was built by first replacing the RNA tag downstream of ACTB with a short g-block sequence consisting of NotI and PmeI sites and flanking KpnI and BamHI sites using KpnI and BamHI sites. Plasmid ACTB-(MS2-SL)24x was then produced by cutting the 24x MS2-SL repeat from plasmid PGK1-24xMS2-SL [reference 12] with NotI and PmeI sites and ligating it downstream of the ACTB sequence via NotI and PmeI sites.

For U1 snRNA fusions, the plasmid pU1(human) [reference 63] was used to produce an $A_T$-tagged U1 snRNA. pU1 was modified to add the sequence of the RNA tag $A_T$ immediately following the first 11 nucleotides of U1, analogous to previous U1 snRNA fusions [reference 55]. Briefly, the parent plasmid was digested with two existing unique restriction sites (BglII is upstream of the U1 coding sequence and PstI is in the 3' region of the U1 coding sequence). An insert that contains the sequence for $A_T$ and the surrounding U1 coding sequence including both restriction sites was purchased as a g-block from IDT and ligated, resulting in $A_T$-U1. Plasmid sequences were verified by sequencing.

An exemplary DNA for U1 small nuclear 1 [*Homo sapiens* (human)]: a gene for U1 snRNA is found within the region encoding human U1 (chromosome 1, gene ID 26871) as gene RNU1-1 (also known as RNU1). Briefly, a U1 snRNA construct [reference 63] has, in operable combination, five snRNA-specific enhancer elements (A through E) in the 315-bp polymerase II promoter, a U1 coding sequence, and a U1 snRNA-specific termination sequence.

Transfections were performed with 10 µg of U1 DNA (plasmid), using a calcium phosphate precipitate protocol.

Cell Culture and Cell Lines.

U2-OS cells (received from Professor Roy Parker [reference 64], HeLa cells and 293T cells (both purchased from ATCC) were maintained in Dulbecco's modified eagle medium (DMEM, Gibco) supplemented with 10% fetal bovine serum (FBS; Gibco) at 37° C. with 5% $CO_2$. To generate a U2-OS cell line that stably produces GFP-G3BP1, the GFP-G3BP1 coding sequence was PCR amplified from a peGFP-C1-based cloning vector (received from Professor Roy Parker) using EcoRI and NotI restriction site overhangs. The PCR product was ligated into a Piggybac Dual Promoter plasmid that includes a Puromycin resistance cassette for selection and a CMV promoter for GFP-G3BP1 expression (System Biosciences, Catalog #PB510B-1), resulting in plasmid pGFP-G3BP1-Piggybac. This plasmid was sequence verified. U2-OS cells were chemically transfected with pGFP-G3BP1-Piggybac and Super PiggyBac Transposase expression vector (System Biosciences, Catalog #PB220PA-1) using the TransIT transfection system according to manufacturer recommendations (Mirus). Selected for genomic integration using was started 3 days after transfection using 1 μg/mL Puromycin and continued for 7-10 days. After selection, U2-OS cells stably producing GFP-G3BP1 were FACS enriched for the brightest 30% of GFP-fluorescent cells. After FACS enrichment, cell aliquots were used for up to 10 additional passages.

To generate a U2-OS cell line that stably produces MS2-GFP, plasmid pMS2-GFP (Addgene plasmid #27121) was PCR amplified with XbaI and NotI restriction site overhangs and ligated into the Piggybac Dual Promoter plasmid described above. Transfection in U2-OS cells with a Halo-G3BP1 genetic background, selection and FACS enrichment was done as described above.

Introduction of an N-terminal 3xFLAG-HALO epitope tag to the endogenous G3BP1 protein was performed as previously described [reference 65] with the following modifications (FIG. 38A-E). First, two single-strand breaks were generated flanking the translational start site of G3BP1 with dual CRISPR-Cas9 nickases (D10A) in U2-OS cells. Correct targeting of CRISPR guides was confirmed by T7 Endonuclease assay (NEB). Cells were selected with Puromyocin to enrich for edited cells containing the sequence for the tags and the LoxP-flanked, SV40-driven Puromycin expression cassette. Removal of the Puromyocin expression cassette and in frame expression of 3xFlag-HALO was achieved by transient transfection of eGFP-Cre plasmid. Transiently transfected cells were enriched by FACS sorting into a population. Correctly edited cells were confirmed by PCR, Western blot and immunofluorescence using standard protocols.

Halo-Staining.

Halo dyes JF585, SiR594 and JF646 were gifts from Professor Luke Lavis. Cells were incubated with 1 μM Halo dye in DMEM/5% FBS media for 20 min at 37° C./5% CO2. Unbound dye was washed out by replacing the media first with PBS and then with DMEM/S % FBS media before further treatment was performed (arsenite treatment, bead loading, see below).

Bead Loading.

Cells were seeded in home-made imaging dishes (35 mm diameter) with a ~10 mm center hole covered by cover glass (No. 1.5, VWR). To introduce the probe, the culture media was removed and the Cbl-fluorophore probe (3 μL of a 50 μM stock in PBS for U-body imaging in HeLa cells, 3 μL of a 0.5 μM stock in PBS for mRNA imaging via Cbl-Cy5 in U2-OS cells and 3 μL of a 5 μM stock in PBS for mRNA imaging via Cbl-5xGly-ATTO590 comprising 4xGly in U2-OS cells) was added directly on the cell in the center of the imaging dish. Microbeads were sprinkled onto the cells [reference 44-46] and the dish was tapped on the cell culture surface 7-8 times. Standard culture media was added immediately. For stress granules imaging, media was supplemented with 0.5 mM sodium arsenite.

Stress Granule (SG) Assay.

U2-OS cells stably producing GFP-G3BP1 or genomically producing Halo-G3BP1 were seeded at $0.25 \times 10^6$ cells in imaging dishes. One day after seeding, cells were chemically transfected with typically 2-μg plasmid DNA (1 μg of the ACTB plasmid fused with an RNA tag of interest mixed with 1 μg of the transfection marker pNLS-TagBFP (in pcDNA)) using the TransIT transfection system following manufacturer recommendations (Mirus). On the next day, cells were stained and bead loaded with the Cbl-fluorophore probe as described above. The media that was added after bead loading contained 0.5 mM sodium arsenite and cells were incubated at 37° C./5% CO 2 for 30-45 min to induce stress granules. Cells were rinsed once in PBS and Fluorobrite media (Gibco), supplemented with 0.5 mM sodium arsenite, was added for live cell imaging. For correlative live/fixed imaging where cells were first imaged live, followed by fixation and FISH/immunofluorescence imaging of the same cells, the following modifications were made to the protocol above. Instead of home-made imaging dishes, gridded imaging dishes (MatTek) were used. Dishes were coated with 1 μg/mL fibronectin (Sigma) for 4 hours and fibronectin was rinsed once with full media before cells were seeded. Because plasmid ACTB-(AT) 4x was used, a higher concentration of Cbl-5xPEG-ATTO590 was bead loaded (3 μL of 50 μM probe).

U-Body Assay.

HeLa cells were seeded at $0.1$-$0.15 \times 10^6$ cells per imaging dish. One day after seeding, cells were chemically transfected with 1 μg plasmid DNA (AT-U1) using the TransIT transfection system following manufacturer recommendations (Mirus). For experiments with marker proteins, 0.25 μg of GFP-SMN 66 (a gift from Greg Matera, Addgene plasmid #37057) was co-transfected. For colocalization experiments with Coilin, 0.5 μg pEGFP-coilin 67 (a gift from Greg Matera, Addgene plasmid #36906) was transfected with or without co-transfection of 0.5 μg plasmid DNA encoding for AT-U1. Imaging or fixation was performed the following day.

For live cell imaging, cells were treated with 10 μM Thapsigargin for 3 hours before bead loading with the Cbl-fluorophore probe and imaged within 1 hour after bead loading.

For immunofluorescence or FISH analysis, cells were fixed 3-4 hours after Thapsigargin treatment.

Fluorescence Microscopy and Image Analysis.

Fluorescence microscopy on live and fixed cells was performed on a Nikon A1R Laser Scanning Confocal Microscope with a 100× oil objective (1.45 NA, Plan Apo I), a pixel size of 0.25 μm and an integration time of 2.2 μsec unless otherwise noted below. Images were acquired at 16-bit depth with Nikon Elements Software and processed in ImageJ2 using the Fiji plugin. Live images were acquired with an environment chamber at 37° C. Laser lines used were 405 nm (for nuclear staining and NLS-TagBFP imaging), 488 nm (for GFP-tagged proteins), 561 nm (for ATTO590 in Cbl-fluorophore probes and Alexa 546, Alexa 594 and Alexa 568 in FISH probes and secondary antibodies and for Halo-dyes JF595 and SiR594) and 638 nm (for Cy5 and Halo-dye JF646).

For live imaging of SGs tagged with the aptamer A bound to the Cbl-Cy5 probe in U2-OS cells, the pinhole was 67.7 μm and the laser settings were as follows. For the DAPI channel, the laser was set at 1.0 (HV=100), for the TRITC channel the laser was set at 0.4 (HV=20), for the Cy5 channel the laser was set at 12.0 (HV=100). The signal was integrated 4× for each acquisition. For live imaging of SGs tagged with the aptamer A bound to the Cbl-5xGly-ATTO590 comprising 4xGly probe in U2-OS cells, the pinhole was 67.7 μm and the laser settings were as follows. For the DAPI channel, the laser was set at 1.0 (HV=100), for the TRITC channel the laser was set at 1.0 (HV=80), for the Cy5 channel the laser was set at 5.0 (HV=100). For correlative imaging to visualize the same stress granules samples live and fixed, the pinhole size was 67.7 µm. In this case, the laser power for live imaging was 1.0 (HV=40) for the 488-laser line and 7.0 (HV=110) for the 638 nm laser line (the signal was not integrated).

Fixed images for correlative imaging of stress granules were collected using a 40× Plan Apo Air objective (26.8 µm pinhole) with Nyquist sampling at 0.16 µm per pixel. The laser power for the 488 nm laser line was 2.0 (HV=40) and the laser power was 1.0 for the 461 nm laser line (HV=40).

For live imaging of SGs tagged with 2xdBroccoli in U2-OS cells, the pinhole was 67.7 µm and the laser settings were as follows. For the DAPI channel, the laser was set at 5.0 (HV=110), for the GFP channel the laser was set at 1.0 (HV=110), for the TRITC channel the laser was set at 1.0 (HV=40). For live imaging of SGs tagged with MS2 stem-loop repeats in U2-OS cells, the pinhole was 67.7 µm and the laser settings were as follows. For the DAPI channel, the laser was set at 5.0 (HV=110), for the GFP channel the laser was adjusted for optimal contrast without detector saturation (approximately 1.0-2.5) (HV approximately 60-100), for the TRITC channel the laser was set at 0.9 (HV=40).

For imaging of transiently produced ACTB mRNA and stress granules in fixed samples, the pinhole size was 63.9 µm, the power of the 488 nm laser line was 1.5 (80 V gain), the power of the 561 nm laser line was 2.0 (110 V gain) and the power of the 636 nm laser line was 6.0 (110 V gain). For imaging of endogenous ACTB mRNA, the pinhole was 58.7 µm, the laser power of the 488 nm laser line was 0.4 (40 V gain) and the laser power of the 638 nm laser line was 12 (120 V gain). The signal from the 638 nm laser line was integrated 16 times.

For live imaging of HeLa cells, the pinhole was 51.1 µm, the laser power for the 561 nm laser line was 2-5 with a gain of 50-80 V (adjusted for optimal contrast to account for differences in bead loading efficiency) and the laser power for the 488 nm laser line was 0.5 (50 V gain).

For live imaging of GFP-SMN with or without co-transfection of a plasmid to produce $A_T$-U1 RNA, the pinhole was 51.1 µm, the laser power for the 561 nm laser line was 2 (50 V gain) and the laser power for the 488 nm laser was 0.5. The gain was adjusted for optimal signal without over-exposure of puncta in the green channel (30 V gain for the single GFP-SMN cells shown in FIG. 37 and 50 V gain for the double transfected cell shown in FIG. 5C).

For imaging of endogenous SMN and DDX20 simultaneous with U1 snRNA (either endogenous U1 snRNA or transfected to produce AT-U1 snRNA) in fixed HeLa cells, the pinhole was 49.8 µm, the laser power for the 405 nm laser line was 2.0 (90 V gain), the laser power for the 561 nm laser line was 0.3 for SMN imaging and 1.0 for DDX20 imaging (40 V gain) and the laser power for the 638 nm laser line was 10.0 (120 V gain). For imaging of transiently co-transfected GFP-SMN and AT-tagged U1 in fixed HeLa cells, the pinhole was 49.8 µm, the laser power for the 488 nm laser line was 0.3 (25 V gain) and the laser power for the 638 nm laser line was 10.0 (120 V gain). For imaging of coilin colocalization in fixed HeLa cells, the pinhole was 0.8 AU, the laser power for the 405 nm laser line was 1.0 (100 V gain), the laser power for the 488 nm laser line was 2.0 (40 V gain) and the laser power for the 638 nm laser line was 4.0 (110 V gain). For live imaging of Broccoli-tagged 5S and U6 RNA, published protocols were used [reference 26]. Briefly, plasmids pAVU6+27-F30-2xdBroccoli and pAV5S-F30-2xdBroccoli [reference 26] were transfected in HEK293T cells and split into imaging dishes 48 h post transfection. 24 h later, DFHBI-1T was added at a final concentration of 40 µM and cells were imaged under widefield illumination conditions as recommended 26 using a 60× oil objective and 250 ms exposure. No ND filters were used.

Immunofluorescence.

Cells were fixed in 4% paraformaldehyde (EM grade, Electron Microscopy Sciences) for 10 min and slides were rinse three times in PBS and permeabilized for 10 min in PBS/0.2% Triton X-100 at room temperature, followed by three rinses in PBS. After blocking for 30 min at room temperature in PBS/5% FBS, slides were incubated with the primary antibody against DDX20 or SMN (both 1:200 dilution) in PBS/5% FBS at 4° C. overnight. The DDX20 antibody was a mouse monoclonal antibody (sc-57007, Santa Cruz Biotechnology) and the SMN antibody was a rabbit polyclonal antibody (sc-15320, Santa Cruz Biotechnology). After three rinses in PBS, slides were incubated with the secondary antibody (1:1,000 dilution in both cases) and Hoechst nuclear dye (1:10,000 dilution) for 90 min at room temperature. The secondary antibody for DDX20 was a goat anti-mouse Alexa 594 antibody (Invitrogen) and the secondary antibody for SMN was a donkey anti-rabbit Alexa 568 antibody (Invitrogen). Slides were rinsed three times in PBS and once in water. If no FISH was performed subsequently, slides were mounted.

Fluorescence In Situ Hybridization (FISH).

When no IF was performed prior to FISH, cells were fixed in 4% paraformaldehyde and permeabilized in 0.2% Triton X-100 as described above. When FISH was performed after IF, no additional permeabilization step was performed. Cells were dehydrated sequentially in 70%, 95% and 100% ethanol for 5 minutes each. After A Two minute drying step, cells were rehydrated in 2×SSC (1× SSC is 150 mM NaCl, 15 mM sodium citrate dihydrate, pH 7.0)/50% formamide (molecular biology grade) for 5 min. Slides were pre-hydrated in pre-hybridization solution for 30 min at 37° C. The pre-hybridization solution contained 50% formamide, 2×SSC, 0.5 mg/mL UltraPure Salmon sperm DNA (ThermoFisher Scientific), 1 mg/mL UltraPure BSA (ThermoFisher Scientific), 0.13 mg/mL *E. coli* tRNA (Sigma Aldrich), 1 mM Vanadyl ribonucleoside complexes solution (Signal Aldrich) and 100 mg/mL dextran sulfate in ultrapure water. After pre-hybridization, samples were hybridized with the probe in pre-hybridization solution (see Table 12 for properties) overnight at 37° C. On the following day, samples were washed twice in 2×SSC/50% formamide for 30 minutes each. Slides were rinsed in PBS once and sealed.

Northern Blotting.

The production and processing of aptamer fusion variants was assessed in 293T cells. Prior to seeding, dishes were coated with 10 µg/mL Poly-L-Lysine for 1 hour (h) and rinsed. For each aptamer variant, approximately 2×10⁶ cells were seeded in a 10 cm dish. On the following day, 15-µg plasmid DNA was transfected per 10 cm dish using the TransIT (Mirus) chemical transfection system according to the manufacturer's recommendations. Cells were harvested 48 h after transfection and cell pellets were frozen at −80° C.

The total RNA was extracted using the RNeasy (Qiagen) kit according to the manufacturer's recommendation. Briefly, cell pellets were thawed on ice, resuspended in buffer RLT and lysed by passing six times through a syringe needle. The lysate was supplemented with 70% ethanol and applied to an RNeasy spin column. After on-column DNase treatment and washing steps, RNA was eluted in water. The final RNA concentration was typically 500-1000 ng/μL. The RNA was stored at −80'C for no longer than one week before proceeding.

Solutions for gel electrophoresis and Northern blotting were made in diethylpyrocarbonate (DEPC)-treated and autoclaved water to ensure removal of RNase. For each blot, RNA samples were normalized for total RNA amount (10 μg total RNA per lane). Samples with the desired amount of total RNA were tried in a SpeedVac and the RNA was brought up in 15 μL of RNA sample buffer (50% v/v formamide, 6.3% v/v formaldehyde, 0.2M MOPS, 50 mM sodium acetate pH 5.2, 10 mM EDTA pH 8.0) plus 2 μL of RNA loading buffer (50% glycerol, 1 mM EDTA pH 8.0, 0.4% Bromophenol blue, 1 mg/mL ethidium bromide). The samples were heated at 65° C. for 5 min and then loaded on a 1% agarose/formaldehyde gel (50 mM sodium acetate pH 5.2, 10 mM EDTA pH 8.0, 1% w/v agarose, 6.3% formaldehyde). 10 μL of a Low Range ssRNA Ladder (New England Biolabs) was loaded as well. The gel was run in running buffer (50 mM sodium acetate pH 5.2, 10 mM EDTA pH 8.0, 6.3% formaldehyde) at 60 V for 2.5 h. To assess the quality of the isolated RNA, the gel was then stained with ethidium bromide (10 μL of 10 mg/mL ethidium bromide in 400 mL running buffer).

After destaining in water for 5 min, the RNA was transferred to a nylon membrane as follows. Immersed in 10×SSC, two pieces of Whatman paper were placed on a stack of blotting paper, followed by the agarose gel and the pre-wet membrane (Amersham Hybond-N+, GE Healthcare). The membrane was covered with two pieces of pre-wet Whatman paper and the RNA was allowed to transfer to the membrane by capillary transfer overnight. The RNA was then crosslinked to the membrane by exposure to UV light, followed by a washing step in 0.1× SSC and 0.1% sodium dodecyl sulfate (SDS) at 65° C. for 1 h. The membrane was prehybridized for 1 h in hybridization solution (6×SSC, 10×Denhardts solution (Life Technologies), 0.1% SDS) at 42° C. The membrane was then incubated with hybridization solution supplemented with the radioactive, labeled probe overnight at 42° C. After 3 wash steps for 5 min at room temperature in washing solution (6×SSC, 0.1% SDS) and an additional wash step at 48° C. for 20 minutes, the membrane was tried and exposed overnight. Exposure and visualization of the $^{32}$P signal was done using the Phosphor Screen and Cassette System from GE Healthcare. The membrane was stripped by repeated microwaving in 0.1×SSC, 0.1% SDS to subsequently hybridize with another probe. Radioactive probes were produced as follows. The sequence of each probe is indicated in Table 6 and probes were purchased as DNA primers from IDT. From a 100 μM stock of this DNA primer, 2 μL were mixed with 2 μL 32 P-ATP, 2 μL T4 Polynucleotide Kinase (PNK) (NEB), 2 μL of 10× T4 PNK buffer (NEB) in water and incubated at 37° C. for at least 1 hour. The DNA was then passed over a G-25 column (GE Healthcare) according to the manufacturer's recommendations to remove unincorporated ATP.

II. Exemplary Methods, Associated at Least in Part, for Embodiments Comprising a 12x Riboglow Tag, are Described as Follows.

Cloning and Mammalian Cell Biology

A construct to tag ACTB with 12 copies of Riboglow was derived from ACTB-A(4×), as described herein. Briefly, the entire region of the four-repeat A sequence was PCR amplified with either PstI or XbaI overhangs. Plasmid ACTB-A (4×) has unique PstI and XbaI sites flanking the A repeat, and the 8mer and 12mer A repeat was generated by sequential ligation using standard molecular cloning protocols (FIG. 39A-B). Relevant DNA coding sequences are listed in Table 16. Constructs were sequence verified.

U2-OS cells were maintained in Dulbecco's modified eagle medium (DMEM, Gibco) supplemented with 10% FBS (Gibco) at 37° C./5% $CO_2$. For imaging experiments, U2-OS cells were seeded at $0.2 \times 10^6$ cells in homemade imaging dishes (as described herein). One day after seeding, cells were chemically transfected with 2 μg plasmid DNA (1 μg of the ACTB-RNA tag fusion mixed with 1 μg of a transfection marker, pNLS-TagBFP, as described herein) using the TransIT transfection system following manufacturer recommendations (Mirus). On the day of the imaging experiment, 3 μL of a 50 μM stock of Cbl-4xGly-ATTO590 were bead loaded [reference 54] per imaging dish, as described herein.

Fab Generation and Dye-Conjugation.

Fab generation was done using the Pierce mouse IgG1 preparation kit (Thermo Fisher Scientific) per the manufacturer's instructions. Briefly, beads conjugated with ficin were incubated in 25 mM cysteine to digest FLAG (Wako, 012-22384 Anti DYKDDDDK mouse $IgG_{2b}$ monoclonal) antibodies to generate Fab. Fab were separated from the digested Fc region using a NAb Protein A column (Thermo Scientific, product #1860592). Fab were concentrated to approximately 1 mg/ml and conjugated to Alexa Fluor 488 (A488). A488 tetrafluorophenyl ester (Invitrogen) was suspended in DMSO and stored at −20° C. 100 μg of Fab were mixed with 10 μL of 1M $NaHCO_3$, to a final volume of 100 μL. 5 μl of A488 was added to this 100 μL mixture and incubated for 2 hours at room temperature with end-over-end rotation. The dye conjugated Fab were eluted from a PBS equilibrated PD-mini G-25 desalting column (GE Healthcare) to remove unconjugated dye. Dye conjugated Fabs then were concentrated in an Ultrafree 0.5 filter (10 k-cut off; Millipore) to 1 mg/ml. This conjugation and concentration process was repeated on occasion to ensure a degree of labeling close to one. The ratio of Fab:dye, $A_{rat}$, was determined using the absorbance at 280 and 495 nm, the extinction coefficient of IgG at 280 nm, $\varepsilon_{IgG}$, the extinction coefficient of the dye, $\varepsilon_{dye}$, provided by the manufacturer, and the dye correction factor at 280 nm, CF, provided by the manufacturer. The degree of labeling, DOL, was calculated with the following formula:

$$DOL = \left(\frac{\varepsilon_{IgG}}{\varepsilon_{dye}}\right)\left(\frac{1}{(A_{rat})^{-1} - CF}\right). \quad \text{(equation 1)}$$

Fab calculated with a DOL approximately 1 were used in experiments.

Single Molecule Live Imaging.

Single molecule live cell imaging was carried out on a Nikon N-STORM microscope, equipped with a TIRF illuminator, 405 nm, 488 nm, 561 nm, and 647 nm laser lines, an environmental chamber to control humidity and temperature, an ORCA-Flash4.0 V2 C11440 sCMOS camera (Hamamatsu) (unless otherwise indicated), a 100× oil-immersion objective (Nikon, NA=1.49), two filter wheels, and the appropriate filter sets. Cells were cultured on homemade imaging dishes as described previously [as described herein]. Unless otherwise noted, cells were transfected with a plasmid to produce tagged mRNA 24 h prior to imaging. For Riboglow imaging, 3 μL of a 5 μM stock of the Cbl-fluorophore probe Cbl-4xGly-ATTO 590 comprising 4xGly were bead loaded immediately prior to imaging as described previously [as described herein], unless otherwise indicated. Cells were washed 3 times with PBS, and medium was replaced with FluoroBrite medium (Gibco). Imaging was performed under HILO conditions [reference 49] at 37° C. and 5% $CO_2$. Details on imaging acquisition conditions are summarized in Table 17.

Particle Detection and Tracking.

Particles were detected using the FIJI plugin TrackMate [reference 52] (version 3.8.0). Movies were divided into small regions of interest (ROI), as illustrated in FIG. 40A. Because a low density of particles is optimal to allow for tracking of the same particles across frames, regions towards the edge of the cell were chosen frequently as ROIs. This was done for 24xMS2-SL tagged mRNA and for Riboglow-tagged mRNA, such that any resulting bias affects both mRNA tags. Detection in TrackMate was performed with the LoG detector, an estimated blob size of 0.5 micron, and a Signal/Noise ratio of 0.5-1.0 was used as a filter for each ROI (adjusted manually). For tracking, the simple LAP tracker was used. Linking maximum distance and Gap-closing maximum distance were both set to 0.5 micron, and Gap-closing maximum frame gap was set as 2. Resulting tracks were further filtered to only include tracks with 30 frames per spot. Spot detection, tracking and filters were manually validated by inspecting each ROI movie.

Classification of tracks was done by the TraJClassifier [reference 53]. The minimal track length was set to 30 frames. Results from tracking are reported as mean values±standard error, unless otherwise indicated.

Translation Assay.

U2-OS cells seeded on home-made imaging dishes as described above were bead loaded with a mix of 1 μg plasmid DNA encoding for the SM-KDM5B translation reporter, 3 μL of a 5 μM stock of the Cbl-fluorophore probe Cbl-4xGly-ATTO 590 and 1 μL of Alexa488-labeled Fab to bind N-terminal FLAG tags in the reporter. After 6-8 hours, cells were washed 3 times with PBS, and medium was replaced with FluoroBrite medium (Gibco). Imaging was performed under HILO conditions [reference 49] at 37° C. and 5% $CO_2$ using an Andor Ixon Ultra DU897U-C50 EMCCD camera. Details on imaging acquisition conditions are summarized in Table 17. When indicated, puromycin was added during the image acquisition at a final concentration of 50 μg/mL.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in medicine, molecular biology, cell biology, microscopy, genetics, statistics or related fields are intended to be within the scope of the following claims.

The invention claimed is:

1. A composition comprising a riboswitch RNA fusion product and a cobalamin conjugate, wherein said riboswitch RNA fusion product has an RNA sequence of interest attached to a RNA tag comprising a cobalamin (Cbl)-binding aptamer and riboswitch sequence.

2. The composition of claim 1, wherein said RNA tag comprises 4 up to 15 copies of a cobalamin (Cbl)-binding aptamer.

3. The composition of claim 1, wherein said RNA tag comprises 8 up to 14 copies of a cobalamin (Cbl)-binding aptamer.

4. The composition of claim 1, wherein said RNA tag comprises 12 copies of a cobalamin (Cbl)-binding aptamer.

5. The composition of claim 1, wherein a plurality of cobalamin conjugates are bound to said aptamers.

6. The composition of claim 1, wherein said cobalamin conjugate is selected from the group consisting of a fluorophore conjugate and a therapeutic drug conjugate.

7. The composition of claim 1, wherein said RNA sequence of interest is a noncoding RNA.

8. The composition of claim 1, wherein said RNA sequence of interest is a mRNA.

9. The composition of claim 8, further comprising a fluorescently tagged protein expressed by said mRNA sequence of interest.

10. The composition of claim 6, wherein said therapeutic drug is selected from the group consisting of a small molecule, GSK2606414, one or more poly-ADP-ribose polymerase (PARP) inhibitors, one or more PARP activators, one or more PARP11 activators, and a therapeutic nucleotide molecule.

11. A method for treating a neurodegenerative disease:
a) providing;
    i) a patient exhibiting at least one symptom of a neurodegenerative disease,
    ii) a riboswitch RNA fusion product, wherein said riboswitch RNA fusion product has a RNA tag attached to a RNA sequence of interest, wherein said RNA tag comprises a cobalamin (Cbl)-binding aptamer and a riboswitch sequence, wherein said RNA sequence of interest is capable of becoming a part of a stress granule; and
    iii) a plurality of Cbl RNA probes, wherein said probes are conjugates of Cbl-therapeutic drug; and
b) administering said riboswitch RNA fusion products to said patient under conditions such that said tag RNA sequence is incorporated into said stress granule; and
c) delivering said plurality of Cbl RNA probes to said patient whereas said probes bind to said cobalamin (Cbl)-binding aptamer of said RNA tag such that said at least one symptom of a neurodegenerative disease is reduced.

12. The method of claim 1, wherein said patient further comprises at least one intraneuronal stress granule.

13. The method of claim 1, wherein said at least one intraneuronal stress granule comprises said at least one RNA molecule of interest.

14. The method of claim 1, wherein said therapeutic drug disrupts said stress granule.

15. The method of claim 1, wherein said therapeutic drug slows or inhibits progression of said neurodegenerative disease selected from the group consisting of amyotrophic lateral sclerosis (ALS), Alzheimer's disease, frontotemporal lobar degeneration (FTLD), repetitive head trauma, and other dementias.

16. The method of claim 1, wherein said therapeutic agent is selected from the group consisting of a small molecule, GSIC-)606414, one or more poly-ADP ribose polymerase (PARP) inhibitors, one or more PARP activators, one or more PARP11 activators, and A therapeutic nucleotide molecule.

17. The method of claim 1, wherein said RNA tag comprises 4 up to 15 copies of a cobalamin (Cbl)-binding aptamer.

18. The method of claim 1, wherein said RNA tag comprises 8 up to 14 copies of a cobalamin (Cbl)-binding aptamer.

19. The method of claim 1, wherein said RNA tag comprises 12 copies of a cobalamin (Cbl)-binding aptamer.

* * * * *

SEQUENCE LISTING

```
<160> NUMBER OF SEQ ID NOS: 19

<210> SEQ ID NO 1
<211> LENGTH: 102
<212> TYPE: RNA
<213> ORGANISM: Artificial Sequence
<220> FEATURE:
<223> OTHER INFORMATION: Synthetic

<400> SEQUENCE: 1
ggccuaaaag cguaguggga aagugacgug aaauucgucc agauuacuug auacgguuau      60
acuccgaaug ccaccuaggc cauacaacga gcaaggagac uc                       102

<210> SEQ ID NO 2
<211> LENGTH: 81
<212> TYPE: RNA
<213> ORGANISM: Artificial Sequence
<220> FEATURE:
<223> OTHER INFORMATION: Synthetic

<400> SEQUENCE: 2
ggccuaaaag cguaguggga aagugacgug aaauucgucc agauuacuug auacgguuau      60
acuccgaaug ccaccuaggc c                                               81

<210> SEQ ID NO 3
<211> LENGTH: 81
<212> TYPE: RNA
<213> ORGANISM: Artificial Sequence
<220> FEATURE:
<223> OTHER INFORMATION: Synthetic

<400> SEQUENCE: 3
ggccuaaaag cguaguggga aagugacgug aaauucgucc agauuacuug auacgguuau      60
```
acuccguuuu ccaccuaggc c                                       81

<210> SEQ ID NO 4
<211> LENGTH: 141
<212> TYPE: RNA
<213> ORGANISM: Artificial Sequence
<220> FEATURE:
<223> OTHER INFORMATION: Synthetic

<400> SEQUENCE: 4
gguacugaaa gcguggcuggg aaacaaugug aaauucauug acuguuccug caacgguaaa     60
aguaaaauug aguccgaaug ccacccagua aaguccgcug ucgagugaag gccaggaaaa    120
gucuaacucu gcaauauuaa a                                      141

<210> SEQ ID NO 5
<211> LENGTH: 149
<212> TYPE: RNA
<213> ORGANISM: Artificial Sequence
<220> FEATURE:
<223> OTHER INFORMATION: Synthetic

<400> SEQUENCE: 5
ggacaucggu uuuaguggg aacagccacu aaaauaaugg ggaaaguuug gugcaaguccc     60 aacacugucc cgcagcugua agcagacuau cucugugagu cagaacgccc accgaugucc    120
cccguaaaca cuucgcgag guacagaaa                               149

<210> SEQ ID NO 6
<211> LENGTH: 130
<212> TYPE: RNA
<213> ORGANISM: Artificial Sequence
<220> FEATURE:
<223> OTHER INFORMATION: Synthetic

<400> SEQUENCE: 6
uacugaaagc gugugggaa acaaugugaa agucauugac uguccugca acgguaagcg      60 cuucggcgcg aguccgaaug ccacccagua aaguccgcug ucgagugaag gccaggaaaa    120
gucuaacuca                                                    130

<210> SEQ ID NO 7
<211> LENGTH: 45
<212> TYPE: DNA
<213> ORGANISM: Artificial Sequence
<220> FEATURE:
<223> OTHER INFORMATION: Synthetic

<400> SEQUENCE: 7
cacagcttct ccttaatgtc acgcacgatt tcccgctcgg ccgtg              45

<210> SEQ ID NO 8
<211> LENGTH: 40
<212> TYPE: DNA
<213> ORGANISM: Artificial Sequence
<220> FEATURE:
<223> OTHER INFORMATION: Synthetic

<400> SEQUENCE: 8
cctaggtggc attcggagta taaccgtatc aagtaatctg                     40

<210> SEQ ID NO 9
<211> LENGTH: 40
<212> TYPE: DNA
<213> ORGANISM: Artificial Sequence

```
<220> FEATURE:
<223> OTHER INFORMATION: Synthetic

<400> SEQUENCE: 9
cctaggtggc attcggagta taaccgtatc aagtaatctg                              40

<210> SEQ ID NO 10
<211> LENGTH: 27
<212> TYPE: DNA
<213> ORGANISM: Artificial Sequence
<220> FEATURE:
<223> OTHER INFORMATION: Synthetic

<400> SEQUENCE: 10
ttgccatgaa tgatccagcc cacactc                                            27

<210> SEQ ID NO 11
<211> LENGTH: 38
<212> TYPE: DNA
<213> ORGANISM: Artificial Sequence
<220> FEATURE:
<223> OTHER INFORMATION: Synthetic

<400> SEQUENCE: 11
gtttaaacga attcgcccct tagatctgatg aaccctgg                               38

<210> SEQ ID NO 12
<211> LENGTH: 44
<212> TYPE: DNA
<213> ORGANISM: Artificial Sequence
<220> FEATURE:
<223> OTHER INFORMATION: Synthetic

<400> SEQUENCE: 12
tcagcacatc cggagtgcaa tggataagcc tcgccctggg aaaa                         44

<210> SEQ ID NO 13
<211> LENGTH: 15
<212> TYPE: DNA
<213> ORGANISM: Artificial Sequence
<220> FEATURE:
<223> OTHER INFORMATION: Synthetic

<400> SEQUENCE: 13
cgcggggcct aggtg                                                         15

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
ggcatggact gtggtcatga g                                                  21

<210> SEQ ID NO 15
<211> LENGTH: 101
<212> TYPE: DNA
<213> ORGANISM: Artificial Sequence
<220> FEATURE:
<223> OTHER INFORMATION: Synthetic

<400> SEQUENCE: 15
cctaaaagcg tagtgggaaa gtgacgtgaa attcgtccag attacttgat acggttatac        60
```
tccgaatgcc acctaggcca tacaacgagc aaggagactc a                101

<210> SEQ ID NO 16
<211> LENGTH: 898
<212> TYPE: DNA
<213> ORGANISM: Artificial Sequence
<220> FEATURE:
<223> OTHER INFORMATION: Synthetic

<400> SEQUENCE: 16
cctaaaagcg tagtgggaaa gtgacgtgaa attcgtccag attacttgat acggttatac     60
tccgaatgcc acctaggcca tacaacgagc aaggagactc aggtaccggc ctaaaagcgt    120
agtgggaaag tgacgtgaaa ttcgtccaga ttacttgata cggttatact ccgaatgcca    180
cctaggccat acaacgagca aggagactca ggatccggcc taaaagcgta gtgggaaagt    240
gacgtgaaat tcgtccagat tacttgatac ggttatactc cgaatgccac ctaggccata    300
caacgagcaa ggagactcag gatccggcct aaaagcgtag tgggaaagtg acgtgaaatt    360
cgtccagatt acttgatacg gttatactcc gaatgccacc taggccatac aacgagcaag    420
gagactcagg atccaccgga tctagctgca gtcgacggta ccggcctaaa agcgtagtgg    480
gaaagtgacg tgaaattcgt ccagattact tgatacggtt atactccgaa tgccacctag    540
gccatacaac gagcaaggag actcaggtac cggcctaaaa gcgtagtggg aaagtgacgt    600
gaaattcgtc cagattactt gatacggtta tactccgaat gccacctagg ccatacaacg    660
agcaaggaga ctcaggatcc ggcctaaaag cgtagtggga aagtgacgtg aaattcgtcc    720
agattacttg atacggttat actccgaatg ccacctaggc catacaacga gcaaggagac    780
tcaggatccg gcctaaaagc gtagtgggaa agtgacgtga aattcgtcca gattacttga    840
tacggttata ctccgaatgc cacctaggcc atacaacgag caaggagact caggatcc     898

<210> SEQ ID NO 17
<211> LENGTH: 1367
<212> TYPE: DNA
<213> ORGANISM: Artificial Sequence
<220> FEATURE:
<223> OTHER INFORMATION: Synthetic

<400> SEQUENCE: 17
cctaaaagcg tagtgggaaa gtgacgtgaa attcgtccag attacttgat acggttatac     60
tccgaatgcc acctaggcca tacaacgagc aaggagactc aggtaccggc ctaaaagcgt    120
agtgggaaag tgacgtgaaa ttcgtccaga ttacttgata cggttatact ccgaatgcca    180
cctaggccat acaacgagca aggagactca ggatccggcc taaaagcgta gtgggaaagt    240
gacgtgaaat tcgtccagat tacttgatac ggttatactc cgaatgccac ctaggccata    300
caacgagcaa ggagactcag gatccggcct aaaagcgtag tgggaaagtg acgtgaaatt    360
cgtccagatt acttgatacg gttatactcc gaatgccacc taggccatac aacgagcaag    420
gagactcagg atccaccgga tctagctgca gtcgacggta ccggcctaaa agcgtagtgg    480
gaaagtgacg tgaaattcgt ccagattact tgatacggtt atactccgaa tgccacctag    540
gccatacaac gagcaaggag actcaggtac cggcctaaaa gcgtagtggg aaagtgacgt    600
gaaattcgtc cagattactt gatacggtta tactccgaat gccacctagg ccatacaacg    660
agcaaggaga ctcaggatcc ggcctaaaag cgtagtggga aagtgacgtg aaattcgtcc    720
agattacttg atacggttat actccgaatg ccacctaggc catacaacga gcaaggagac    780
tcaggatccg gcctaaaagc gtagtgggaa agtgacgtga aattcgtcca gattacttga    840

```
tacggttata ctccgaatgc cacctaggcc atacaacgag caaggagact caggatccac    900
cgagtctaga agcattgcag tcgacggtac cggcctaaaa gcgtagtggg aaagtgacgt    960
gaaattcgtc cagattactt gatacggtta tactccgaat gccacctagg ccatacaacg   1020
agcaaggaga ctcaggtacc ggcctaaaag cgtagtggga agtgacgtg aaattcgtcc    1080 agattacttg atacggttat actccgaatg ccacctaggc catacaacga gcaaggagac   1140
tcaggatccg gcctaaaagc gtagtgggaa agtgacgtga attcgtcca gattacttga    1200 tacggttata ctccgaatgc cacctaggcc atacaacgag caaggagact caggatccgg   1260
cctaaaagcg tagtgggaaa gtgacgtgaa attcgtccag attacttgat acggttatac   1320
tccgaatgcc acctaggcca tacaacgagc aaggagactc aggatcc                 1367

<210> SEQ ID NO 18
<211> LENGTH: 62
<212> TYPE: DNA
<213> ORGANISM: Artificial Sequence
<220> FEATURE:
<223> OTHER INFORMATION: Synthetic

<400> SEQUENCE: 18
ggagcgcgga gacggtcggg tccagatatt cgtatctgtc gagtagagtg tgggctccgc     60
gc                                                                   62

<210> SEQ ID NO 19
<211> LENGTH: 1852
<212> TYPE: DNA
<213> ORGANISM: Artificial Sequence
<220> FEATURE:
<223> OTHER INFORMATION: Synthetic

<400> SEQUENCE: 19
accgccgaga ccgcgtccgc cccgcgagca cagagcctcg cctttgccga tccgccgccc     60
gtccacaccc gccgccagct caccatggat gatgatatcg ccgcgctcgt cgtcgacaac    120
ggctccggca tgtgcaaggc cggcttcgcg ggcgacgatg ccccccgggc cgtcttcccc    180
tccatcgtgg ggcgccccag gcaccagggc gtgatggtgg gcatgggtca gaaggattcc    240
tatgtgggcg acgaggccca gagcaagaga ggcatcctca ccctgaagta ccccatcgag    300
cacggcatcg tcaccaactg ggacgacatg gagaaatct ggcaccacac cttctacaat    360
gagctgcgtg tggctcccga ggagcacccc gtgctgctga ccgaggcccc cctgaacccc    420
aaggccaacc gcgagaagat gacccagatc atgtttgaga ccttcaacac cccagccatg    480
tacgttgcta tccaggctgt gctatccctg tacgcctctg gccgtaccac tggcatcgtg    540
atggactccg gtgacgggt cacccacact gtgcccatct cgagggta tgccctcccc    600 catgccatcc tgcgtctgga cctggctggc cgggacctga ctgactacct catgaagatc    660
ctcaccgagc gcggctacag cttcaccacc acggccgagc gggaaatcgt gcgtgacatt    720
aaggagaagc tgtgctacgt cgccctggac ttcgagcaag atggccac ggctgcttcc    780 agctcctccc tggagaagag ctacgagctg cctgacggcc aggtcatcac cattggcaat    840
gagcggttcc gctgccctga ggcactcttc cagccttcct tcctgggcat ggagtcctgt    900
ggcatccacg aaactacctt caactccatc atgaagtgtg acgtggacat ccgcaaagac    960
ctgtacgcca acacagtgct gtctggcggc accaccatgt accctggcat tgccgacagg   1020
atgcagaagg agatcactgc cctggcaccc agcacaatga agatcaagat cattgctcct   1080
```

```
cctgagcgca agtactccgt gtggatcggc ggctccatcc tggcctcgct gtccaccttc    1140
cagcagatgt ggatcagcaa gcaggagtat gacgagtccg gcccctccat cgtccaccgc    1200
aaatgcttct aggcggacta tgacttagtt gcgttacacc ctttcttgac aaaacctaac    1260
ttgcgcagaa aacaagatga gattggcatg gctttatttg ttttttttgt tttgttttgg    1320
tttttttttt tttttggct tgactcagga tttaaaaact ggaacggtga aggtgacagc     1380
agtcggttgg agcgagcatc ccccaaagtt cacaatgtgg ccgaggactt tgattgcaca    1440
ttgttgtttt tttaatagtc attccaaata tgagatgcgt tgttacagga agtcccttgc    1500
catcctaaaa gccaccccac ttctctctaa ggagaatggc ccagtcctct cccaagtcca    1560
cacaggggag gtgatagcat tgctttcgtg taaattatgt aatgcaaaat tttttaatc     1620 ttcgccttaa tactttttta ttttgtttta ttttgaatga tgagccttcg tgccccccct    1680
tccccctttt ttgtccccca acttgagatg tatgaaggct tttggtctcc ctgggagtgg    1740
gtggaggcag ccagggctta cctgtacact gacttgagac cagttgaata aaagtgcaca    1800
ccttaaaaat gaaaaaaaaa aaaaaaaaaa aaaaaaaaaa aaaaaaaaaa aa            1852
```